US011547709B2

(12) United States Patent
Jackowski et al.

(10) Patent No.: US 11,547,709 B2
(45) Date of Patent: Jan. 10, 2023

(54) METHODS OF TREATING DISORDERS ASSOCIATED WITH CASTOR

(71) Applicants: ST. JUDE CHILDREN'S RESEARCH HOSPITAL, INC., Memphis, TN (US); COA THERAPEUTICS, INC., San Francisco, CA (US)

(72) Inventors: Suzanne Jackowski, Bartlett, TN (US); Charles O. Rock, Bartlett, TN (US); Richard E. Lee, Cordova, TN (US); Lalit Kumar Sharma, South San Francisco, CA (US); Mi Kyung Yun, Collierville, TN (US); Chitra Subramanian, Cordova, TN (US); Rajendra P. Tangallapally, Collierville, TN (US); Anne V. Edwards, Memphis, TN (US); Robert Zamboni, Beaconsfield (CA); T. Jagadeeswar Reddy, Pierrefonds (CA); Jiuyu Liu, Collierville, TN (US)

(73) Assignees: ST. JUDE CHILDREN'S RESEARCH HOSPITAL, INC., Memphis, TN (US); COA THERAPEUTICS, INC., San Francisco, CA (US)

( * ) Notice: Subject to any disclaimer, the term of this patent is extended or adjusted under 35 U.S.C. 154(b) by 115 days.

(21) Appl. No.: 16/957,996

(22) PCT Filed: Dec. 26, 2018

(86) PCT No.: PCT/US2018/067536
§ 371 (c)(1),
(2) Date: Jun. 25, 2020

(87) PCT Pub. No.: WO2019/133632
PCT Pub. Date: Jul. 4, 2019

(65) Prior Publication Data
US 2021/0023081 A1   Jan. 28, 2021

Related U.S. Application Data

(60) Provisional application No. 62/751,210, filed on Oct. 26, 2018, provisional application No. 62/610,839, filed on Dec. 27, 2017.

(51) Int. Cl.
*A61K 31/501* (2006.01)
*A61P 3/00* (2006.01)
*A61K 31/197* (2006.01)
*A61K 31/205* (2006.01)

(52) U.S. Cl.
CPC .......... *A61K 31/501* (2013.01); *A61K 31/197* (2013.01); *A61K 31/205* (2013.01); *A61P 3/00* (2018.01)

(58) Field of Classification Search
CPC .. A61K 31/197; A61K 31/205; A61K 31/501; A61K 38/43; A61K 31/22; A61K 31/444; A61K 31/496; A61K 31/5377; A61K 31/551; A61K 49/00; A61K 2300/00; A61P 3/00; A61P 21/04; A61P 25/02; A61P 25/28; A61P 35/00; A61P 39/02; A61P 3/10; A61P 43/00
See application file for complete search history.

(56) References Cited

U.S. PATENT DOCUMENTS

| 7,754,724 | B2 | 7/2010 | Lorsbach et al. |
| 8,153,633 | B2 | 4/2012 | Austin et al. |
| 8,227,467 | B2 | 7/2012 | Kyle et al. |
| 8,975,398 | B2 | 3/2015 | Hansen et al. |
| 10,899,734 | B2 | 1/2021 | Sharma et al. |
| 2003/0114517 | A1 | 6/2003 | Greenlee et al. |
| 2006/0035884 | A1 | 2/2006 | Neitzel et al. |
| 2009/0306100 | A1 | 12/2009 | Barbosa et al. |
| 2010/0004254 | A1 | 1/2010 | Sun et al. |
| 2010/0041663 | A1 | 2/2010 | He et al. |
| 2010/0210594 | A1 | 8/2010 | Wagner et al. |
| 2011/0021530 | A1 | 1/2011 | Billich et al. |
| 2011/0053233 | A1 | 3/2011 | Brown et al. |
| 2013/0072497 | A1 | 3/2013 | Lorsbach et al. |

(Continued)

FOREIGN PATENT DOCUMENTS

| WO | WO-2003105853 A1 | 12/2003 |
| WO | WO-2004011441 A1 | 2/2004 |

(Continued)

OTHER PUBLICATIONS

NINDS ((https://www.ninds.nih.gov/Disorders/All-Disorders/Refsum-Disease-Information-Page), 2019 (Year: 2019).*
(Yang, Biochem Soc Trans (2019) 47 (1): 149-155). (Year: 2019).*
Mitchell, Mol Genet Metab May 2008;94(1):4-15 (Year: 2008).*
CAS Registry No. 1183793-26-1, Entered STN Sep. 13, 2009.
Bennett et al., Cecil Textbook of Medicine,1996, 20th edition, vol. 1, 1004-1010.
Cohen et al., the development and therapeutic potential of protein kinase inhibitors, Current Opinion in Chemical Biology, 1999, vol. 3, pp. 459-465.

(Continued)

*Primary Examiner* — Umamaheswari Ramachandran
(74) *Attorney, Agent, or Firm* — Mintz, Levin, Cohn, Ferris, Glovsky and Popeo, P.C.

(57) ABSTRACT

The present disclosure relates to methods of treating a coenzyme A reduction, elevation, sequestration, toxicity, or redistribution (CASTOR) disease such as, for example, defects in fatty acid oxidation enzymes, methylmalonic acidemia, glutaric acidemia, propionic academia, and HMG-CoA lyase, via small molecule modulators of CoA levels. This abstract is intended as a scanning tool for purposes of searching in the particular art and is not intended to be limiting of the present invention.

19 Claims, 8 Drawing Sheets

(56) References Cited

U.S. PATENT DOCUMENTS

| | | |
|---|---|---|
| 2013/0157330 A1 | 6/2013 | Zhang et al. |
| 2014/0275095 A1 | 9/2014 | Dvorak et al. |
| 2015/0284746 A1 | 10/2015 | Zhang et al. |
| 2019/0300499 A1 | 10/2019 | Sharma et al. |
| 2020/0330450 A1 | 10/2020 | Smith et al. |
| 2021/0061788 A1 | 3/2021 | Lee et al. |

FOREIGN PATENT DOCUMENTS

| | | |
|---|---|---|
| WO | WO-2004058754 A1 | 7/2004 |
| WO | WO-2005011653 A2 | 2/2005 |
| WO | WO-2005056015 A1 | 6/2005 |
| WO | WO-2009106991 A2 | 9/2009 |
| WO | WO-2010007120 A1 | 1/2010 |
| WO | WO-2013004642 A1 | 1/2013 |
| WO | WO-2016168619 A1 | 10/2016 |
| WO | 2017223474 A1 | 12/2017 |
| WO | WO-2019133632 A1 | 7/2019 |
| WO | WO-2019133634 A1 | 7/2019 |
| WO | WO-2019133635 A1 | 7/2019 |
| WO | WO-2022133034 A1 | 6/2022 |

OTHER PUBLICATIONS

Dansie et al., Physiological roles of the pantothenate kinases, Biochem. Soc. Trans., 2014, 42:1033-1036.
Database BIOSIS, Accession No. PREV198631080811, 1986, Abstract.
Database BIOSIS, Accession No. PREV200100537451, Oct. 2001, Abstract.
Database Registry (STN) Registry No. 19544999-65-0, entered Jul. 18, 2016.
Database Registry (STN) Registry No. 1956298-43-3, entered Jul. 20, 2016.
Dermer et al., Bio/Technology, 1994, 12:320.
European Patent Office, Extended European Search Report for EP Application No. 17816310.1, dated Oct. 29, 2019, 9 pages.
European Patent Office, Extended European Search Report for EP Application No. 18894179.3, dated Jul. 19, 2021, 7 pages.
European Patent Office, Extended European Search Report for EP Application No. 18895007.5, dated Aug. 19, 2021, 9 pages.
Freshney, Culture of Animal Cells, A Manual of Basic Technique, Alan R. Liss, Inc., 1983, New York, pp. 1-4.
Garcia et al., Germline Deletion of Pantothenate Kinases 1 and 2 Reveals the Key Roles for CoA in Postnatal Metabolism, PLoS One, 2012, vol. 7, Issue 7: e40871, 13 pages.
Horig et al., From bench to clinic and back: Perspective on the 1$^{st}$ IQPC Translational Research Conference, Journal of Translational Medicine, Dec. 20, 2004, vol. 2, p. 44.
International Preliminary Report on Patentability dated Dec. 25, 2018 by the International Searching Authority for International Application No. PCT/US2017/039037, 6 Pages.
International Search Report, dated Nov. 9, 2017 by the International Searching Authority for International Application No. PCT/US2017/039037, 4 Pages.
International Search Report, dated Mar. 27, 2019 by the International Searching Authority for International Application No. PCT/US2018/067538, 3 pages.
International Search Report, dated Mar. 27, 2019 by the International Searching Authority for International Application No. PCT/US2018/067539, 2 pages.
Jackowski et al., Regulation of Coenzyme A Biosynthesis, Journal of Bacteriology, Dec. 1981, vol. 148, N. 3, pp. 926-932.
Johnson et al. (2004) Mitochondrial Llocalization of Human PANK2 and Hypotheses of Secondary Iron Accumulation in Pantothenate Kinase-Associated Neurodegeneration, Ann. New York Academy of Sciences, 2004, 1012: 282-298.
Kotzbauer et al., Altered Neuronal Mitochondrial Coenzyme A Synthesis in Neurodegeneration with Brain Iron Accumulation Caused by Abnormal Processing, Stability, and Catalytic Activity of Mutant Pantothenate Kinase 2, Journal of Neuroscience, Jan. 19, 2005, vol. 25, No. 3, pp. 689-698.
Kuo et al., Deficiency of pantothenate kinase 2 (Pank2) in mice leads to retinal degeneration and azoospermia, Hum. Mol. Genet., Jan. 1, 2005, vol. 14, No. 1, pp. 49-57.
Leeson et al., The influence of drug-like concepts on decision-making in medicinal chemistry, Nature Review Drug Discovery, Nov. 2007, vol. 6, pp. 881-890.
Leonardi et al., Coenzyme A: back in action, Progress in Lipid Research, 2005, vol. 44, pp. 125-153.
Leonardi et al., Localization and Regulation of Mouse Pantothenate Kinase 2, FEBS Lett., Oct. 2, 2007, vol. 581, pp. 4639-4644.
Leonardi et al., Pantothenate Kinase 1 is Required to Support the Metabolic Transition from the Fed to the Fasted State, PloS One, Jun. 14, 2010, vol. 5, Issue 6, e11107, 12 pages.
Leonardi et al., Pank1 Deletion in Leptin-deficient Mice Reduces Hyperglycaemia and Hyperinsulinaemia and Modifies Global Metabolism without Affecting Insulin Resistance, Diabetologia, Jul. 2014, vol. 57, pp. 1466-1475.
Pratini et al., Treatment of Classic Pantothenate Kinase-Associated Neurodegeneration (PKAN) with Deferiprone and Intrathecal Baclofen, American Journal of Physical Medicine & Rehabilitation, Aug. 2013, vol. 98, pp. 728-733.
PUBCHEM Compound Summary for CID 110727414, 'AKOS027640281', U.S. National Library of Medicine, 2016, (https://pubchem.ncbi.nlm.nih.gov/compound/110727414); p. 3.
PUBCHEM Compound Summary For CID 121060331 deposited on Jun. 17, 2016, pp. 1-10., p. 3.
PUBMED Compound Summary for CID 53621124, 'MolPort-020-021-215', U.S. National Library of Medicine, 2011,(https://pubchem.ncbi.nlm.nih.gov/compound/53621124); p. 3.
Rinaldo et al., Effect of treatment with glycine and L-carnitine in medium-chain acyl-coenzyme a dehydrogenase deficiency, Journal of Pediatrics, Mosby-Year Book, St. Louis, MO, Apr. 1, 1993, vol. 122, No. 4, pp. 580-584.
Rock et al., The murine pantothenate kinase (Pank1) gene encodes two differentially regulated pantothenate kinase isozymes, Gene, 2002, vol. 291, pp. 35-43.
Sabatti et al., Genome-wide association analysis of metabolic traits in a birth cohort from a founder population, Nature Genet., Jan. 2009, vol. 41, No. 1, pp. 35-46.
Schafer et al., Failure is an option: learning from unsuccessful proof-of-concept trials, Drug Discovery Today, Nov. 2008, vol. 13, Nos. 21/22, pp. 913-916.
Sharma et. al., A High-Throughput Screen Reveals New Small-Molecule Activators and Inhibitors of Pantothenate Kinases, Journal of Medicinal Chemistry, 2015, vol. 58, pp. 1563-1568.
Shultz, Setting expectations in molecular optimizations: Strengths and limitations of commonly used composite parameters, Bioorganic & Medicinal Chemistry Letters, 2013, vol. 23, pp. 5980-5991.
Tafesse et al., Synthesis and evaluation of pyridazinylpiperazines as vanilloid receptor 1 antagonists, Bioorganic & Medicinal Chemistry Letters, Nov. 15, 2004, vol. 14, pp. 5513-5519.
Zhang et al., Feedback Regulation of Murine Pantothenate Kinase 3 by Coenzyme A and Coenzyme A thioesters, The Journal of Biological Chemistry, Sep. 23, 2005, vol. 280, No. 1, pp. 32594-32601.
Zhang et al., Biochemical Properties of Human Pantothenate Kinase 2 Isoforms and Mutations Linked to Pantothenate Kinase-associated Neurodegeneration, The Journal of Biological Chemistry, Jan. 6, 2006, vol. 281, No. 1, pp. 107-114.
Zhou et al., A novel pantothenate kinase gene (PANK2) is defective in Hallervorden-Spatz syndrome, Nature Genetics, Aug. 2001, vol. 28, pp. 345-349.
Written Opinion, dated Nov. 9, 2017 by the International Searching Authority for International Application No. PCT/US2017/039037, 5 pages.
Written Opinion, dated Mar. 27, 2019 by the International Searching Authority for International Application No. PCT/US2018/067538, 4 pages.
Written Opinion, dated Mar. 27, 2019 by the International Searching Authority for International Application No. PCT/US2018/067539, 5 pages.
International Search Report for PCT/US2018/067536 dated Mar. 21, 2019, 2 pages.

(56) References Cited

OTHER PUBLICATIONS

PUBCHEM CID 75373203, "2-Methyl-8-[4-(pyridazin-3-yl)piperazine-1-carbonyl]quinoline", Create Date: Jul. 12, 2014, p. 4, compound listed.
Written Opinion of the International Searching Authority for PCT/US2018/067536 dated Mar. 21, 2019, 3 pages.
International Search Report for International Application No. PCT/US2021/063717, dated May 12, 2022, 4 pages.
Mitchell et al., Hereditary and acquired diseases of acyl-coenzyme A metabolism, Molecular Genetics and Metabolism, 2008, vol. 94, pp. 415.
National Institute of Neurological Disorders and Stroke, Refsum Disease Information Page, https://www.ninds.nih.gov/Disorders/All-Disorders/Refsum-Disease-Information-Page), 2019 (year:2019), 4 pages.
Waack et al., L-Malate's Plasma and Excretion Profile in the Treatment of Moderate and Severe Hemorrhagic Shock in Rats, BioMed Research International, 2016, vol. 2016, 9 pages.
Written Opinion for International Application No. PCT/US2021/063717, dated May 12, 2022, 6 pages.
Yang et al., Hereditary diseases of coenzyme A thioester metabolism, Biochemical Society Transactions, 2019, vol. 47, pp. 149-155.

* cited by examiner

PZ-2891

PZ-3022

METHODS OF TREATING DISORDERS ASSOCIATED WITH CASTOR

CROSS-REFERENCE TO RELATED APPLICATIONS

This Application is the U.S. National Stage Entry under § 371 of International Application No. PCT/US2018/067536, filed Dec. 26, 2018, which claims the priority benefit of U.S. Provisional Application No. 62/751,210, filed on Oct. 26, 2018, and 62/610,839, filed on Dec. 27, 2017, the contents of which are incorporated herein by reference in their entireties.

BACKGROUND

Coenzyme A (CoA) is a cofactor derived from vitamin B5 (pantothenate) that is covalently bound to the organic acids in cells, thereby enabling the organic acids to participate in the biochemical reactions that govern energy production and lipid metabolism. The CoA-bound organic acids, called acyl-CoAs, constitute a small, but significant portion of the total CoA pool under normal healthy conditions. A number of inborn errors of metabolism result from the genetic deficiency of one of the enzymes acting on acyl-CoAs, leading to the accumulation of acyl-CoAs to high levels. 'CASTOR' is the term that has been given to these diseases and stands for CoA sequestration, toxicity or redistribution (Mitchell et al. (2008) *Mol. Genet. Metab.* 94:4-15). Acyl-CoAs are known feedback inhibitors of pantothenate kinase (PANK) enzymes that catalyze the first step in CoA biosynthesis (Leonardi et al. (2005) *Prog. Lipid Res.* 44:125-153). Under CASTOR conditions the synthesis of CoA becomes inhibited and energy production and lipid metabolism are limited as a result.

Despite the documented association of PanK with acyl-CoAs, methods of treating CASTOR diseases using small molecule modulators of CoA levels have yet to be realized. Thus, there remains a need for methods of treating CASTOR diseases via modulation of CoA levels. These needs and others are met by the present invention.

SUMMARY

In accordance with the purpose(s) of the invention, as embodied and broadly described herein, the invention, in one aspect, relates to compositions and methods for use in the prevention and treatment of disorders associated with pantothenate kinase activity such as, for example, PKAN and diabetes.

Disclosed are of treating a coenzyme A reduction, elevation, sequestration, toxicity, or redistribution (CASTOR) disease in a subject, the method comprising the step of administering to the subject a therapeutically effective amount of a compound having a structure represented by a formula:

$$Ar^1-Z-Q^2-R^6,$$

wherein Z is selected from A(C=O), COCH$_2$,

[cyclopropane-carbonyl structure]

CO, NHCO, NHCS, CH$_2$SO$_2$, and SO$_2$; wherein A is selected from O, CO, CH$_2$, CF$_2$, NH, N(CH$_3$), and CH(OH); wherein Q$^2$ is a structure selected from:

[structures]

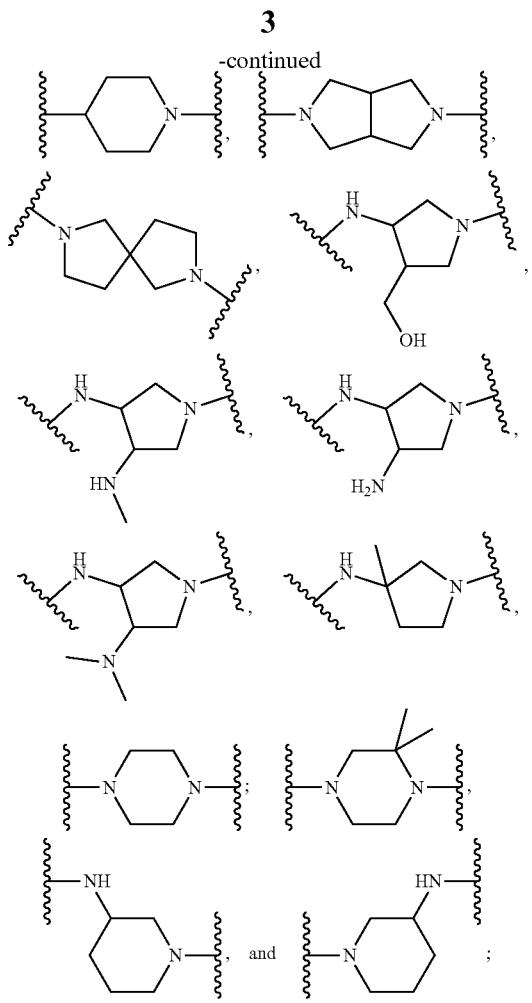

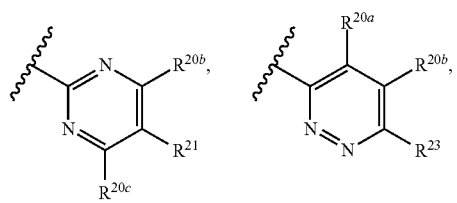

wherein Ar$^1$ is selected from aryl and heteroaryl and substituted with 0, 1, 2, or 3 groups independently selected from halogen, —NO$_2$, —CN, —OH, —SH, —NH$_2$, C1-C8 thioalkyl, C1-C8 acyclic alkyl, C2-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, —CO(C1-C8 acyclic alkyl), C1-C8 alkoxyhaloalkyl, and cyclopropyl, cyclobutyl, and oxetane, wherein the cyclopropyl, cyclobutyl, and oxetane are optionally substituted with 1, 2, 3, or 4 groups independently selected from halogen, —NO$_2$, —CN, —OH, —SH, —NH$_2$, C1-C4 acyclic alkyl, C1-C4 hydroxyalkyl, C1-C4 monohaloalkyl, C1-C4 polyhaloalkyl, C1-C4 alkoxy, C1-C4 monohaloalkoxy, C1-C4 polyhaloalkoxy, C1-C4 acyclic alkylamino, (C1-C4)(C1-C4)dialkylamino, and —CO(C1-C4 acyclic alkyl); wherein R$^6$ is selected from —NHCH$_2$C$_6$H$_5$ and Ar$^2$; wherein Ar$^2$ is a structure represented by a formula selected from:

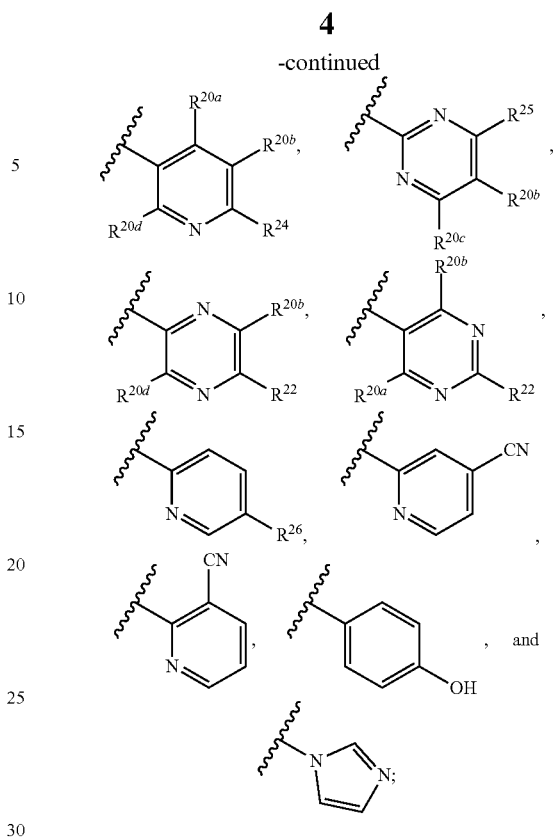

wherein each of R$^{20a}$, R$^{20b}$, R$^{20c}$, and R$^{20d}$, when present, is independently selected from hydrogen, halogen, —CN, —NO$_2$, —NH$_2$, C1-C4 alkyl, C1-C4 monohaloalkyl, C1-C4 polyhaloalkyl, C1-C4 alkoxy, C1-C4 monohaloalkoxy, C1-C4 polyhaloalkoxy, C1-C4 alkylamino, (C1-C4)(C1-C4) dialkylamino, and cyclopropyl; wherein R$^{21}$, when present, is selected from hydrogen, halogen, —CN, —NO$_2$, —SO$_2$NH$_2$, —SO$_2$CH$_3$, —SO$_2$CF$_3$, and Cy$^1$; wherein Cy$^1$, when present, is selected from cycle, heterocycle, aryl, and heteroaryl and substituted with 0, 1, 2, or 3 groups independently selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino; wherein R$^{22}$, when present, is selected from —CN, halogen, —NO$_2$, SO$_2$NH$_2$, SO$_2$CH$_3$, and SO$_2$CF$_3$; wherein R$^{23}$, when present, is selected from hydrogen, halogen, —CN, —NO$_2$, —SO$_2$NH$_2$, —SO$_2$CH$_3$, —SO$_2$CF$_3$, cyclohexyl,

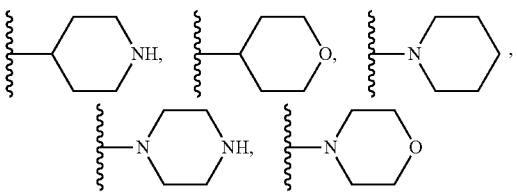

and Cy$^1$; wherein R$^{24}$, when present, is selected from —CN, halogen, —NO$_2$, SO$_2$NH$_2$, SO$_2$CH$_3$, and SO$_2$CF$_3$; wherein R$^{25}$, when present, is selected from —CN, —NO$_2$, SO$_2$NH$_2$, SO$_2$CH$_3$, and SO$_2$CF$_3$; wherein R$^{26}$, when present, is selected from —Br, —Cl, —F, —CN, —NO$_2$, —CF$_3$, and methyl; or a pharmaceutically acceptable salt thereof.

Also disclosed are kits comprising an effective amount of a compound of claim 1, and one or more of: (a) at least one agent known to treat a CASTOR disease; and (b) instructions for treating a CASTOR disease.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying figures, which are incorporated in and constitute a part of this specification, illustrate several aspects and together with the description serve to explain the principles of the invention.

Figure 1A:
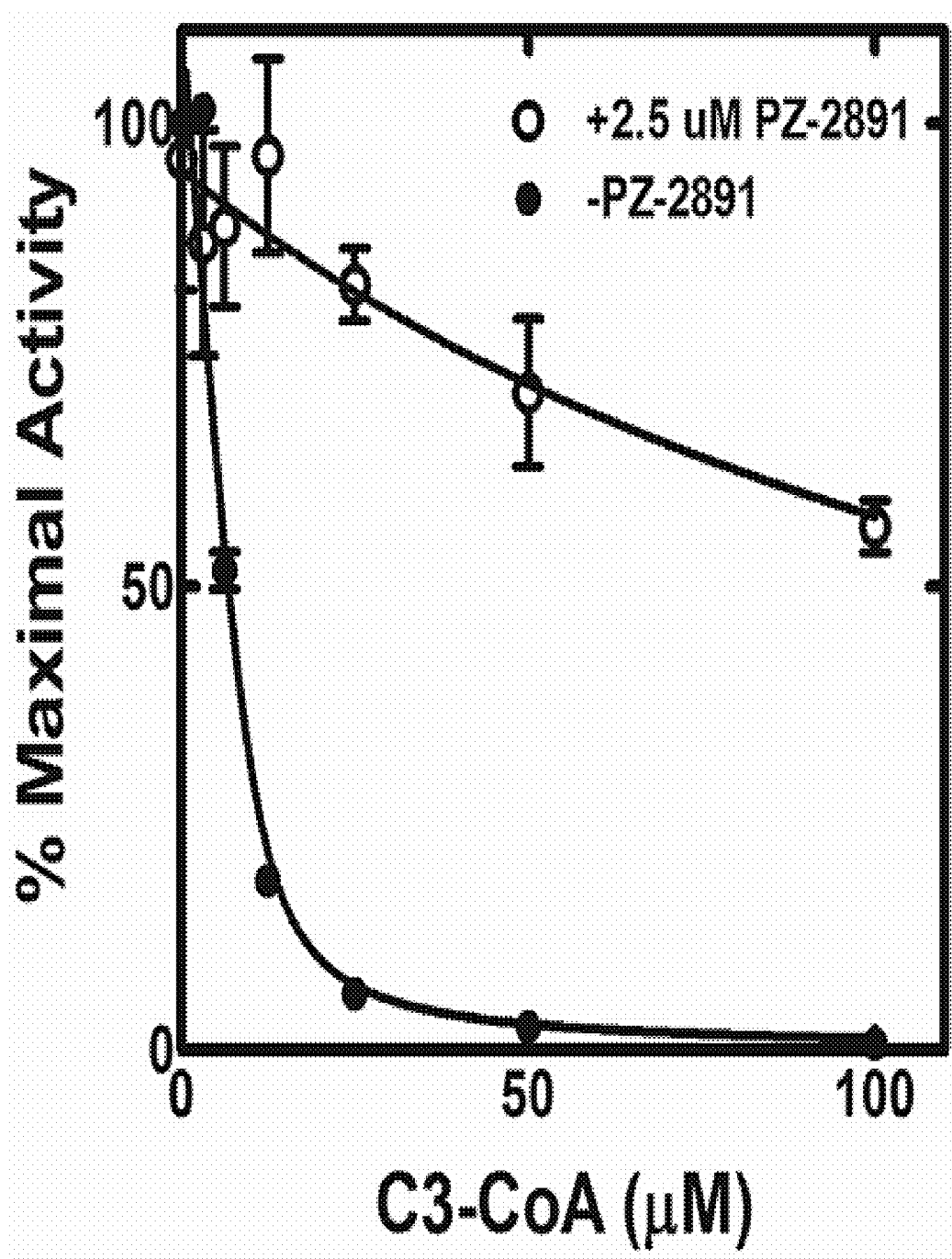
FIG. 1A shows representative data demonstrating that PZ-2891 prevents inhibition of purified human PANK3 by propionyl-CoA.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage form can comprise a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), anti-foaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an interne website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an interne website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. For example, the cycloalkyl group and heterocycloalkyl group can be substituted with 0, 1, 2, 3, or 4 groups independently selected from C1-C4 alkyl, C3-C7 cycloalkyl, C1-C4 alkoxy, $-NH_2$, (C1-C4)alkylamino, (C1-C4)(C1-C4)dialkylamino, ether, halogen, $-OH$, C1-C4 hydroxyalkyl, $-NO_2$, silyl, sulfo-oxo, $-SH$, and C1-C4 thioalkyl, as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. For example, the cycloalkenyl group and heterocycloalkenyl group can be substituted with 0, 1, 2, 3, or 4 groups independently selected from C1-C4 alkyl, C3-C7 cycloalkyl, C1-C4 alkoxy, C2-C4 alkenyl, C3-C6 cycloalkenyl, C2-C4 alkynyl, aryl, heteroaryl, aldehyde, $-NH_2$, (C1-C4)alkylamino, (C1-C4)(C1-C4)dialkylamino, carboxylic acid, ester, ether, halogen, $-OH$, C1-C4 hydroxyalkyl, ketone, azide, $-NO_2$, silyl, sulfo-oxo, $-SH$, and C1-C4 thioalkyl, as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkynyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, $-NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" or "CO" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(0)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$- or -($A^1$O(O)C-$A^2$-OC(O))$_a$-, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1$O$A^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$-$A^2$O)$_a$-, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN or —C≡N.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$(CH_2)_{0-4}O(CH_2)_{0-1}$-pyridyl which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR—$, $SC(S)SR°$; —$(CH_2)_{0-4}SC(O)R°$; —$(CH_2)_{0-4}C(O)NR°_2$; —$C(S)NR°_2$; —$C(S)SR°$; —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2R°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°_2$; $SiR°_3$; —$(C_{1-4}$ straight or branched)alkylene)O—$N(R°)_2$; or —$(C_{1-4}$ straight or branched)alkylene)C(O)O—$N(R°)_2$, wherein each $R°$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet{}_2$, —NO$_2$, —SiR$^\bullet{}_3$, —OSiR$^\bullet{}_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR°$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger{}_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger{}_2$, —C(S)NR$^\dagger{}_2$, —C(NH)NR$^\dagger{}_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

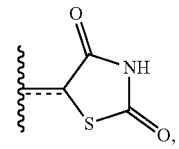

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an a-hydrogen can exist in an equilibrium of the keto form and the enol form.

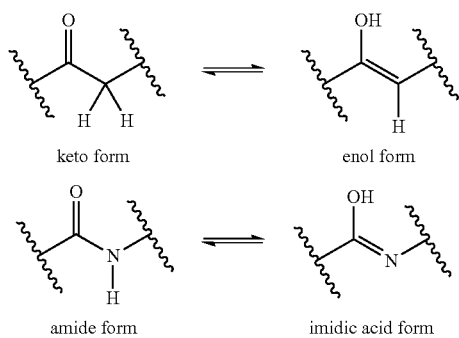

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

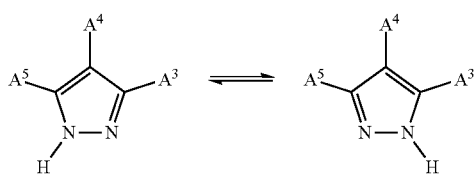

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

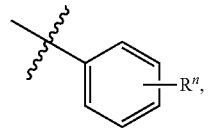

which is understood to be equivalent to a formula:

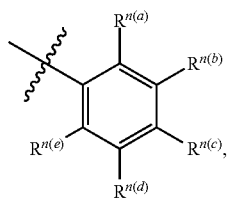

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. METHODS OF TREATING A CASTOR DISEASE IN A SUBJECT

In one aspect, disclosed are methods of treating a coenzyme A reduction, elevation, sequestration, toxicity, or redistribution (CASTOR) disease in a subject, the method comprising the step of administering to the subject a therapeutically effective amount of at least one disclosed compound or a pharmaceutically acceptable salt thereof. Examples of CASTOR diseases include, but are not limited to, defects in fatty acid oxidation enzymes, methylmalonic acidemia, glutaric acidemia, propionic academia, and HMG-CoA lyase deficiency.

In one aspect, disclosed are methods of treating a coenzyme A reduction, elevation, sequestration, toxicity, or redistribution (CASTOR) disease in a subject, the method comprising the step of administering to the subject a therapeutically effective amount of a compound having a structure represented by a formula:

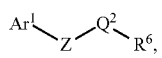

wherein Z is selected from A(C=O), COCH$_2$,

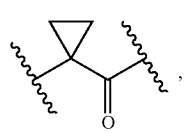

CO, NHCO, NHCS, CH$_2$SO$_2$, and SO$_2$; wherein A is selected from O, CO, CH$_2$, CF$_2$, NH, N(CH$_3$), and CH(OH); wherein Q$^2$ is a structure selected from:

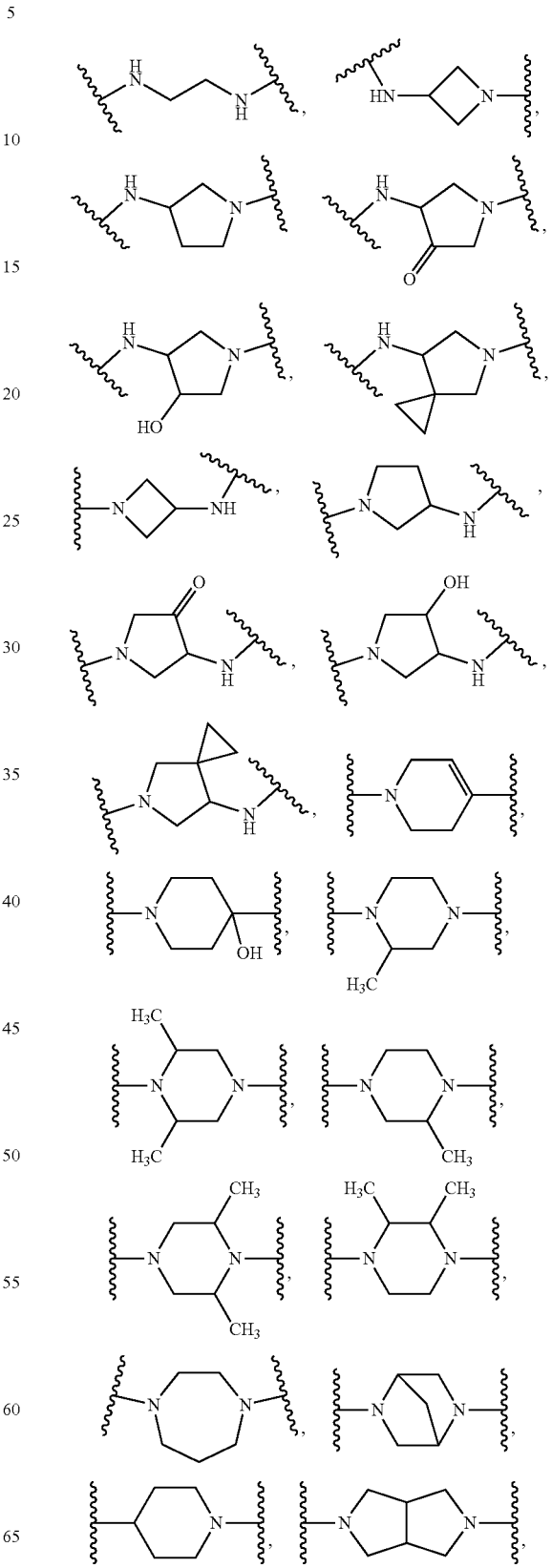

-continued

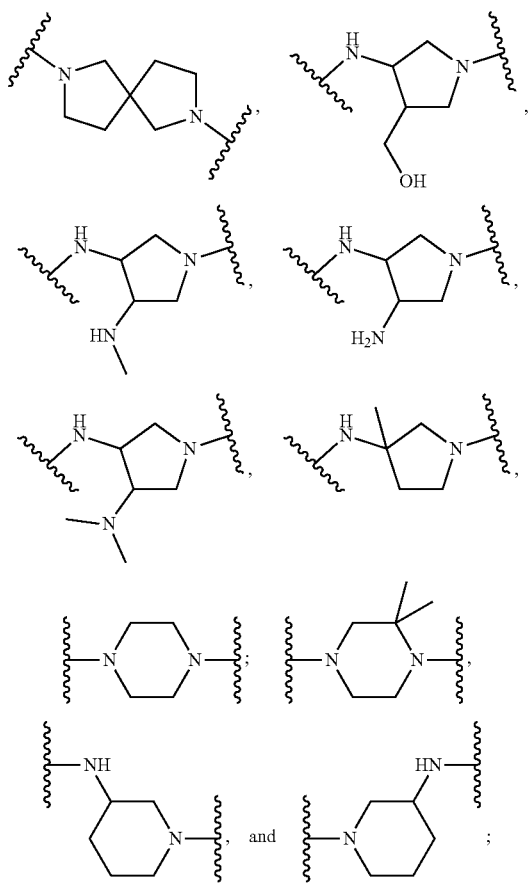

wherein Ar¹ is selected from aryl and heteroaryl and substituted with 0, 1, 2, or 3 groups independently selected from halogen, —NO₂, —CN, —OH, —SH, —NH₂, C1-C8 thioalkyl, C1-C8 acyclic alkyl, C2-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, —CO(C1-C8 acyclic alkyl), C1-C8 alkoxyhaloalkyl, and cyclopropyl, cyclobutyl, and oxetane, wherein the cyclopropyl, cyclobutyl, and oxetane are optionally substituted with 1, 2, 3, or 4 groups independently selected from halogen, —NO₂, —CN, —OH, —SH, —NH₂, C1-C4 acyclic alkyl, C1-C4 hydroxyalkyl, C1-C4 monohaloalkyl, C1-C4 polyhaloalkyl, C1-C4 alkoxy, C1-C4 monohaloalkoxy, C1-C4 polyhaloalkoxy, C1-C4 acyclic alkylamino, (C1-C4)(C1-C4)dialkylamino, and —CO(C1-C4 acyclic alkyl); wherein R⁶ is selected from —NHCH₂C₆H₅ and Ar²; wherein Ar² is a structure represented by a formula selected from:

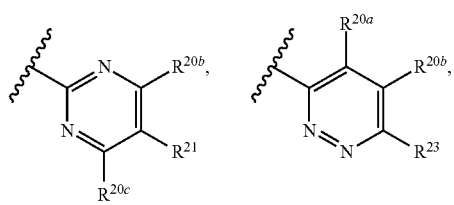

-continued (structures with R²⁰ᵃ, R²⁰ᵇ, R²⁰ᶜ, R²⁰ᵈ, R²¹, R²², R²³, R²⁴, R²⁵, R²⁶ as shown)

wherein each of R²⁰ᵃ, R²⁰ᵇ, R²⁰ᶜ, and R²⁰ᵈ, when present, is independently selected from hydrogen, halogen, —CN, —NO₂, —NH₂, C1-C4 alkyl, C1-C4 monohaloalkyl, C1-C4 polyhaloalkyl, C1-C4 alkoxy, C1-C4 monohaloalkoxy, C1-C4 polyhaloalkoxy, C1-C4 alkylamino, (C1-C4)(C1-C4) dialkylamino, and cyclopropyl; wherein R²¹, when present, is selected from hydrogen, halogen, —CN, —NO₂, —SO₂NH₂, —SO₂CH₃, —SO₂CF₃, and Cy¹; wherein Cy¹, when present, is selected from cycle, heterocycle, aryl, and heteroaryl and substituted with 0, 1, 2, or 3 groups independently selected from halogen, —NO₂, —CN, —OH, —SH, —NH₂, C1-C4 alkyl, C1-C4 monohaloalkyl, C1-C4 polyhaloalkyl, C1-C4 alkoxy, C1-C4 alkylamino, and (C1-C4)(C1-C4)dialkylamino; wherein R²², when present, is selected from —CN, halogen, —NO₂, SO₂NH₂, SO₂CH₃, and SO₂CF₃; wherein R²³, when present, is selected from hydrogen, halogen, —CN, —NO₂, —SO₂NH₂, —SO₂CH₃, —SO₂CF₃, cyclohexyl,

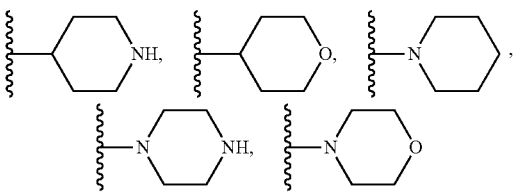

and Cy¹; wherein R²⁴, when present, is selected from —CN, halogen, —NO₂, SO₂NH₂, SO₂CH₃, and SO₂CF₃; wherein R²⁵, when present, is selected from —CN, —NO₂, SO₂NH₂, SO₂CH₃, and SO₂CF₃; wherein R²⁶, when present, is selected from —Br, —Cl, —F, —CN, —NO₂, —CF₃, and methyl; or a pharmaceutically acceptable salt thereof.

The disclosed small molecule modulators of pantothenate kinases counteract the feedback inhibition of the PANK enzyme(s) by cellular acyl-coenzyme A molecules (acyl-CoAs), thereby releasing the PANK catalytic capacity to initiate CoA biosynthesis. Treatment with the disclosed small molecules resulted in elevated levels of CoA that can accommodate the acyl-CoA accumulation under CASTOR conditions while maintaining a rate of energy production and lipid metabolism that is sufficient to ameliorate the pathology, morbidity, and mortality that are associated with acyl-CoA imbalances.

In various aspects, the CASTOR disease may be associated with inhibition of one or more pantothenate kinases by one or more acyl Coenzyme A (acyl-CoA) species. In a further aspect, the CASTOR disease is associated with accumulation of one or more acyl Coenzyme A (acyl-CoA) species in a subject having a CASTOR disease in an amount greater than that of a subject not having a CASTOR disease. In a still further aspect, the CASTOR disease is associated with a decrease of CoA and/or acetyl-CoA in a subject having a CASTOR disease in an amount lower than that of a subject not having the CASTOR disease. In yet a further aspect, the CASTOR disease is associated with impaired or inhibited degradation of the one or more acyl-CoA species in the subject having a CASTOR disease. In an even further aspect, the one or more acyl-CoA species are not acetyl Coenzyme A (acetyl-CoA).

In various aspects, the CASTOR disease is associated with accumulation of one or more fatty acids in a subject having a CASTOR disease in an amount greater than that of a subject not having the CASTOR disease. In a further aspect, the CASTOR disease is associated with impaired or inhibited degradation of the one or more fatty acids in the subject having a CASTOR disease.

In various aspects, the CASTOR disease is selected from medium-chain acyl-CoA dehydrogenase deficiency, biotinidase deficiency, isovaleric acidemia, very long-chain acyl-CoA dehydrogenase deficiency, long-chain L-3-OH acyl-CoA dehydrogenase deficiency, glutaric acidemia type I, 3-hydroxy-3-methylglutaric acidemia, trifunctional protein deficiency, multiple carboxylase deficiency, methylmalonic acidemia (methylmalonyl-CoA mutase deficiency), 3-methylcrotonyl-CoA carboxylase deficiency, methylmalonic acidemia (Cbl A,B), propionic acidemia, carnitine uptake defect, beta-ketothiolase deficiency, short-chain acyl-CoA dehydrogenase deficiency, glutaric acidemia type II, medium/short-chain L-3-OH acyl-CoA dehydrogenase deficiency, medium-chain ketoacyl-CoA thiolase deficiency, carnitine palmitoyltransferase II deficiency, methylmalonic acidemia (Cbl C,D), malonic acidemia, carnitine: acylcarnitine translocase deficiency, isobutyryl-CoA dehydrogenase deficiency, 2-methyl 3-hydroxybutyric aciduria, dienoyl-CoA reductase deficiency, 3-methylglutaconic aciduria, PLA2G6-associated neurodegeneration, glycine N-acyltransferase deficiency, 2-methylbutyryl-CoA-dehydrogenase-deficiency, mitochondrial acetoacetyl-CoA thiolase deficiency, dihydrolipoamide dehydrogenase deficiency/Branched chain alpha-ketoacid dehydrogenase (BCKDH) deficiency, 3-methylglutaconyl-CoA hydratase deficiency, 3-hydroxyisobutyrate dehydrogenase deficiency, 3-hydroxy-isobutyryl-CoA hydrolase deficiency, isobutyryl-CoA dehydrogenase deficiency, methylmalonate semialdehyde dehydrogenase deficiency, bile acid-Co A: amino acid N-acyltransferase deficiency, bile acid-CoA ligase deficiency, holocarboxylase synthetase deficiency, succinate dehydrogenase deficiency, a-ketoglutarate dehydrogenase deficiency, CoASY, glutaric acidemia type II/multiple acyl-CoA dehydrogenase deficiency, long chain 3-ketoacyl-CoA thiolase, D-3-hydroxyacyl-CoA dehydrogenase deficiency (part of DBD), acyl-CoA dehydrogenase 9 deficiency, Systemic primary carnitine deficiency, carnitine: acylcarnitine translocase deficiency I and II, acetyl-CoA carboxylase deficiency, malonyl-CoA decarboxylase deficiency, Mitochondrial HMG-CoA synthase deficiency, succinyl-CoA:3-ketoacid CoA transferase deficiency, phytanoyl-CoA hydroxylase deficiency/Refsum disease, D-bifunctional protein deficiency (2-enoyl-CoA-hydratase and D-3-hydroxyacyl-CoA-dehydrogenase deficiency.), acyl-CoA oxidase deficiency, alpha-methylacyl-CoA racemase (AMACR) deficiency, sterol carrier protein x deficiency, 2,4-dienoyl-CoA reductase deficiency, cytosolic acetoacetyl-CoA thiolase deficiency, cytosolic HMG-CoA synthase deficiency, lecithin cholesterol acyltransferase deficiency, choline acetyl transferase deficiency, congenital myasthenic syndrome, pyruvate dehydrogenase deficiency, phosphoenolpyruvate carboxykinase deficiency, pyruvate carboxylase deficiency, serine palmiotyl-CoA transferase deficiency/Hereditary sensory and autonomic neuropathy type I, and ethylmalonic encephalopathy.

In various aspects, the CASTOR disease is selected from medium-chain acyl-CoA dehydrogenase deficiency, biotinidase deficiency, isovaleric acidemia, very long-chain acyl-CoA dehydrogenase deficiency, long-chain L-3-OH acyl-CoA dehydrogenase deficiency, glutaric acidemia type I, 3-hydroxy-3-methylglutaric acidemia, trifunctional protein deficiency, multiple carboxylase deficiency, methylmalonic acidemia (methylmalonyl-CoA mutase deficiency), 3-methylcrotonyl-CoA carboxylase deficiency, methylmalonic acidemia (Cbl A,B), propionic acidemia, carnitine uptake defect, beta-ketothiolase deficiency, short-chain acyl-CoA dehydrogenase deficiency, glutaric acidemia type II, medium/short-chain L-3-OH acyl-CoA dehydrogenase deficiency, medium-chain ketoacyl-CoA thiolase deficiency, carnitine palmitoyltransferase II deficiency, methylmalonic acidemia (Cbl C,D), malonic acidemia, carnitine: acylcarnitine translocase deficiency, isobutyryl-CoA dehydrogenase deficiency, 2-methyl 3-hydroxybutyric aciduria, dienoyl-CoA reductase deficiency, 3-methylglutaconic aciduria, and PLA2G6-associated neurodegeneration.

In various aspects, the CASTOR disease is selected from glycine N-acyltransferase deficiency, 2-methylbutyryl-CoA-dehydrogenase-deficiency, mitochondrial acetoacetyl-CoA thiolase deficiency, dihydrolipoamide dehydrogenase deficiency/Branched chain alpha-ketoacid dehydrogenase (BCKDH) deficiency, 3-methylglutaconyl-CoA hydratase deficiency, 3-hydroxyisobutyrate dehydrogenase deficiency, 3-hydroxy-isobutyryl-CoA hydrolase deficiency, isobutyryl-CoA dehydrogenase deficiency, methylmalonate semialdehyde dehydrogenase deficiency, bile acid-CoA: amino acid N-acyltransferase deficiency, bile acid-CoA ligase deficiency, holocarboxylase synthetase deficiency, succinate dehydrogenase deficiency, a-ketoglutarate dehydrogenase deficiency, CoASY, glutaric acidemia type II/multiple acyl-CoA dehydrogenase deficiency, long chain 3-ketoacyl-CoA thiolase, D-3-hydroxyacyl-CoA dehydrogenase deficiency (part of DBD), acyl-CoA dehydrogenase 9 deficiency, systemic primary carnitine deficiency, carnitine: acylcarnitine translocase deficiency I and II, acetyl-CoA carboxylase deficiency, malonyl-CoA decarboxylase deficiency, mitochondrial HMG-CoA synthase deficiency, succinyl-CoA:3-ketoacid CoA transferase deficiency, phytanoyl-CoA hydroxylase deficiency/Refsum disease, D-bifunctional protein deficiency (2-enoyl-CoA-hydratase and D-3-hydroxyacyl-CoA-dehydrogenase deficiency.), acyl-CoA oxidase deficiency, alpha-methylacyl-CoA racemase (AMACR) deficiency, sterol carrier protein x deficiency, 2,4-dienoyl- CoA reductase deficiency, cytosolic acetoacetyl-CoA thiolase deficiency, cytosolic HMG-CoA synthase deficiency, lecithin cholesterol, acyltransferase deficiency, choline acetyl transferase deficiency/Congenital myasthenic syndrome, pyruvate dehydrogenase deficiency, phosphoenolpyruvate carboxykinase deficiency, pyruvate carboxylase deficiency, serine palmiotyl-CoA transferase deficiency/Hereditary sensory and autonomic neuropathy type I, and ethylmalonic encephalopathy.

In various aspects, the CASTOR disease is selected from medium chain acyl-CoA dehydrogenase deficiency, short chain acyl-CoA dehydrogenase deficiency, very long chain acyl-CoA dehydrogenase deficiency, and D-bifunctional protein deficiency. In a further aspect, the CASTOR disease is medium chain acyl-CoA dehydrogenase deficiency. In a still further aspect, the CASTOR disease is short chain acyl-CoA dehydrogenase deficiency. In yet a further aspect, the CASTOR disease is very long chain acyl-CoA dehydrogenase deficiency. For yet another example, the CASTOR disease is D-bifunctional protein deficiency.

In various aspects, the CASTOR disease is selected from glutaric acidemia type 1, methylmalonic academia, propionyl-CoA carboxylase deficiency, propionic academia, 3-methylcrotonyl carboxylase deficiency, and isovaleryl-CoA dehydrogenase deficiency. In a further aspect, the CASTOR disease is Glutaric acidemia type 1. In a still further aspect, the CASTOR disease is methylmalonic academia. In yet a further aspect, the CASTOR disease is propionyl-CoA carboxylase deficiency. In an even further aspect, the CASTOR disease is propionic academia. In a still further aspect, the CASTOR disease is 3-methylcrotonyl carboxylase deficiency. In yet a further aspect, the CASTOR disease is isovaleryl-CoA dehydrogenase deficiency.

In various aspects, the disclosed compounds can be used in combination with one or more other drugs in the treatment, prevention, control, amelioration, or reduction of risk of CASTOR diseases for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly. Accordingly, the pharmaceutical compositions include those that contain one or more other active ingredients, in addition to a compound of the present invention.

In a further aspect, the subject is a mammal. In a still further aspect, the mammal is human.

In a further aspect, the subject has been diagnosed with a need for treatment of the CASTOR disease prior to the administering step. In a still further aspect, the subject is at risk for developing the CASTOR disease prior to the administering step.

In a further aspect, the method further comprises identifying a subject at risk for developing the CASTOR disease prior to the administering step.

In a further aspect, the method further comprises the step of administering to the subject a therapeutically effective amount of carnitine, pantothenate, and/or pantothenic acid. In a still further aspect, the method further comprises the step of administering to the subject a therapeutically effective amount of carnitine, pantothenate, and pantothenic acid. In yet a further aspect, the method further comprises the step of administering to the subject a therapeutically effective amount of carnitine, pantothenate, or pantothenic acid. In an even further aspect, the method further comprises the step of the step of administering to the subject a therapeutically effective amount of carnitine. In a still further aspect, the method further comprises the step of administering to the subject a therapeutically effective amount of pantothenate. In yet a further aspect, the method further comprises the step of administering to the subject a therapeutically effective amount of pantothenic acid.

In a further aspect, the CASTOR disease is hereditary. In a still further aspect, the CASTOR disease is acquired.

C. COMPOUNDS

In one aspect, disclosed are compounds useful in treating or preventing a CASTOR disease such as, for example, defects in fatty acid oxidation enzymes, methylmalonic acidemia, glutaric acidemia, propionic academia, and HMG-CoA lyase deficiency.

In one aspect, the compounds of the invention are useful in the treatment or prevention of CASTOR diseases in which PanKs or altered levels of CoA and CoA esters are involved, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

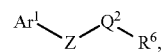

wherein Z is selected from A(C=O), COCH$_2$,

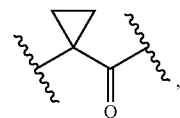

CO, NHCO, NHCS, CH$_2$SO$_2$, and SO$_2$; wherein A is selected from O, CO, CH$_2$, CF$_2$, NH, N(CH$_3$), and CH(OH); wherein Q$^2$ is a structure selected from:

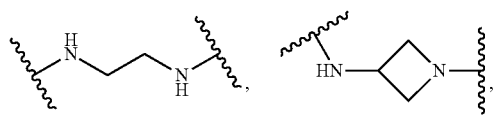

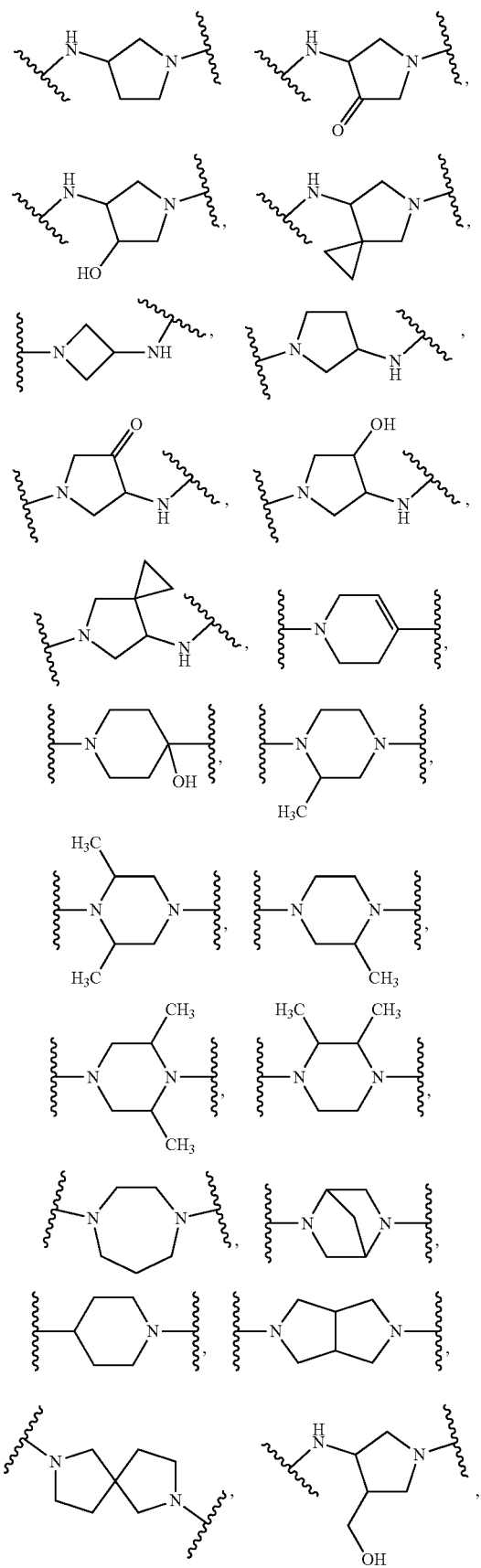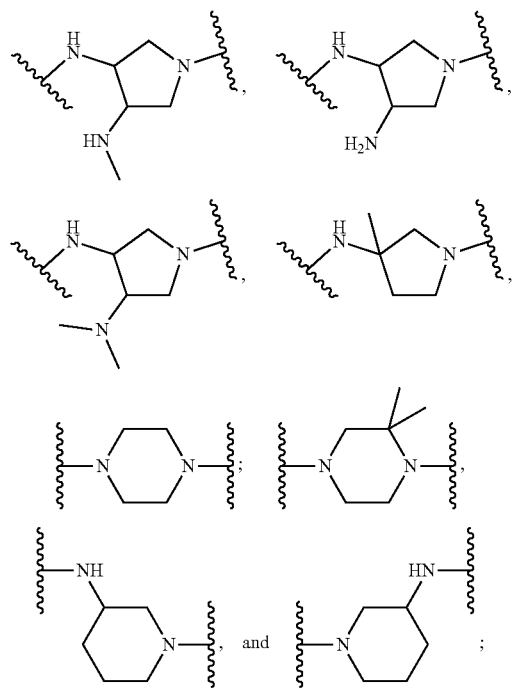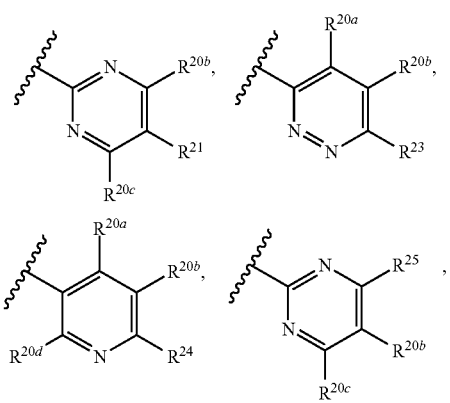

wherein Ar¹ is selected from aryl and heteroaryl and substituted with 0, 1, 2, or 3 groups independently selected from halogen, —NO₂, —CN, —OH, —SH, —NH₂, C1-C8 thioalkyl, C1-C8 acyclic alkyl, C2-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, —CO(C1-C8 acyclic alkyl), C1-C8 alkoxyhaloalkyl, and cyclopropyl, cyclobutyl, and oxetane, wherein the cyclopropyl, cyclobutyl, and oxetane are optionally substituted with 1, 2, 3, or 4 groups independently selected from halogen, NO₂, —CN, —OH, —SH, —NH₂, C1-C4 acyclic alkyl, C1-C4 hydroxyalkyl, C1-C4 monohaloalkyl, C1-C4 polyhaloalkyl, C1-C4 alkoxy, C1-C4 monohaloalkoxy, C1-C4 polyhaloalkoxy, C1-C4 acyclic alkylamino, (C1-C4)(C1-C4)dialkylamino, and —CO(C1-C4 acyclic alkyl); wherein R⁶ is selected from —NHCH₂C₆H₅ and Ar²; wherein Ar² is a structure represented by a formula selected from:

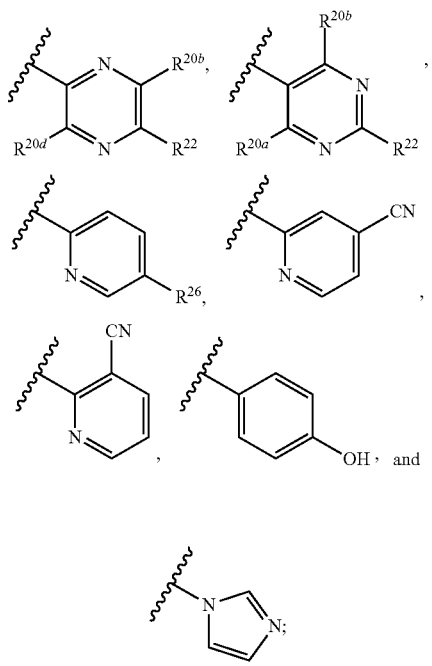

wherein each of $R^{20a}$, $R^{20b}$, $R^{20c}$, and $R^{20d}$, when present, is independently selected from hydrogen, halogen, —CN, —NO$_2$, —NH$_2$, C1-C4 alkyl, C1-C4 monohaloalkyl, C1-C4 polyhaloalkyl, C1-C4 alkoxy, C1-C4 monohaloalkoxy, C1-C4 polyhaloalkoxy, C1-C4 alkylamino, (C1-C4)(C1-C4) dialkylamino, and cyclopropyl; wherein $R^{21}$, when present, is selected from hydrogen, halogen, —CN, —NO$_2$, —SO$_2$NH$_2$, —SO$_2$CH$_3$, —SO$_2$CF$_3$, and $Cy^1$; wherein $Cy^1$, when present, is selected from cycle, heterocycle, aryl, and heteroaryl and substituted with 0, 1, 2, or 3 groups independently selected from halogen, NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino; wherein $R^{22}$, when present, is selected from —CN, halogen, —NO$_2$, SO$_2$NH$_2$, SO$_2$CH$_3$, and SO$_2$CF$_3$; wherein $R^{23}$, when present, is selected from hydrogen, halogen, —CN, —NO$_2$, —SO$_2$NH$_2$, —SO$_2$CH$_3$, —SO$_2$CF$_3$, cyclohexyl,

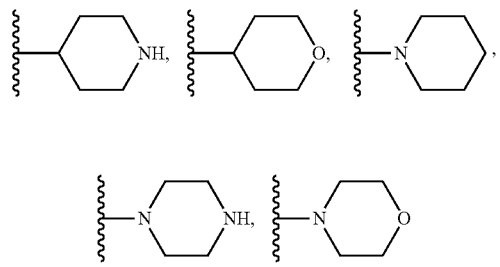

and $Cy^1$; wherein $R^{24}$, when present, is selected from —CN, halogen, —NO$_2$, SO$_2$NH$_2$, SO$_2$CH$_3$, and SO$_2$CF$_3$; wherein $R^{25}$, when present, is selected from —CN, —NO$_2$, SO$_2$NH$_2$, SO$_2$CH$_3$, and SO$_2$CF$_3$; wherein $R^{26}$, when present, is selected from —Br, —Cl, —F, —CN, —NO$_2$, —CF$_3$, and methyl; or a pharmaceutically acceptable salt thereof.

In a further aspect, disclosed are compounds having a structure represented by a formula:

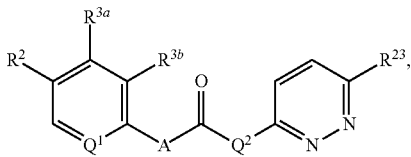

wherein A is selected from O, CO, CH$_2$, CF$_2$, NH, N(CH$_3$), and CH(OH); wherein $Q^1$ is CH; and wherein $R^2$ is selected from —SCH$_3$, C1-C8 acyclic alkyl, C1-C8 acyclic alkenyl, C1-C8 monohaloalkyl, C1-C8 polyhaloalkyl, C1-C8 alkoxyhaloalkyl, cyclopropyl, cyclobutyl, and oxetane, wherein the cyclopropyl, cyclobutyl, and oxetane are optionally substituted with 1, 2, or 3 groups independently selected from —OH, C1-C4 alkyl, and C1-C4 alkoxy; or wherein $Q^1$ is N; and $R^2$ is selected from halogen, —SCH$_3$, C1-C8 acyclic alkyl, C1-C8 acyclic alkenyl, C1-C8 monohaloalkyl, C1-C8 polyhaloalkyl, C1-C8 alkoxyhaloalkyl, cyclopropyl, cyclobutyl, and oxetane, wherein the cyclopropyl, cyclobutyl, and oxetane are optionally substituted with 1, 2, or 3 groups independently selected from —OH, C1-C4 alkyl, and C1-C4 alkoxy; wherein $Q^2$ is a structure selected from:

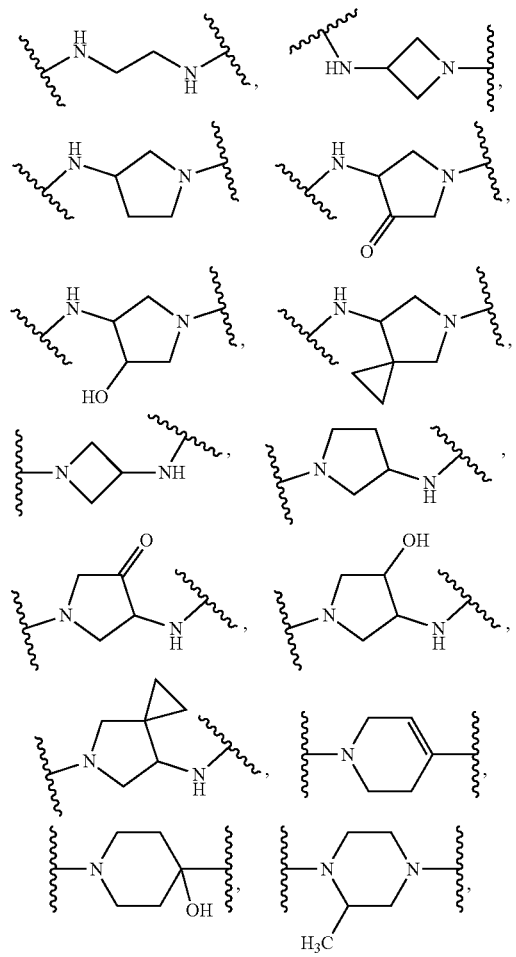

-continued

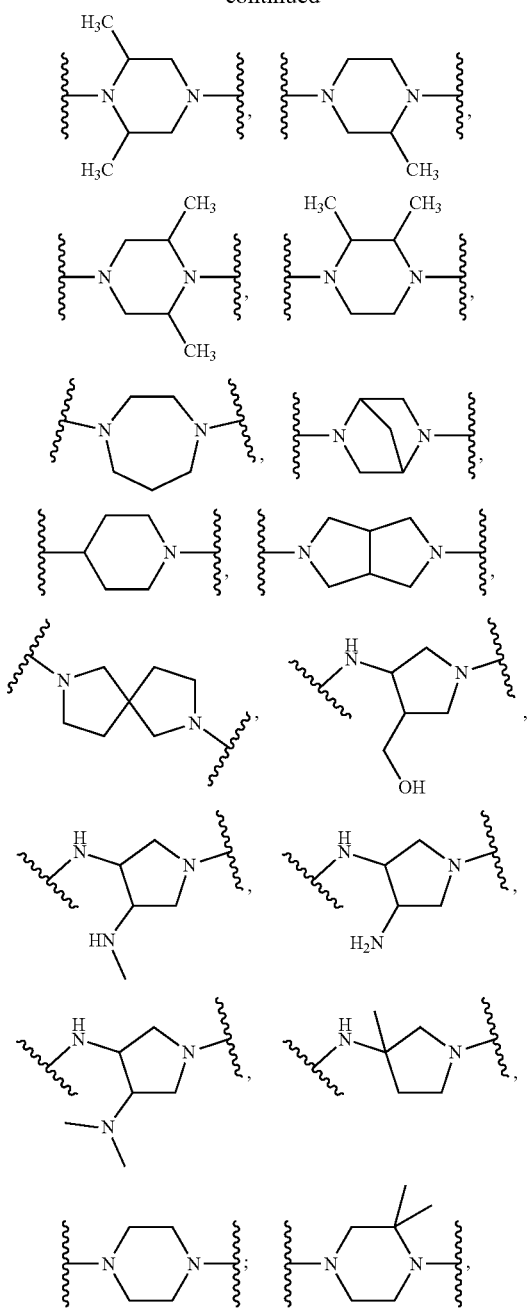

wherein each of $R^{3a}$ and $R^{3b}$ is independently selected from hydrogen, halogen, —OH, C1-C4 alkoxy, and C1-C4 alkyl; and wherein $R^{23}$ is selected form hydrogen, halogen, —CN, $SO_2NH_2$, $SO_2CH_3$, $SO_2CF_3$, and $NO_2$, or a pharmaceutically acceptable salt thereof.

In a still further aspect, the compound has a structure represented by a formula:

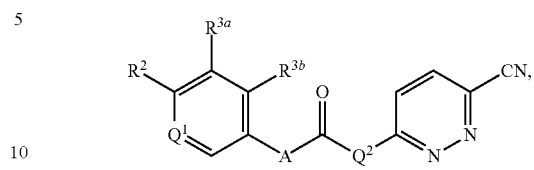

or a pharmaceutically acceptable salt thereof.

In yet a further aspect, the compound has a structure represented by a formula:

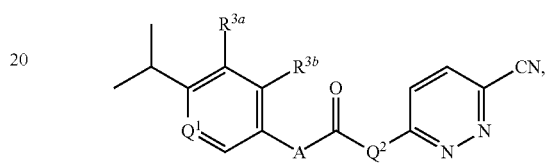

or a pharmaceutically acceptable salt thereof.

In an even further aspect, the compound is selected from:

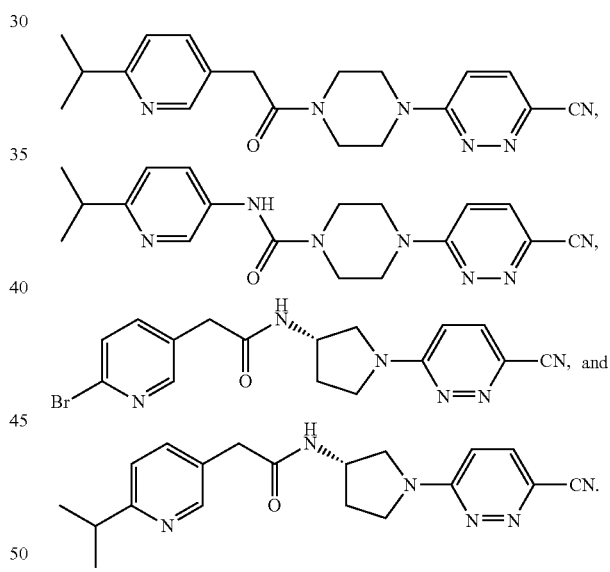

or a pharmaceutically acceptable salt thereof.

In a still further aspect, the compound is selected from:

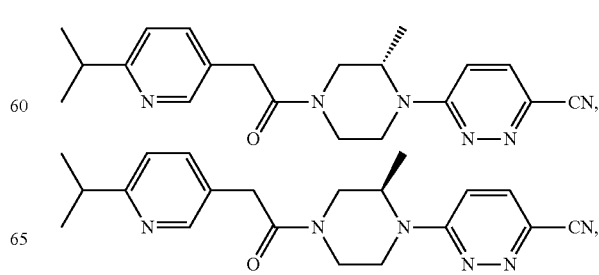

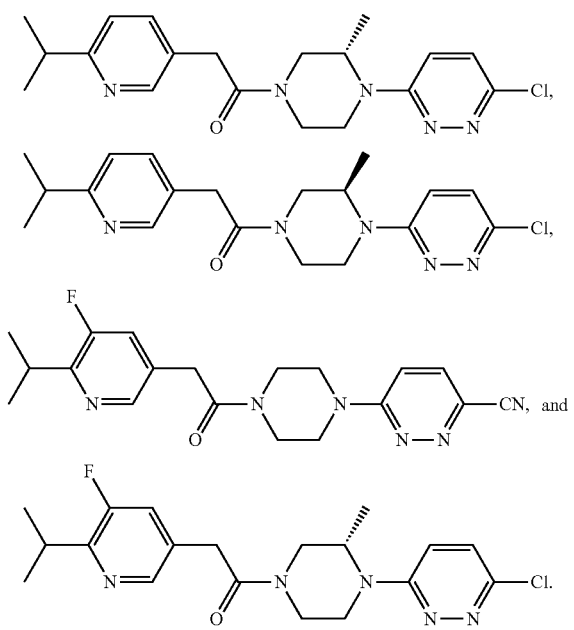
In yet a further aspect, the compound is:
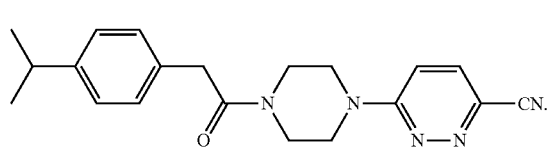
In a further aspect, a compound can be present as one or more of the following structures:
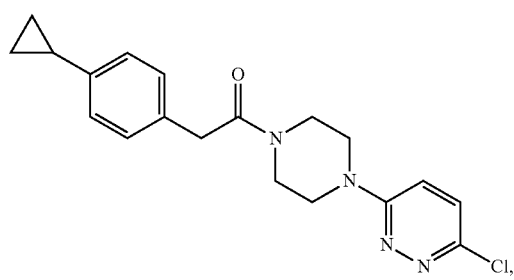
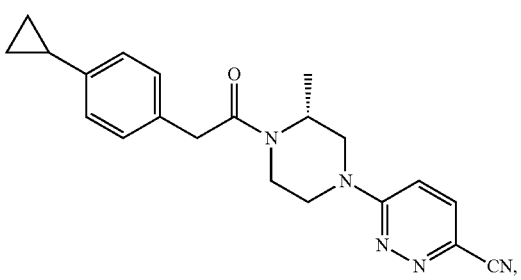
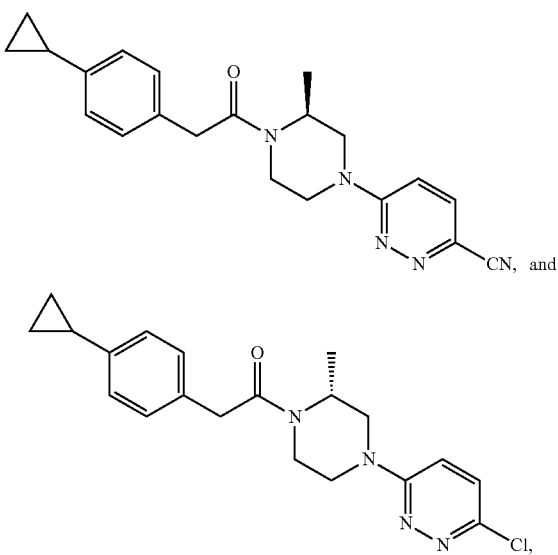
or a pharmaceutically acceptable salt thereof.
In a further aspect, the compound has a structure a structure represented by a formula:
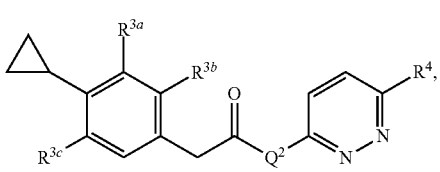
wherein $Q^2$ is a structure selected from:
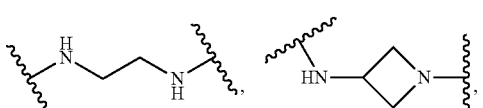
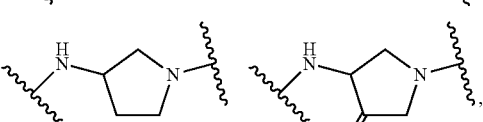
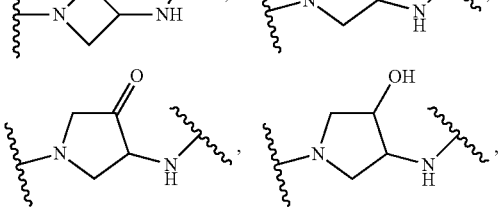

-continued

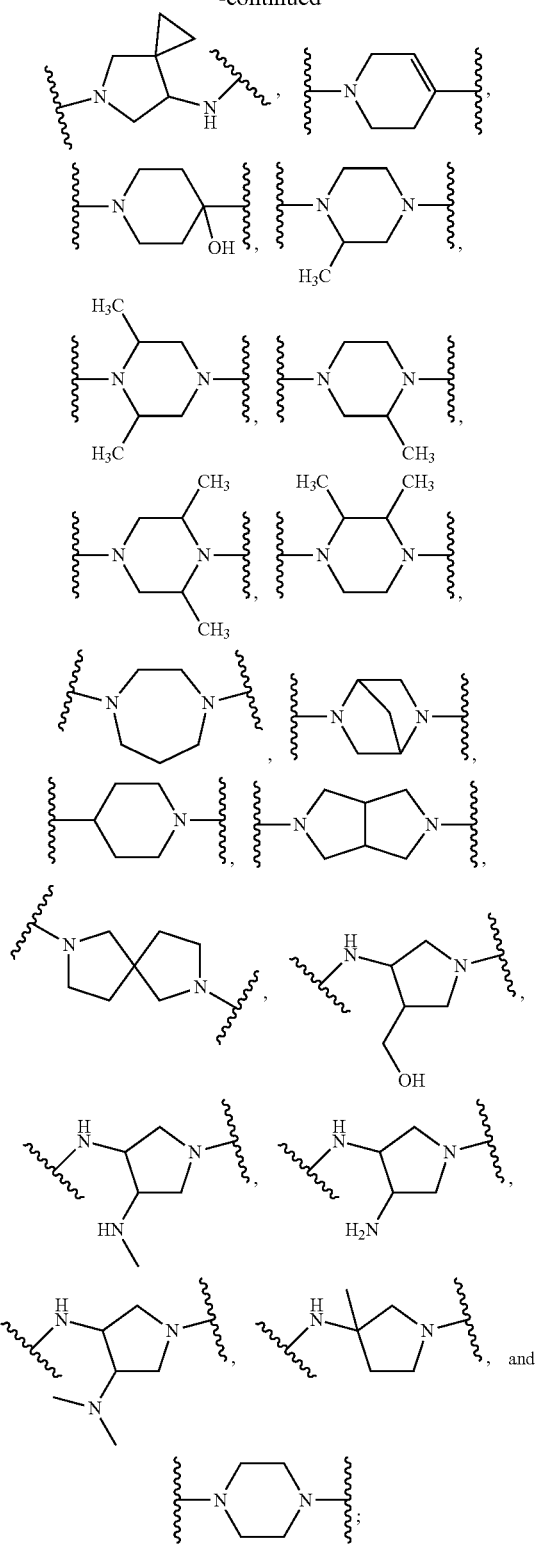

wherein each of $R^{3a}$, $R^{3b}$, and $R^{3c}$ is independently selected from hydrogen, halogen, C1-C4 alkoxy and C1-C4 alkyl, provided at least one of $R^{3a}$, $R^{3b}$, and $R^{3c}$ is halogen; and wherein $R^4$ is selected form hydrogen, halogen, —CN, $SO_2NH_2$, $SO_2CH_3$, $SO_2CF_3$, and $NO_2$, or a pharmaceutically acceptable salt thereof.

In a still further aspect, the compound is selected from:

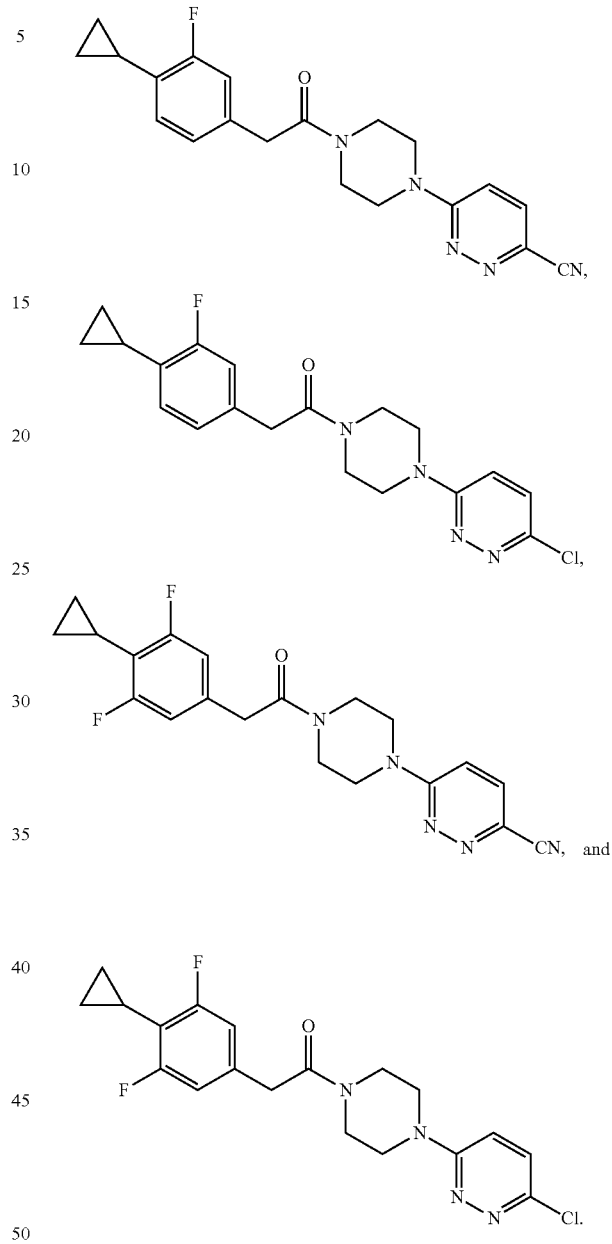

In a further aspect, a compound can be present as one or more of the following structures:

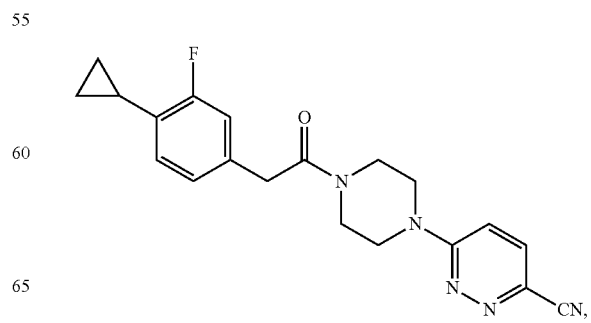

-continued

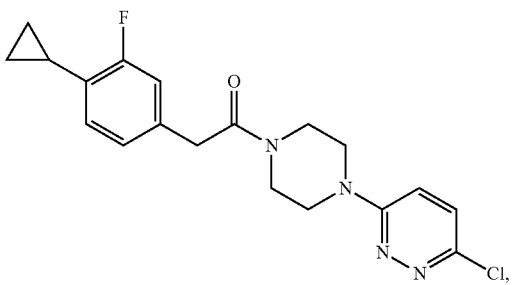

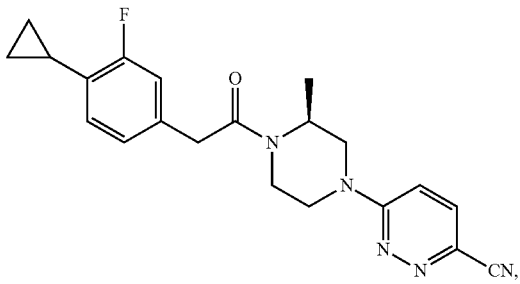

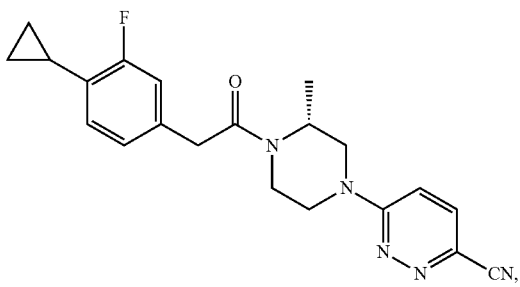

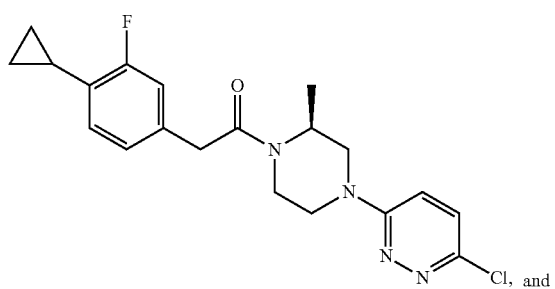

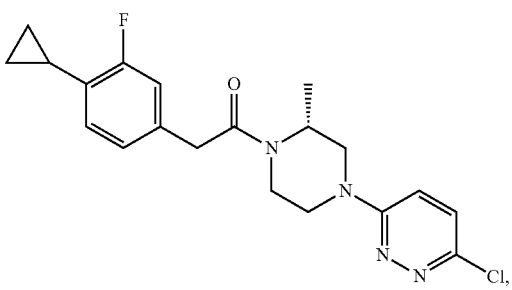

or a pharmaceutically acceptable salt thereof.

In a further aspect, disclosed are compounds having a structure represented by a formula:

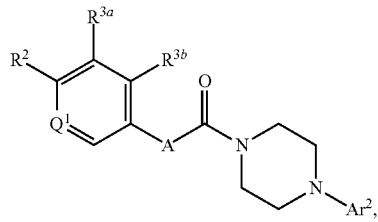

wherein A is selected from O, CO, $CH_2$, $CF_2$, NH, $N(CH_3)$ and CH(OH); wherein $Q^1$ is selected from N and CH; wherein $R^2$ is selected from C1-C8 acyclic alkyl, C1-C8 acyclic alkenyl, C1-C8 monohaloalkyl, C1-C8 polyhaloalkyl, (C1-C8)(C1-C8)dialkylamino, cyclopropyl, cyclobutyl, and oxetane, wherein the cyclopropyl, cyclobutyl, and oxetane are optionally substituted with 1, 2, or 3 groups independently selected from —OH, C1-C4 alkyl, and C1-C4 alkoxy; wherein each of $R^{3a}$ and $R^{3b}$ is independently selected from hydrogen, halogen, C1-C4 alkyl, and C1-C4 alkoxy; wherein $Ar^2$ is a structure represented by a formula selected from:

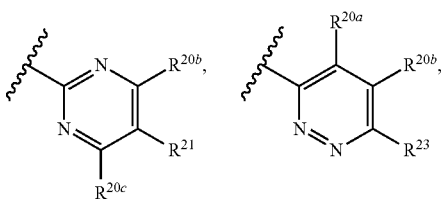

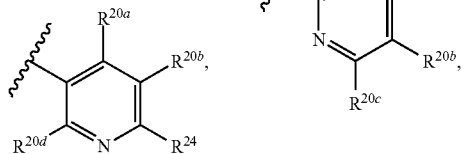

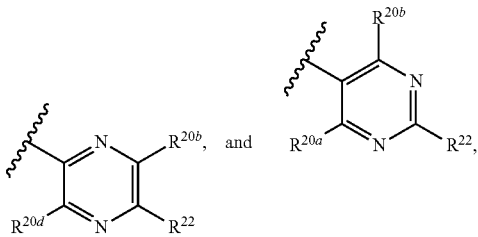

wherein each of $R^{20a}$, $R^{20b}$, $R^{20c}$, and $R^{20d}$, when present, is independently selected from hydrogen, halogen, —CN, —$NO_2$, —$NH_2$, C1-C4 alkyl, C1-C4 monohaloalkyl, C1-C4 polyhaloalkyl, C1-C4 alkoxy, C1-C4 monohaloalkoxy, C1-C4 polyhaloalkoxy, C1-C4 alkylamino, (C1-C4)(C1-C4) dialkylamino, and cyclopropyl; wherein $R^{21}$, when present, is selected from —CN, —$NO_2$, $SO_2NH_2$, $SO_2CH_3$, $SO_2CF_3$, and $Cy^1$; wherein $Cy^1$, when present, is selected from cycle, heterocycle, aryl, and heteroaryl and substituted with 0, 1, 2, or 3 groups independently selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino; wherein $R^{22}$, when present, is selected from —CN, halogen, —NO$_2$, SO$_2$NH$_2$, SO$_2$CH$_3$, and SO$_2$CF$_3$; wherein R$^{23}$, when present, is selected from —CN, —NO$_2$, SO$_2$NH$_2$, SO$_2$CH$_3$, SO$_2$CF$_3$, cyclohexyl,

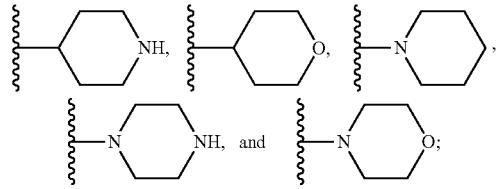

wherein R$^{24}$, when present, is selected from —CN, halogen, —NO$_2$, SO$_2$NH$_2$, SO$_2$CH$_3$, and SO$_2$CF$_3$, provided that if A is NH or N(CH$_3$) then R$^{24}$ is not —NO$_2$; and wherein R$^{25}$, when present, is selected from —CN, —NO$_2$, SO$_2$NH$_2$, SO$_2$CH$_3$, and SO$_2$CF$_3$; or a pharmaceutically acceptable salt thereof.

In a further aspect, disclosed are compounds having a structure represented by a formula:

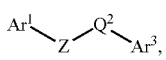

wherein Q$^2$ is a structure selected from:

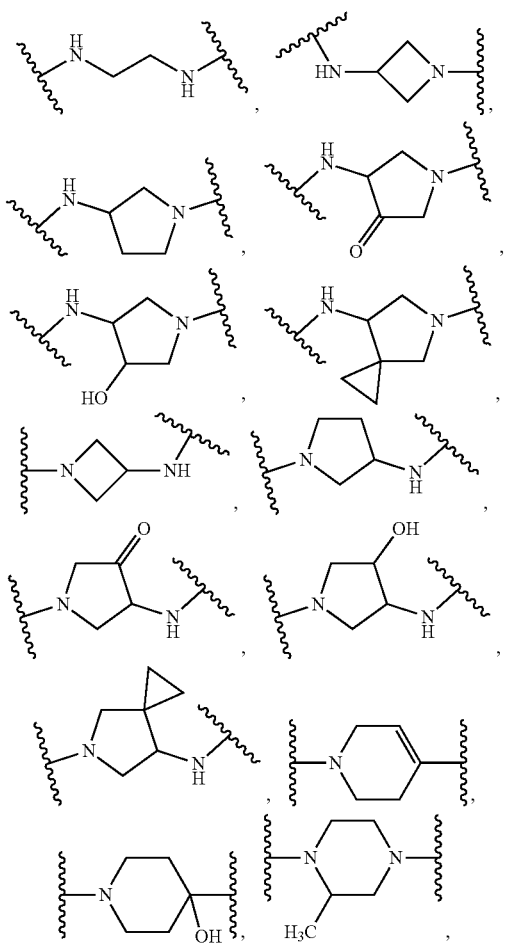

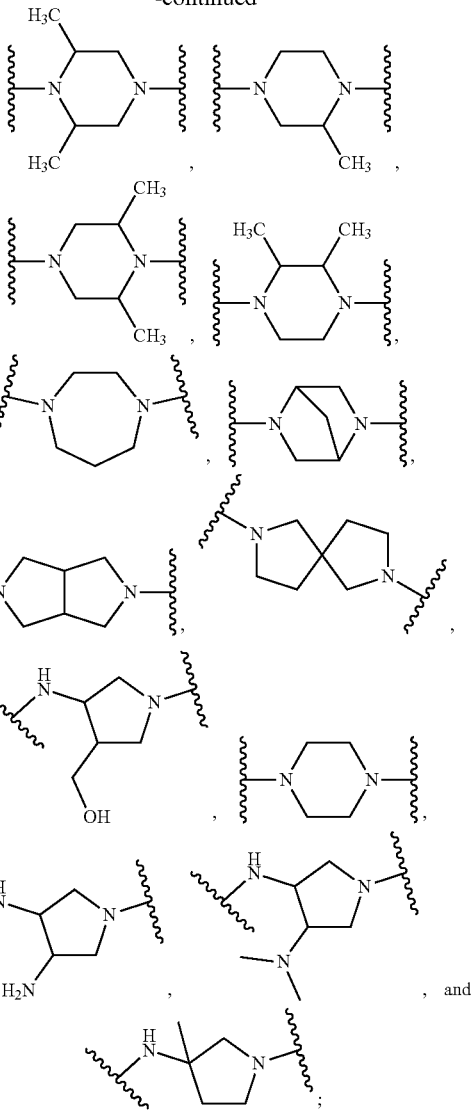

wherein Z is selected from O(C=O), CF$_2$CO, COCH$_2$, CH$_2$CO,

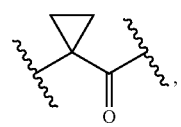 [SMILES: *C(=O)C1(*)CC1]

CO, CH$_2$SO$_2$, SO$_2$, NHCO, N(CH$_3$)CO, and CH(OH)CO; wherein Ar$^1$ is selected from aryl and heteroaryl and substituted with 1, 2, or 3 groups independently selected from halogen, —NO$_2$, —CN, —OH, —SH, —NH$_2$, C1-C8 acyclic alkyl, C1-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, —CO(C1-C8 acyclic alkyl), cyclopropyl, cyclobutyl, and oxetane, wherein the cyclopropyl, cyclobutyl, and oxetane are optionally substituted with 1, 2, or 3 groups independently selected from —OH, C1-C4 alkyl, and C1-C4 alkoxy; and wherein Ar$^3$ is a structure selected from:

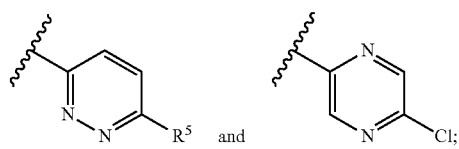

wherein R⁵, when present, is selected from CN, halogen, —NO₂, SO₂NH₂, and SO₂CH₃, provided that if R⁵ is CN and Z is CO then Ar¹ is not substituted with C1-C8 monohaloalkyl or C1-C8 polyhaloalkyl; provided that if R⁵ is halogen then Ar¹ is selected from 5- and 6-membered heteroaryl and Z cannot be CO, or a pharmaceutically acceptable salt thereof.

In a still further aspect, Ar¹ is selected from aryl and heteroaryl and substituted with 1, 2, or 3 groups independently selected from halogen, —NO₂, —CN, —OH, —SH, —NH₂, C1-C8 acyclic alkyl, C2-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, —CO(C1-C8 acyclic alkyl), and cyclopropyl.

In yet a further aspect, Ar³ is:

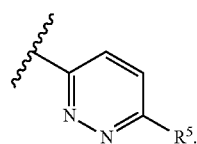

In an even further aspect, R⁵ is CN. In a still further aspect, R⁵ is —Cl. In yet a further aspect, R⁵ is selected from halogen, —NO₂, SO₂NH₂, and SO₂CH₃.

In an even further aspect, the compound is:

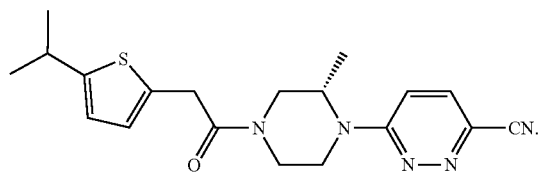 [SMILES: CC(C)c1ccc(CC(=O)N2CCN(c3ccc(C#N)nn3)[C@@H](C)C2)s1]

In a further aspect, disclosed are compounds having a structure represented by a formula:

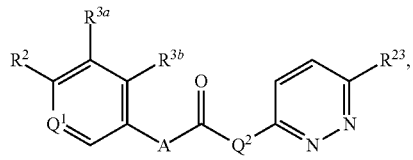

wherein A is selected from O, CO, CH₂, CF₂, NH, N(CH₃), and CH(OH); wherein Q¹ is CH; and wherein R² is selected from —SCH₃, C1-C8 acyclic alkyl, C1-C8 acyclic alkenyl, C1-C8 monohaloalkyl, C1-C8 polyhaloalkyl, C1-C8 alkoxyhaloalkyl, cyclopropyl, cyclobutyl, and oxetane, wherein the cyclopropyl, cyclobutyl, and oxetane are optionally substituted with 1, 2, or 3 groups independently selected from —OH, C1-C4 alkyl, and C1-C4 alkoxy; or wherein Q¹ is N; and R² is selected from halogen, —SCH₃, C1-C8 acyclic alkyl, C1-C8 acyclic alkenyl, C1-C8 monohaloalkyl, C1-C8 polyhaloalkyl, C1-C8 alkoxyhaloalkyl, cyclopropyl, cyclobutyl, and oxetane, wherein the cyclopropyl, cyclobutyl, and oxetane are optionally substituted with 1, 2, or 3 groups independently selected from —OH, C1-C4 alkyl, and C1-C4 alkoxy; wherein Q² is a structure selected from:

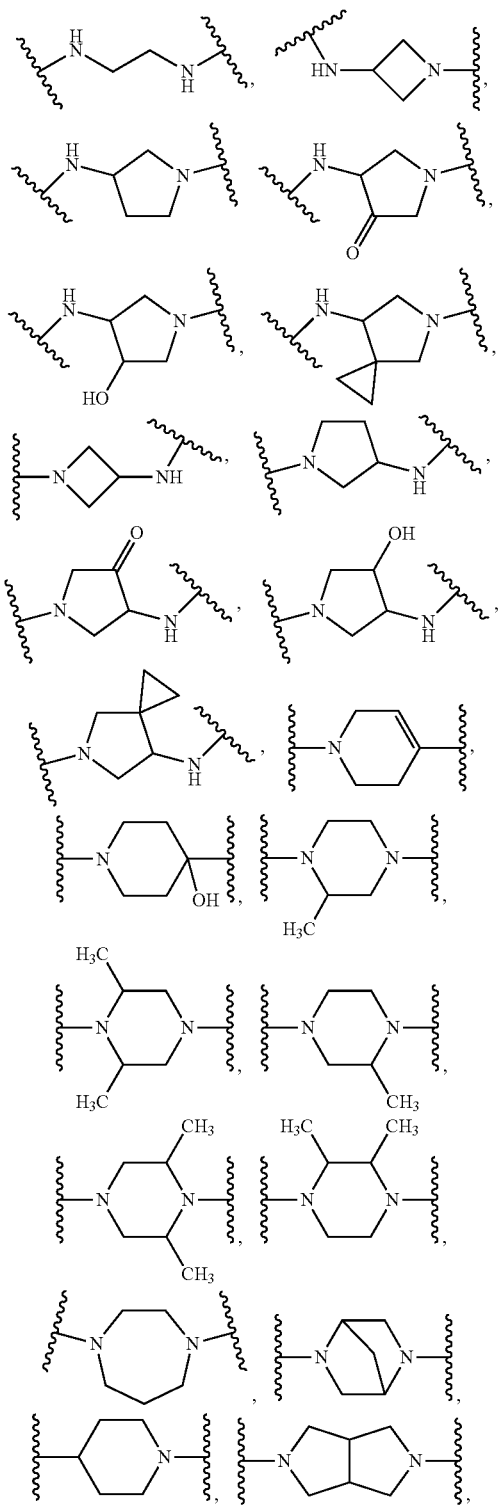

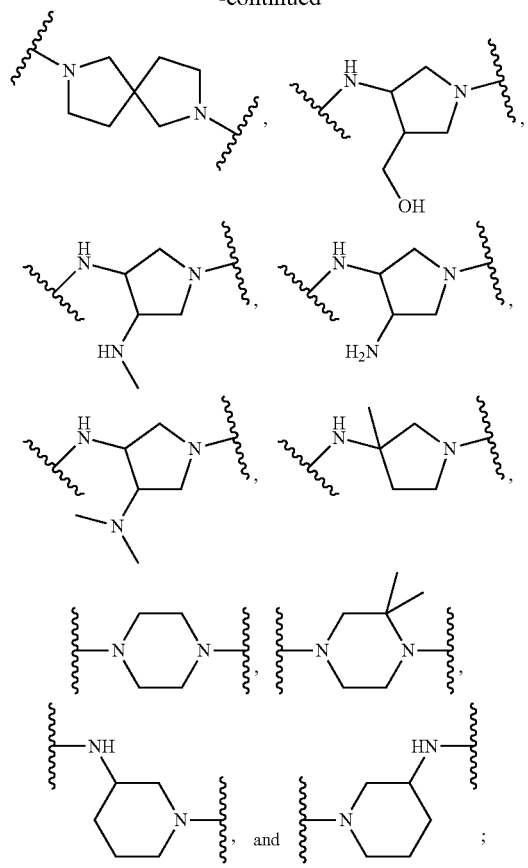

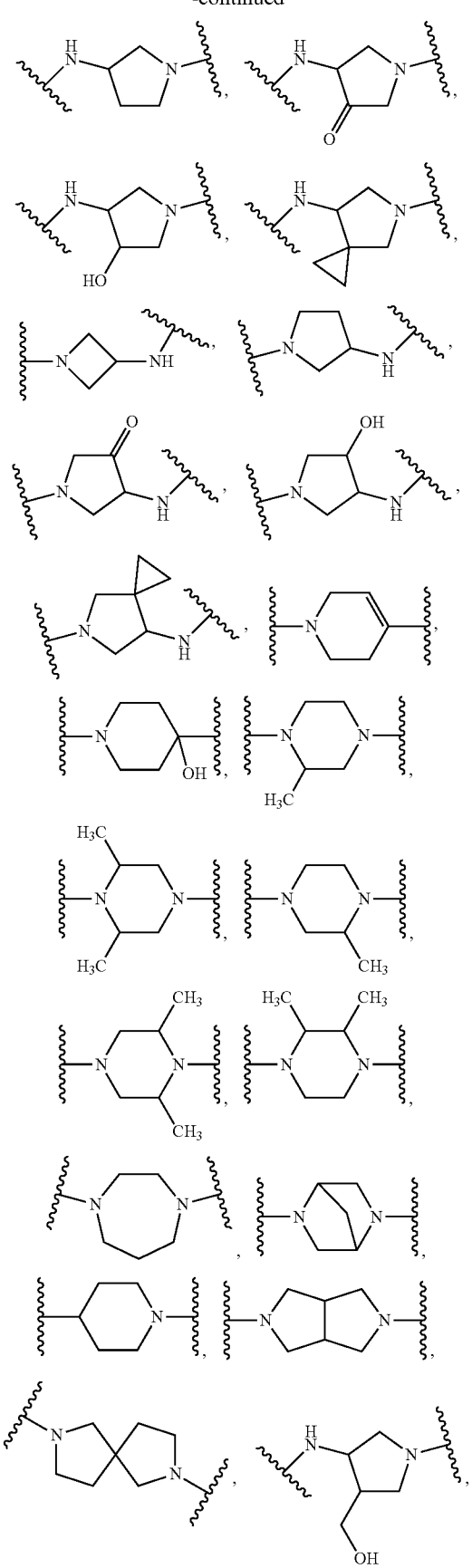

wherein each of $R^{3a}$ and $R^{3b}$ is independently selected from hydrogen, halogen, —OH, C1-C4 alkoxy, and C1-C4 alkyl; and wherein $R^{23}$ is selected form hydrogen, halogen, —CN, $SO_2NH_2$, $SO_2CH_3$, $SO_2CF_3$, and $NO_2$, or a pharmaceutically acceptable salt thereof.

In a further aspect, disclosed are compounds having a structure represented by a formula:

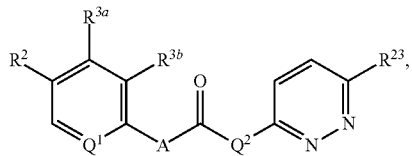

wherein A is selected from O, CO, $CH_2$, $CF_2$, NH, $N(CH_3)$, and CH(OH); wherein $Q^1$ is CH; and wherein $R^2$ is selected from C1-C8 acyclic alkyl, C1-C8 acyclic alkenyl, C1-C8 monohaloalkyl, C1-C8 polyhaloalkyl, and cyclopropyl, or wherein A is selected from O, CO, $CH_2$, $CF_2$, $N(CH_3)$, and CH(OH); wherein $Q^1$ is N; and $R^2$ is selected from halogen, C1-C8 acyclic alkyl, C1-C8 acyclic alkenyl, C1-C8 monohaloalkyl, C1-C8 polyhaloalkyl, and cyclopropyl; wherein $Q^2$ is a structure selected from:

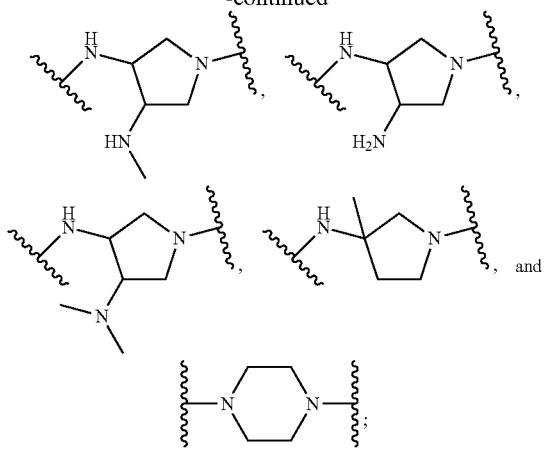

wherein each of $R^{3a}$ and $R^{3b}$ is independently selected from hydrogen, halogen, C1-C4 alkyl, and C1-C4 alkoxy; and wherein $R^4$ is selected form hydrogen, halogen, —CN, $SO_2NH_2$, $SO_2CH_3$, $SO_2CF_3$, and $NO_2$, or a pharmaceutically acceptable salt thereof.

In a further aspect, disclosed are compounds having a structure represented by a formula:

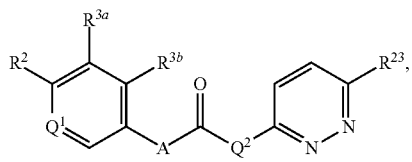

wherein A is selected from O, CO, $CH_2$, $CF_2$, NH, $N(CH_3)$, and CH(OH); wherein $Q^1$ is CH; and wherein $R^2$ is selected from C1-C8 acyclic alkyl, C1-C8 acyclic alkenyl, C1-C8 monohaloalkyl, C1-C8 polyhaloalkyl, and cyclopropyl, or wherein A is selected from O, CO, $CH_2$, $CF_2$, $N(CH_3)$, and CH(OH); wherein $Q^1$ is N; and $R^2$ is selected from halogen, C1-C8 acyclic alkyl, C1-C8 acyclic alkenyl, C1-C8 monohaloalkyl, C1-C8 polyhaloalkyl, and cyclopropyl; wherein $Q^2$ is a structure selected from:

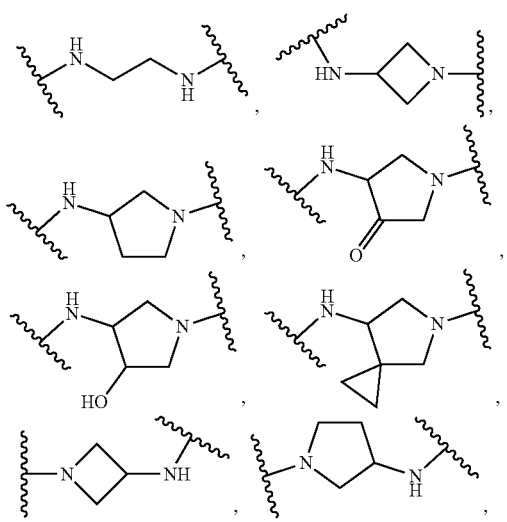

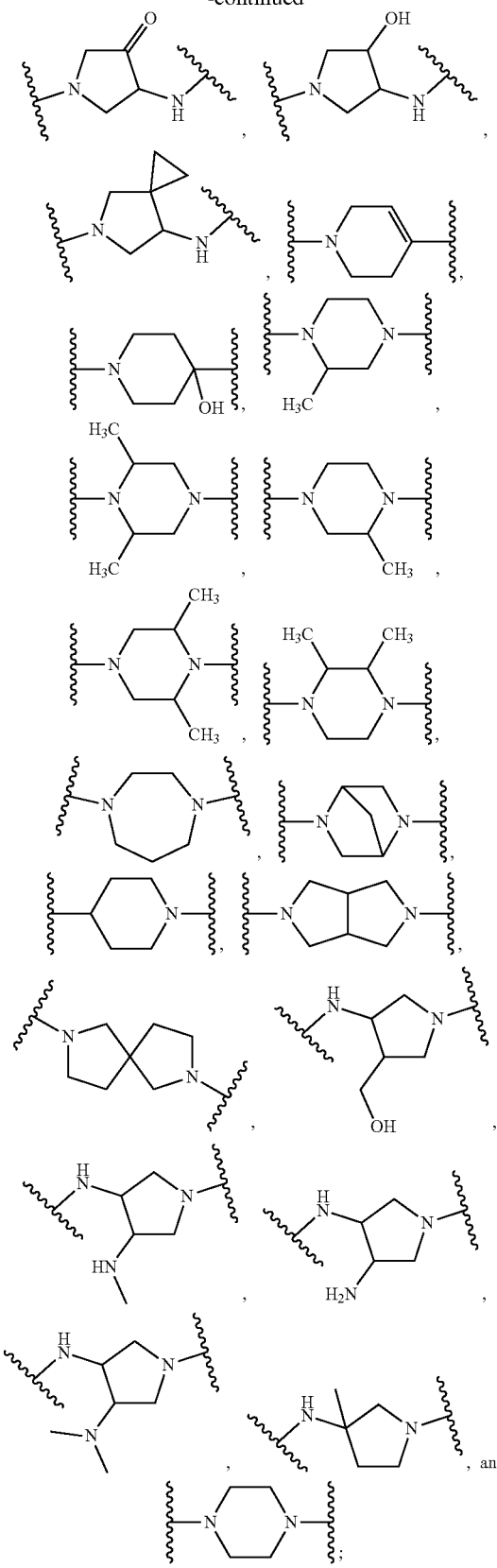

wherein each of $R^{3a}$ and $R^{3b}$ is independently selected from hydrogen, halogen, C1-C4 alkyl, and C1-C4 alkoxy; and wherein R⁴ is selected form hydrogen, halogen, —CN, SO₂NH₂, SO₂CH₃, SO₂CF₃, and NO₂, or a pharmaceutically acceptable salt thereof.

In a further aspect, disclosed are compounds having a structure represented by a formula:

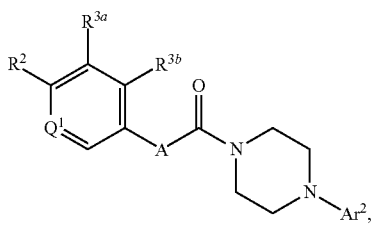

wherein A is selected from O, CO, CH₂, CF₂, NH, N(CH₃) and CH(OH); wherein Q¹ is selected from N and CH; wherein R² is selected from C1-C8 acyclic alkyl, C1-C8 acyclic alkenyl, C1-C8 monohaloalkyl, C1-C8 polyhaloalkyl, (C1-C8)(C1-C8)dialkylamino, and cyclopropyl; wherein each of $R^{3a}$ and $R^{3b}$ is independently selected from hydrogen, halogen, C1-C4 alkyl, and C1-C4 alkoxy; wherein Are is a structure represented by a formula selected from:

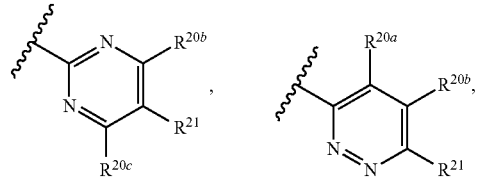

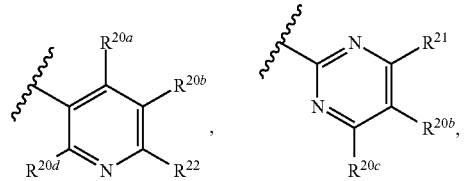

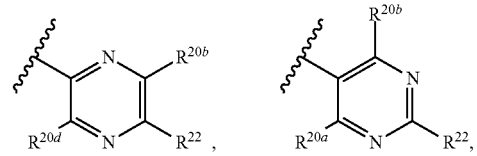

wherein each of $R^{20a}$, $R^{20b}$, $R^{20c}$, and $R^{20d}$, when present, is independently selected from hydrogen, halogen, —CN, —NO₂, C1-C4 alkyl, C1-C4 monohaloalkyl, C1-C4 polyhaloalkyl, C1-C4 alkoxy, C1-C4 monohaloalkoxy, C1-C4 polyhaloalkoxy, C1-C4 alkylamino, (C1-C4)(C1-C4)dialkylamino, and cyclopropyl; wherein $R^{21}$, when present, is selected from —CN, —NO₂, SO₂NH₂, SO₂CH₃, SO₂CF₃, and Cy¹; and wherein $R^{22}$, when present, is selected from —CN, halogen, —NO₂, SO₂NH₂, SO₂CH₃, and SO₂CF₃, or a pharmaceutically acceptable salt thereof.

In a further aspect, disclosed are compounds having a structure represented by a formula:

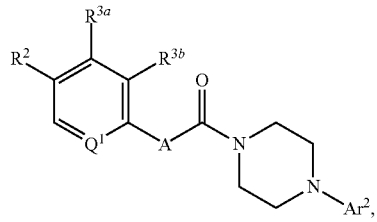

wherein A is selected from O, CO, CH₂, CF₂, NH, N(CH₃) and CH(OH); wherein Q¹ is selected from N and CH; wherein R² is selected from C1-C8 acyclic alkyl, C1-C8 acyclic alkenyl, C1-C8 monohaloalkyl, C1-C8 polyhaloalkyl, (C1-C8)(C1-C8)dialkylamino, and cyclopropyl; wherein each of $R^{3a}$ and $R^{3b}$ is independently selected from hydrogen, halogen, C1-C4 alkyl, and C1-C4 alkoxy; wherein Are is a structure represented by a formula selected from:

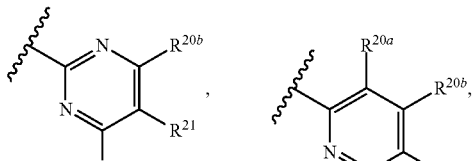

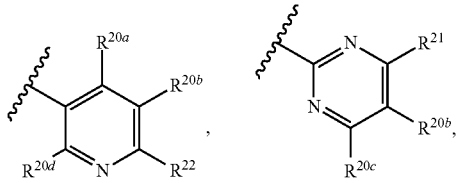

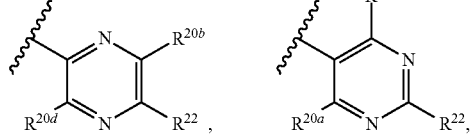

wherein each of $R^{20a}$, $R^{20b}$, $R^{20c}$, and $R^{20d}$, when present, is independently selected from hydrogen, halogen, —CN, —NO₂, C1-C4 alkyl, C1-C4 monohaloalkyl, C1-C4 polyhaloalkyl, C1-C4 alkoxy, C1-C4 monohaloalkoxy, C1-C4 polyhaloalkoxy, C1-C4 alkylamino, (C1-C4)(C1-C4)dialkylamino, and cyclopropyl; wherein $R^{21}$, when present, is selected from —CN, —NO₂, SO₂NH₂, SO₂CH₃, SO₂CF₃, and Cy¹; and wherein $R^{22}$, when present, is selected from —CN, halogen, —NO₂, SO₂NH₂, SO₂CH₃, and SO₂CF₃, or a pharmaceutically acceptable salt thereof.

In a further aspect, disclosed are compounds having a structure represented by a formula:

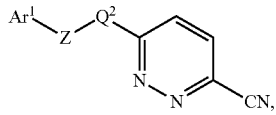

wherein $Q^2$ is a structure selected from:

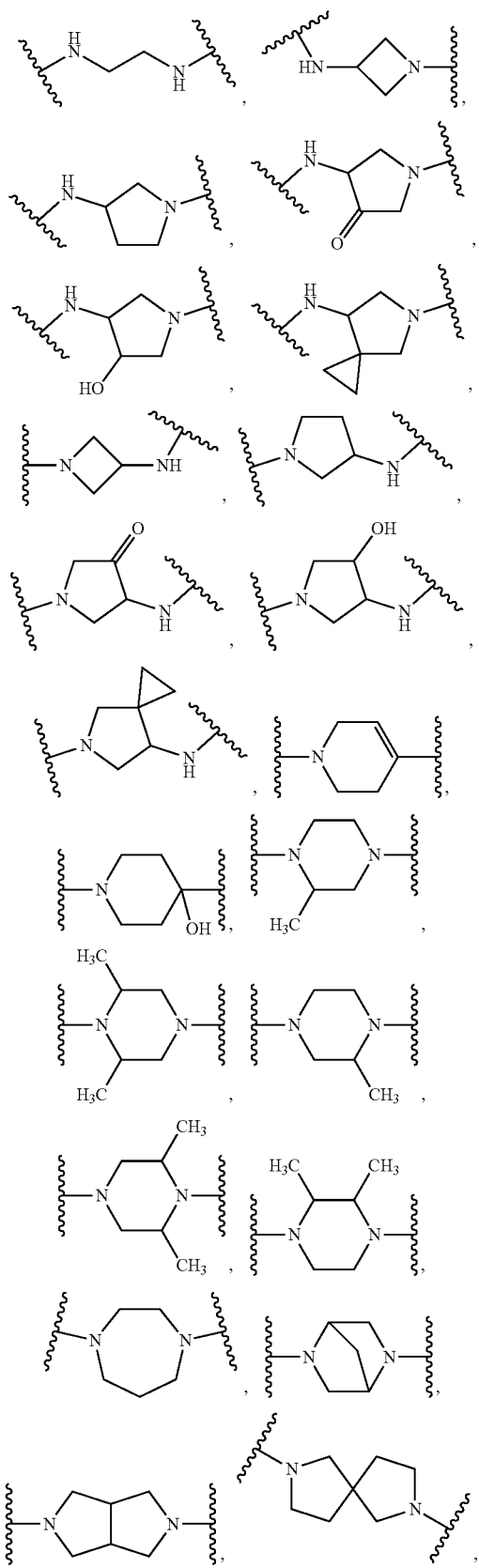

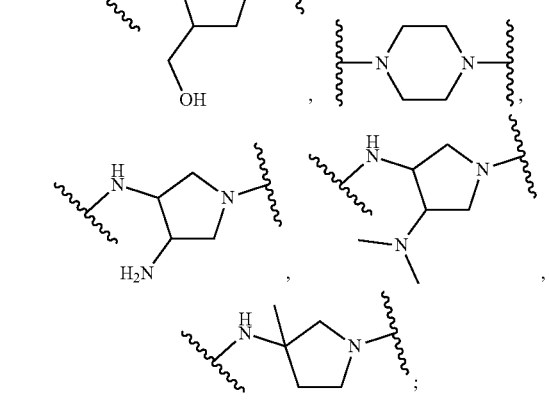

wherein Z is selected from O(C=O), $CF_2CO$, $COCH_2$, $CH_2CO$,

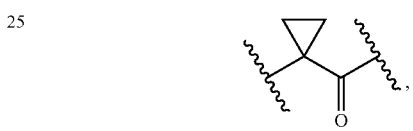

CO, $CH_2SO_2$, $SO_2$, NHCO, and CH(OH)CO; and wherein $Ar^1$ is selected from aryl and heteroaryl and substituted with 1, 2, or 3 groups independently selected from halogen, $-NO_2$, $-CN$, $-OH$, $-SH$, $-NH_2$, C1-C8 acyclic alkyl, C1-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, $-CO$(C1-C8 acyclic alkyl), and cyclopropyl, cyclobutyl, and oxetane, wherein the cyclopropyl, cyclobutyl, and oxetane are optionally substituted with 1, 2, or 3 groups independently selected from $-OH$, C1-C4 alkyl, and C1-C4 alkoxy, or a pharmaceutically acceptable salt thereof.

In a further aspect, disclosed are compounds having a structure represented by a formula:

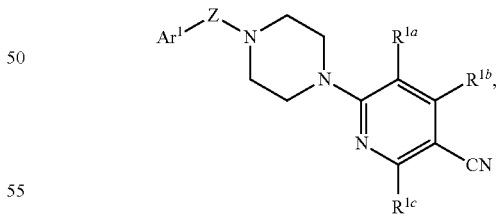

wherein each of $R^{1a}$, $R^{1b}$, and $R^{1c}$ is independently selected from hydrogen, halogen, $-NO_2$, $-CN$, $-OH$, $-SH$, $-NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino; and wherein Z is selected from $COCH_2$, O(C=O), $CF_2CO$, and CH(OH)CO; and wherein $Ar^1$ is selected from aryl and heteroaryl and substituted with 1, 2, or 3 groups independently selected from halogen, $-NO_2$, $-CN$, $-OH$, $-SH$, $-NH_2$, C1-C8 acyclic alkyl, C1-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, —CO(C1-C8 acyclic alkyl), and cyclopropyl, or wherein Z is selected from CO,

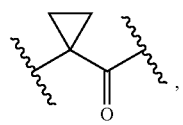 [SMILES: *C(=O)C1(*)CC1]

$CH_2CO$, $COCH_2$, NHCO, and NHCS; and wherein $Ar^1$ is selected from furanyl, 3-isopropylisoxazole, 6-isopropylpyridin-2-yl, 5-isopropylpyridin-2-yl, 5-tertbutylpyridin-2-yl, 5-bromopyridin-2-yl, 5-(prop-1-en-2-yl)pyridin-2-yl, 3-pyridinyl, 4-pyridinyl, and pyrimidinyl, and substituted with 0, 1, 2, or 3 groups independently selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino, or a pharmaceutically acceptable salt thereof.

In a further aspect, disclosed are compounds having a structure represented by a formula:

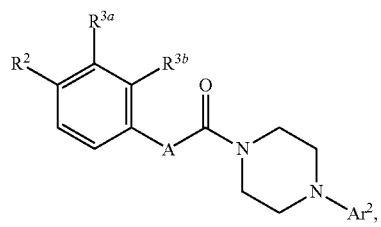

wherein A is selected from O, CO, $CH_2$, $CF_2$, NH, and CH(OH); wherein $R^2$ is selected from isopropyl and cyclopropyl; wherein $Ar^2$ is a structure represented by a formula selected from:

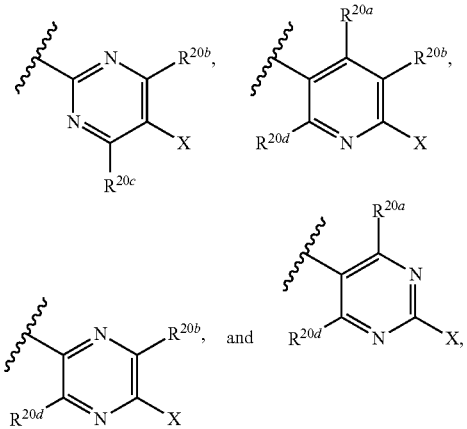

wherein X is halogen; and wherein each of $R^{20a}$, $R^{20b}$, $R^{20c}$, and $R^{20d}$, when present, is independently selected from hydrogen, halogen, —CN, C1-C4 alkyl, C1-C4 monohaloalkyl, C1-C4 polyhaloalkyl, C1-C4 alkoxy, C1-C4 monohaloalkoxy, C1-C4 polyhaloalkoxy, C1-C4 alkylamino, (C1-C4)(C1-C4)dialkylamino, and cyclopropyl; or wherein A is selected from O, CO, $CH_2$, $CF_2$, and CH(OH); and wherein $Ar^2$ is a structure represented by a formula:

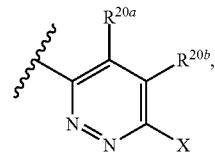

or a pharmaceutically acceptable salt thereof.

Also disclosed are compounds selected from:

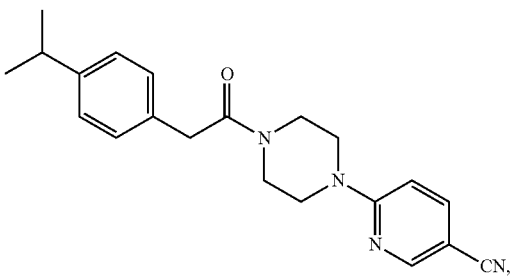

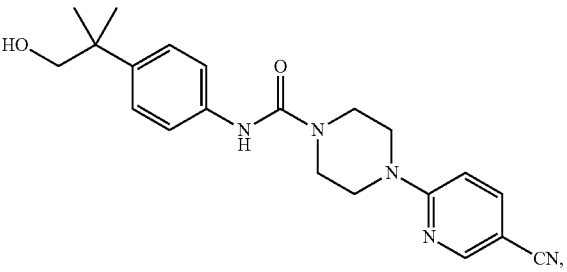

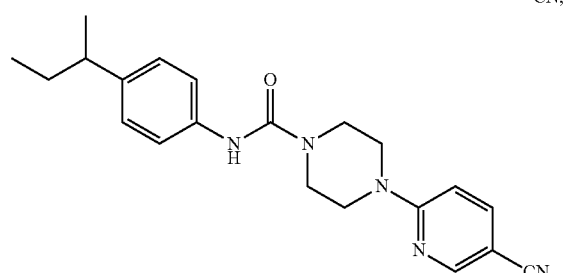

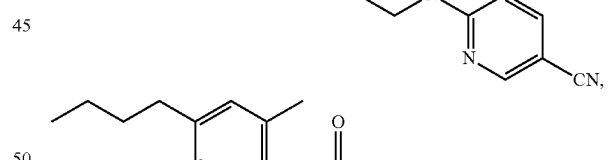

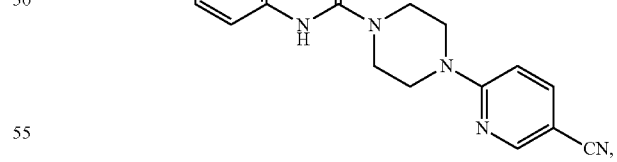

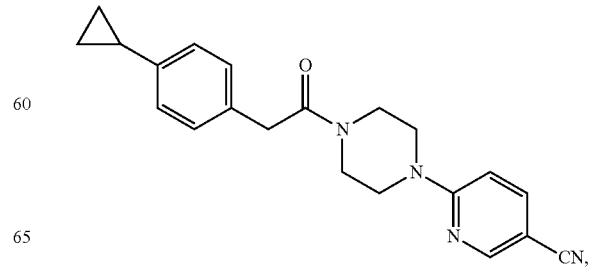

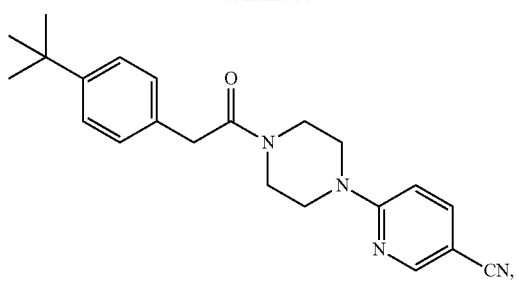
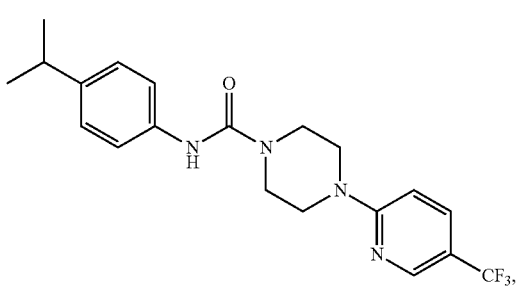
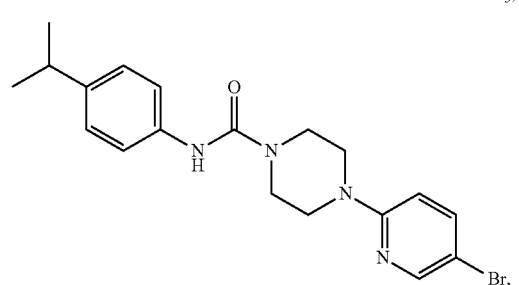
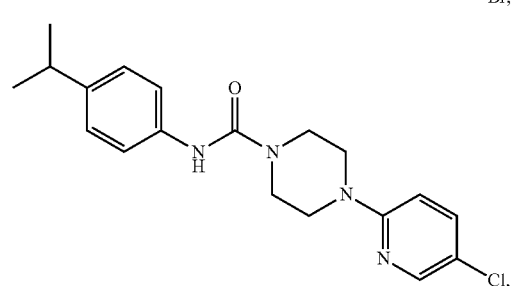
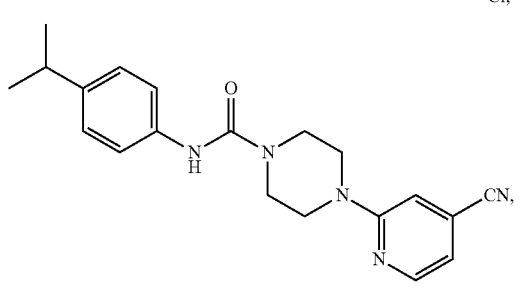
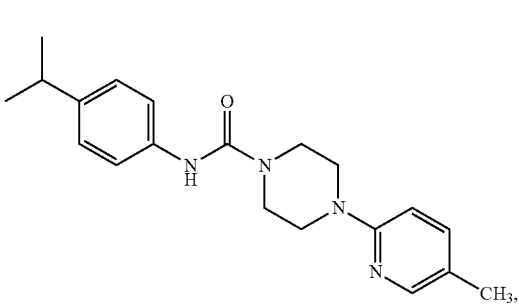
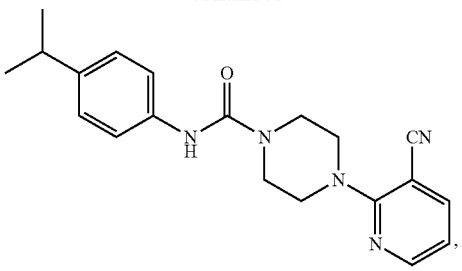
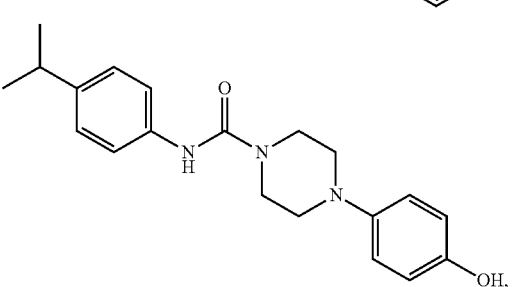
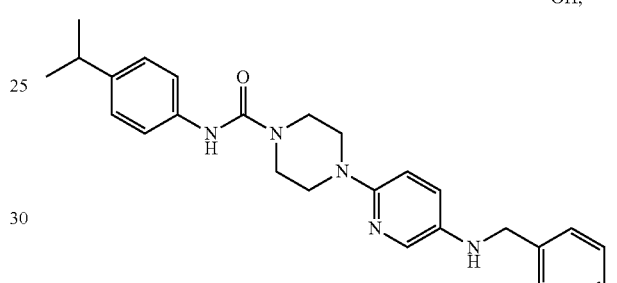
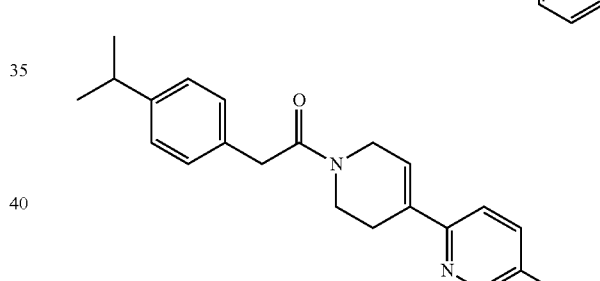
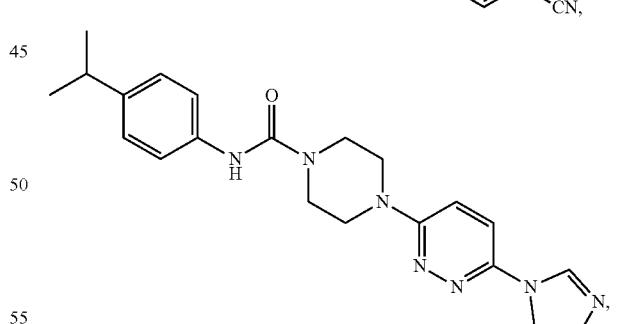
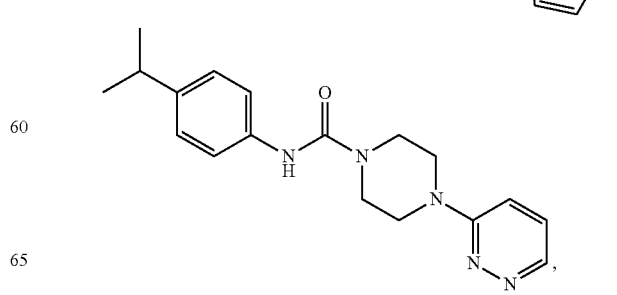

-continued

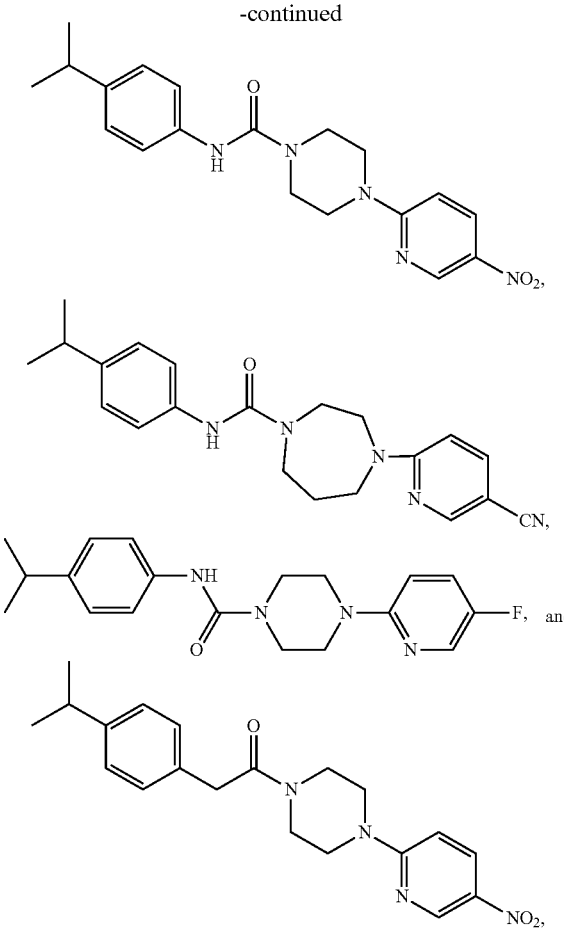

or a pharmaceutically acceptable salt thereof.

In a further aspect, $Q^1$ is CH and $R^2$ is selected from C1-C8 acyclic alkyl, C1-C8 acyclic alkenyl, C1-C8 monohaloalkyl, C1-C8 polyhaloalkyl, and cyclopropyl; or $Q^1$ is N and $R^2$ is selected from halogen, C1-C8 acyclic alkyl, C1-C8 acyclic alkenyl, C1-C8 monohaloalkyl, C1-C8 polyhaloalkyl, and cyclopropyl; and $Q^2$ is a structure selected from:

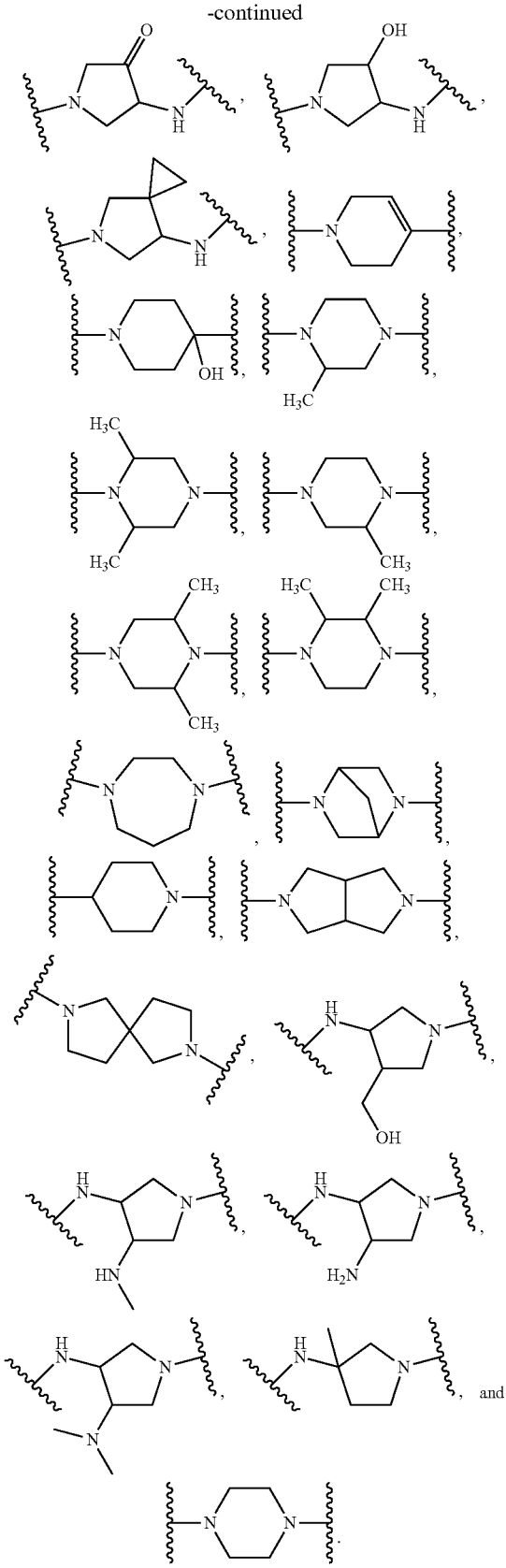

In a further aspect, $Q^1$ is CH; and $R^2$ is selected from C1-C8 acyclic alkyl, C1-C8 acyclic alkenyl, C1-C8 monohaloalkyl, C1-C8 polyhaloalkyl, and cyclopropyl; or $Q^1$ is N; and $R^2$ is selected from halogen, C1-C8 acyclic alkyl, C1-C8 acyclic alkenyl, C1-C8 monohaloalkyl, C1-C8 polyhaloalkyl, and cyclopropyl.

In a further aspect, $Q^1$ is CH or N; and $R^2$ is selected from —SCH$_3$, C1-C8 alkoxyhaloalkyl, cyclobutyl, and oxetane, wherein the cyclopropyl, cyclobutyl, and oxetane are optionally substituted with 1, 2, or 3 groups independently selected from —OH, C1-C4 alkyl, and C1-C4 alkoxy.

In a further aspect, the compound has a structure represented by a formula:

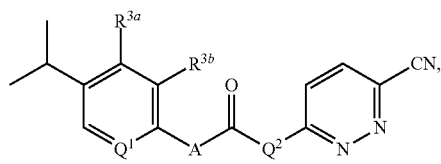

or a pharmaceutically acceptable salt thereof.

In a still further aspect, the compound has a structure represented by a formula selected from:

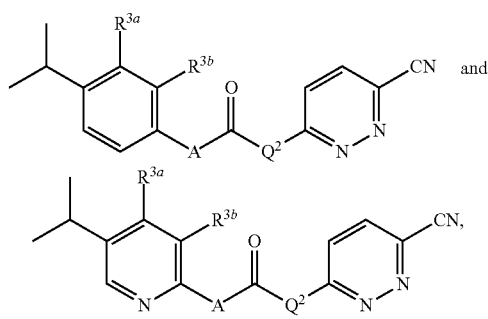

or a pharmaceutically acceptable salt thereof.

In yet a further aspect, the compound has a structure represented by a formula:

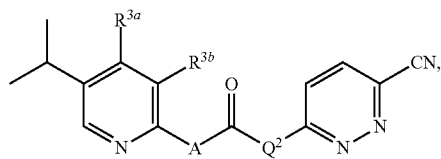

or a pharmaceutically acceptable salt thereof.

In an even further aspect, the compound has a structure represented by a formula:

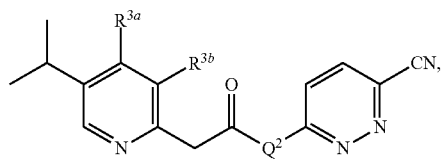

or a pharmaceutically acceptable salt thereof.

In a still further aspect, the compound has a structure represented by a formula:

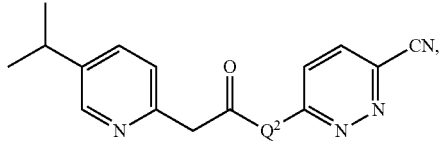

or a pharmaceutically acceptable salt thereof.

In yet a further aspect, the compound is:

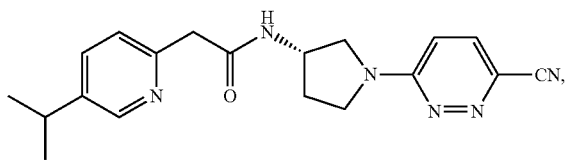 [SMILES: CC(C)c1ccc(CC(=O)N[C@H]2CCN(c3ccc(C#N)nn3)C2)nc1]

or a pharmaceutically acceptable salt thereof.

In a further aspect, the compound has a structure represented by a formula:

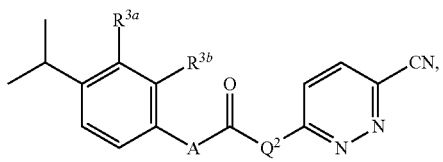

or a pharmaceutically acceptable salt thereof.

In yet a further aspect, the compound has a structure represented by a formula selected from:

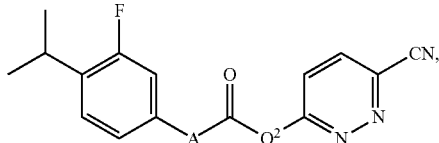

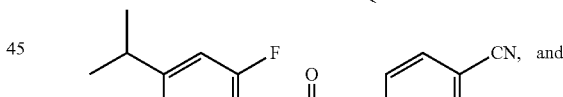

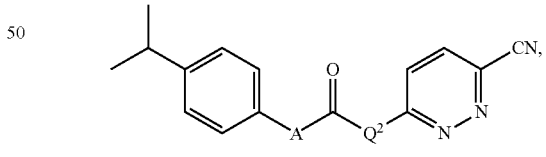

or a pharmaceutically acceptable salt thereof.

In an even further aspect, the compound has a structure represented by a formula selected from:

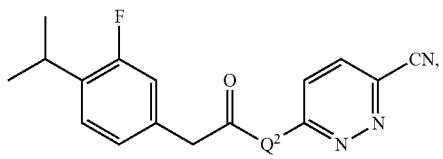

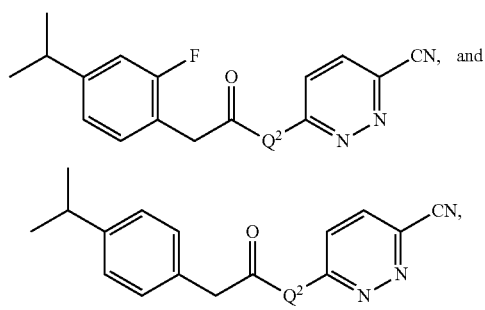

or a pharmaceutically acceptable salt thereof.

In a still further aspect, the compound is selected from:

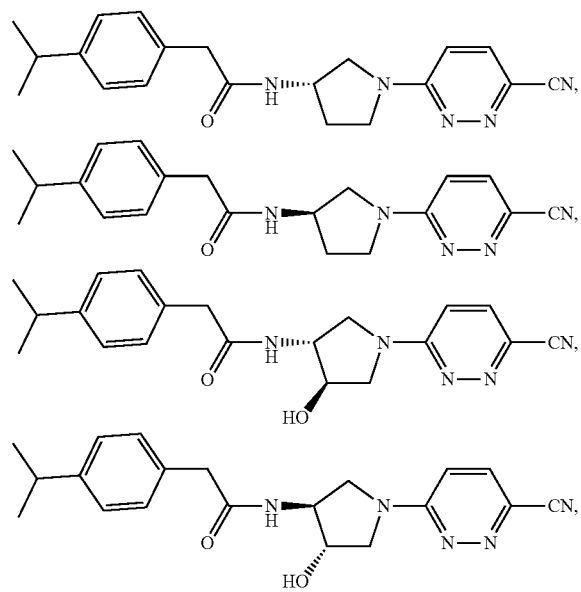

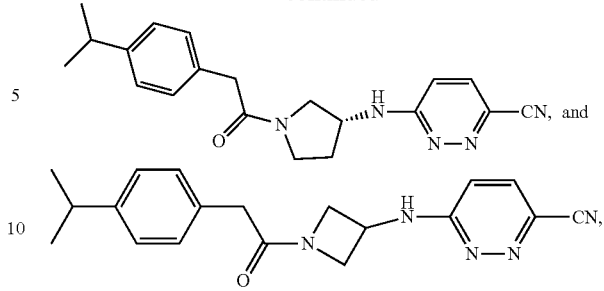

or a pharmaceutically acceptable salt thereof.

In yet a further aspect, the compound has a structure represented by a formula selected from:

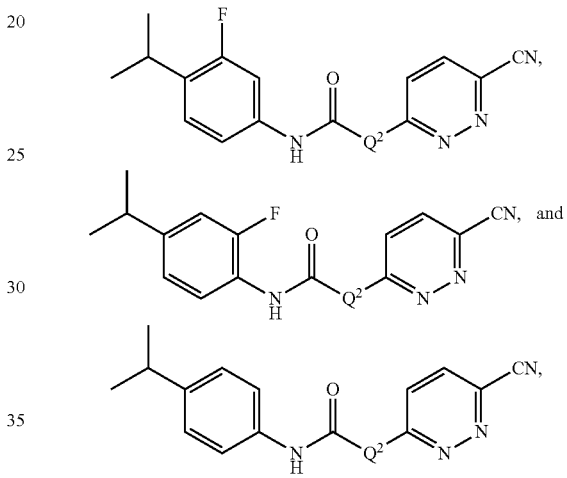

or a pharmaceutically acceptable salt thereof.

In an even further aspect, the compound is selected from:

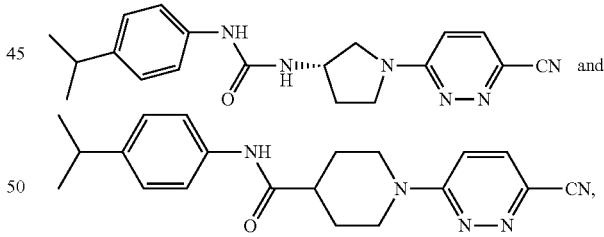

or a pharmaceutically acceptable salt thereof.

In a further aspect, the compound has a structure represented by a formula:

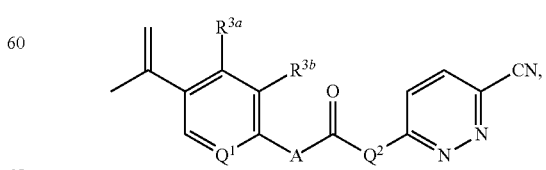

or a pharmaceutically acceptable salt thereof.

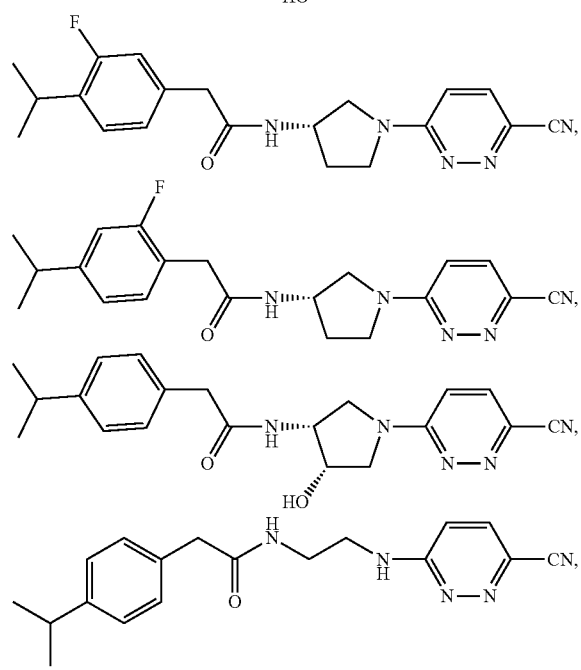

In a still further aspect, the compound has a structure represented by a formula selected from:

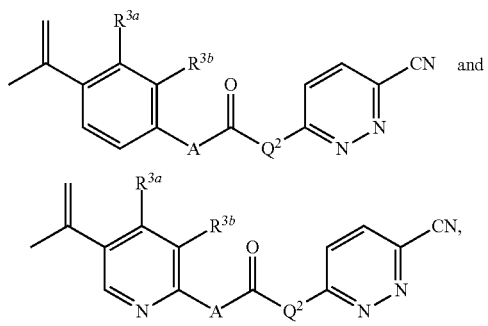

or a pharmaceutically acceptable salt thereof.

In yet a further aspect, the compound has a structure represented by a formula:

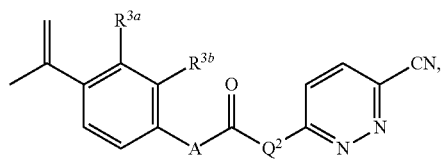

or a pharmaceutically acceptable salt thereof.

In an even further aspect, the compound has a structure represented by a formula selected from:

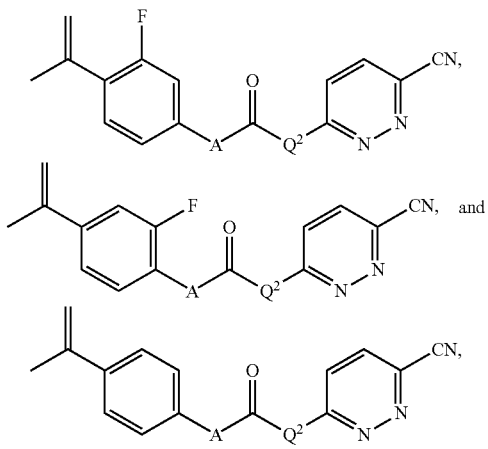

or a pharmaceutically acceptable salt thereof.

In a still further aspect, the compound has a structure represented by a formula selected from:

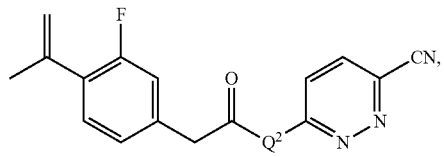

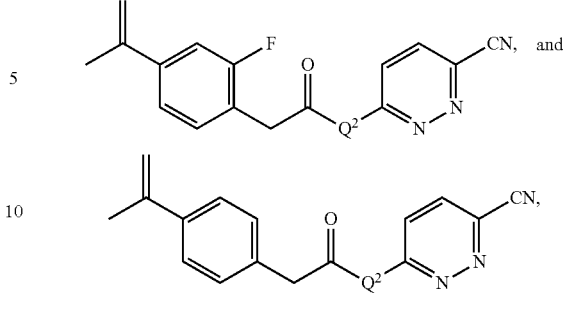

or a pharmaceutically acceptable salt thereof.

In yet further aspect, the compound is selected from:

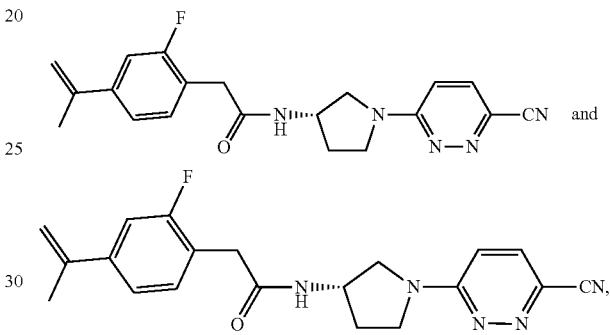

or a pharmaceutically acceptable salt thereof.

In a further aspect, the compound has a structure represented by a formula:

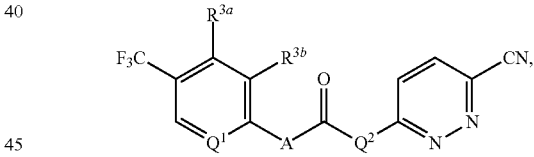

or a pharmaceutically acceptable salt thereof.

In a still further aspect, the compound has a structure represented by a formula selected from:

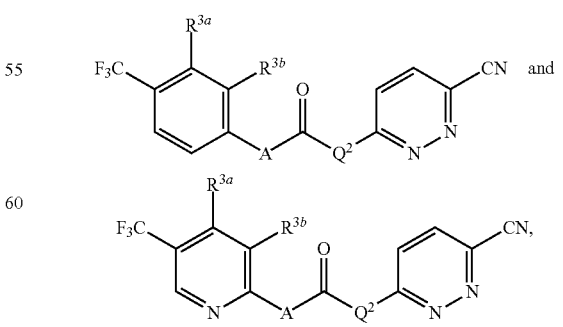

or a pharmaceutically acceptable salt thereof.

In yet a further aspect, the compound has a structure represented by a formula:

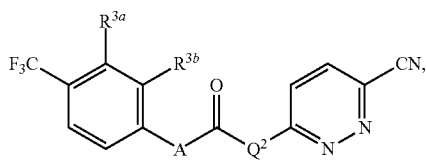

or a pharmaceutically acceptable salt thereof.

In an even further aspect, the compound has a structure represented by a formula selected from:

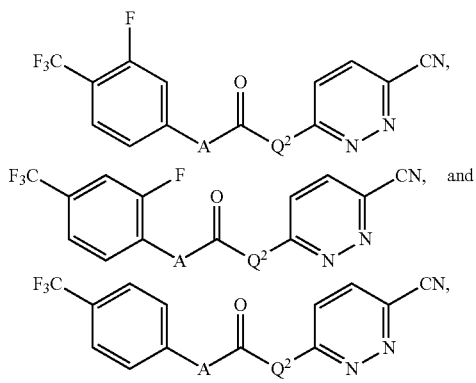

or a pharmaceutically acceptable salt thereof.

In a still further aspect, the compound has a structure represented by a formula:

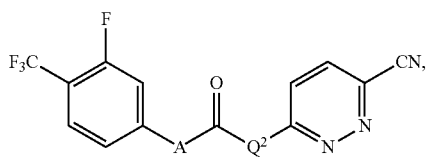

or a pharmaceutically acceptable salt thereof.

In yet a further aspect, the compound is:

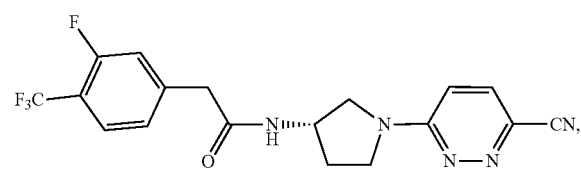 [SMILES: N#Cc1ccc(N2CC[C@H](NC(=O)Cc3ccc(C(F)(F)F)c(F)c3)C2)nn1]

or a pharmaceutically acceptable salt thereof.

In a further aspect, the compound is selected from:

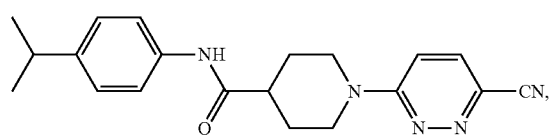

-continued

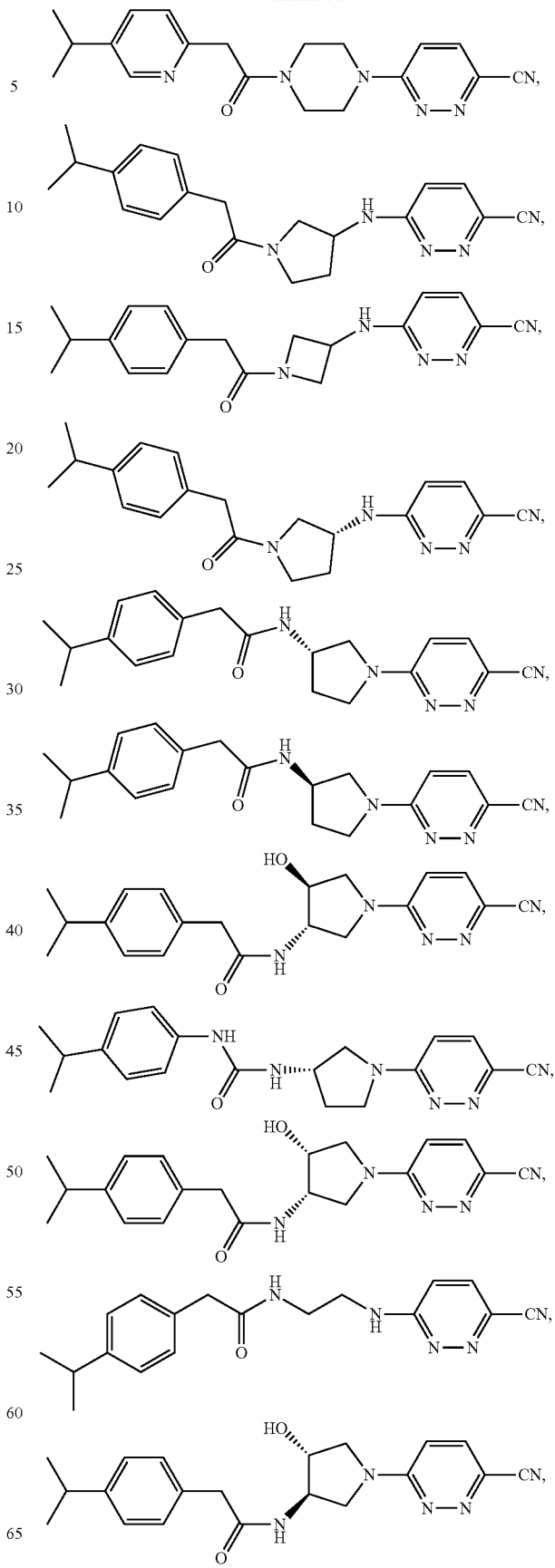

-continued
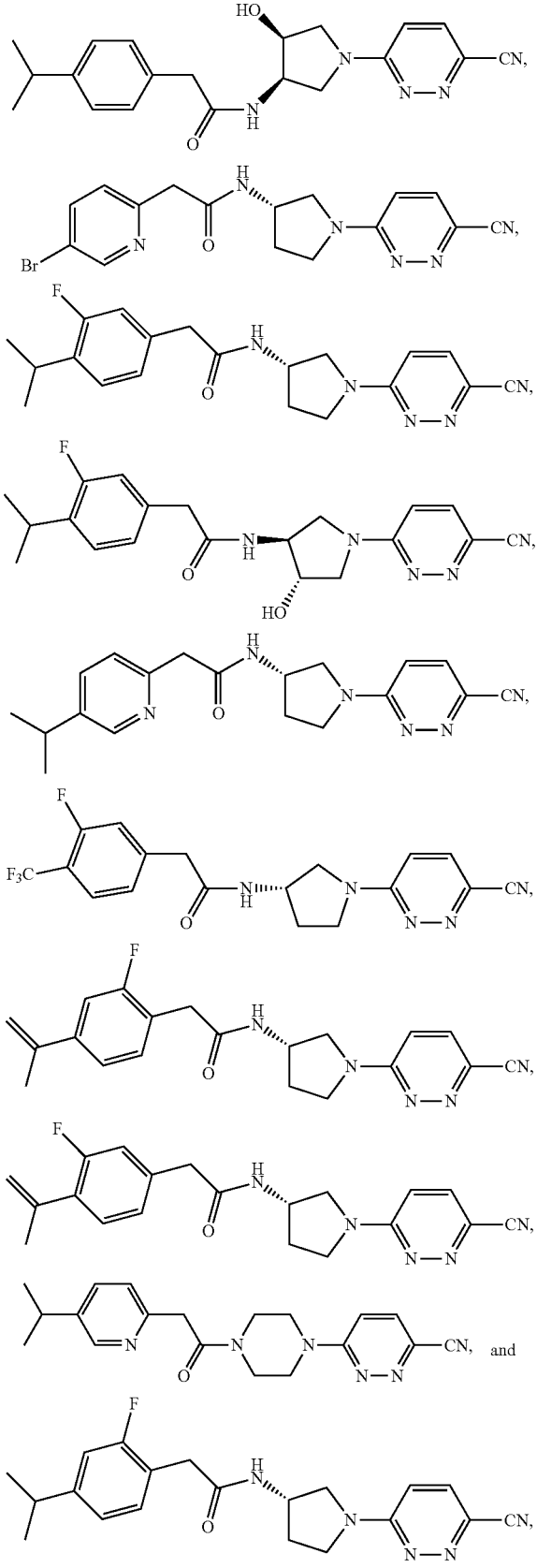
or a pharmaceutically acceptable salt thereof.
In a further aspect, the compound is selected from:
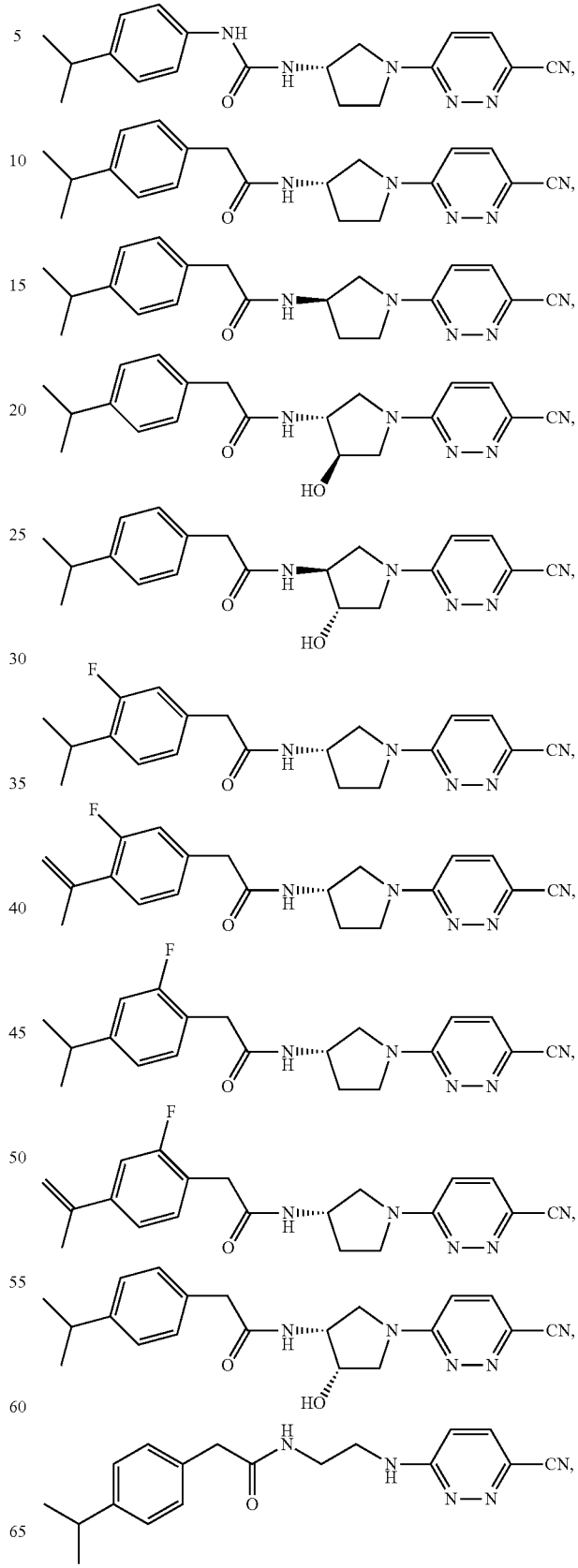

-continued

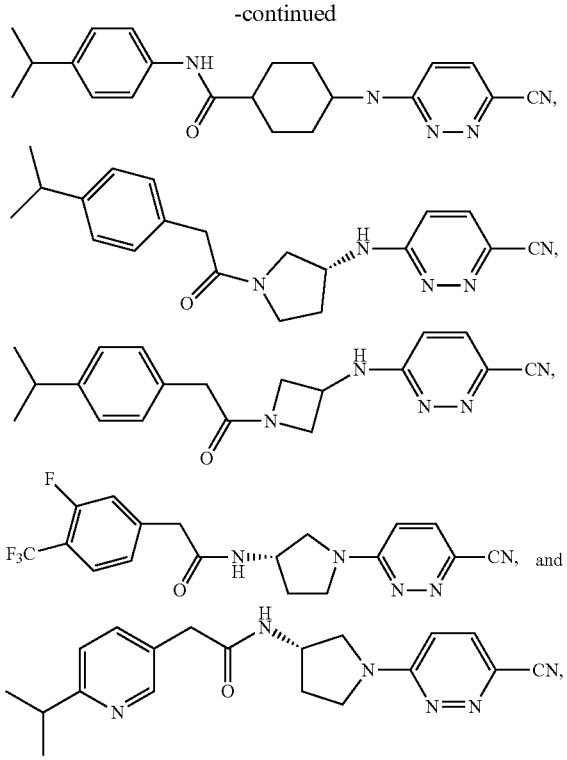

or a pharmaceutically acceptable salt thereof.

In a further aspect, the compound has a structure represented by a formula:

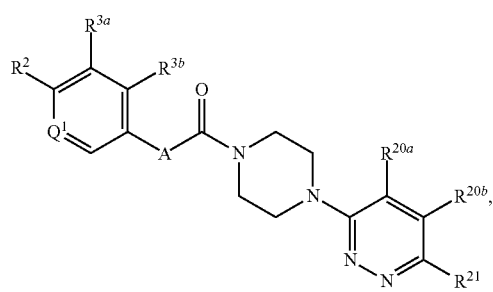

or a pharmaceutically acceptable salt thereof.

In a still further aspect, the compound has a structure represented by a formula:

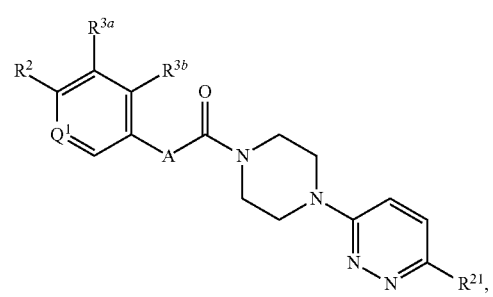

or a pharmaceutically acceptable salt thereof.

In yet a further aspect, the compound has a structure represented by a formula selected from:

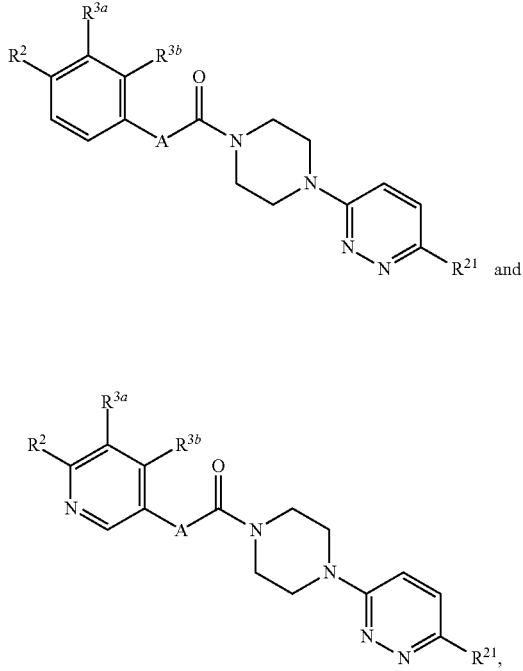

or a pharmaceutically acceptable salt thereof.

In an even further aspect, the compound has a structure represented by a formula:

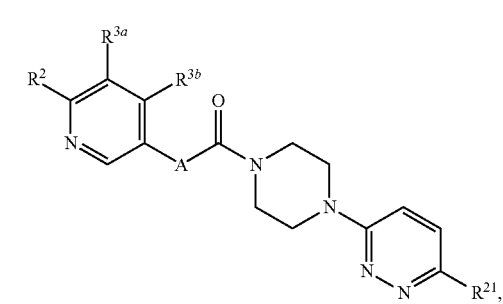

or a pharmaceutically acceptable salt thereof.

In a still further aspect, the compound has a structure represented by a formula:

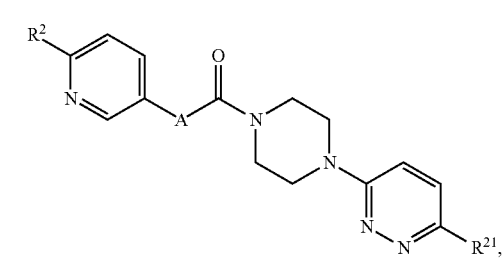

or a pharmaceutically acceptable salt thereof.

In yet a further aspect, the compound is selected from:

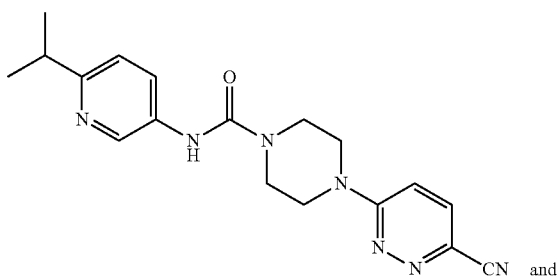

and

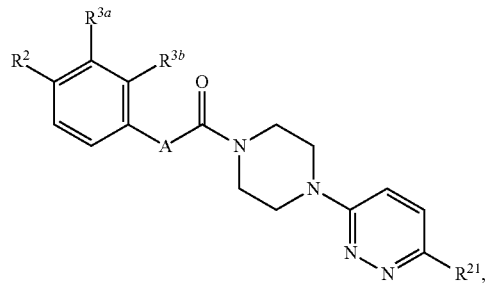

or a pharmaceutically acceptable salt thereof.

In a further aspect, the compound has a structure represented by a formula:

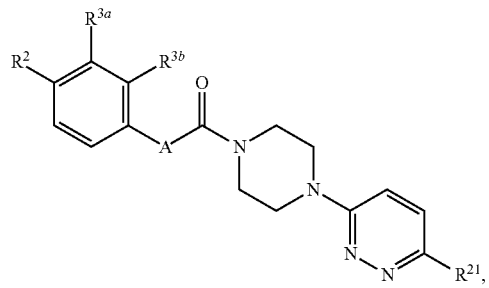

or a pharmaceutically acceptable salt thereof.

In a still further aspect, the compound has a structure represented by a formula:

In yet a further aspect, the compound has a structure represented by a formula:

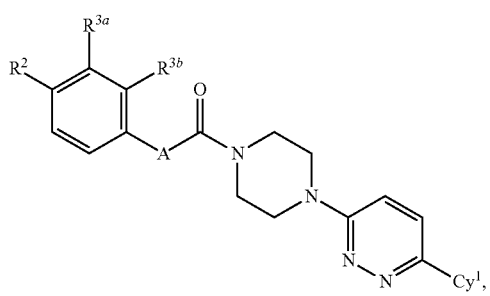

or a pharmaceutically acceptable salt thereof.

In an even further aspect, the compound is:

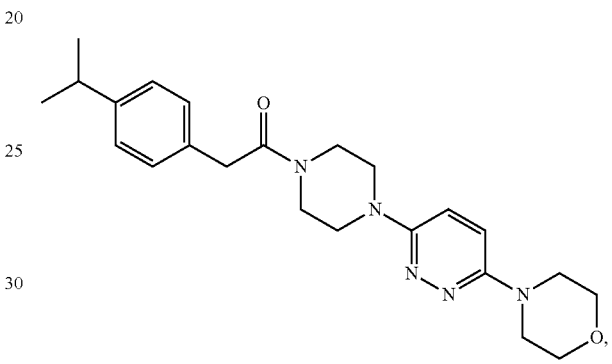

or a pharmaceutically acceptable salt thereof.

In a further aspect, the compound has a structure represented by a formula:

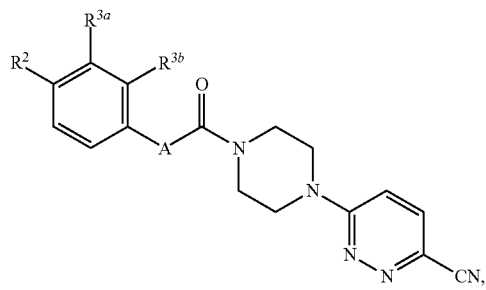

or a pharmaceutically acceptable salt thereof.

In a still further aspect, the compound has a structure represented by a formula:

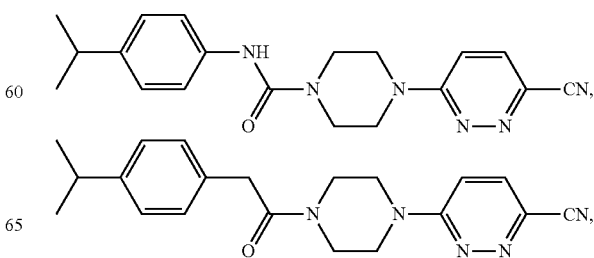

or a pharmaceutically acceptable salt thereof.

-continued

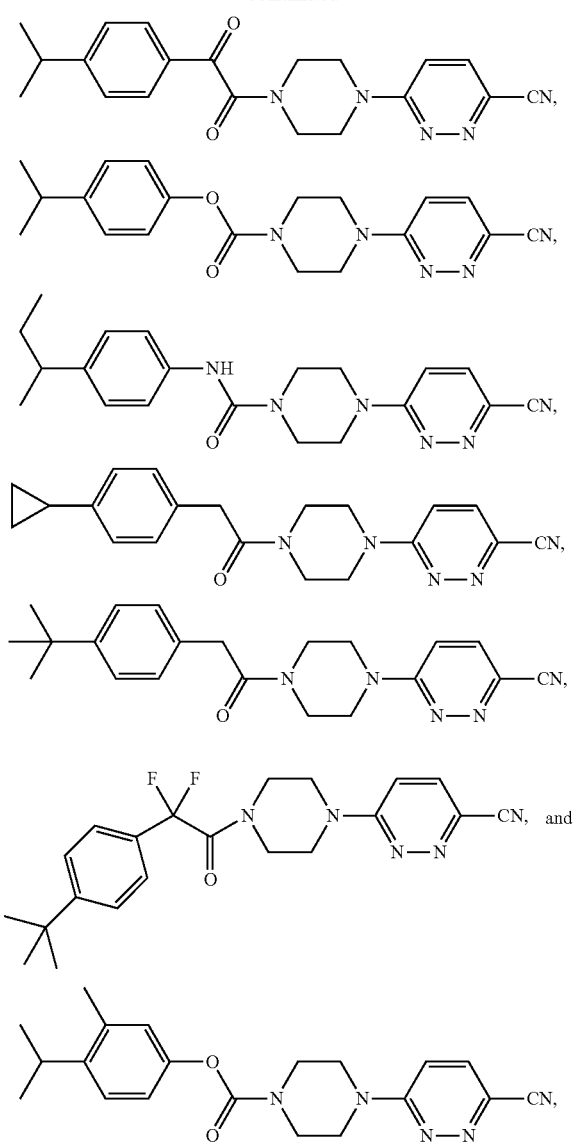

or a pharmaceutically acceptable salt thereof.

In a further aspect, the compound has a structure represented by a formula:

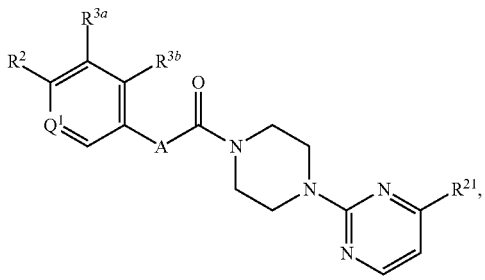

or a pharmaceutically acceptable salt thereof.

In a still further aspect, the compound has a structure represented by a formula:

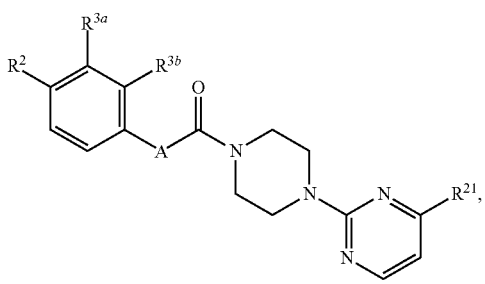

or a pharmaceutically acceptable salt thereof.

In yet a further aspect, the compound has a structure represented by a formula:

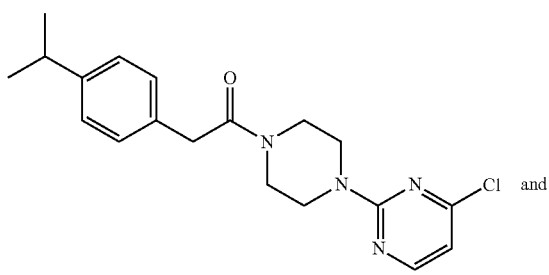

or a pharmaceutically acceptable salt thereof.

In an even further aspect, the compound is selected from:

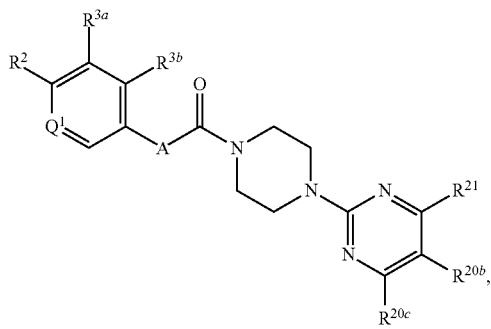

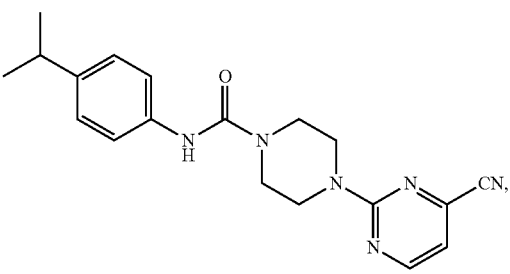

or a pharmaceutically acceptable salt thereof.

In a further aspect, the compound has a structure represented by a formula:

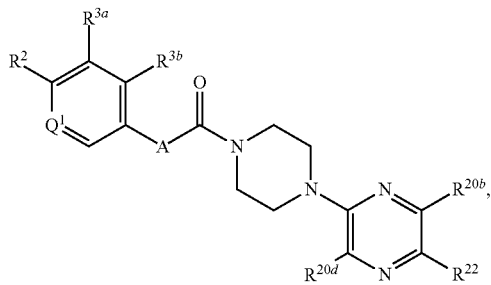

or a pharmaceutically acceptable salt thereof.

In a still further aspect, the compound has a structure represented by a formula:

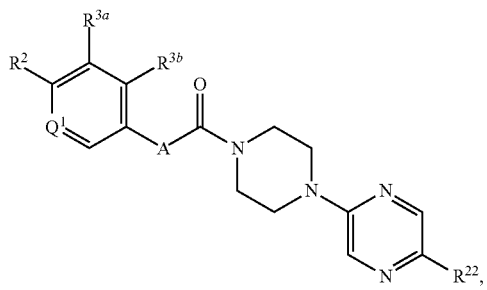

or a pharmaceutically acceptable salt thereof.

In yet a further aspect, the compound has a structure represented by a formula:

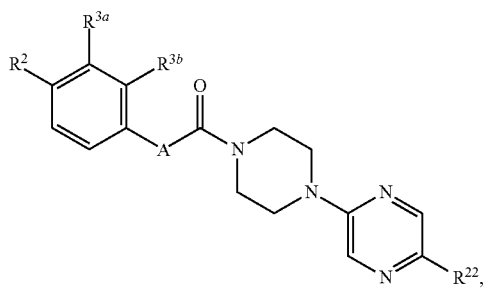

or a pharmaceutically acceptable salt thereof.

In an even further aspect, the compound is selected from:

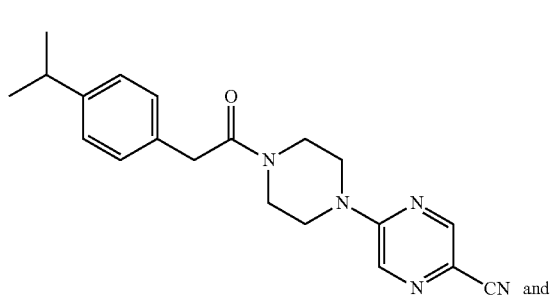

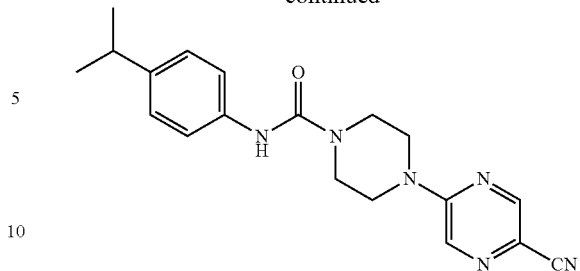

or a pharmaceutically acceptable salt thereof.

In a further aspect, the compound has a structure represented by a formula:

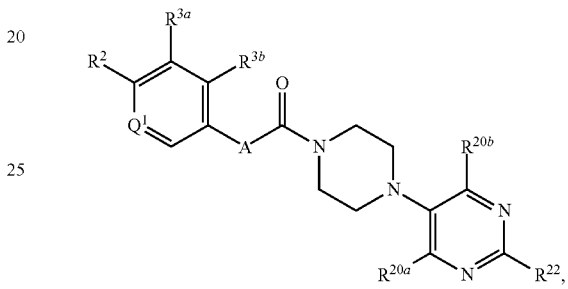

or a pharmaceutically acceptable salt thereof.

In a still further aspect, the compound has a structure represented by a formula:

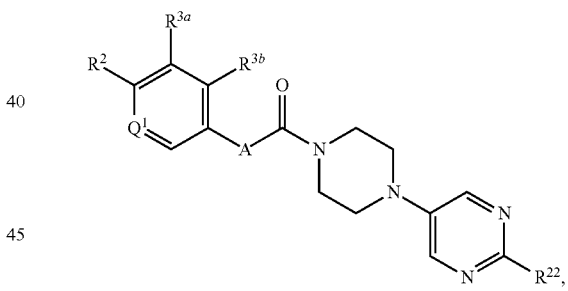

or a pharmaceutically acceptable salt thereof.

In yet a further aspect, the compound has a structure represented by a formula:

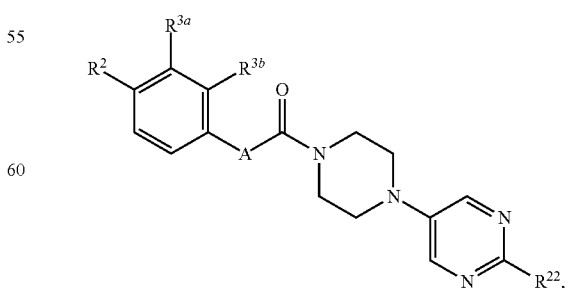

or a pharmaceutically acceptable salt thereof.

In an even further aspect, the compound has a structure represented by a formula:
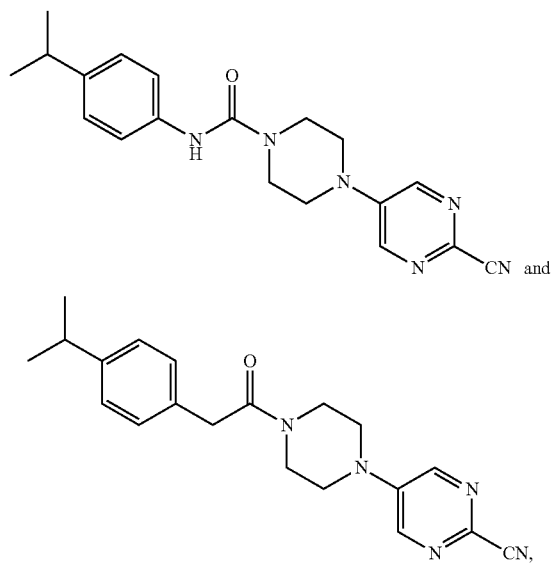
or a pharmaceutically acceptable salt thereof.
In a further aspect, the compound is selected from:
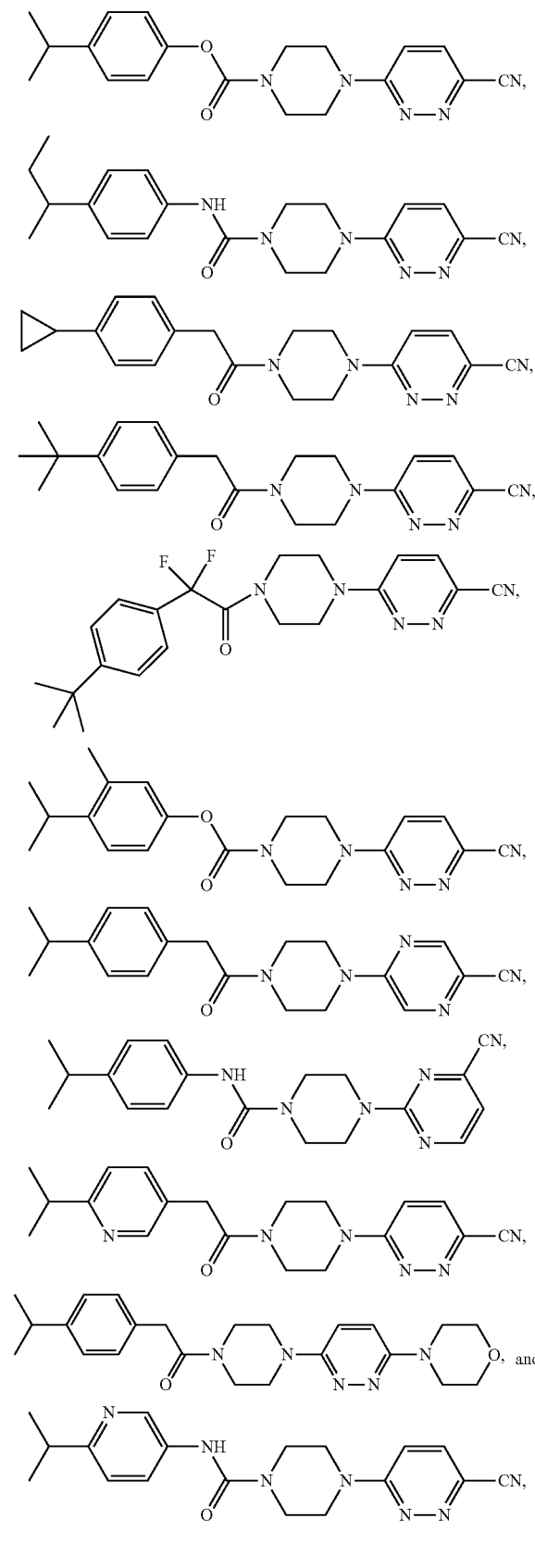
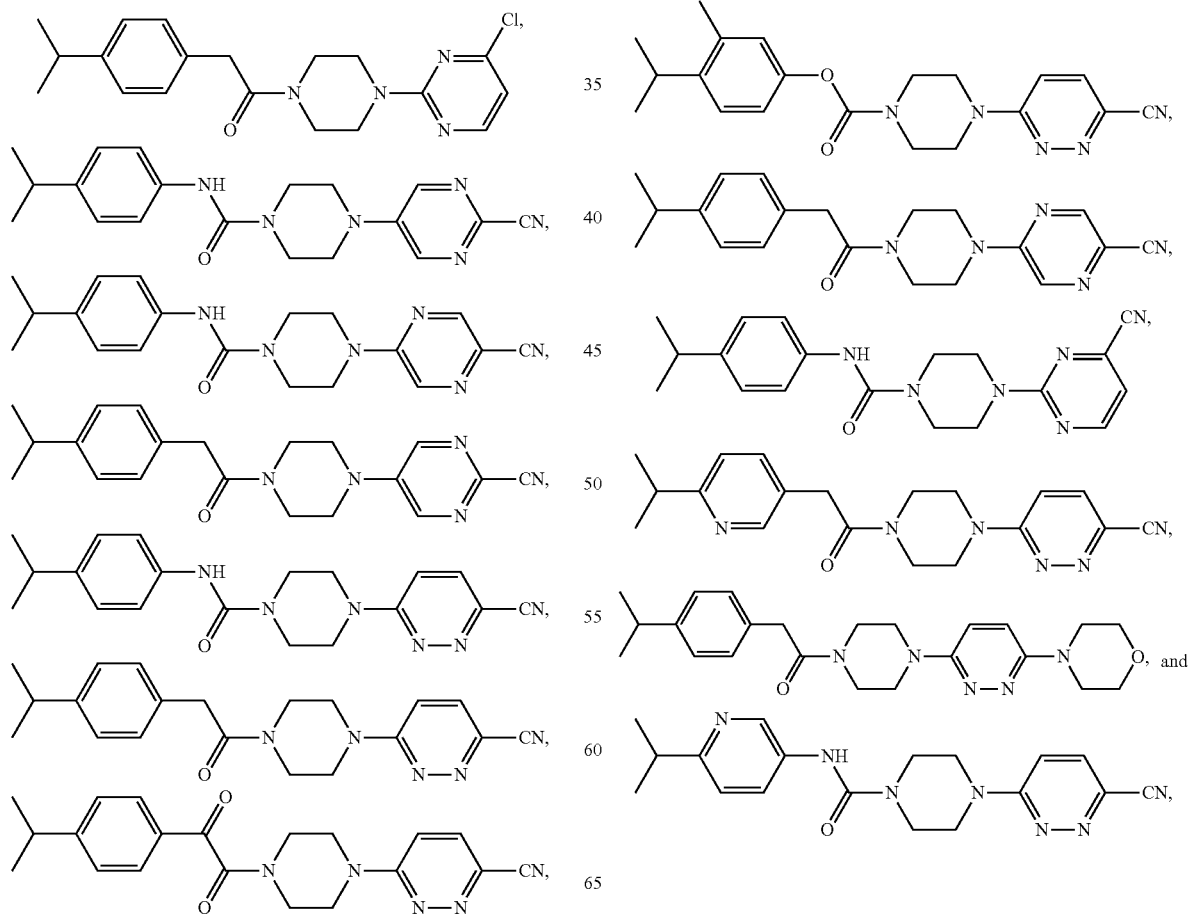
or a pharmaceutically acceptable salt thereof.

In a further aspect, the compound has a structure represented by a formula selected from:
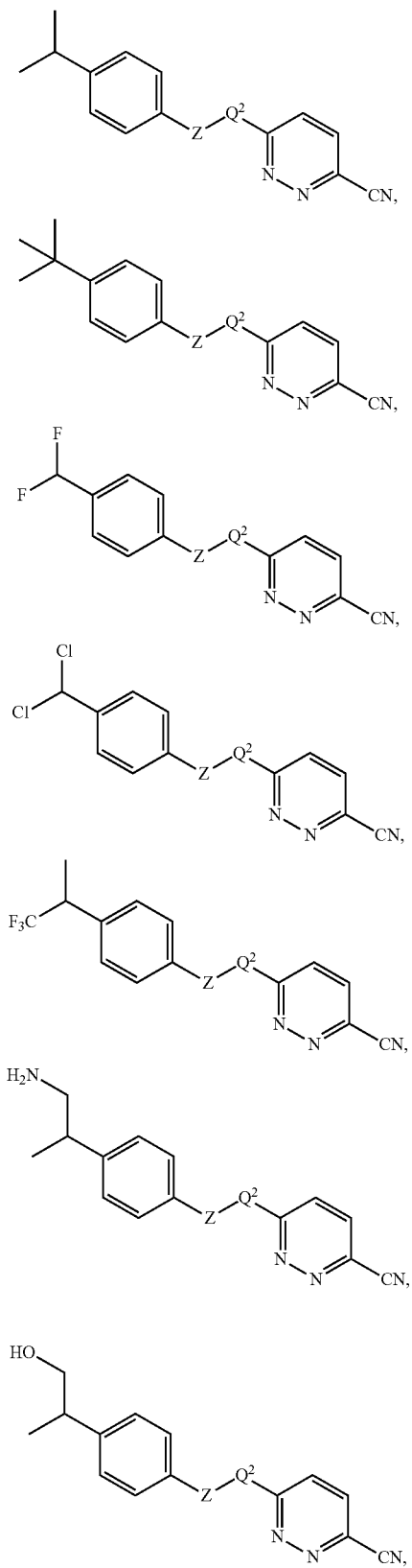
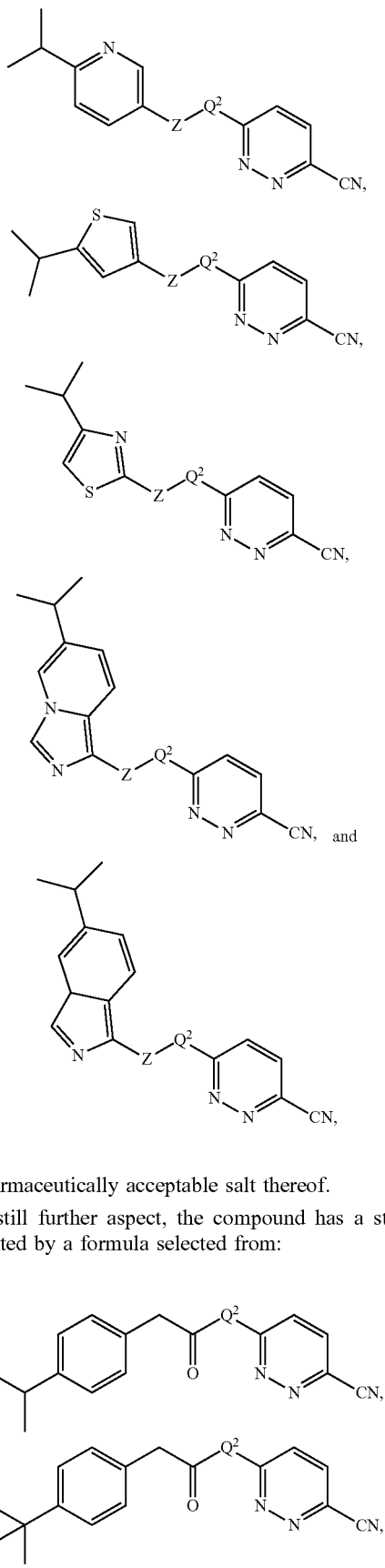
or a pharmaceutically acceptable salt thereof.
In a still further aspect, the compound has a structure represented by a formula selected from:

-continued
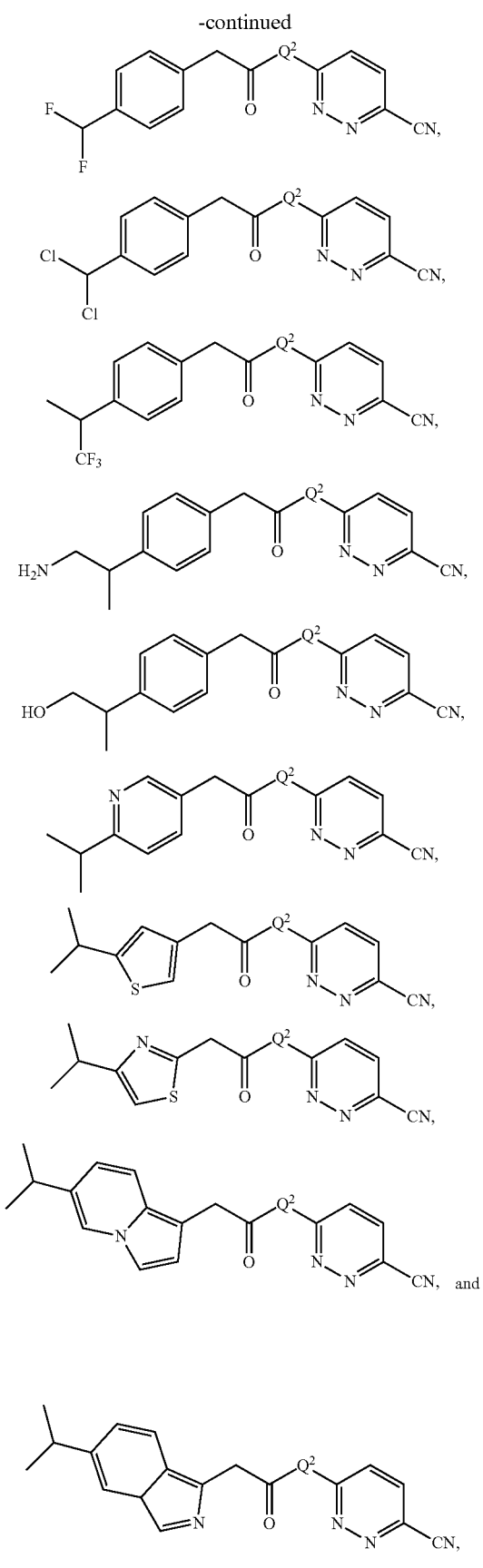
or a pharmaceutically acceptable salt thereof.
In yet a further aspect, the compound has a structure represented by a formula selected from:
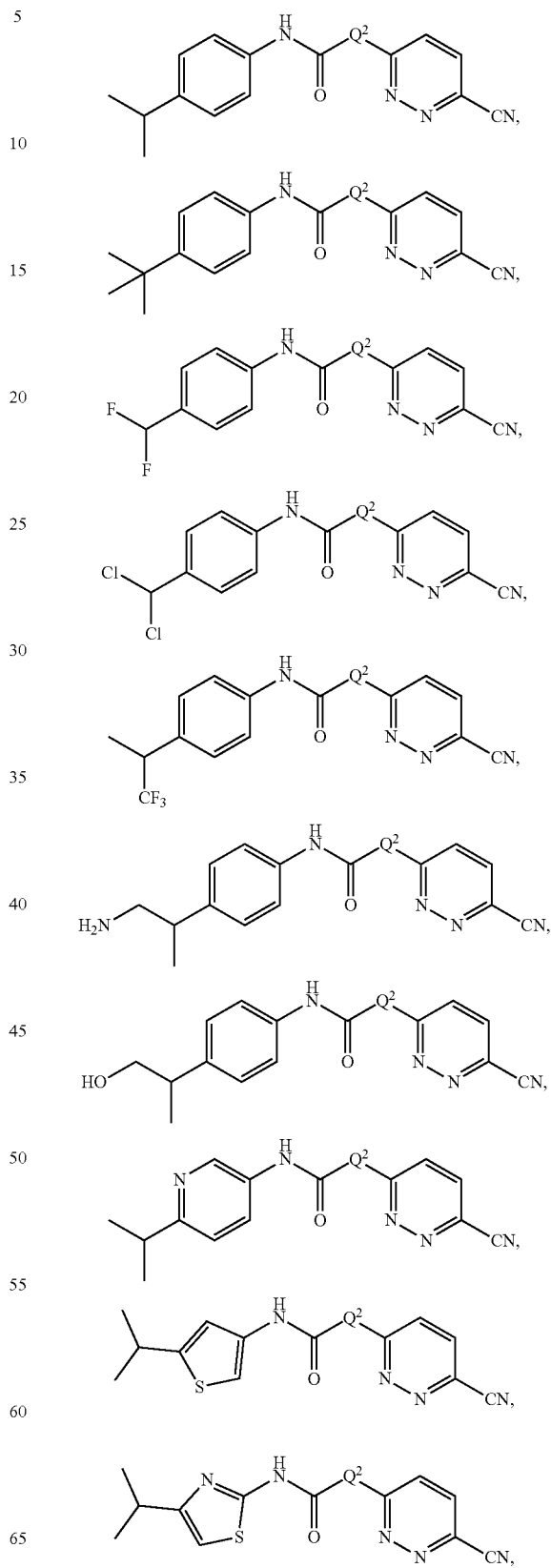

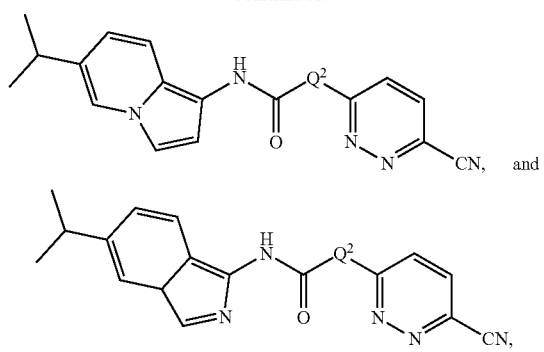
or a pharmaceutically acceptable salt thereof.
In an even further aspect, the compound has a structure represented by a formula selected from:
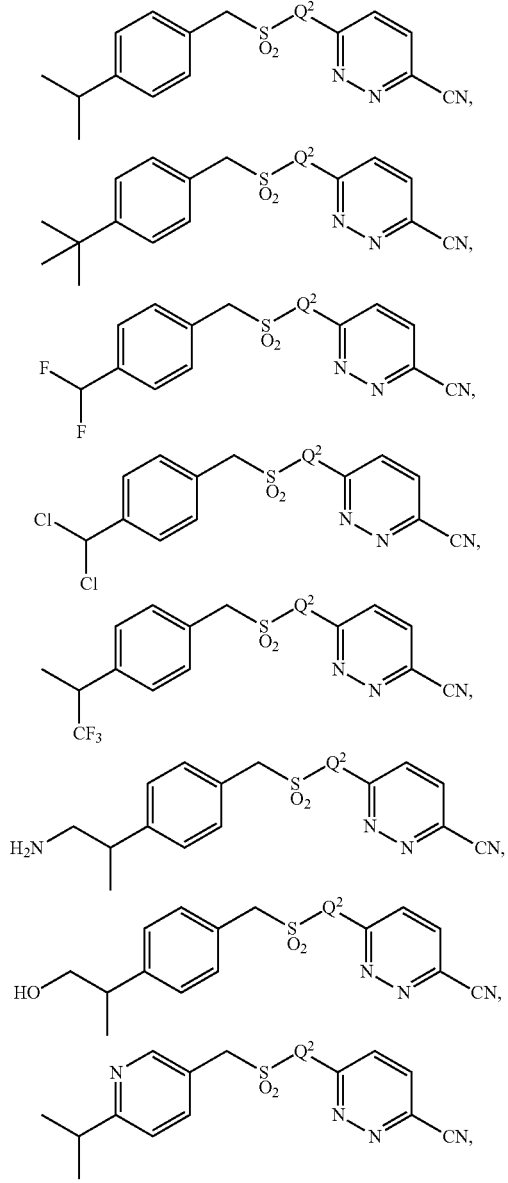
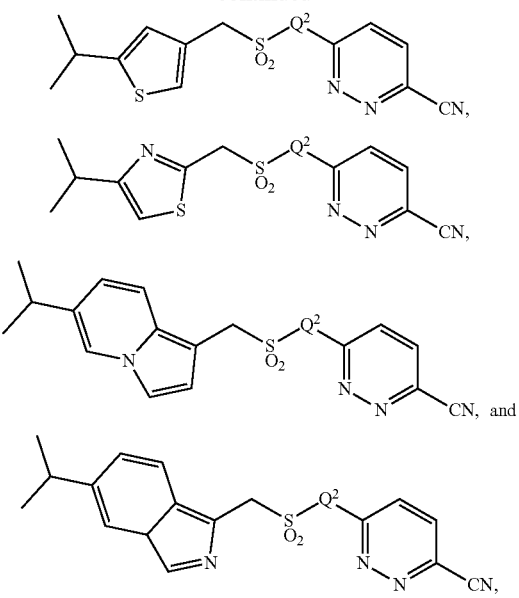
or a pharmaceutically acceptable salt thereof.
In a still further aspect, the compound has a structure represented by a formula selected from:
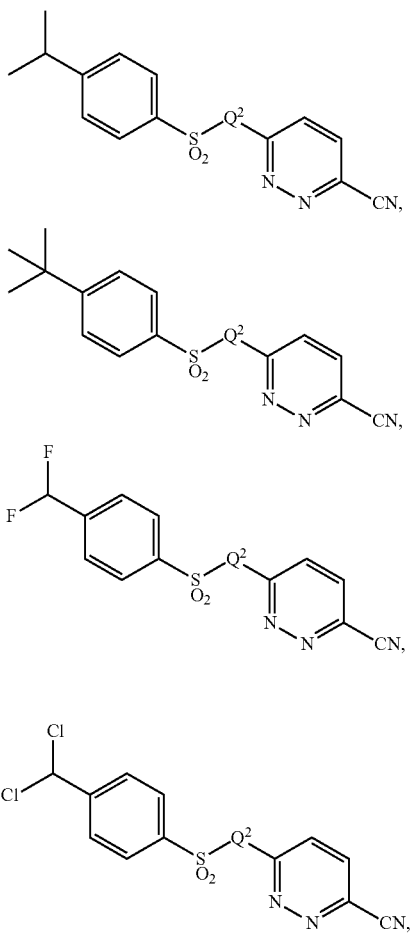

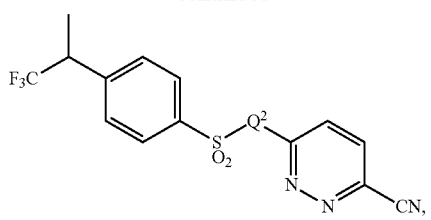
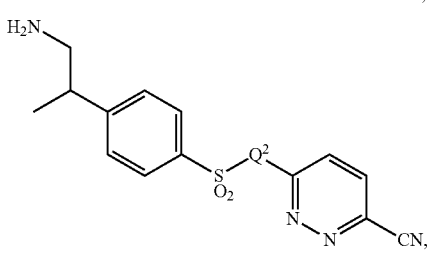
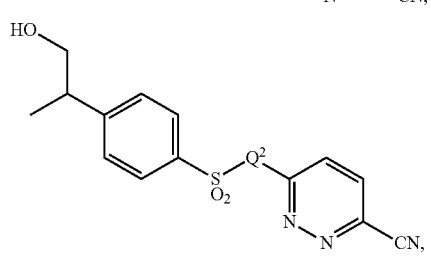
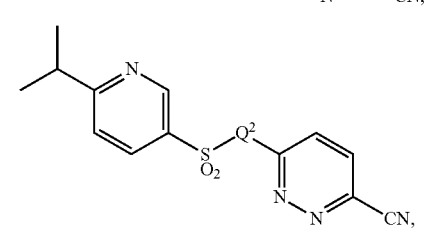
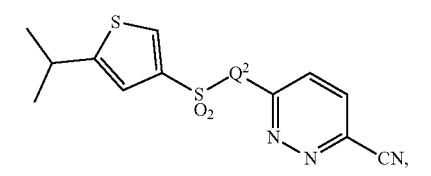
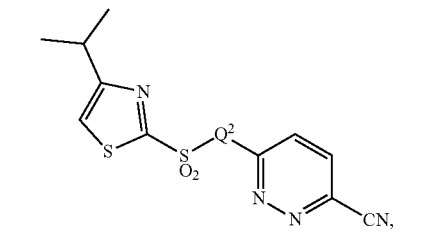
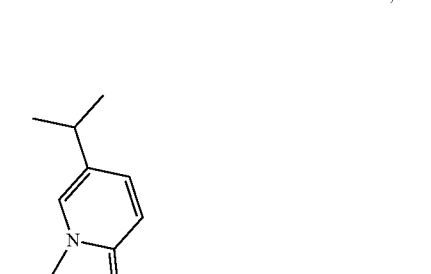
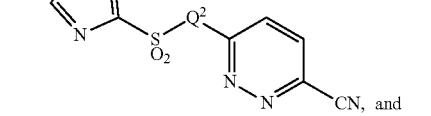
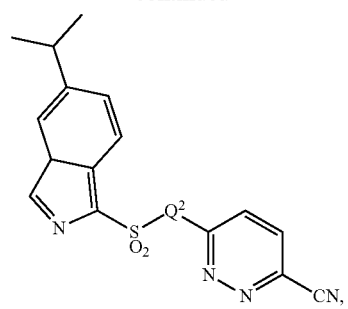
or a pharmaceutically acceptable salt thereof.
In yet a further aspect, the compound has a structure represented by a formula selected from:
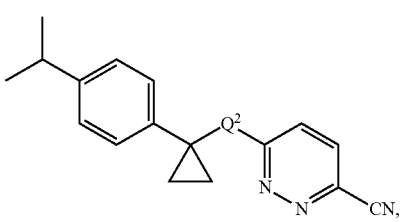
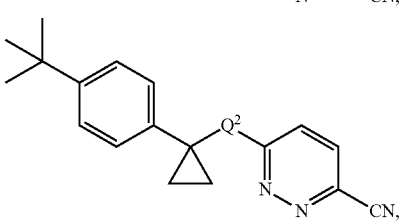
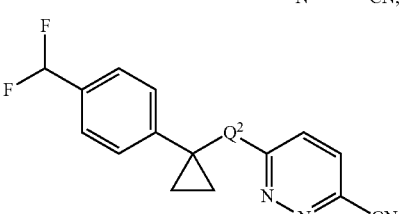
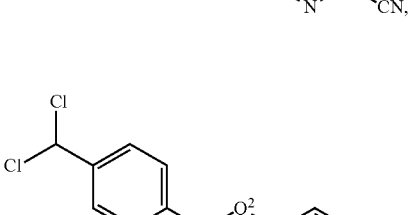
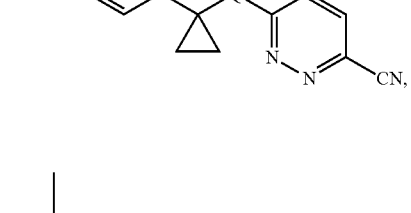
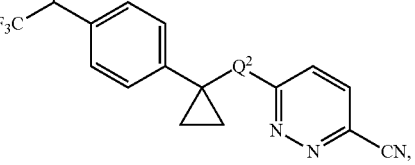

-continued
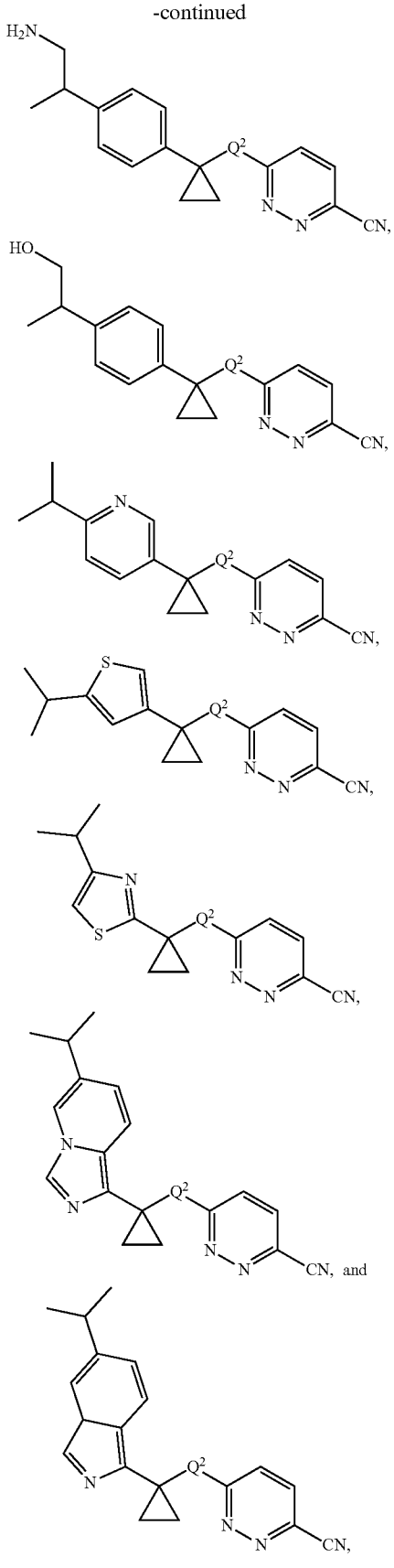
or a pharmaceutically acceptable salt thereof.
In an even further aspect, the compound has a structure represented by a formula selected from:
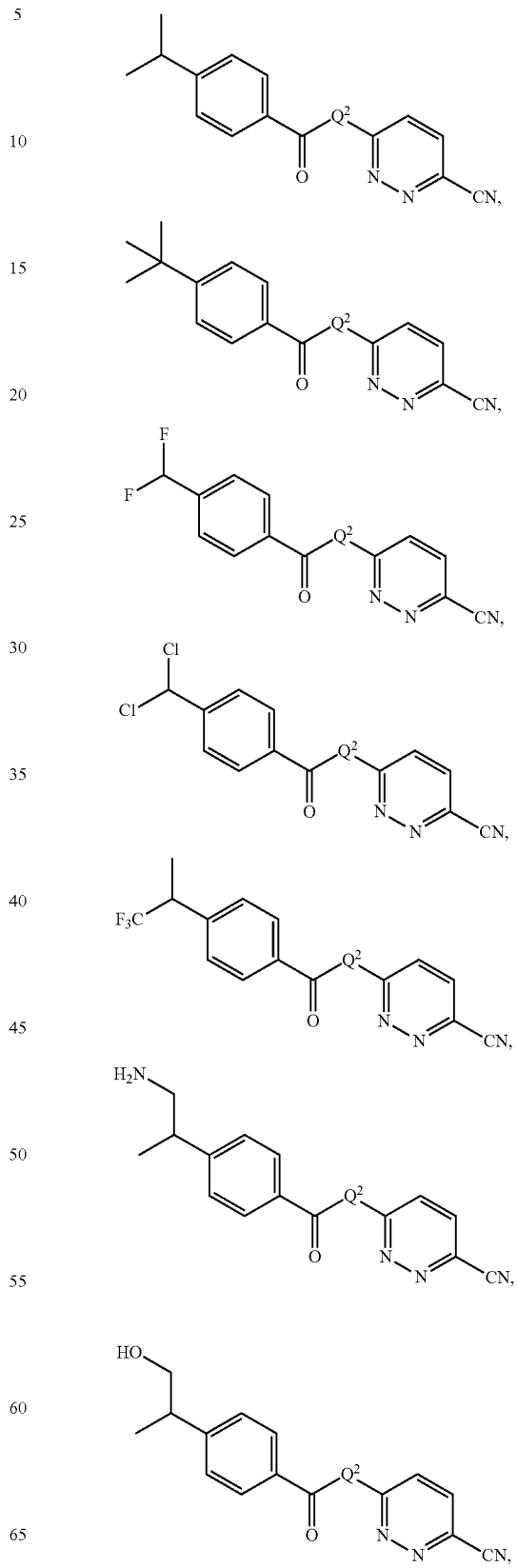

93
-continued

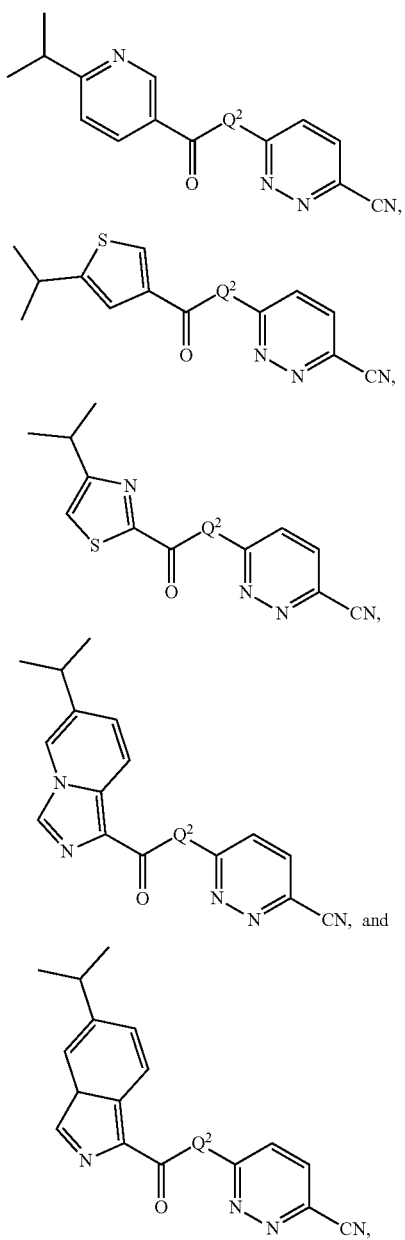

or a pharmaceutically acceptable salt thereof.

In a further aspect, the compound has a structure represented by a formula:

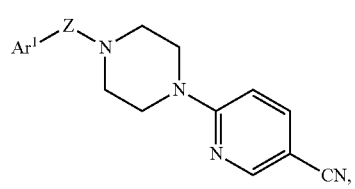

or a pharmaceutically acceptable salt thereof.

94

In a still further aspect, the compound has a structure represented by a formula selected from:

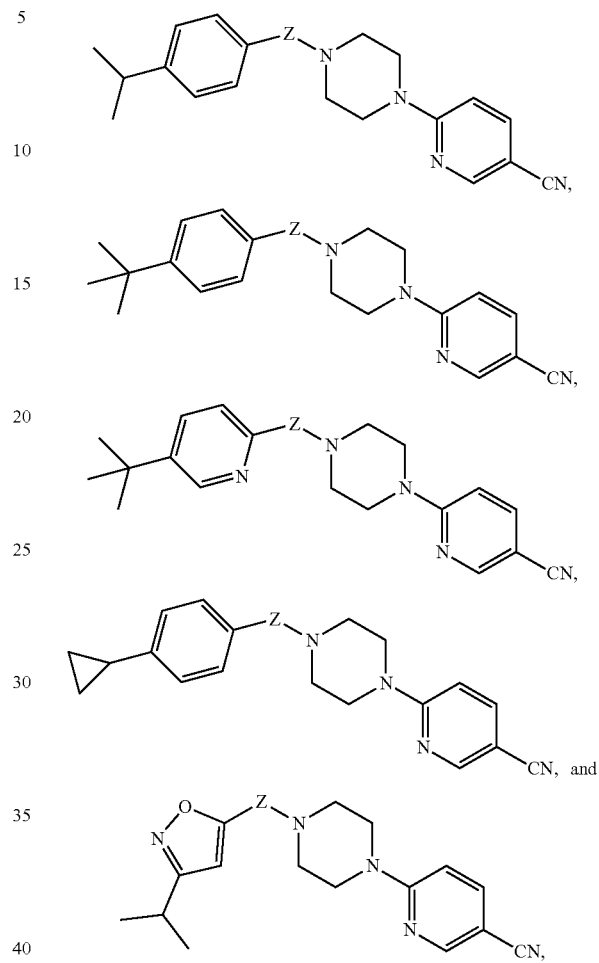

or a pharmaceutically acceptable salt thereof.

In yet a further aspect, the compound is selected from:

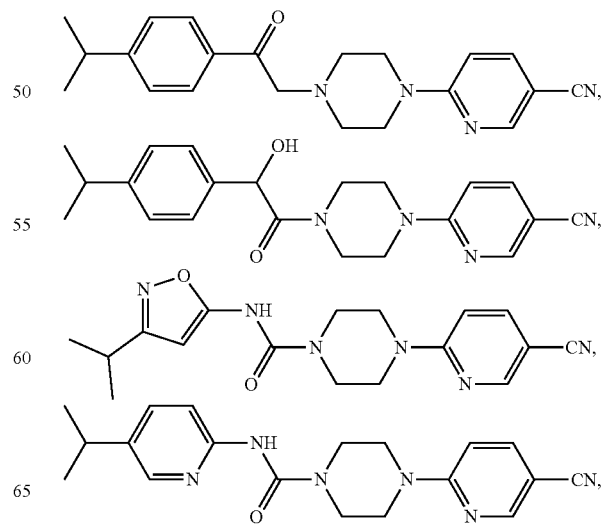

-continued

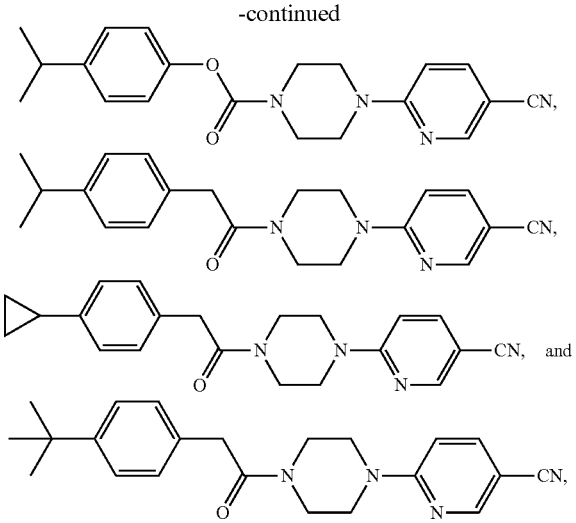

or a pharmaceutically acceptable salt thereof.

In a further aspect, the compound has a structure represented by a formula selected from:

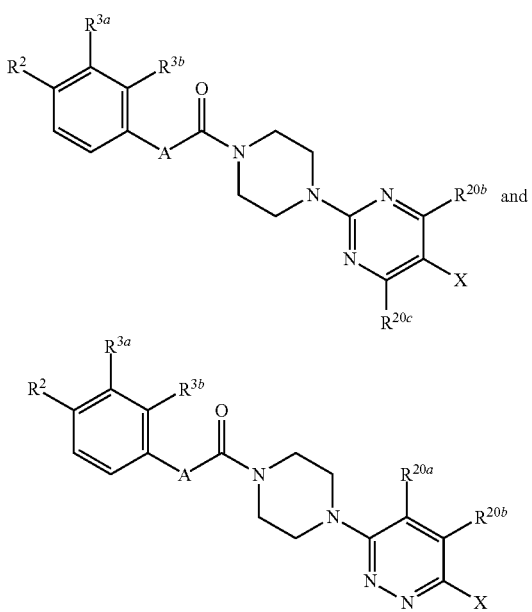

or a pharmaceutically acceptable salt thereof.

In a still further aspect, the compound has a structure represented by a formula selected from:

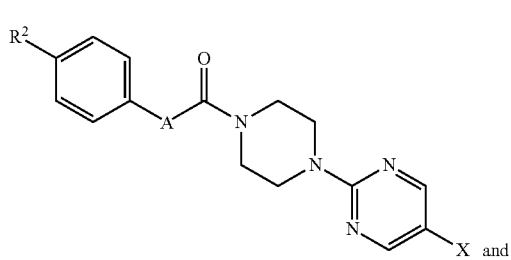

-continued

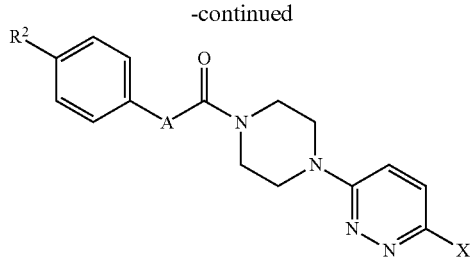

or a pharmaceutically acceptable salt thereof.

In yet a further aspect, the compound is selected from:

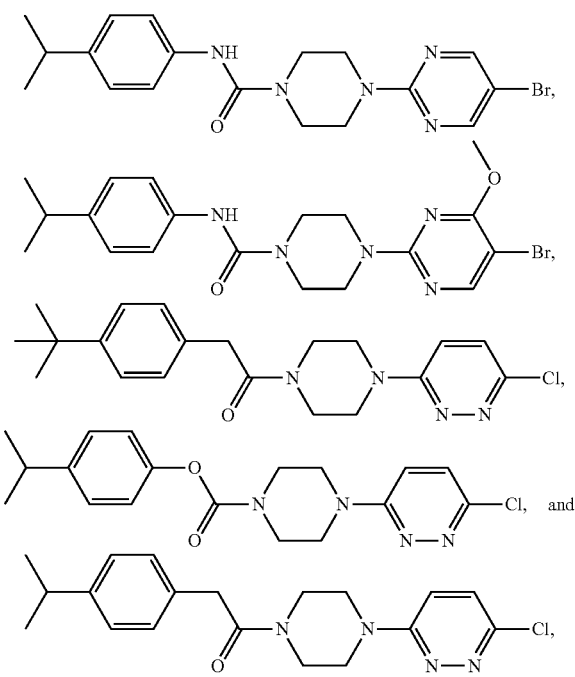

or a pharmaceutically acceptable salt thereof.

In a further aspect, the compound is selected from:

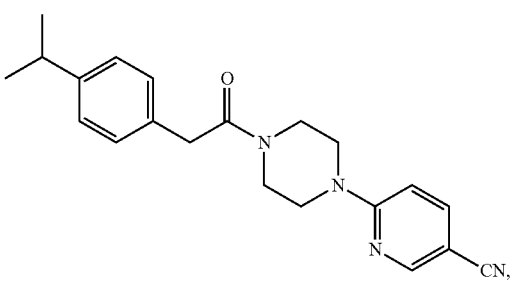

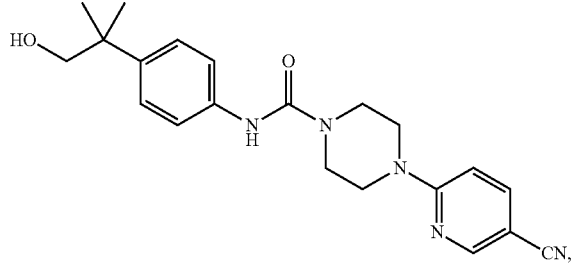

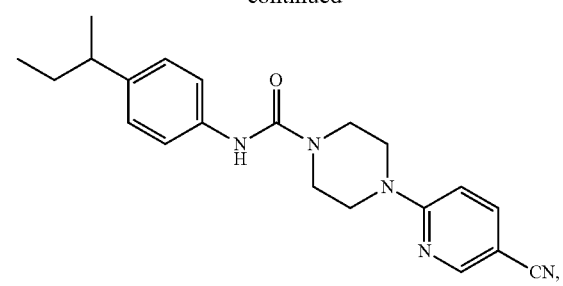
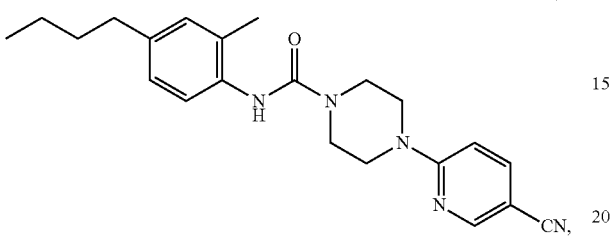
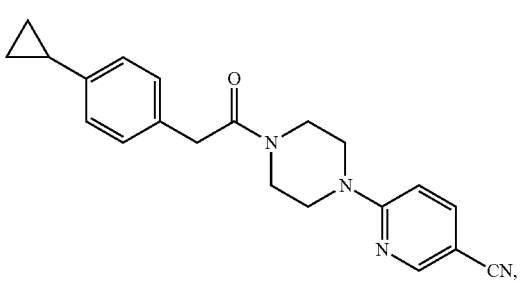
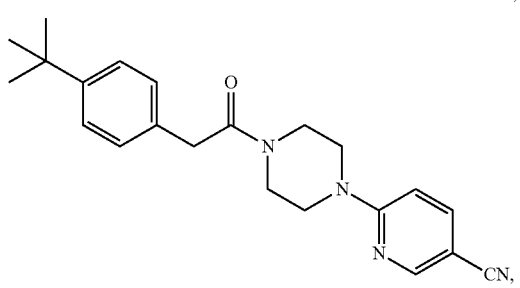
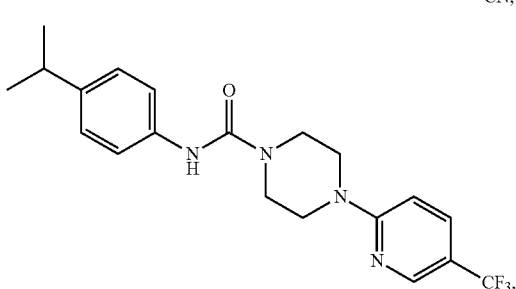
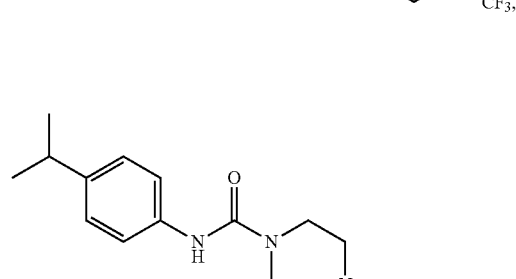
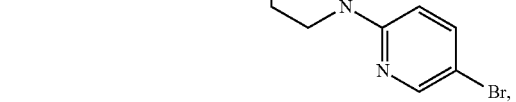
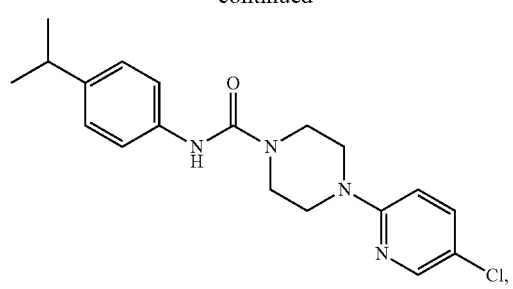
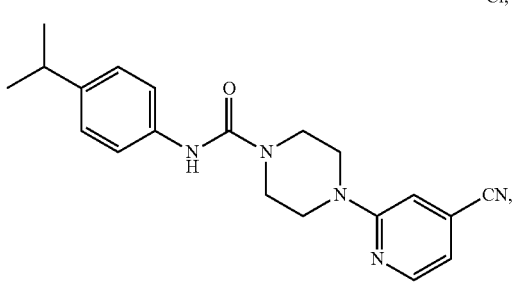
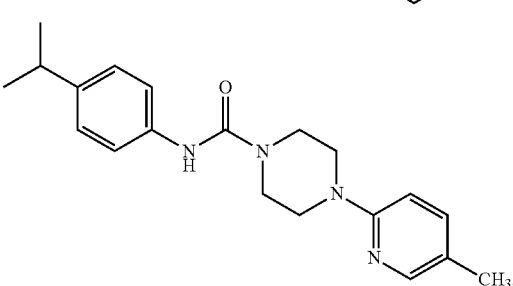
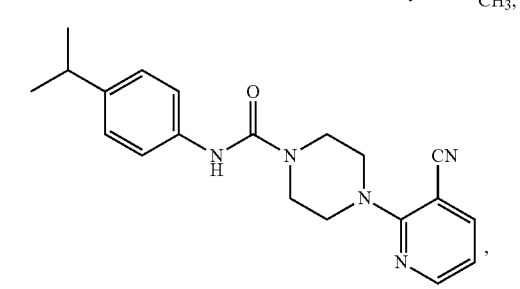
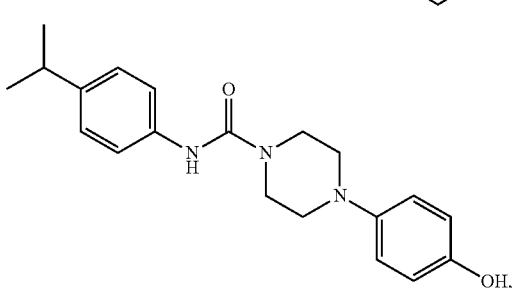
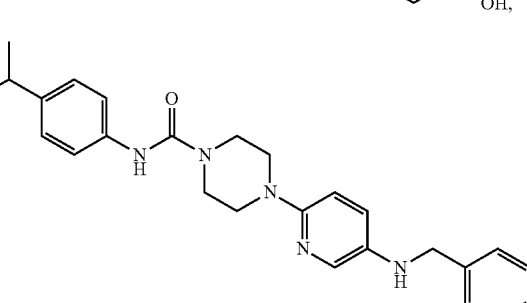

-continued
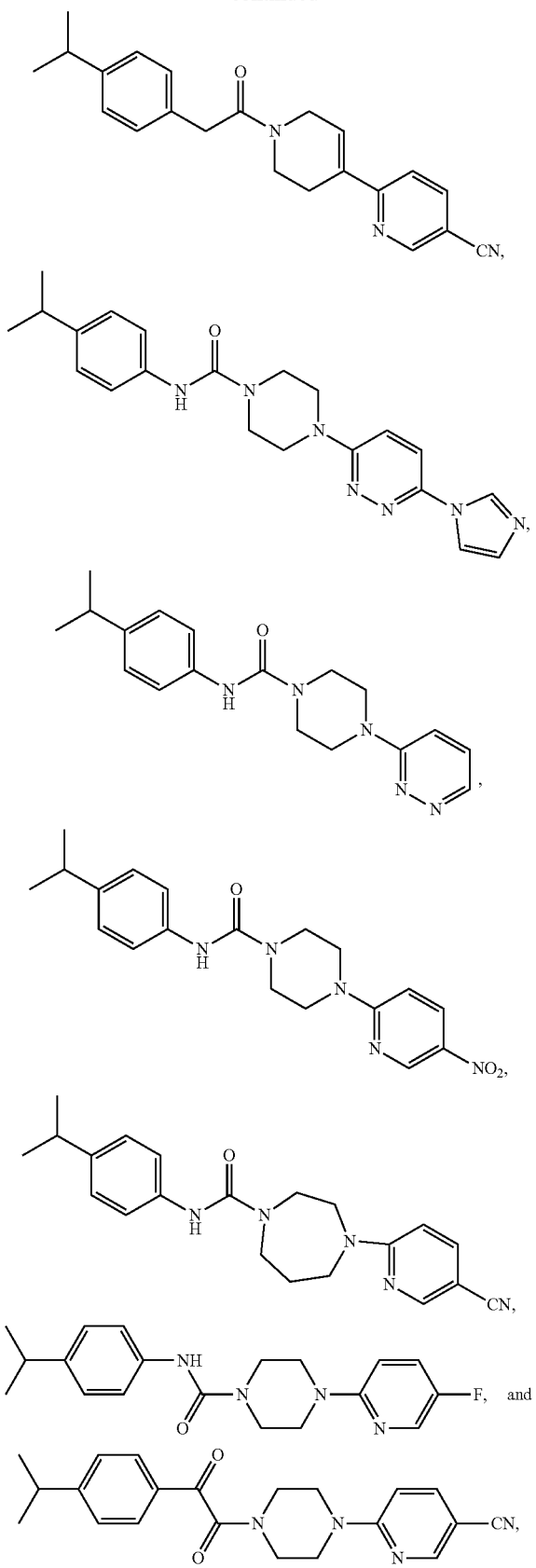
or a pharmaceutically acceptable salt thereof.
In a further aspect, the compound is selected from:
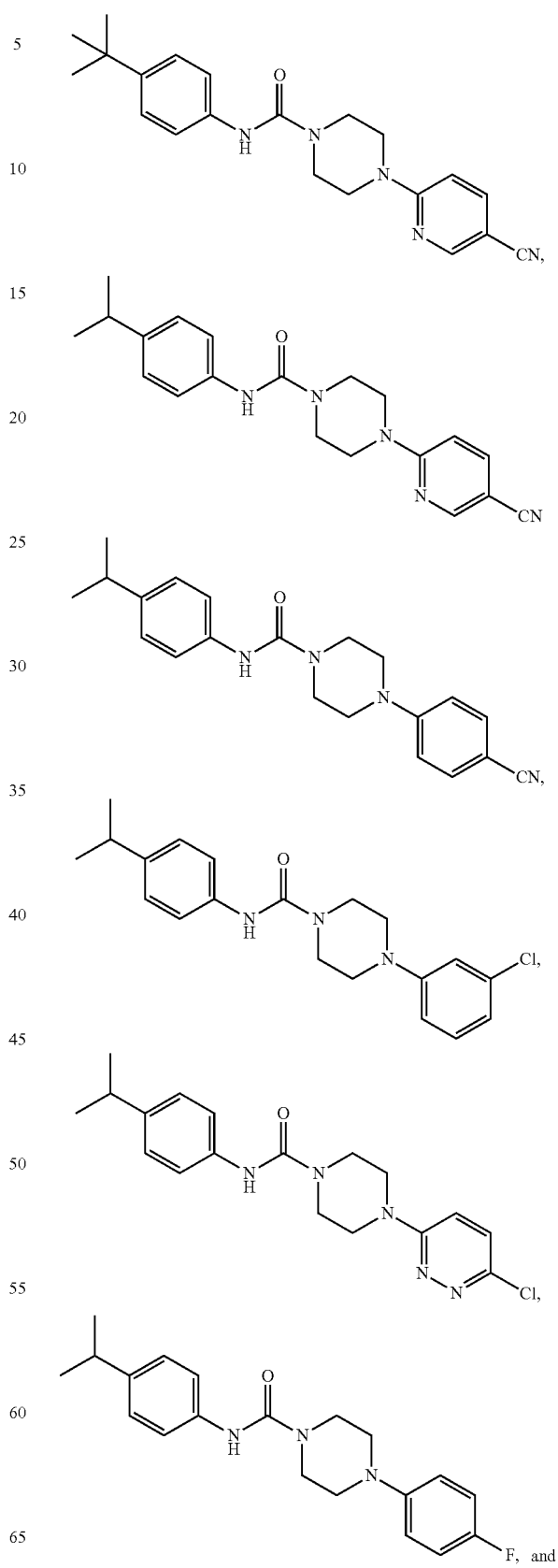

101

-continued

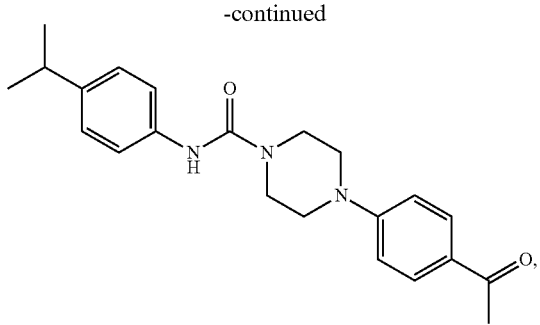

or a pharmaceutically acceptable salt thereof.

In a further aspect, the compound has a structure represented by a formula selected from:

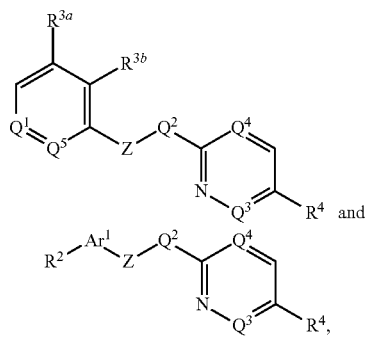

wherein Z is selected from A(C=O), C(O)CH$_2$, C(O), CH$_2$SO$_2$, and SO$_2$; wherein A is selected from O, CH$_2$, CF$_2$, NH, N(CH$_3$), and CH(OH); wherein each of Q$^1$ and Q$^5$, when present, is independently selected from N and CH; wherein Q$^3$ is N and Q$^4$ is CH or wherein Q$^4$ is N and Q$^3$ is CH; wherein Q$^2$ is a structure selected from:

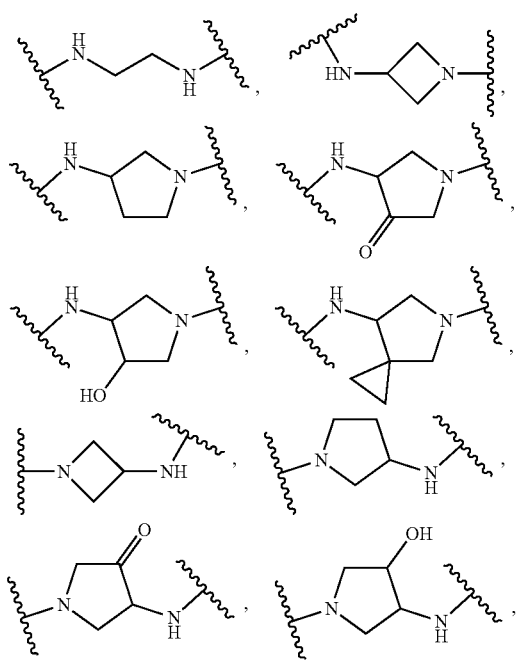

102

-continued

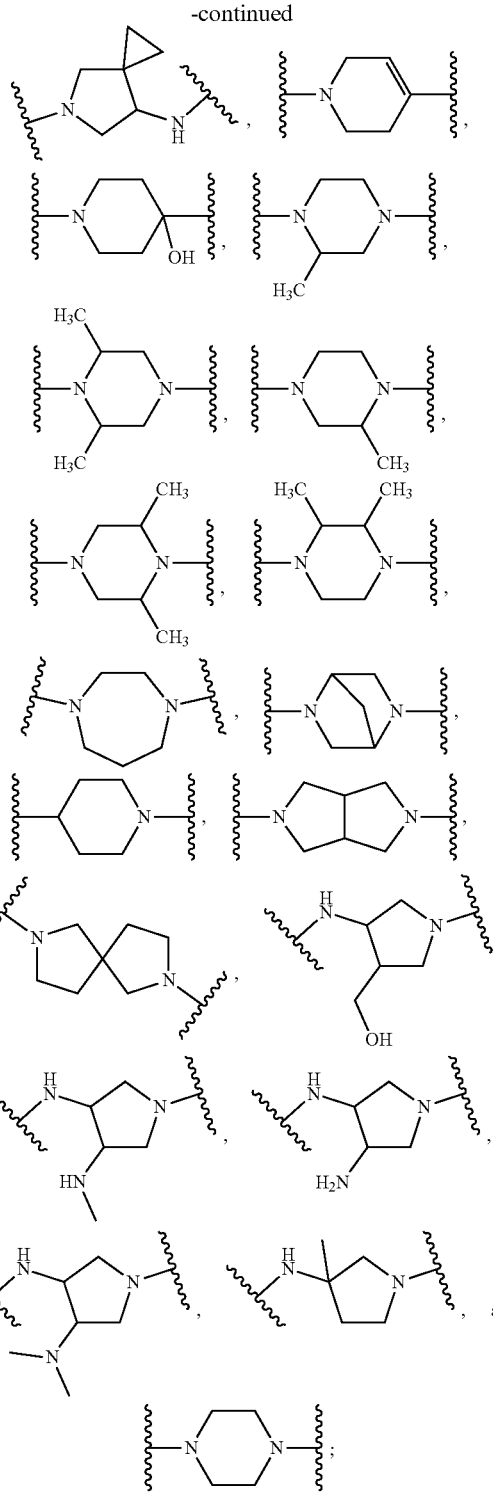

wherein R$^2$, when present, is selected from C1-C8 hydroxyalkyl, C1-C8 alkoxy, and cyclopropyl substituted with 1, 2, 3, or 4 groups independently selected from halogen, —NO$_2$, —CN, —OH, —SH, —NH$_2$, C1-C4 acyclic alkyl, C1-C4 hydroxyalkyl, C1-C4 monohaloalkyl, C1-C4 polyhaloalkyl, C1-C4 alkoxy, C1-C4 monohaloalkoxy, C1-C4 polyhaloalkoxy, C1-C4 acyclic alkylamino, (C1-C4)(C1-C4)dialkylamino, and —CO(C1-C4 acyclic alkyl), provided that cyclopropyl, when present, is substituted with at least one halogen group; wherein each of $R^{3a}$ and $R^{3b}$, when present, is independently selected from hydrogen, halogen, —OH, C1-C4 alkyl, C1-C4 thioalkyl, and C1-C4 alkoxy; wherein $R^4$ is selected from hydrogen, halogen, —CN, —NO$_2$, —SO$_2$NH$_2$, and —SO$_2$CH$_3$; and wherein $Ar^1$, when present, is selected from aryl and heteroaryl and is substituted with 0, 1, 2, or 3 groups independently selected from halogen, —NO$_2$, —CN, —OH, —SH, —NH$_2$, C1-C8 acyclic alkyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, and —CO(C1-C8 acyclic alkyl), provided that when $R^3$ is C1-C8 hydroxy or C1-C8 alkoxy then $R^2$ is not hydrogen, or a pharmaceutically acceptable salt thereof.

In a further aspect, each of $Q^1$ and $Q^5$ is CH.

In a further aspect, $Q^3$ is N and $Q^4$ is CH.

In a further aspect, $Q^2$ is a structure:

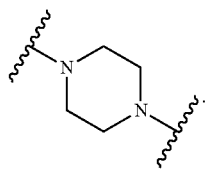 [SMILES: *N1CCN(*)CC1]

In a further aspect, $R^2$ is cyclopropyl substituted with 1, 2, or 3 groups independently selected from halogen and C1-C4 acyclic alkyl, provided that cyclopropyl is substituted with at least one halogen group. In a still further aspect, $R^2$ is a structure selected from:

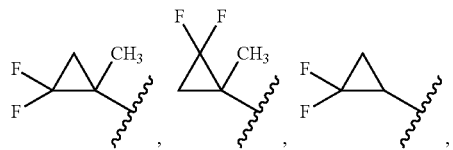

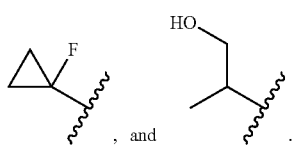

In a further aspect, each of $R^{3a}$ and $R^{3b}$ is hydrogen.

In a further aspect, $R^4$ is CN.

In a further aspect, $Ar^1$ is a structure:

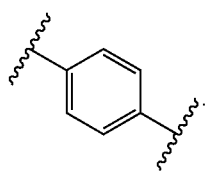 [SMILES: *c1ccc(*)cc1]

In a further aspect, the compound has a structure represented by a formula selected from:

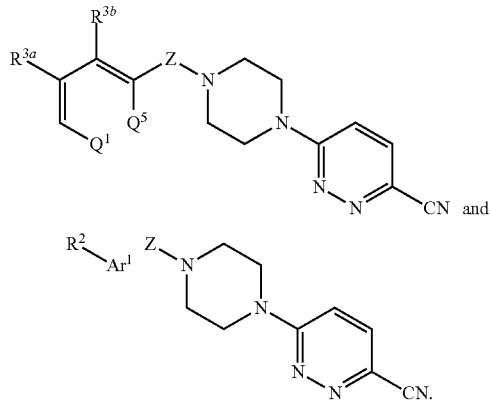

In a further aspect, the compound is selected from:

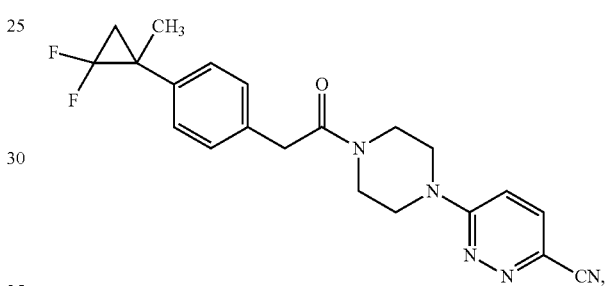

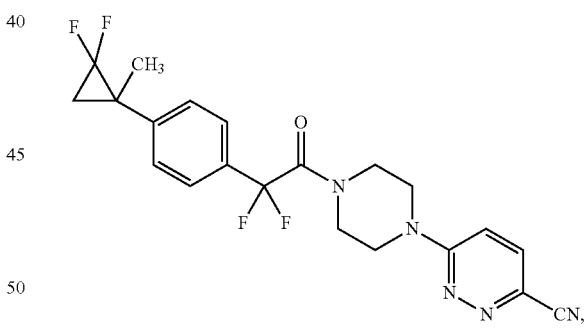

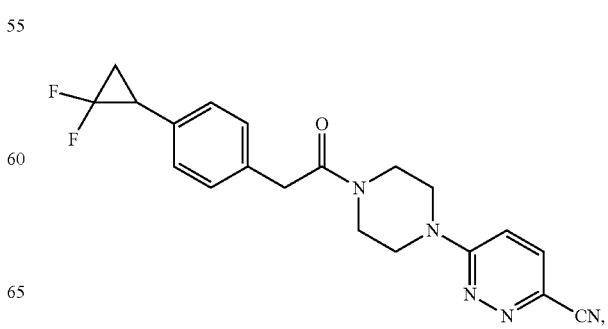

-continued

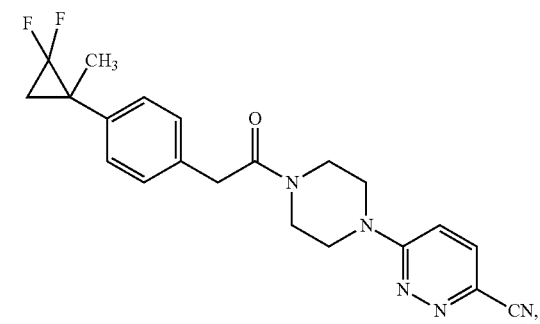

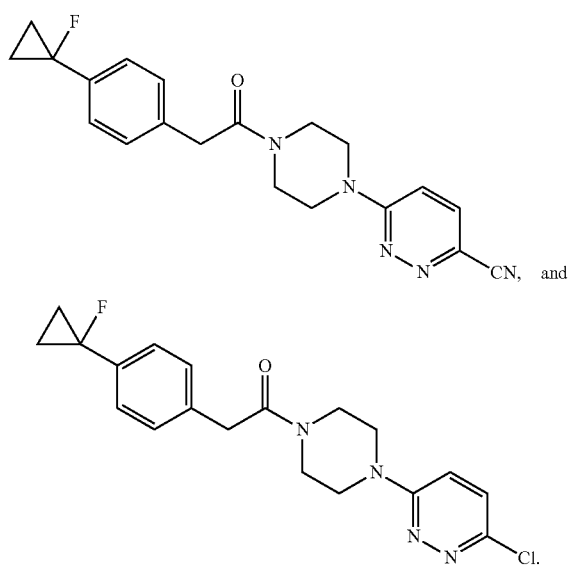

In a further aspect, the compound is:

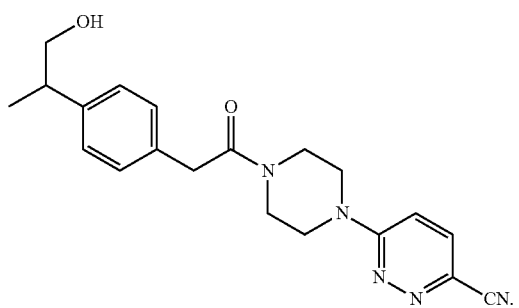 [SMILES: CC(CO)c1ccc(CC(=O)N2CCN(c3ccc(C#N)nn3)CC2)cc1]

a. A Groups

In one aspect, A is selected from O, CO, $CH_2$, $CF_2$, NH, $N(CH_3)$, and CH(OH). In one aspect, A is selected from O, CO, $CH_2$, $CF_2$, NH, and CH(OH). In one aspect, O, CO, $CH_2$, $CF_2$, $N(CH_3)$, and CH(OH). In one aspect, A is selected from O, CO, $CH_2$, $CF_2$, and CH(OH).

In a further aspect, A is selected from O, CO, $CH_2$, and $CF_2$. In a still further aspect, A is selected from O, CO, and $CH_2$. In yet a further aspect, A is selected from O and CO. In an even further aspect, A is O. In a still further aspect, A is CO. In yet a further aspect, A is $CH_2$. In an even further aspect, A is $CF_2$.

In a further aspect, A is selected from NH and $N(CH_3)$. In a still further aspect, A is NH. In yet a further aspect, A is $N(CH_3)$.

In a further aspect, A is selected from NH and $CH_2$.

In a further aspect, A is CH(OH).

b. $Q^1$ and $Q^5$ Groups

In one aspect, $Q^1$ is selected from N and CH. In one aspect, $Q^1$ is N. In one aspect, $Q^1$ is CH.

In one aspect, each of $Q^1$ and $Q^5$, when present, is independently selected from N and CH. In a further aspect, each of $Q^1$ and $Q^5$, when present, is N. In a still further aspect, each of $Q^1$ and $Q^5$, when present, is CH. In yet a further aspect, $Q^1$, when present, is N and $Q^5$, when present, is CH. In an even further aspect, $Q^1$, when present, is CH and $Q^5$, when present, is N.

C. $Q^2$ Groups

In one aspect, $Q^2$ is a structure selected from:

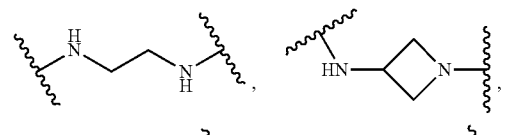

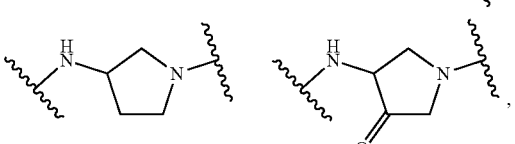

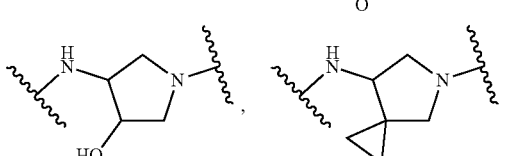

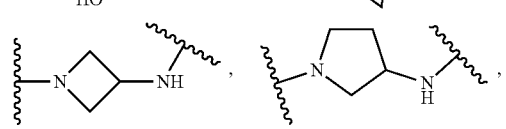

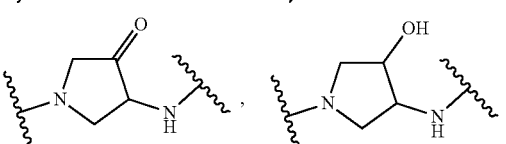

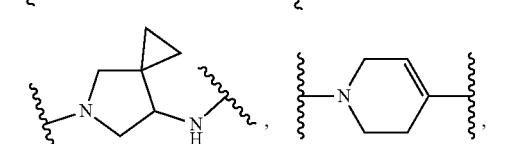

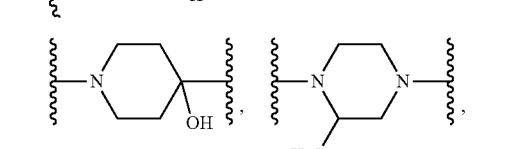

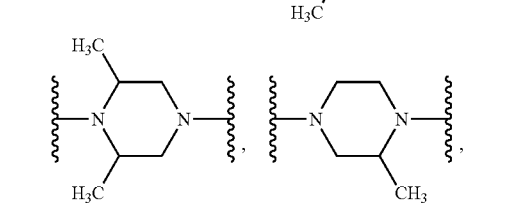

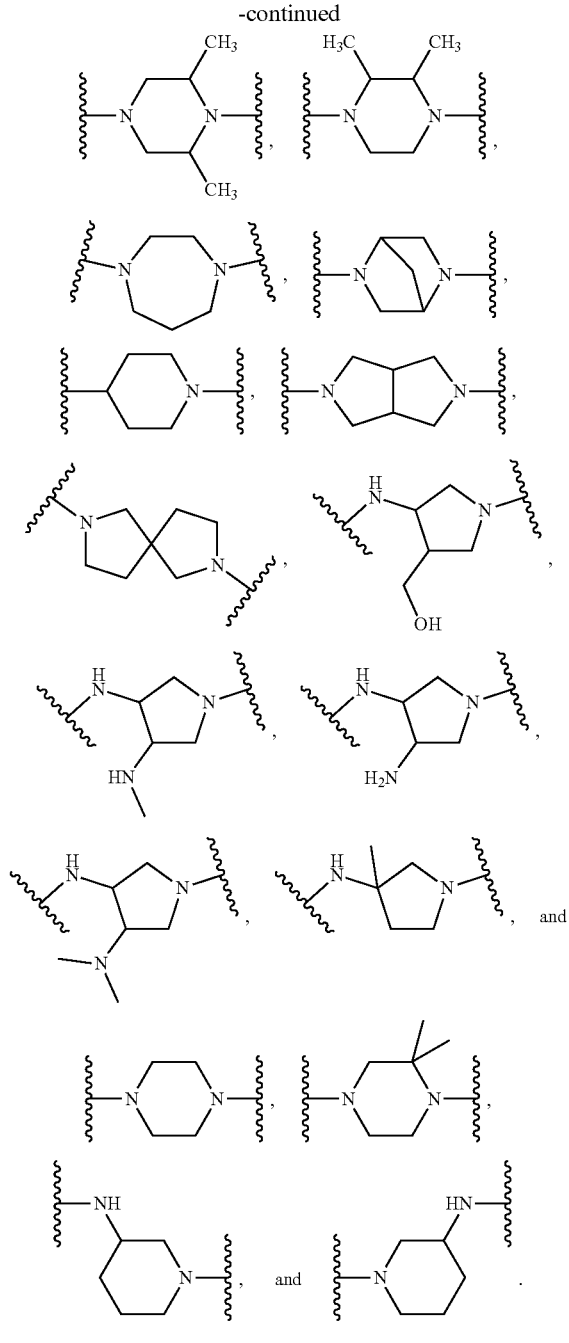
In one aspect, $Q^2$ is a structure selected from:
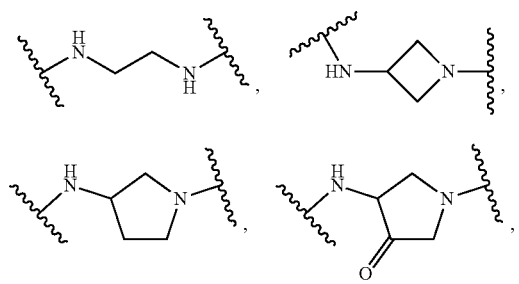
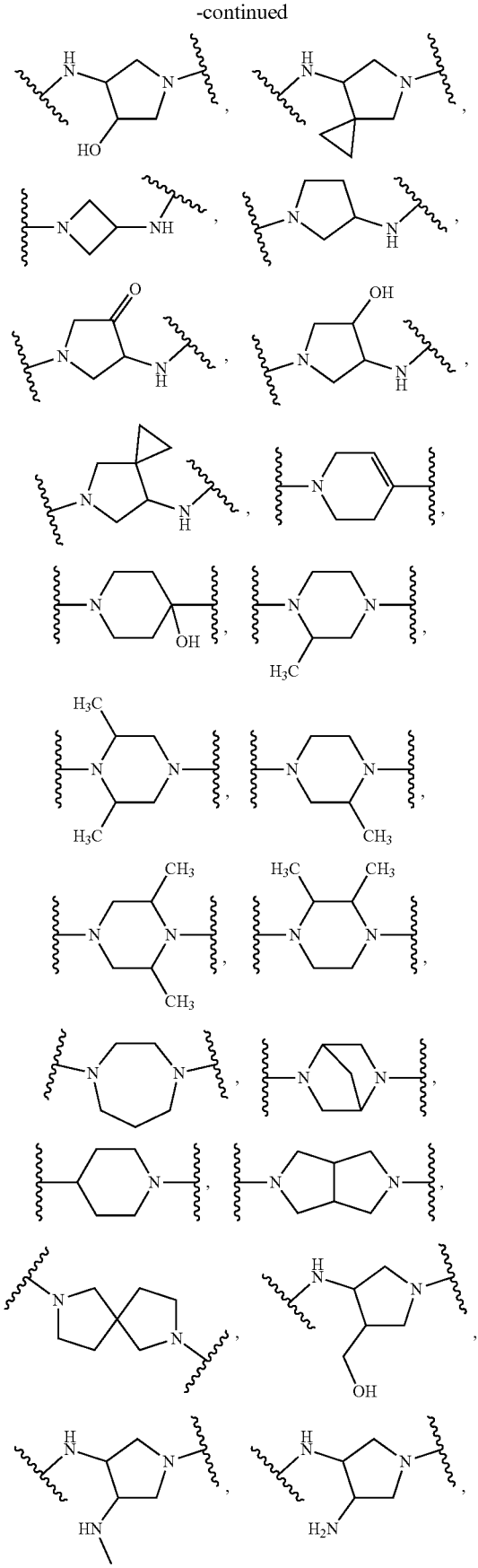

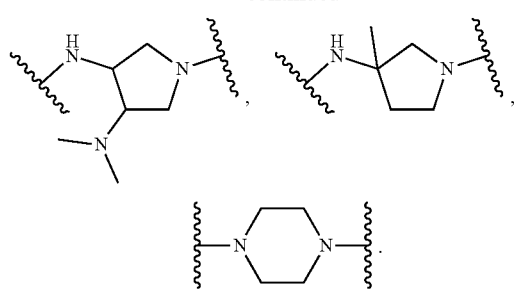
In one aspect, Q² is a structure selected from:
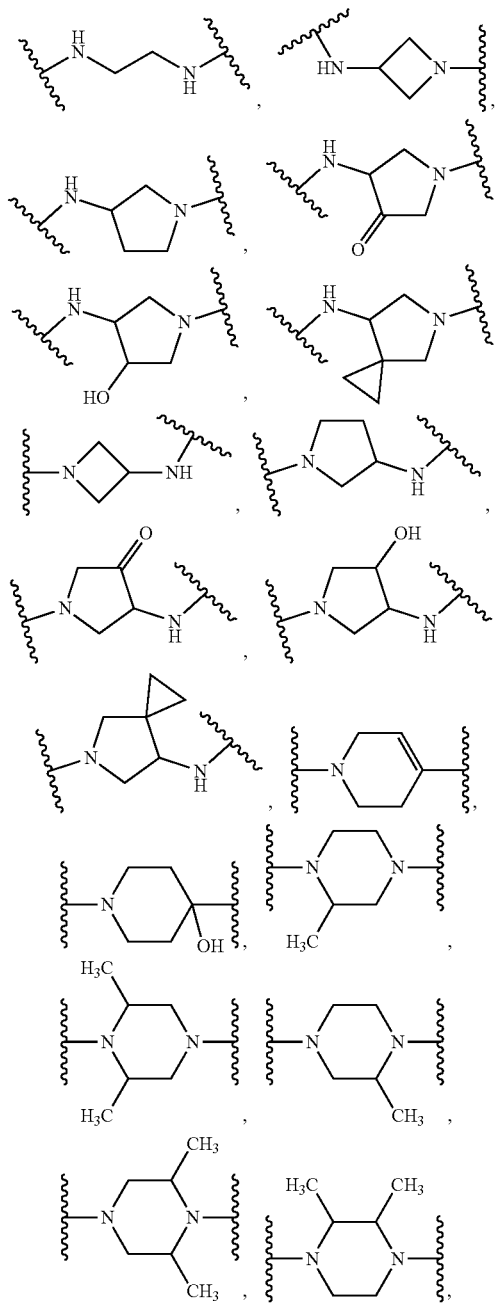
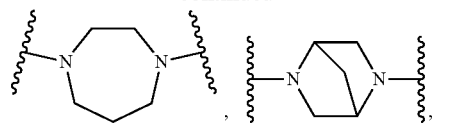
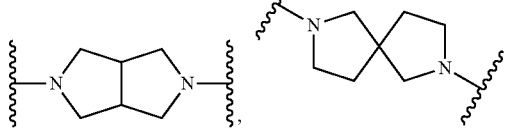
, and
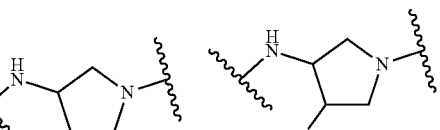
In a further aspect, Q² is a structure selected from:
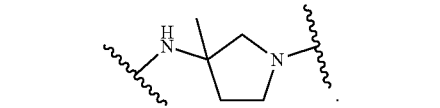
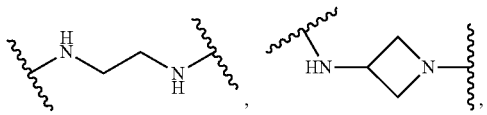
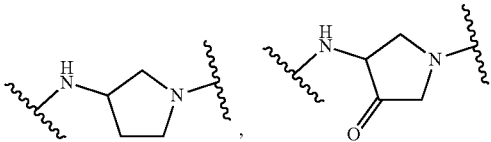
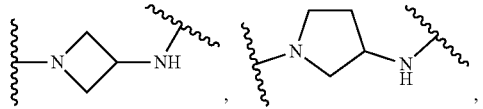
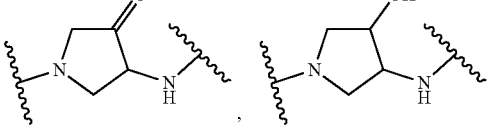
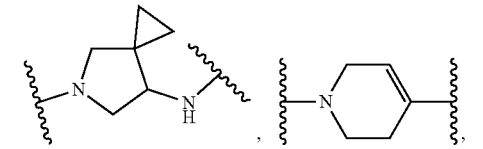

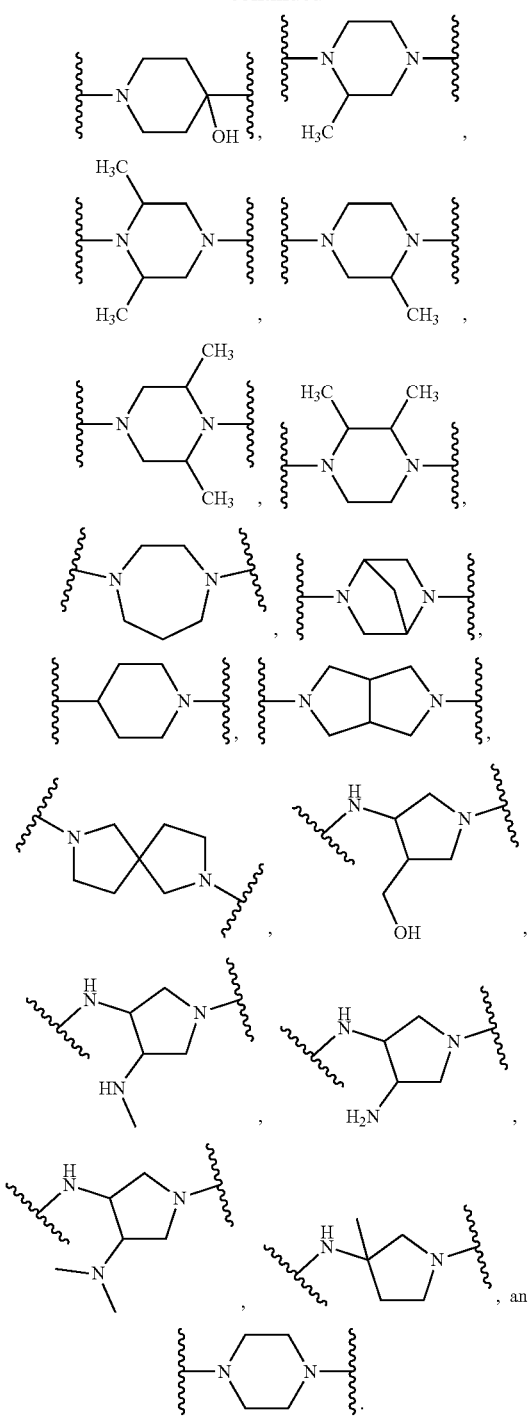
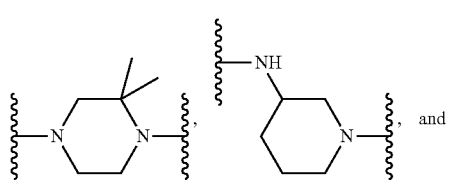
In a further aspect, $Q^2$ is a structure selected from:
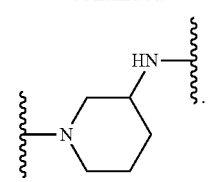
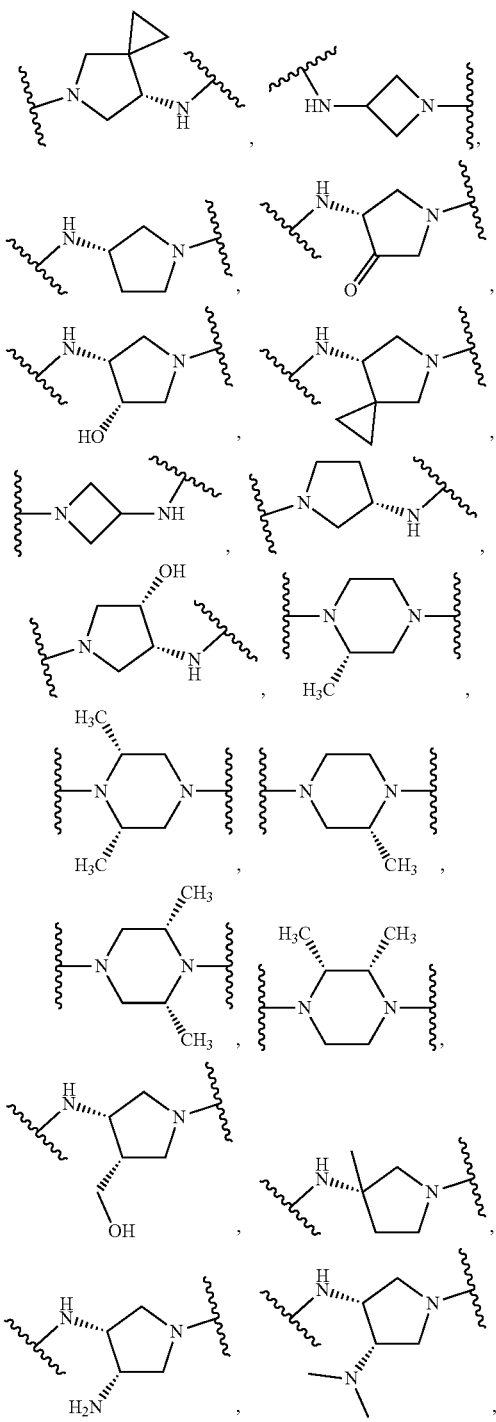

-continued
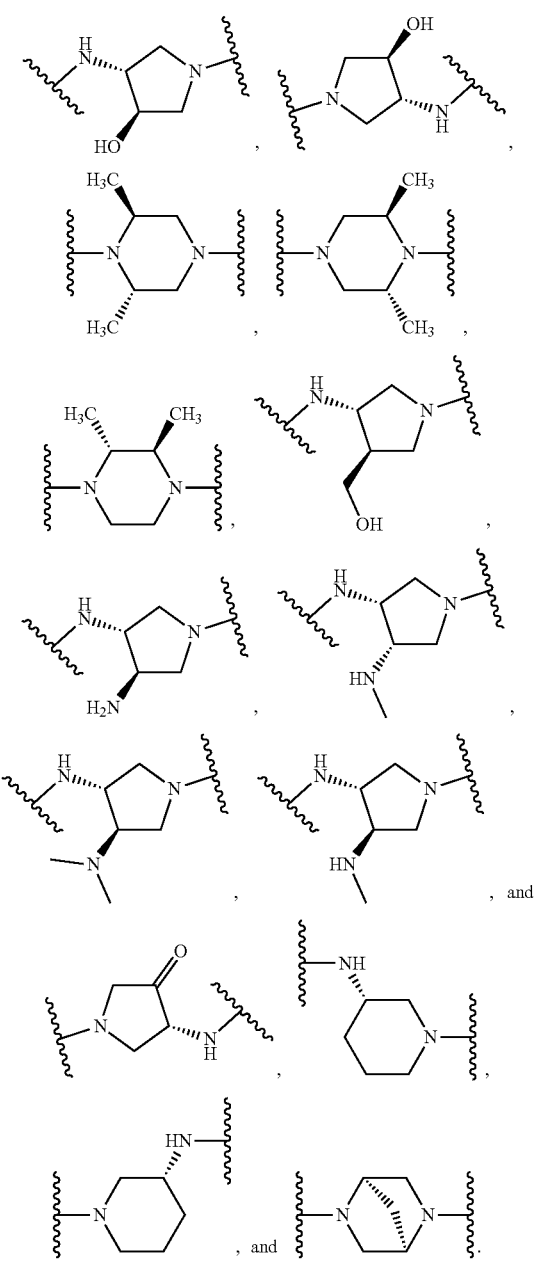
In a further aspect, wherein $Q^2$ is a structure selected from:
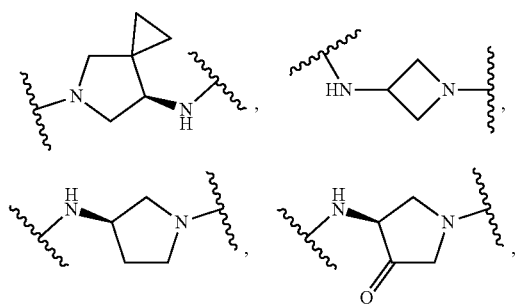
-continued
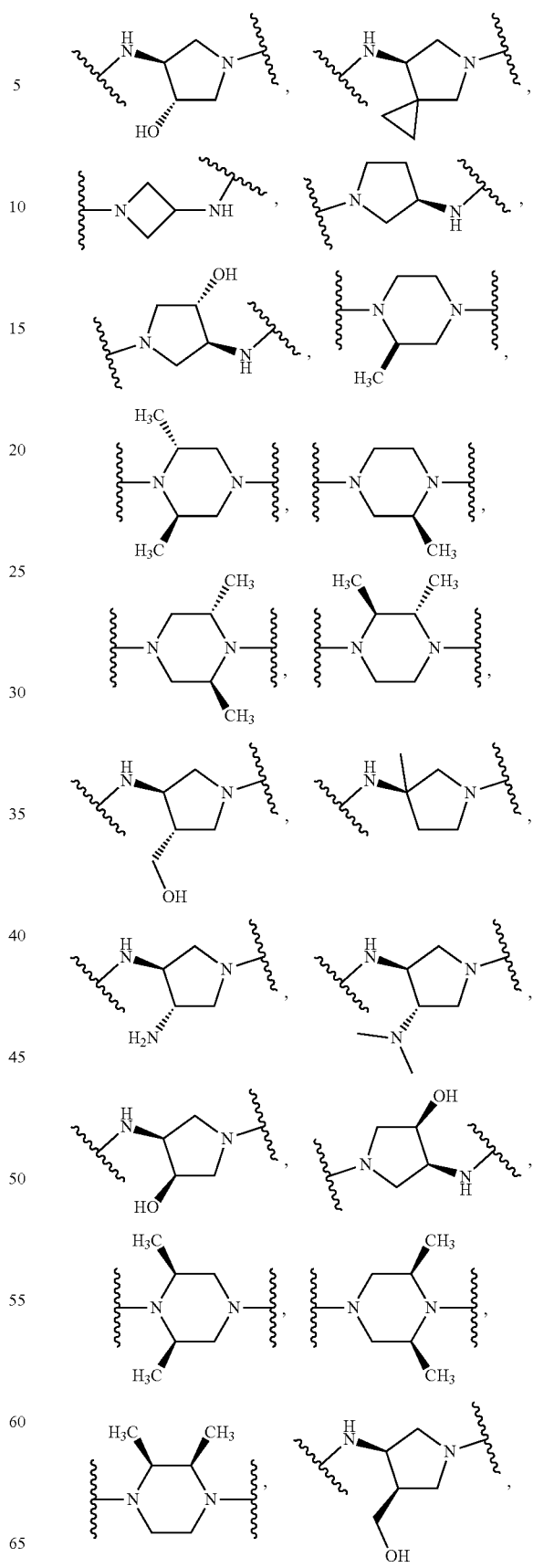

-continued
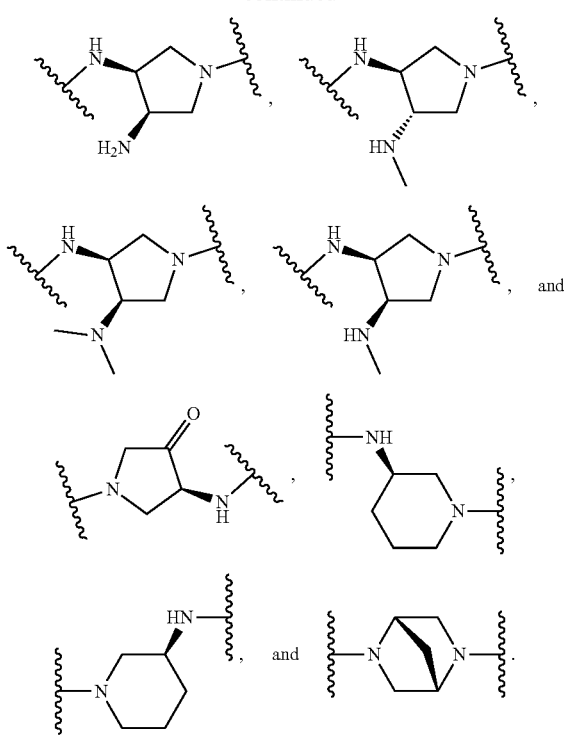
In a further aspect, $Q^2$ is a structure selected from:
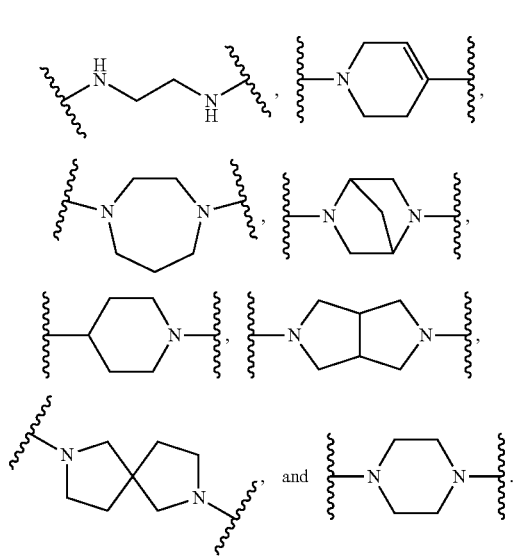
In a still further aspect, $Q^2$ is:
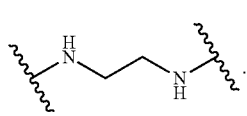 [SMILES: *NCCN*]
In yet a further aspect, $Q^2$ is a structure selected from:
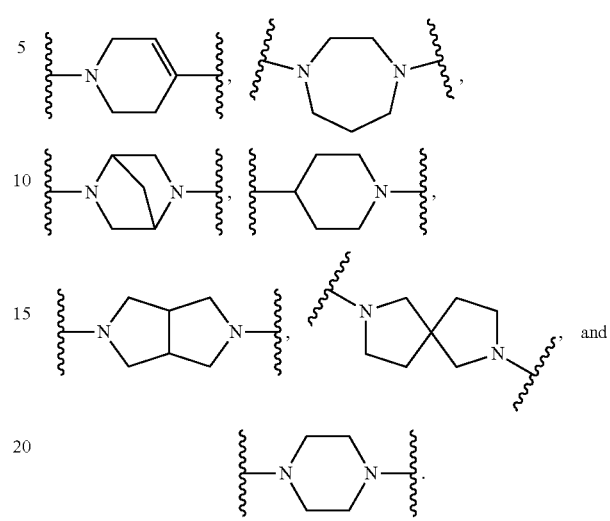
In an even further aspect, $Q^2$ is a structure selected from:
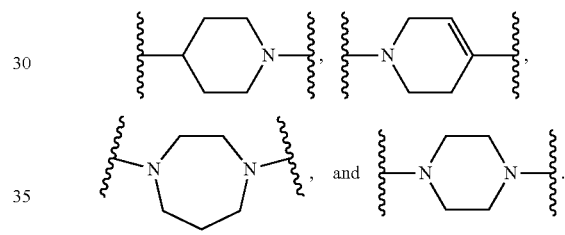
In a still further aspect, $Q^2$ is a structure selected from:
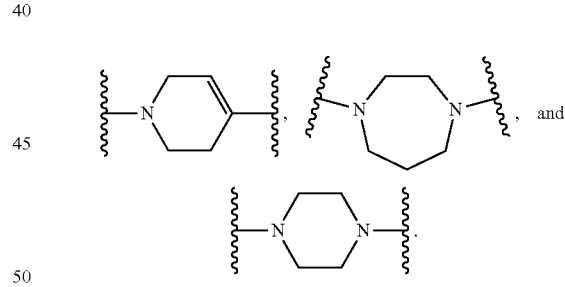
In yet a further aspect, $Q^2$ is a structure selected from:
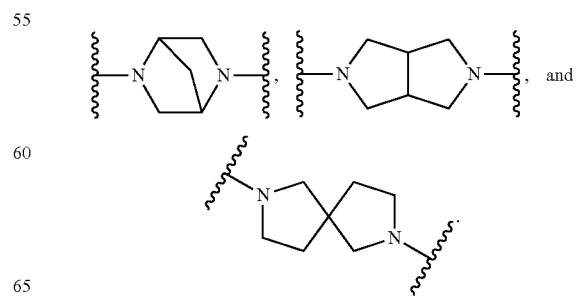

In a further aspect, $Q^2$ is a structure selected from:
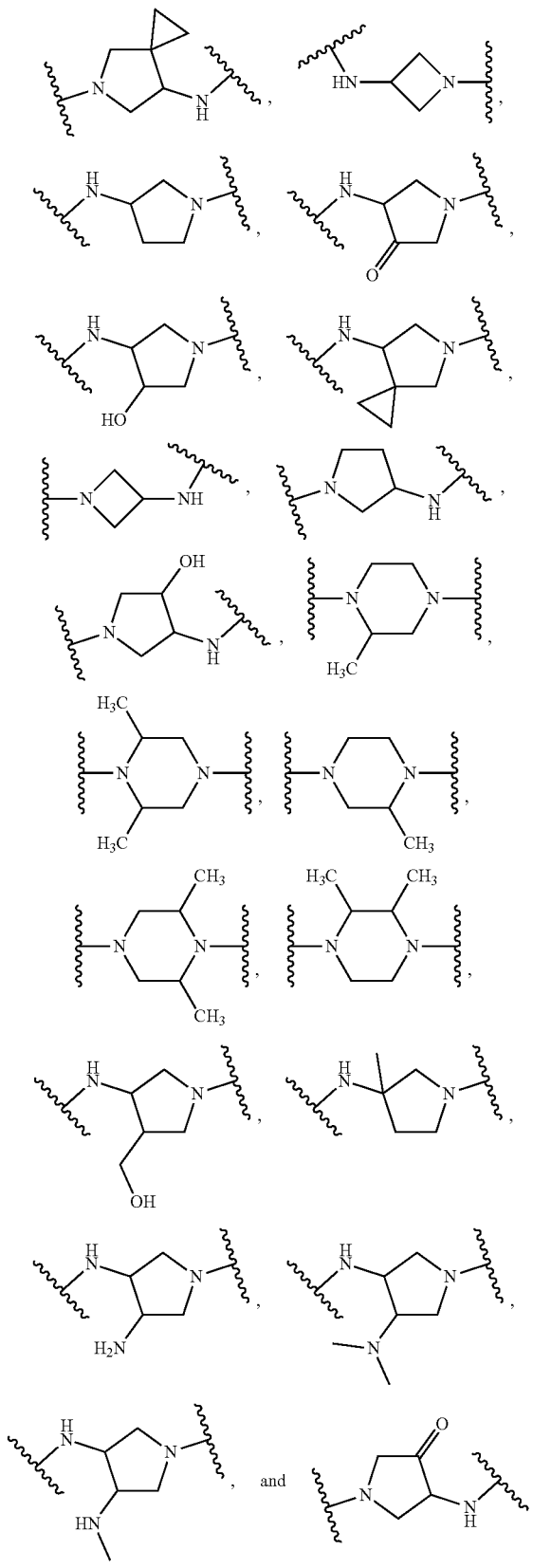
In a still further aspect, $Q^2$ is a structure selected from:
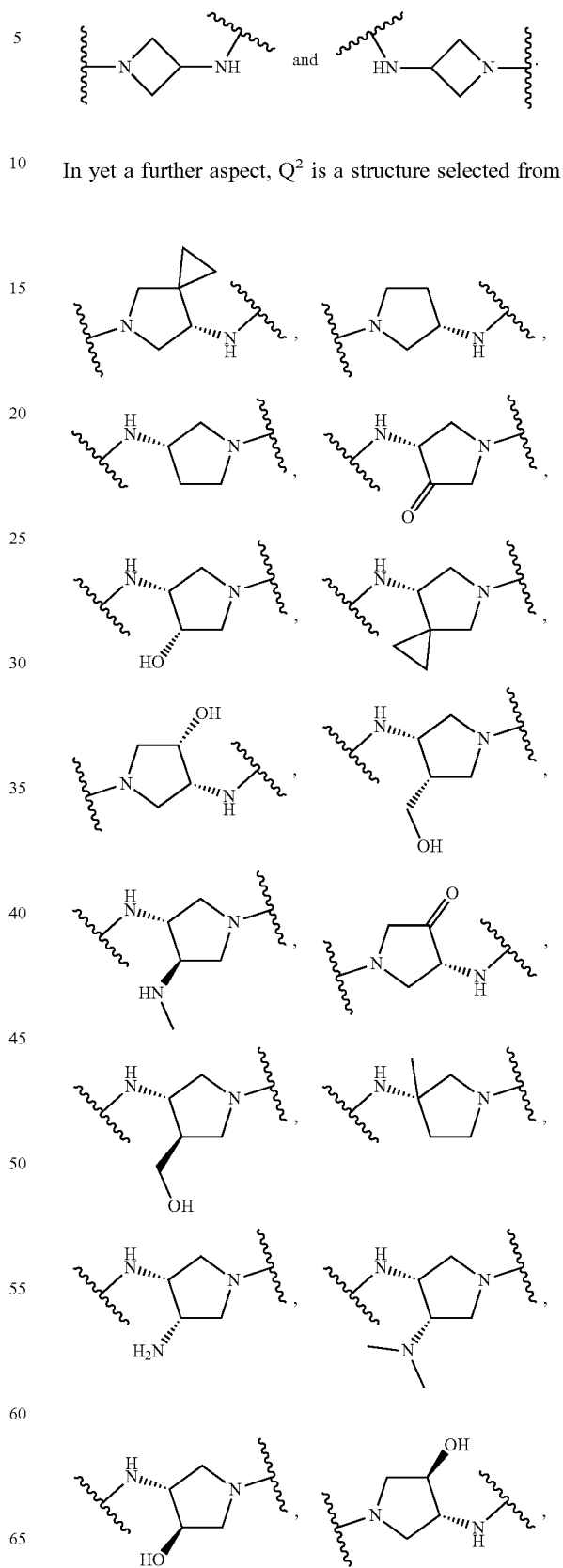
In yet a further aspect, $Q^2$ is a structure selected from:

-continued
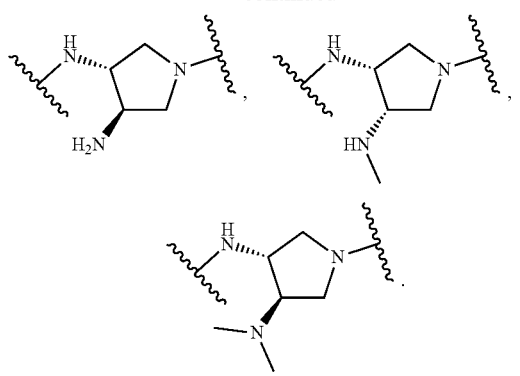
In an even further aspect, $Q^2$ is a structure selected from:
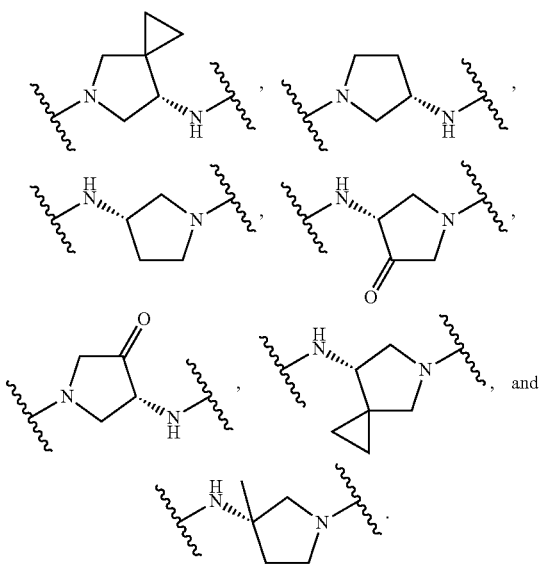
In a still further aspect, $Q^2$ is a structure selected from:
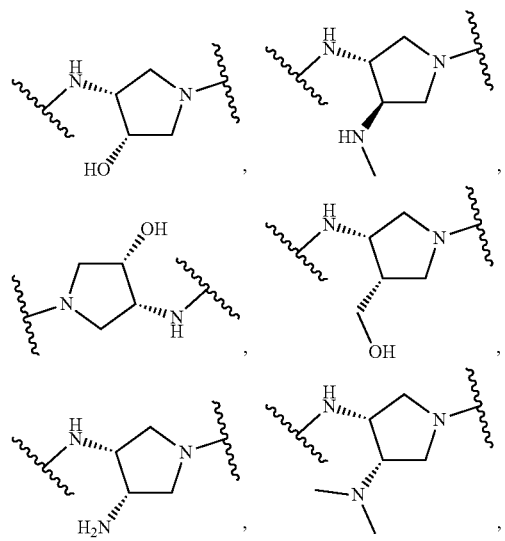
-continued
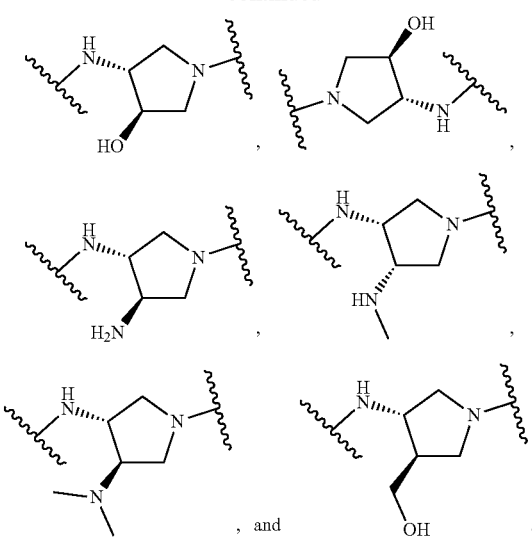
In yet a further aspect, $Q^2$ is a structure selected from:
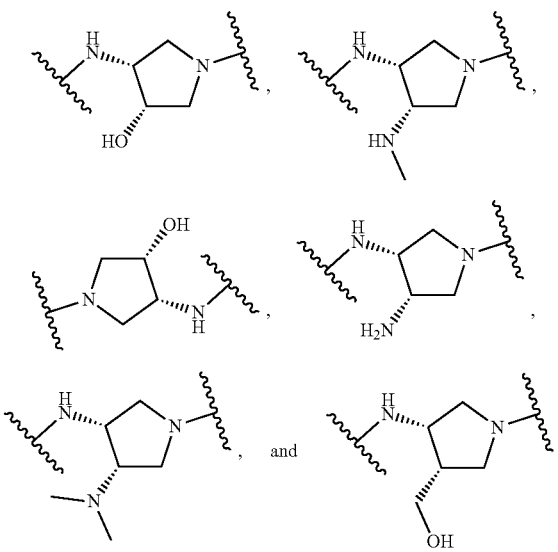
In an even further aspect, $Q^2$ is a structure selected from:
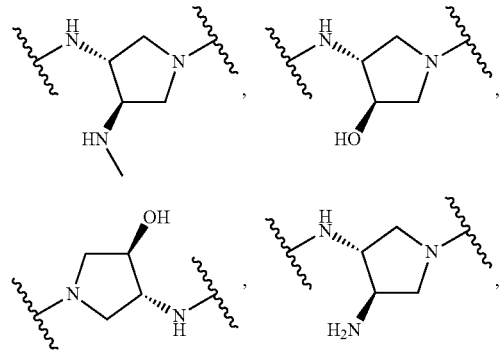

-continued

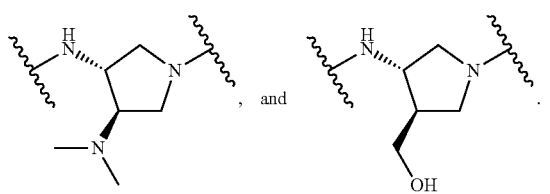, and

In a still further aspect, $Q^2$ is a structure selected from:

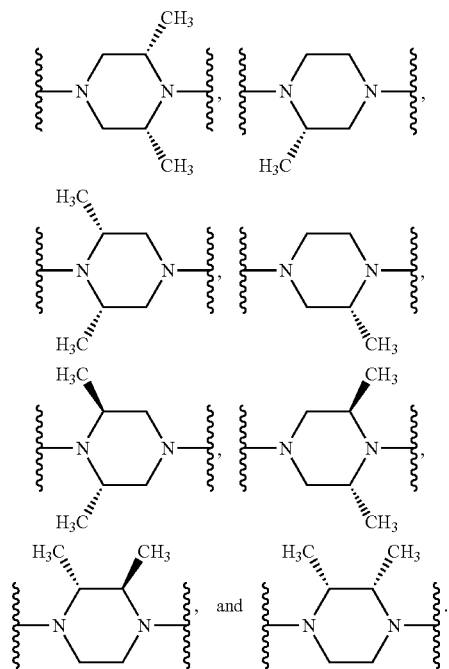

In yet a further aspect, $Q^2$ is a structure selected from:

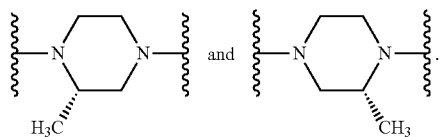

In an even further aspect, $Q^2$ is a structure selected from:

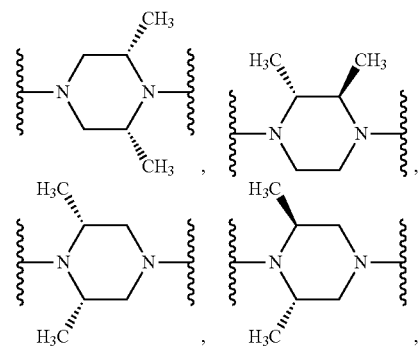

-continued

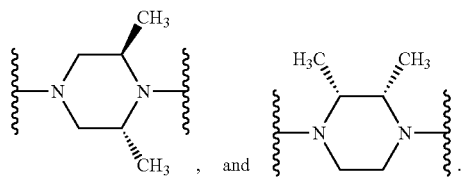, and

In a still further aspect, $Q^2$ is a structure selected from:

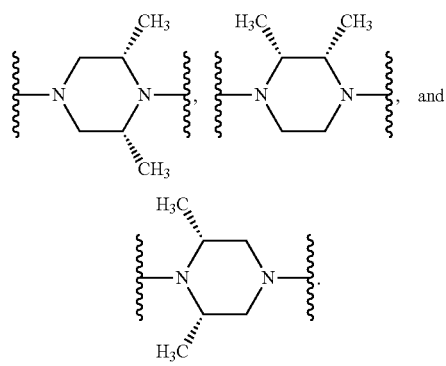

In yet a further aspect, $Q^2$ is a structure selected from:

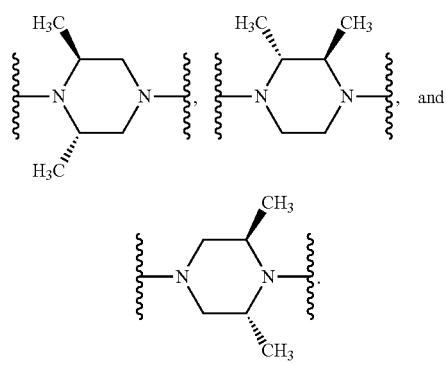

In a further aspect, $Q^2$ is a structure selected from:

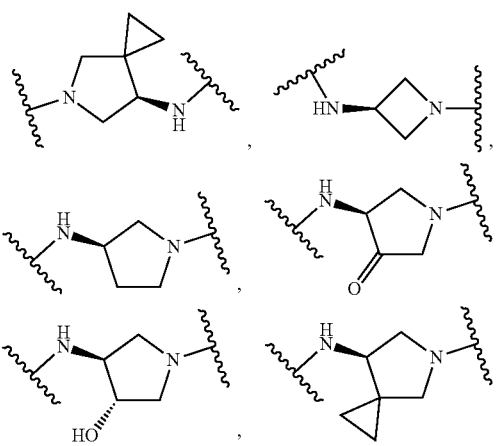

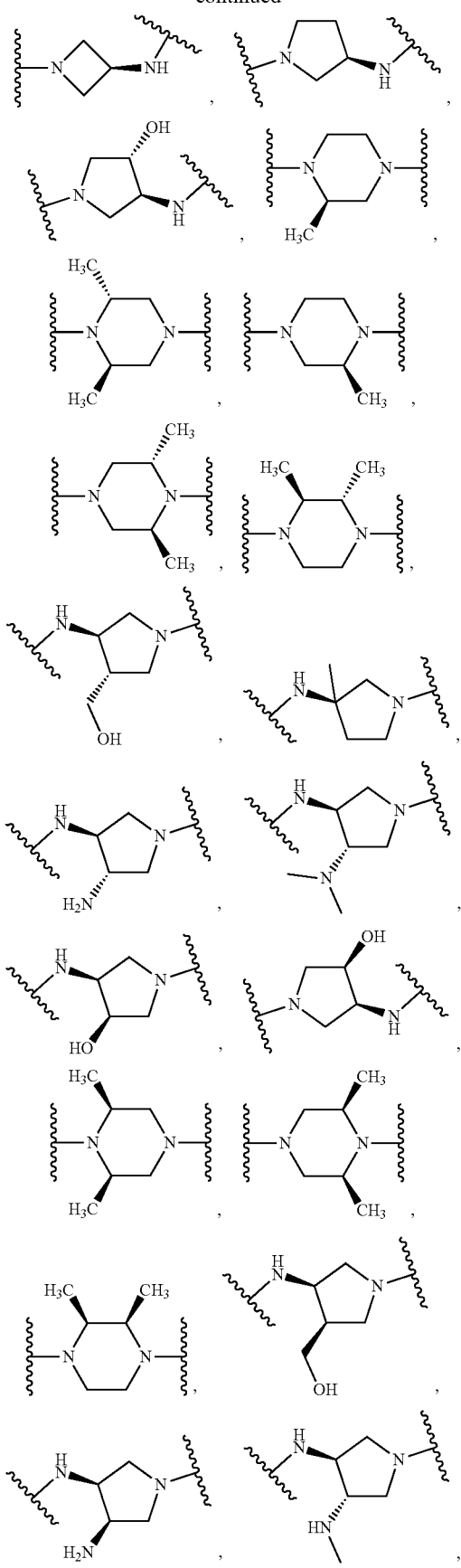
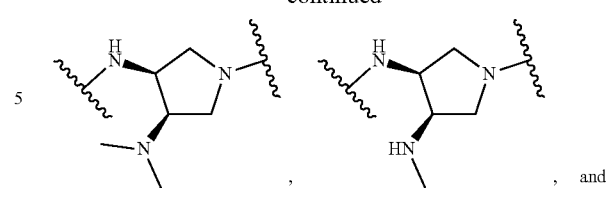
In a still further aspect, $Q^2$ is a structure selected from:
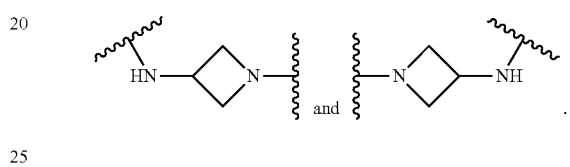
In yet a further aspect, $Q^2$ is a structure selected from:
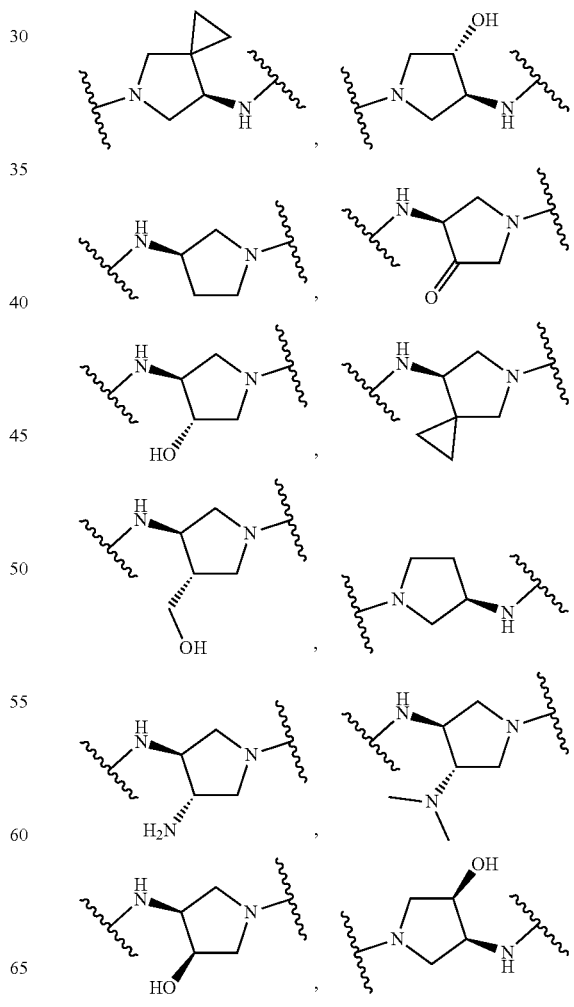

125
-continued
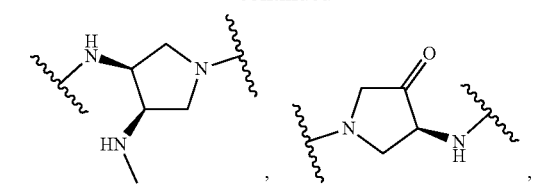
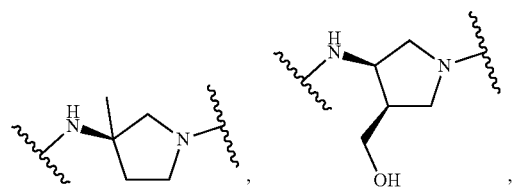
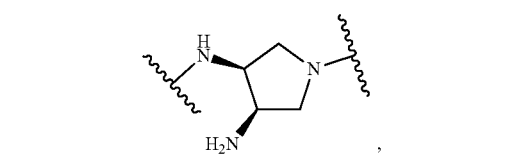
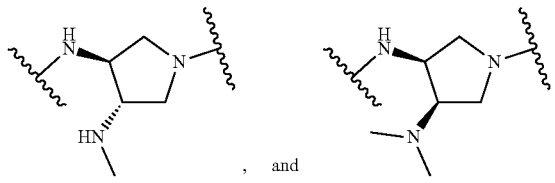
, and
In an even further aspect, $Q^2$ is a structure selected from:
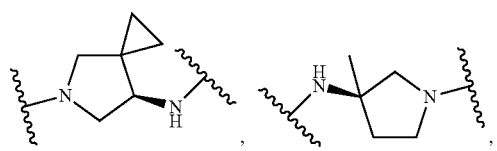
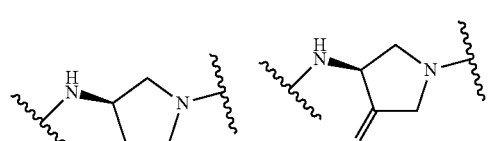
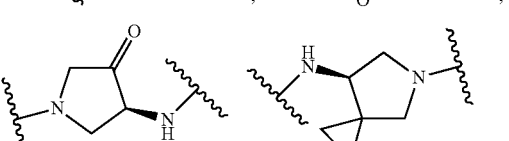
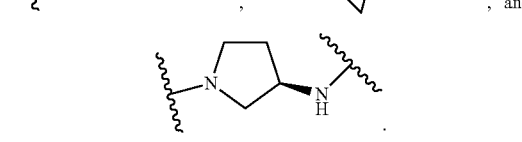, and
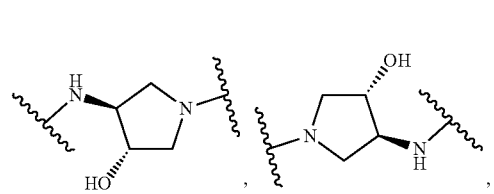
In a still further aspect, $Q^2$ is a structure selected from:
126
-continued
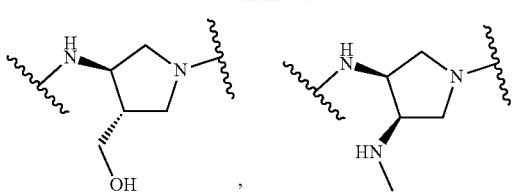
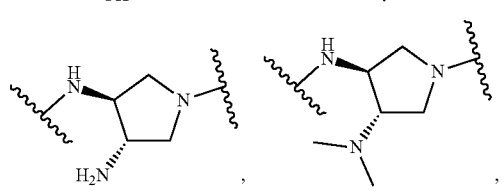
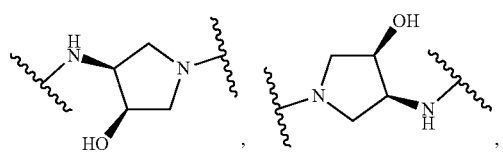
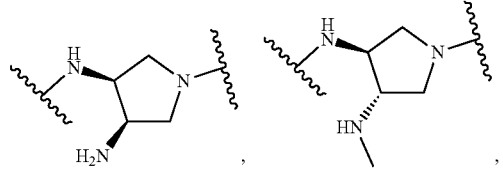
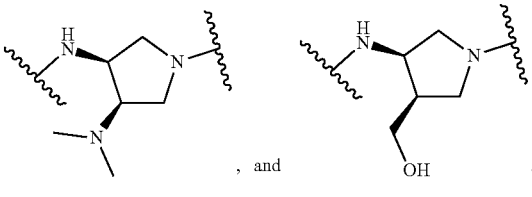, and
In yet a further aspect, $Q^2$ is a structure selected from:
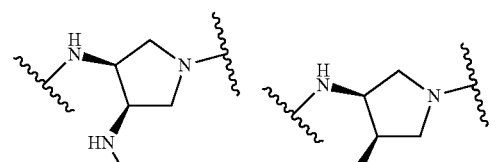
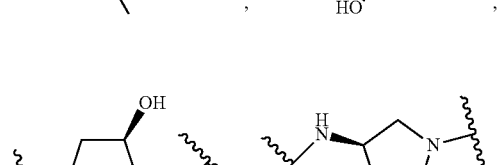
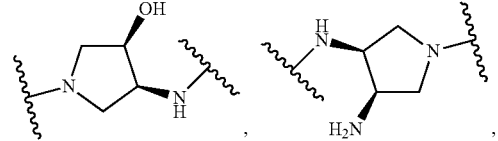
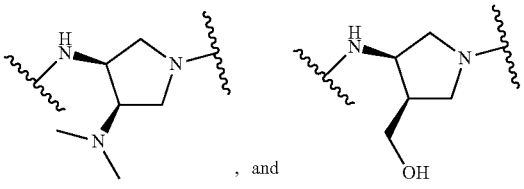, and In an even further aspect, Q² is a structure selected from:

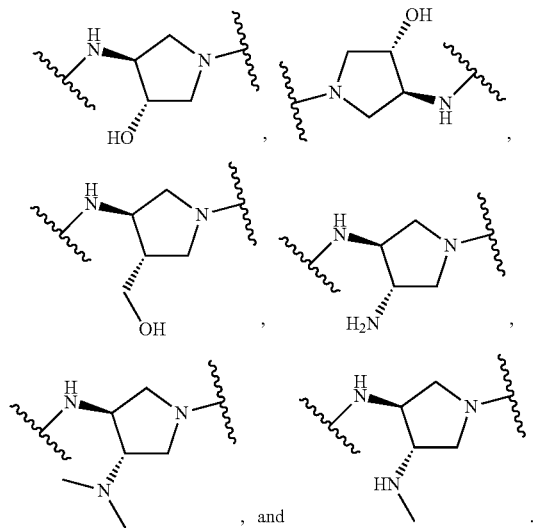

In a still further aspect, Q² is a structure selected from:

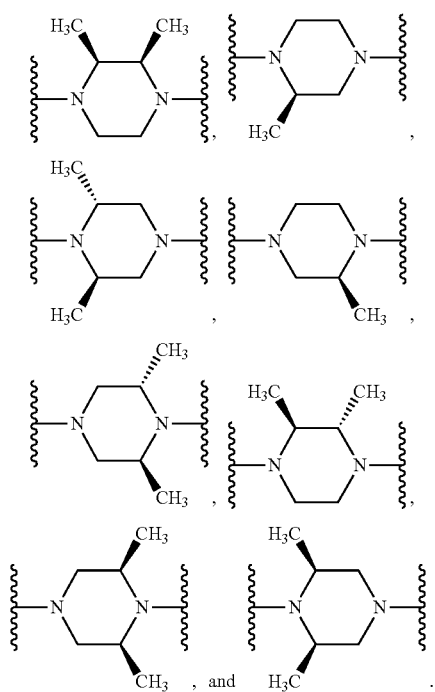

In yet a further aspect, Q² is a structure selected from:

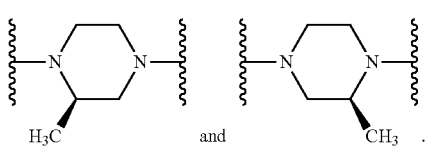

In an even further aspect, Q² is a structure selected from:

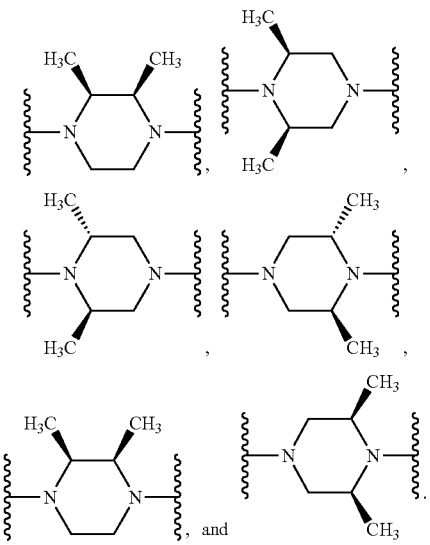

In a still further aspect, Q² is a structure selected from:

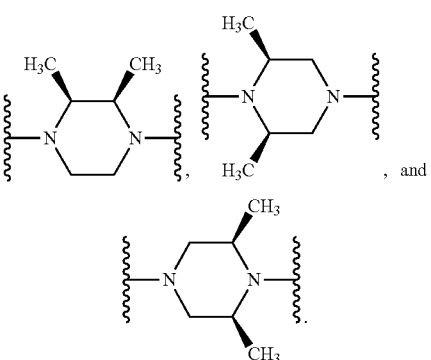

In yet a further aspect, Q² is a structure selected from:

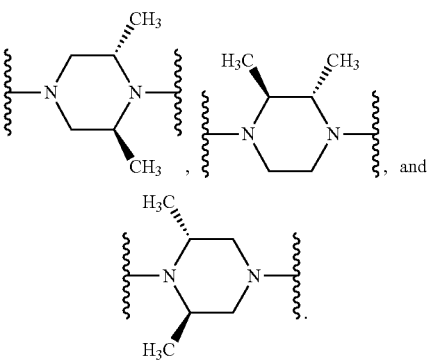

d. Q³ and Q⁴ Groups

In one aspect, Q³ is N and Q⁴ is CH or Q⁴ is N and Q³ is CH. In a further aspect, Q³ is N and Q⁴ is CH. In a still further aspect, Q⁴ is N and Q³ is CH.

e. $Q^5$ Groups

In one aspect, f. Z Groups

In one aspect, Z is selected from A(C=O), COCH$_2$,

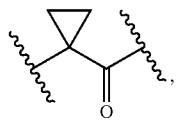

CO, NHCO, NHCS, CH$_2$SO$_2$, and SO$_2$. In a further aspect, Z is A(C=O).

In a further aspect, Z is selected from O(C=O), CF$_2$CO, COCH$_2$, CH$_2$CO,

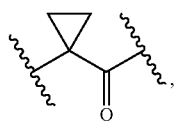

CO, CH$_2$SO$_2$, SO$_2$, NHCO, and CH(OH)CO.

In a further aspect, Z is selected from O(C=O), CF$_2$CO, COCH$_2$, CH$_2$CO,

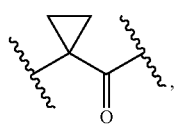

CO, CH$_2$SO$_2$, SO$_2$, and NHCO. In a still further aspect, Z is selected from O(C=O), CF$_2$CO, COCH$_2$, CH$_2$CO,

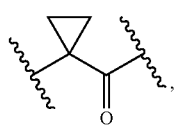 [SMILES: *C(=O)C1(*)CC1]

CO, CH$_2$SO$_2$, and SO$_2$. In yet a further aspect, Z is selected from O(C=O), CF$_2$CO, COCH$_2$, CH$_2$CO,

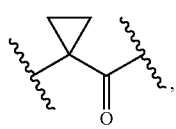

CO, and CH$_2$SO$_2$. In an even further aspect, Z is selected from O(C=O), CF$_2$CO, COCH$_2$, CH$_2$CO,

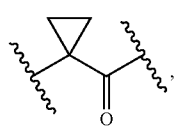 [SMILES: *C(=O)C1(*)CC1]

and CO. In a still further aspect, Z is selected from O(C=O), CF$_2$CO, COCH$_2$, and CH$_2$CO. In yet a further aspect, Z is selected from O(C=O), CF$_2$CO, and COCH$_2$. In an even further aspect, Z is selected from O(C=O) and CF$_2$CO. In a still further aspect, Z is O(C=O). In yet a further aspect, Z is CF$_2$CO. In an even further aspect, Z is COCH$_2$. In a still further aspect, Z is CH$_2$CO. In yet a further aspect, Z is CO. In an even further aspect, Z is

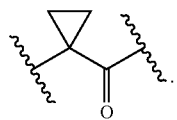 [SMILES: *C(=O)C1(*)CC1]

In a still further aspect, Z is CH$_2$SO$_2$. In yet a further aspect, Z is SO$_2$. In an even further aspect, Z is NHCO. In a still further aspect, Z is CH(OH)CO.

In one aspect, Z is selected from COCH$_2$, O(C=O), CF$_2$CO, and CH(OH)CO. In a further aspect, Z is selected from COCH$_2$, O(C=O), and CF$_2$CO. In a still further aspect, Z is selected from COCH$_2$ and O(C=O).

In one aspect, Z is selected from CO,

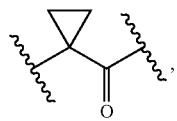

CH$_2$CO, COCH$_2$, NHCO, and NHCS. In a further aspect, Z is selected from CO,

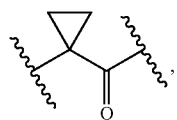

CH$_2$CO, COCH$_2$, and NHCO. In a still further aspect, Z is selected from CO,

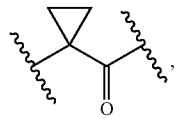 [SMILES: *C(=O)C1(*)CC1]

CH$_2$CO, and COCH$_2$. In yet a further aspect, Z is selected from CO,

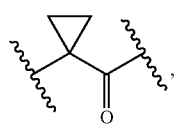 [SMILES: *C(=O)C1(*)CC1]

and CH$_2$CO. In an even further aspect, Z is selected from CO and

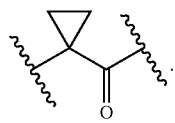

In a still further aspect, Z is NHCS.

g. $R^{1A}$, $R^{1B}$, and $R^{1C}$ Groups

In one aspect, each of $R^{1a}$, $R^{1b}$, and $R^{1c}$ is independently selected from hydrogen, halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a further aspect, each of $R^{1a}$, $R^{1b}$, and $R^{1c}$ is hydrogen.

In a further aspect, each of $R^{1a}$, $R^{1b}$, and $R^{1c}$ is independently selected from hydrogen, —F, —Cl, —Br, —NO$_2$, —CN, —OH, —SH, —NH$_2$, C1-C4 alkyl, C1-C4 monohaloalkyl, C1-C4 polyhaloalkyl, C1-C4 alkylamino, and (C1-C4)(C1-C4)dialkylamino. In a still further aspect, each of $R^{1a}$, $R^{1b}$, and $R^{1c}$ is independently selected from hydrogen, —F, —Cl, —Br, —NO$_2$, —CN, —OH, —SH, —NH$_2$, methyl, ethyl, n-propyl, i-propyl, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_2$CH$_3$)$_2$, —N((CH$_2$)$_2$CH$_3$)$_2$, —N(CH(CH$_3$)$_2$)$_2$, —N(CH$_3$)CH$_2$CH$_3$, —N(CH$_3$)(CH$_2$)$_2$CH$_3$, and —N(CH$_3$)CH(CH$_3$)$_2$. In yet a further aspect, each of $R^{1a}$, $R^{1b}$, and $R^{1c}$ is independently selected from hydrogen, —F, —Cl, —Br, —NO$_2$, —CN, —OH, —SH, —NH$_2$, methyl, ethyl, —CH$_2$F, —CH$_2$Cl, —CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —NHCH$_3$, —NHCH$_2$CH$_3$, —N(CH$_3$)$_2$, —N(CH$_2$CH$_3$)$_2$, and —N(CH$_3$)CH$_2$CH$_3$. In an even further aspect, each of $R^{1a}$, $R^{1b}$, and $R^{1c}$ is independently selected from hydrogen, —F, —Cl, —Br, —NO$_2$, —CN, —OH, —SH, —NH$_2$, methyl, —CH$_2$F, —CH$_2$Cl, —CH$_2$Br, —CHF$_2$, —CF$_3$, —CHCl$_2$, —CCl$_3$, —CHBr$_2$, —CBr$_3$, —NHCH$_3$, and —N(CH$_3$)$_2$.

In a further aspect, each of $R^{1a}$, $R^{1b}$, and $R^{1c}$ is independently selected from hydrogen, —F, —Cl, —Br, —NO$_2$, —CN, —OH, —SH, —NH$_2$, C1-C4 alkyl, C1-C4 alkoxy, C1-C4 alkylamino, and (C1-C4)(C1-C4)dialkylamino. In a still further aspect, each of $R^{1a}$, $R^{1b}$, and $R^{1c}$ is independently selected from hydrogen, —F, —Br, —NO$_2$, —CN, —OH, —SH, —NH$_2$, methyl, ethyl, n-propyl, i-propyl, —OCH$_3$, —OCH$_2$CH$_3$, —O(CH$_2$)$_2$CH$_3$, —OCH(CH$_3$)$_2$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_2$CH$_3$)$_2$, —N((CH$_2$)$_2$CH$_3$)$_2$, —N(CH(CH$_3$)$_2$)$_2$, —N(CH$_3$)CH$_2$CH$_3$, —N(CH$_3$)(CH$_2$)$_2$CH$_3$, and —N(CH$_3$)CH(CH$_3$)$_2$. In yet a further aspect, each of $R^{1a}$, $R^{1b}$, and $R^{1c}$ is independently selected from hydrogen, —F, —Cl, —Br, —NO$_2$, —CN, —OH, —SH, —NH$_2$, methyl, ethyl, —OCH$_3$, —OCH$_2$CH$_3$, —NHCH$_3$, —NHCH$_2$CH$_3$, —N(CH$_3$)$_2$, —N(CH$_2$CH$_3$)$_2$, and —N(CH$_3$)CH$_2$CH$_3$. In an even further aspect, each of $R^{1a}$, $R^{1b}$, and $R^{1c}$ is independently selected from hydrogen, —F, —Cl, —Br, —NO$_2$, —CN, —OH, —SH, —NH$_2$, methyl, —OCH$_3$, —NHCH$_3$, —N(CH$_3$)$_2$.

In a further aspect, each of $R^{1a}$, $R^{1b}$, and $R^{1c}$ is independently selected from hydrogen and C1-C4 alkyl. In a still further aspect, each of $R^{1a}$, $R^{1b}$, and $R^{1c}$ is independently selected from hydrogen, methyl, ethyl, n-propyl, and i-propyl. In yet a further aspect, each of $R^{1a}$, $R^{1b}$, and $R^{1c}$ is independently selected from hydrogen, methyl, and ethyl. In an even further aspect, each of $R^{1a}$, $R^{1b}$, and $R^{1c}$ is independently selected from hydrogen and ethyl. In a still further aspect, each of $R^{1a}$, $R^{1b}$, and $R^{1c}$ is independently selected from hydrogen and methyl.

In a further aspect, each of $R^{1a}$, $R^{1b}$, and $R^{1c}$ is independently selected from hydrogen, C1-C4 monohaloalkyl, and C1-C4 polyhaloalkyl. In a still further aspect, each of $R^{1a}$, $R^{1b}$, and $R^{1c}$ is independently selected from hydrogen, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$. In yet a further aspect, each of $R^{1a}$, $R^{1b}$, and $R^{1c}$ is independently selected from hydrogen, —CH$_2$F, —CH$_2$Cl, —CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, and —CH$_2$CBr$_3$. In an even further aspect, each of $R^{1a}$, $R^{1b}$, and $R^{1c}$ is independently selected from hydrogen, —CH$_2$F, —CH$_2$Cl, —CH$_2$Br, —CHF$_2$, —CF$_3$, —CHCl$_2$, —CCl$_3$, —CHBr$_2$, and —CBr$_3$.

In a further aspect, each of $R^{1a}$, $R^{1b}$, and $R^{1c}$ is independently selected from hydrogen and halogen. In a still further aspect, each of $R^{1a}$, $R^{1b}$, and $R^{1c}$ is independently selected from hydrogen, —F, —Cl, and —Br. In yet a further aspect, each of $R^{1a}$, $R^{1b}$, and $R^{1c}$ is independently selected from hydrogen, —F, and —Cl. In an even further aspect, each of $R^{1a}$, $R^{1b}$, and $R^{1c}$ is independently selected from hydrogen and —Br. In a still further aspect, each of $R^{1a}$, $R^{1b}$, and $R^{1c}$ is independently selected from hydrogen and —Cl. In yet a further aspect, each of $R^{1a}$, $R^{1b}$, and $R^{1c}$ is independently selected from hydrogen and —F.

h. $R^2$ Groups

In one aspect, $R^2$ is selected from —SCH$_3$, C1-C8 acyclic alkyl, C1-C8 acyclic alkenyl, C1-C8 monohaloalkyl, C1-C8 polyhaloalkyl, C1-C8 alkoxyhaloalkyl, cyclopropyl, cuclobutyl, and oxetane, wherein the cyclopropyl, cyclobutyl, and oxetane are optionally substituted with 1, 2, or 3 groups independently selected from —OH, C1-C4 alkyl, and C1-C4 alkoxy. In a further aspect, $R^2$ is selected from —SCH$_3$, C1-C4 acyclic alkyl, C1-C4 acyclic alkenyl, C1-C4 monohaloalkyl, C1-C4 polyhaloalkyl, C1-C4 alkoxyhaloalkyl, cyclopropyl, cuclobutyl, and oxetane.

In one aspect, $R^2$ is selected from halogen, —SCH$_3$, C1-C8 acyclic alkyl, C1-C8 acyclic alkenyl, C1-C8 monohaloalkyl, C1-C8 polyhaloalkyl, C1-C8 alkoxyhaloalkyl, cyclopropyl, cuclobutyl, and oxetane, wherein the cyclopropyl, cyclobutyl, and oxetane are optionally substituted with 1, 2, or 3 groups independently selected from —OH, C1-C4 alkyl, and C1-C4 alkoxy. In a further aspect, $R^2$ is selected from halogen, —SCH$_3$, C1-C4 acyclic alkyl, C1-C4 acyclic alkenyl, C1-C4 monohaloalkyl, C1-C4 polyhaloalkyl, C1-C4 alkoxyhaloalkyl, cyclopropyl, cuclobutyl, and oxetane.

In one aspect, $R^2$ is selected from C1-C8 acyclic alkyl, C1-C8 acyclic alkenyl, C1-C8 monohaloalkyl, C1-C8 polyhaloalkyl, and cyclopropyl. In a further aspect, $R^2$ is selected from C1-C4 acyclic alkyl, C1-C4 acyclic alkenyl, C1-C4 monohaloalkyl, C1-C4 polyhaloalkyl, and cyclopropyl.

In one aspect, $R^2$ is selected from halogen, C1-C8 acyclic alkyl, C1-C8 acyclic alkenyl, C1-C8 monohaloalkyl, C1-C8 polyhaloalkyl, and cyclopropyl. In a further aspect, $R^2$ is selected from halogen, C1-C4 acyclic alkyl, C1-C4 acyclic alkenyl, C1-C4 monohaloalkyl, C1-C4 polyhaloalkyl, and cyclopropyl.

In one aspect, $R^2$ is selected from C1-C8 acyclic alkyl, C1-C8 acyclic alkenyl, C1-C8 monohaloalkyl, C1-C8 polyhaloalkyl, (C1-C8)(C1-C8)dialkylamino, and cyclopropyl. In a further aspect, $R^2$ is selected from C1-C4 acyclic alkyl, C1-C4 acyclic alkenyl, C1-C4 monohaloalkyl, C1-C4 polyhaloalkyl, (C1-C4)(C1-C4)dialkylamino, and cyclopropyl.

In one aspect, $R^2$ is selected from isopropyl and cyclopropyl. In a further aspect, $R^2$ is isopropyl. In a further aspect, $R^2$ is cyclopropyl.

In a further aspect, $R^2$ is selected from C1-C4 acyclic alkyl, C1-C4 acyclic alkenyl, and cyclopropyl. In a still further aspect, $R^2$ is selected from methyl, ethyl, n-propyl, i-propyl, ethenyl, 1-propenyl, 2-propenyl, and cyclopropyl. In yet a further aspect, $R^2$ is selected from ethyl, n-propyl, i-propyl, ethenyl, 1-propenyl, 2-propenyl, and cyclopropyl. In an even further aspect, $R^2$ is selected from n-propyl, i-propyl, 1-propenyl, 2-propenyl, and cyclopropyl.

In a further aspect, $R^2$ is selected from cyclopropyl, cyclobutyl, and oxetane and substituted with 1, 2, or 3 groups independently selected from —OH, C1-C4 alkyl, and C1-C4 alkoxy. In a still further aspect, $R^2$ is selected from cyclopropyl, cyclobutyl, and oxetane and substituted with 1 or 2 groups independently selected from —OH, C1-C4 alkyl, and C1-C4 alkoxy. In yet a further aspect, $R^2$ is selected from cyclopropyl, cyclobutyl, and oxetane and substituted with a group selected from —OH, C1-C4 alkyl, and C1-C4 alkoxy. In an even further aspect, $R^2$ is selected from cyclopropyl, cyclobutyl, and oxetane and substituted with a —OH group. In still further aspect, $R^2$ is selected from cyclopropyl, cyclobutyl, and oxetane and substituted with a C1-C4 alkyl group. In yet a further aspect, $R^2$ is selected from cyclopropyl, cyclobutyl, and oxetane and substituted with a methyl group. In an even further aspect, $R^2$ is selected from cyclopropyl, cyclobutyl, and oxetane and is unsubstituted.

In a further aspect, $R^2$ is selected from C1-C4 acyclic alkyl, C1-C4 monohaloalkyl, C1-C4 polyhaloalkyl, C1-C4 alkoxyhaloalkyl, cyclopropyl, cyclobutyl, and oxetane. In a still further aspect, $R^2$ is selected from methyl, ethyl, n-propyl, i-propyl, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —OCH$_2$F, —OCHF$_2$, —OCF$_3$, cyclopropyl, cyclobutyl, and oxetane. In yet a further aspect, $R^2$ is selected from ethyl, n-propyl, i-propyl, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —OCH$_2$F, —OCHF$_2$, —OCF$_3$, cyclopropyl, cyclobutyl, and oxetane. In an even further aspect, $R^2$ is selected from n-propyl, i-propyl, —(CH$_2$)$_2$CH$_2$F, —(CH$_2$)$_2$CH$_2$Cl, —(CH$_2$)$_2$CH$_2$Br, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CBr$_3$, —OCH$_2$F, —OCHF$_2$, —OCF$_3$, cyclopropyl, cyclobutyl, and oxetane.

In a further aspect, $R^2$ is selected from —SCH$_3$, halogen, C1-C4 acyclic alkyl, C1-C4 acyclic alkenyl, cyclopropyl, cyclobutyl, and oxetane. In a still further aspect, $R^2$ is selected from —SCH$_3$, —F, —Cl, —Br, methyl, ethyl, n-propyl, i-propyl, ethenyl, 1-propenyl, 2-propenyl, cyclopropyl, cyclobutyl, and oxetane. In yet a further aspect, $R^2$ is selected from —SCH$_3$, —F, —Cl, —Br, ethyl, n-propyl, i-propyl, 1-propenyl, 2-propenyl, cyclopropyl, cyclobutyl, and oxetane. In an even further aspect, $R^2$ is selected from —SCH$_3$, —F, —Cl, —Br, n-propyl, i-propyl, 1-propenyl, 2-propenyl, cyclopropyl, cyclobutyl, and oxetane.

In a further aspect, $R^2$ is selected from C1-C4 acyclic alkyl, C1-C4 acyclic alkenyl, (C1-C4)(C1-C4)dialkylamino, cyclopropyl, cyclobutyl, and oxetane. In a still further aspect, $R^2$ is selected from methyl, ethyl, n-propyl, i-propyl, ethenyl, 1-propenyl, 2-propenyl, —NHCH$_3$, —NHCH$_2$CH$_3$, —NH(CH$_2$)$_2$CH$_3$, —NHCH(CH$_3$)$_2$, —N(CH$_3$)$_2$, —N(CH$_2$CH$_3$)$_2$, —N((CH$_2$)$_2$CH$_3$)$_2$, —N(CH(CH$_3$)$_2$)$_2$, —N(CH$_3$)CH$_2$CH$_3$, —N(CH$_3$)(CH$_2$)$_2$CH$_3$, —N(CH$_3$)CH(CH$_3$)$_2$, cyclopropyl, cyclobutyl, and oxetane. In yet a further aspect, $R^2$ is selected from ethyl, n-propyl, i-propyl, ethenyl, 1-propenyl, 2-propenyl, —NHCH$_2$CH$_3$, —NH(CH$_2$)$_2$CH$_3$, —NHCH(CH$_3$)$_2$, —N(CH$_2$CH$_3$)$_2$, —N((CH$_2$)$_2$CH$_3$)$_2$, —N(CH(CH$_3$)$_2$)$_2$, —N(CH$_3$)CH$_2$CH$_3$, —N(CH$_3$)(CH$_2$)$_2$CH$_3$, —N(CH$_3$)CH(CH$_3$)$_2$, cyclopropyl, cyclobutyl, and oxetane. In an even further aspect, $R^2$ is selected from n-propyl, i-propyl, 1-propenyl, 2-propenyl, —NH(CH$_2$)$_2$CH$_3$, —NHCH(CH$_3$)$_2$, —N((CH$_2$)$_2$CH$_3$)$_2$, —N(CH(CH$_3$)$_2$)$_2$, —N(CH$_3$)(CH$_2$)$_2$CH$_3$, —N(CH$_3$)CH(CH$_3$)$_2$, cyclopropyl, cyclobutyl, and oxetane.

i. $R^{3A}$ and $R^{3B}$ Groups

In one aspect, each of $R^{3a}$ and $R^{3b}$ is independently selected from hydrogen, halogen, —OH, C1-C4 alkoxy, and C1-C4 alkyl. In a further aspect, each of $R^{3a}$ and $R^{3b}$ is independently selected from hydrogen, halogen, C1-C4 alkoxy, and C1-C4 alkyl. In a still further aspect, one of $R^{3a}$ and $R^{3b}$ is hydrogen and one of $R^{3a}$ and $R^{3b}$ is —OH.

In one aspect, each of $R^{3a}$ and $R^{3b}$ is independently selected from hydrogen, halogen, and C1-C4 alkyl. In a further aspect, each of $R^{3a}$ and $R^{3b}$ is hydrogen.

In one aspect, each of $R^{3a}$ and $R^{3b}$ is independently selected from hydrogen, halogen, C1-C4 alkyl, and C1-C4 alkoxy.

In a further aspect, each of $R^{3a}$ and $R^{3b}$ is independently selected from hydrogen, —F, —Cl, —Br, methyl, ethyl, n-propyl, i-propyl, n-butyl, i-butyl, t-butyl, and s-butyl. In a still further aspect, each of $R^{3a}$ and $R^{3b}$ is independently selected from hydrogen, —F, —Cl, —Br, methyl, ethyl, n-propyl, and i-propyl. In yet a further aspect, each of $R^{3a}$ and $R^{3b}$ is independently selected from hydrogen, —F, —Cl, —Br, methyl, and ethyl. In an even further aspect, each of $R^{3a}$ and $R^{3b}$ is independently selected from hydrogen, —F, —Cl, —Br, and methyl.

In a further aspect, each of $R^{3a}$ and $R^{3b}$ is independently selected from hydrogen, —F, —Cl, —Br, methyl, ethyl, n-propyl, i-propyl, —OCH$_3$, —OCH$_2$CH$_3$, —O(CH$_2$)$_2$CH$_3$, and —OCH(CH$_3$)$_2$. In a still further aspect, each of $R^{3a}$ and $R^{3b}$ is independently selected from hydrogen, —F, —Cl, —Br, methyl, ethyl, —OCH$_3$, and —OCH$_2$CH$_3$. In yet a further aspect, each of $R^{3a}$ and $R^{3b}$ is independently selected from hydrogen, —F, —Cl, —Br, methyl, and —OCH$_3$.

In a further aspect, each of $R^{3a}$ and $R^{3b}$ is independently selected from hydrogen and C1-C4 alkyl. In a still further aspect, each of $R^{3a}$ and $R^{3b}$ is independently selected from hydrogen, methyl, ethyl, n-propyl, and i-propyl. In yet a further aspect, each of $R^{3a}$ and $R^{3b}$ is independently selected from hydrogen, methyl, and ethyl. In an even further aspect, each of $R^{3a}$ and $R^{3b}$ is independently selected from hydrogen and ethyl. In a still further aspect, each of $R^{3a}$ and $R^{3b}$ is independently selected from hydrogen and methyl.

In a further aspect, each of $R^{3a}$ and $R^{3b}$ is independently selected from hydrogen, —F, —Cl, and —Br. In a still further aspect, each of $R^{3a}$ and $R^{3b}$ is independently selected from hydrogen, —F, and —Cl. In yet a further aspect, each of $R^{3a}$ and $R^{3b}$ is independently selected from hydrogen and —I. In an even further aspect, each of $R^{3a}$ and $R^{3b}$ is independently selected from hydrogen and —Br. In a still further aspect, each of $R^{3a}$ and $R^{3b}$ is independently selected from hydrogen and —Cl. In yet a further aspect, each of $R^{3a}$ and $R^{3b}$ is independently selected from hydrogen and —F.

j. $R^5$ Groups

In one aspect, $R^5$, when present, is selected from CN, halogen, —NO$_2$, SO$_2$NH$_2$, and SO$_2$CH$_3$, provided that if $R^5$ is CN and Z is CO then $Ar^1$ is not substituted with C1-C8 monohaloalkyl or C1-C8 polyhaloalkyl; and provided that if $R^5$ is halogen then $Ar^1$ is selected from 5- and 6-membered heteroaryl and Z cannot be CO. In a further aspect, $R^5$, when present, is CN.

In a further aspect, $R^5$, when present, is selected from —NO$_2$, SO$_2$NH$_2$, and SO$_2$CH$_3$. In a still further aspect, $R^5$, when present, is selected from SO$_2$NH$_2$ and SO$_2$CH$_3$. In yet a further aspect, $R^5$, when present, is —NO$_2$. In an even further aspect, $R^5$, when present, is SO$_2$NH$_2$. In a still further aspect, $R^5$, when present, is SO$_2$CH$_3$.

In a further aspect, $R^5$ is selected from halogen, —NO$_2$, SO$_2$NH$_2$, and SO$_2$CH$_3$. In a still further aspect, $R^5$ is selected from —Cl, —F, —NO$_2$, SO$_2$NH$_2$, and SO$_2$CH$_3$.

In a further aspect, $R^5$, when present, is selected from CN and halogen. In a still further aspect, $R^5$, when present, is selected from CN, —Cl, and —F. In yet a further aspect, $R^5$, when present, is selected from CN and —F. In an even further aspect, $R^5$, when present, is selected from CN and —Cl.

In a further aspect, $R^5$, when present, is selected from —I, —Br, —Cl, and —F. In a still further aspect, $R^5$, when present, is —I. In yet a further aspect, $R^5$, when present, is —Br. In an even further aspect, $R^5$, when present, is —Cl. In a still further aspect, $R^5$, when present, is —F.

k. $R^6$ Groups

In one aspect, $R^6$ is selected from —NHCH$_2$C$_6$H$_5$ and $Ar^2$. In a further aspect, $R^6$ is —NHCH$_2$C$_6$H$_5$. In a still further aspect, $R^6$ is $Ar^2$.

l. $R^{20A}$, $R^{20B}$, $R^{20C}$, and $R^{20D}$ Groups

In one aspect, each of $R^{20a}$, $R^{20b}$, $R^{20c}$, and $R^{20d}$, when present, is independently selected from hydrogen, halogen, —CN, —NO$_2$, —NH$_2$, C1-C4 alkyl, C1-C4 monohaloalkyl, C1-C4 polyhaloalkyl, C1-C4 alkoxy, C1-C4 monohaloalkoxy, C1-C4 polyhaloalkoxy, C1-C4 alkylamino, (C1-C4)(C1-C4)dialkylamino, and cyclopropyl.

In one aspect, each of $R^{20a}$, $R^{20b}$, $R^{20c}$, and $R^{20d}$, when present, is independently selected from hydrogen, halogen, —CN, —NO$_2$, —NH$_2$, —C1-C4 alkyl, C1-C4 monohaloalkyl, C1-C4 polyhaloalkyl, C1-C4 alkoxy, C1-C4 monohaloalkoxy, C1-C4 polyhaloalkoxy, C1-C4 alkylamino, (C1-C4)(C1-C4)dialkylamino, and cyclopropyl.

In one aspect, each of $R^{20a}$, $R^{20b}$, $R^{20c}$, and $R^{20d}$, when present, is independently selected from hydrogen, halogen, —CN, —NO$_2$, C1-C4 alkyl, C1-C4 monohaloalkyl, C1-C4 polyhaloalkyl, C1-C4 alkoxy, C1-C4 monohaloalkoxy, C1-C4 polyhaloalkoxy, C1-C4 alkylamino, (C1-C4)(C1-C4)dialkylamino, and cyclopropyl. In a further aspect, each of $R^{20a}$, $R^{20b}$, $R^{20c}$, and $R^{20d}$, when present, is hydrogen.

In one aspect, each of $R^{20a}$, $R^{20b}$, $R^{20c}$, and $R^{20d}$, when present, is independently selected from hydrogen, halogen, —CN, C1-C4 alkyl, C1-C4 monohaloalkyl, C1-C4 polyhaloalkyl, C1-C4 alkoxy, C1-C4 monohaloalkoxy, C1-C4 polyhaloalkoxy, C1-C4 alkylamino, (C1-C4)(C1-C4)dialkylamino, and cyclopropyl.

In a further aspect, each of $R^{20a}$, $R^{20b}$, $R^{20c}$, and $R^{20d}$, when present, is independently selected from hydrogen, —F, —Cl, —Br, —CN, —NO$_2$, —NH$_2$, C1-C4 alkyl, C1-C4 monohaloalkyl, C1-C4 polyhaloalkyl, C1-C4 alkoxy, C1-C4 monohaloalkoxy, C1-C4 polyhaloalkoxy, C1-C4 alkylamino, (C1-C4)(C1-C4)dialkylamino, and cyclopropyl. In a still further aspect, each of $R^{20a}$, $R^{20b}$, $R^{20c}$, and $R^{20d}$, when present, is independently selected from hydrogen, —F, —Cl, —Br, —CN, —NO$_2$, —NH$_2$, methyl, ethyl, n-propyl, i-propyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_2$CH$_3$)$_2$, —N((CH$_2$)$_2$CH$_3$)$_2$, —N(CH(CH$_3$)$_2$)$_2$, —N(CH$_3$)CH$_2$CH$_3$, —N(CH$_3$)(CH$_2$)$_2$CH$_3$, —N(CH$_3$)CH(CH$_3$)$_2$. and cyclopropyl. In yet a further aspect, each of $R^{20a}$, $R^{20b}$, $R^{20c}$, and $R^{20d}$, when present, is independently selected from hydrogen, —F, —Cl, —Br, —CN, NO$_2$, —NH$_2$, methyl, ethyl, —OCH$_3$, —OCH$_2$CH$_3$, —CH$_2$F, —CH$_2$Cl, —CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —NHCH$_3$, —NHCH$_2$CH$_3$, —N(CH$_3$)$_2$, —N(CH$_2$CH$_3$)$_2$, —N(CH$_3$)CH$_2$CH$_3$, and cyclopropyl. In an even further aspect, each of $R^{20a}$, $R^{20b}$, $R^{20c}$, and $R^{20d}$, when present, is independently selected from hydrogen, —F, —Cl, —Br, —CN, —NO$_2$, —NH$_2$, methyl, —OCH$_3$, —OCH$_2$CH$_3$, —CH$_2$F, —CH$_2$Cl, —CH$_2$Br, —CHF$_2$, —CF$_3$, —CHCl$_2$, —CCl$_3$, —CHBr$_2$, —CBr$_3$, —NHCH$_3$, —N(CH$_3$)$_2$, and cyclopropyl.

In a further aspect, each of $R^{20a}$, $R^{20b}$, $R^{20c}$, and $R^{20d}$, when present, is independently selected from hydrogen, —F, —Cl, —Br, —CN, C1-C4 alkyl, C1-C4 monohaloalkyl, C1-C4 polyhaloalkyl, C1-C4 alkoxy, C1-C4 monohaloalkoxy, C1-C4 polyhaloalkoxy, C1-C4 alkylamino, (C1-C4)(C1-C4)dialkylamino, and cyclopropyl. In a still further aspect, each of $R^{20a}$, $R^{20b}$, $R^{20c}$, and $R^{20d}$, when present, is independently selected from hydrogen, —F, —Cl, —Br, —CN, methyl, ethyl, n-propyl, i-propyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$CH$_2$F, —CH$_2$CH$_2$Cl, —CH$_2$CH$_2$Br, —(CH$_2$)$_2$CH$_2$F, —(CH$_2$)$_2$CH$_2$Cl, —(CH$_2$)$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_2$CH$_3$)$_2$, —N((CH$_2$)$_2$CH$_3$)$_2$, —N(CH(CH$_3$)$_2$)$_2$, —N(CH$_3$)CH$_2$CH$_3$, —N(CH$_3$)(CH$_2$)$_2$CH$_3$, —N(CH$_3$)CH(CH$_3$)$_2$. and cyclopropyl. In yet a further aspect, each of $R^{20a}$, $R^{20b}$, $R^{20c}$, and $R^{20d}$, when present, is independently selected from hydrogen, —F, —Cl, —Br, —CN, methyl, ethyl, —OCH$_3$, —OCH$_2$CH$_3$, —CH$_2$F, —CH$_2$Cl, —CH$_2$Br, —CH$_2$CH$_2$F, —CH$_2$CH$_2$Cl, —CH$_2$CH$_2$Br, —CHF$_2$, —CF$_3$, —CHCl$_2$, —CCl$_3$, —CHBr$_2$, —CBr$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —NHCH$_3$, —NHCH$_2$CH$_3$, —N(CH$_3$)$_2$, —N(CH$_2$CH$_3$)$_2$, —N(CH$_3$)CH$_2$CH$_3$, and cyclopropyl. In an even further aspect, each of R$^{20a}$, R$^{20b}$, R$^{20c}$, and R$^{20d}$, when present, is independently selected from hydrogen, —F, —Cl, —Br, —CN, methyl, —OCH$_3$, —OCH$_2$CH$_3$, —CH$_2$F, -CH$_2$Cl, —CH$_2$Br, —CHF$_2$, —CF$_3$, —CHCl$_2$, —CCl$_3$, —CHBr$_2$, —CBr$_3$, —NHCH$_3$, —N(CH$_3$)$_2$, and cyclopropyl.

In a further aspect, each of R$^{20a}$, R$^{20b}$, R$^{20c}$, and R$^{20d}$, when present, is independently selected from hydrogen and C1-C4 alkyl. In a still further aspect, each of R$^{20a}$, R$^{20b}$, R$^{20c}$, and R$^{20d}$, when present, is independently selected from hydrogen, methyl, ethyl, n-propyl, and i-propyl. In yet a further aspect, each of R$^{20a}$, R$^{20b}$, R$^{20c}$, and R$^{20d}$, when present, is independently selected from hydrogen, methyl, and ethyl. In an even further aspect, each of R$^{20a}$, R$^{20b}$, R$^{20c}$, and R$^{20d}$, when present, is independently selected from hydrogen and ethyl. In a still further aspect, each of R$^{20a}$, R$^{20b}$, R$^{20c}$, and R$^{20d}$, when present, is independently selected from hydrogen and methyl.

In a further aspect, each of R$^{20a}$, R$^{20b}$, R$^{20c}$, and R$^{20d}$, when present, is independently selected from hydrogen and halogen. In a still further aspect, each of R$^{20a}$, R$^{20b}$, R$^{20c}$, and R$^{20d}$, when present, is independently selected from hydrogen, —F, —Cl, and —Br. In yet a further aspect, each of R$^{20a}$, R$^{20b}$, R$^{20c}$, and R$^{20d}$, when present, is independently selected from hydrogen, —F, and —Cl. In an even further aspect, each of R$^{20a}$, R$^{20b}$, R$^{20c}$, and R$^{20d}$, when present, is independently selected from hydrogen and —I. In a still further aspect, each of R$^{20a}$, R$^{20b}$, R$^{20c}$, and R$^{20d}$, when present, is independently selected from hydrogen and —Br. In yet a further aspect, each of R$^{20a}$, R$^{20b}$, R$^{20c}$, and R$^{20d}$, when present, is independently selected from hydrogen and —Cl. In an even further aspect, each of R$^{20a}$, R$^{20b}$, R$^{20c}$, and R$^{20d}$, when present, is independently selected from hydrogen and —F.

m. R$^{21}$ Groups

In one aspect, R$^{21}$, when present, is selected from hydrogen, halogen, —CN, —NO$_2$, —SO$_2$NH$_2$, —SO$_2$CH$_3$, —SO$_2$CF$_3$, and Cy$^1$.

In one aspect, R$^{21}$, when present, is selected from —CN, —NO$_2$, SO$_2$NH$_2$, SO$_2$CH$_3$, SO$_2$CF$_3$, and Cy$^1$. In a further aspect, R$^{21}$, when present, is selected from —CN, —NO$_2$, SO$_2$NH$_2$, SO$_2$CH$_3$, and SO$_2$CF$_3$. In a still further aspect, R$^{21}$, when present, is selected from —CN, —NO$_2$, SO$_2$NH$_2$, and SO$_2$CH$_3$. In yet a further aspect, R$^{21}$, when present, is selected from —CN, —NO$_2$, and SO$_2$NH$_2$. In an even further aspect, R$^{21}$, when present, is selected from —CN, and —NO$_2$.

In a further aspect, R$^{21}$, when present, is —CN. In a still further aspect, R$^{21}$, when present, is —NO$_2$. In yet a further aspect, R$^{21}$, when present, is SO$_2$NH$_2$. In an even further aspect, R$^{21}$, when present, is SO$_2$CH$_3$. In a still further aspect, R$^{21}$, when present, is SO$_2$CF$_3$. In yet a further aspect, R$^{21}$, when present, is Cy$^1$.

In a further aspect, R$^{21}$, when present, is —CN and R$^{22}$, when present, is selected from —CN and halogen. In a still further aspect, R$^{21}$, when present, is —CN and R$^{22}$, when present, is selected from —CN, —F, and —Br. In yet a further aspect, R$^{21}$, when present, is —CN and R$^{22}$, when present, is selected from —CN, —F, and —Cl. In an even further aspect, R$^{21}$, when present, is —CN and R$^{22}$, when present, is —CN. In a still further aspect, R$^{21}$, when present, is —CN and R$^{22}$, when present, is —I. In yet a further aspect, R$^{21}$, when present, is —CN and R$^{22}$, when present, is —Br. In an even further aspect, R$^{21}$, when present, is —CN and R$^{22}$, when present, is —Cl. In a still further aspect, R$^{21}$, when present, is —CN and R$^{22}$, when present, is —F.

n. R$^{22}$ Groups

In one aspect, R$^{22}$, when present, is selected from —CN, halogen, —NO$_2$, SO$_2$NH$_2$, SO$_2$CH$_3$, and SO$_2$CF$_3$.

In one aspect, R$^{22}$, when present, is selected from —CN, halogen, —NO$_2$, SO$_2$NH$_2$, SO$_2$CH$_3$, and SO$_2$CF$_3$. In a further aspect, R$^{22}$, when present, is selected from —CN, halogen, —NO$_2$, SO$_2$NH$_2$, and SO$_2$CH$_3$. In yet a further aspect, R$^{22}$, when present, is selected from —CN, halogen, —NO$_2$, and SO$_2$NH$_2$. In an even further aspect, R$^{22}$, when present, is selected from —CN, halogen, and —NO$_2$. In a still further aspect, R$^{22}$, when present, is selected from —CN and halogen.

In a further aspect, R$^{22}$, when present, is —CN. In a still further aspect, R$^{22}$, when present, is —NO$_2$. In yet a further aspect, R$^{22}$, when present, is SO$_2$NH$_2$. In an even further aspect, R$^{22}$, when present, is SO$_2$CH$_3$. In a still further aspect, R$^{22}$, when present, is SO$_2$CF$_3$.

In a further aspect, R$^{22}$, when present, is halogen. In a still further aspect, R$^{22}$, when present, is selected from —F, —Cl, and —Br. In yet a further aspect, R$^{22}$, when present, is selected from —F and —Br. In an even further aspect, R$^{22}$, when present, is selected from —F and —Cl. In a still further aspect, R$^{22}$, when present, is —I. In yet a further aspect, R$^{22}$, when present, is —Br. In an even further aspect, R$^{22}$, when present, is —Cl. In a still further aspect, R$^{22}$, when present, is —F.

o. R$^{23}$ Groups

In one aspect, R$^{23}$, when present, is selected from hydrogen, halogen, —CN, —NO$_2$, —SO$_2$NH$_2$, —SO$_2$CH$_3$, —SO$_2$CF$_3$, cyclohexyl,

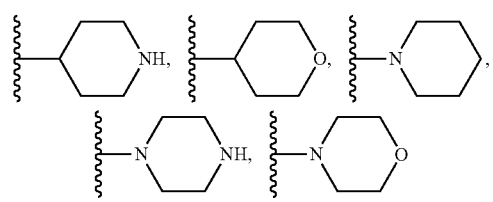

and Cy$^1$.

In one aspect, R$^{23}$, when present, is selected from —CN, —NO$_2$, SO$_2$NH$_2$, SO$_2$CH$_3$, SO$_2$CF$_3$, cyclohexyl,

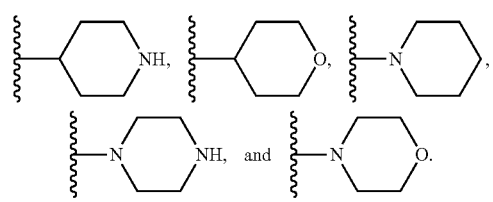

In a further aspect, R$^{23}$, when present, is selected from —CN, —NO$_2$, SO$_2$NH$_2$, and SO$_2$CH$_3$. In yet a further aspect, R$^{23}$, when present, is selected from —CN, —NO$_2$, and SO$_2$NH$_2$. In an even further aspect, R$^{23}$, when present, is selected from —CN, and —NO$_2$.

In a further aspect, $R^{23}$, when present, is —CN. In a still further aspect, $R^{23}$, when present, is —NO$_2$. In yet a further aspect, $R^{23}$, when present, is SO$_2$NH$_2$. In an even further aspect, $R^{23}$, when present, is SO$_2$CH$_3$. In a still further aspect, $R^{23}$, when present, is SO$_2$CF$_3$.

In a further aspect, $R^{23}$, when present, is selected from cyclohexyl,

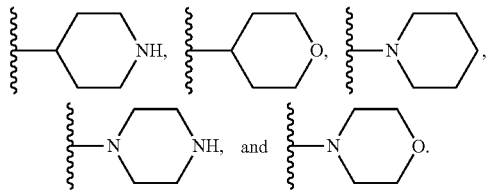

In a stil further aspect, $R^{23}$, when present, is selected from

In yet a further aspect, $R^{23}$, when present, is selected from cyclohexyl,

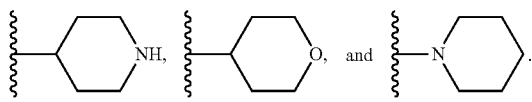

In an even further aspect, $R^{23}$, when present, is selected from

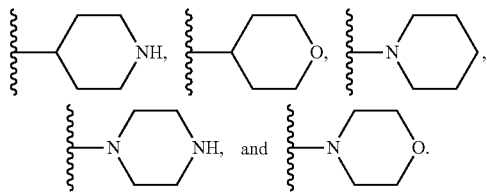

In a still further aspect, $R^{23}$, when present, is cyclohexyl.

In a further aspect, $R^{23}$ is selected from hydrogen, halogen, —CN, SO$_2$NH$_2$, SO$_2$CH$_3$, SO$_2$CF$_3$, and NO$_2$. In a further aspect, $R^{23}$ is hydrogen.

In a further aspect, $R^{23}$ is selected from —CN, SO$_2$NH$_2$, SO$_2$CH$_3$, SO$_2$CF$_3$, and NO$_2$. In a still further aspect, $R^{23}$ is selected from —CN, SO$_2$NH$_2$, SO$_2$CH$_3$, and SO$_2$CF$_3$. In yet a further aspect, $R^{23}$ is selected from —CN, SO$_2$NH$_2$, and SO$_2$CH$_3$. In an even further aspect, $R^{23}$ is selected from —CN and SO$_2$NH$_2$. In a still further aspect, $R^{23}$ is NO$_2$. In yet a further aspect, $R^{23}$ is SO$_2$CF$_3$. In an even further aspect, $R^{23}$ is SO$_2$CH$_3$. In a still further aspect, $R^{23}$ is SO$_2$NH$_2$. In yet a further aspect, $R^{23}$ is —CN.

In a further aspect, $R^{23}$ is selected from hydrogen and halogen. In a still further aspect, $R^{23}$ is selected from hydrogen, —F, —Cl, and —Br. In yet a further aspect, $R^{23}$ is selected from hydrogen, —F, and —Cl. In an even further aspect, $R^{23}$ is selected from hydrogen and —I. In a still further aspect, $R^{23}$ is selected from hydrogen and —Br. In yet a further aspect, $R^{23}$ is selected from hydrogen and —Cl. In an even further aspect, $R^{23}$ is selected from hydrogen and —F.

p. $R^{24}$ Groups

In one aspect, $R^{24}$, when present, is selected from —CN, halogen, —NO$_2$, SO$_2$NH$_2$, SO$_2$CH$_3$, and SO$_2$CF$_3$.

In one aspect, $R^{24}$, when present, is selected from —CN, halogen, —NO$_2$, SO$_2$NH$_2$, SO$_2$CH$_3$, and SO$_2$CF$_3$, provided that if A is NH or N(CH$_3$), then $R^{24}$ is not —NO$_2$. In a further aspect, $R^{24}$, when present, is selected from —CN, halogen, —NO$_2$, SO$_2$NH$_2$, and SO$_2$CH$_3$. In yet a further aspect, $R^{24}$, when present, is selected from —CN, halogen, —NO$_2$, and SO$_2$NH$_2$. In an even further aspect, $R^{24}$, when present, is selected from —CN, halogen, and —NO$_2$. In a still further aspect, $R^{24}$, when present, is selected from —CN and halogen.

In a further aspect, $R^{24}$, when present, is —CN. In a still further aspect, $R^{24}$, when present, is —NO$_2$. In yet a further aspect, $R^{24}$, when present, is SO$_2$NH$_2$. In an even further aspect, $R^{24}$, when present, is SO$_2$CH$_3$. In a still further aspect, $R^{24}$, when present, is SO$_2$CF$_3$.

In a further aspect, $R^{24}$, when present, is halogen. In a still further aspect, $R^{24}$, when present, is selected from —F, —Cl, and —Br. In yet a further aspect, $R^{24}$, when present, is selected from —F and —Br. In an even further aspect, $R^{24}$, when present, is selected from —F and —Cl. In a still further aspect, $R^{24}$, when present, is —I. In yet a further aspect, $R^{24}$, when present, is —Br. In an even further aspect, $R^{24}$, when present, is —Cl. In a still further aspect, $R^{24}$, when present, is —F.

q. $R^{25}$ Groups

In one aspect, $R^{25}$, when present, is selected from —CN, —NO$_2$, SO$_2$NH$_2$, SO$_2$CH$_3$, and SO$_2$CF$_3$.

In one aspect, $R^{25}$, when present, is selected from —CN, —NO$_2$, SO$_2$NH$_2$, SO$_2$CH$_3$, and SO$_2$CF$_3$. In a further aspect, $R^{25}$, when present, is selected from —CN, —NO$_2$, SO$_2$NH$_2$, and SO$_2$CH$_3$. In yet a further aspect, $R^{25}$, when present, is selected from —CN, —NO$_2$, and SO$_2$NH$_2$. In an even further aspect, $R^{25}$, when present, is selected from —CN and —NO$_2$.

In a further aspect, $R^{25}$, when present, is —CN. In a still further aspect, $R^{25}$, when present, is —NO$_2$. In yet a further aspect, $R^{25}$, when present, is SO$_2$NH$_2$. In an even further aspect, $R^{25}$, when present, is SO$_2$CH$_3$. In a still further aspect, $R^{25}$, when present, is SO$_2$CF$_3$.

r. $R^{26}$ Groups

In one aspect, $R^{26}$, when present, is selected from —Br, —Cl, —F, —CN, —NO$_2$, —CF$_3$, and methyl.

s. AR$^1$ Groups

In one aspect, Ar$^1$ is selected from aryl and heteroaryl and substituted with 0, 1, 2, or 3 groups independently selected from halogen, —NO$_2$, —CN, —OH, —SH, —NH$_2$, C1-C8 thioalkyl, C1-C8 acyclic alkyl, C2-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, —CO(C1-C8 acyclic alkyl), C1-C8 alkoxyhaloalkyl, and cyclopropyl, cyclobutyl, and oxetane, wherein the cyclopropyl, cyclobutyl, and oxetane are optionally substituted with 1, 2, 3, or 4 groups independently selected from halogen, —NO$_2$, —CN, —OH, —SH, —NH$_2$, C1-C4 acyclic alkyl, C1-C4 hydroxyalkyl, C1-C4 monohaloalkyl, C1-C4 polyhaloalkyl, C1-C4 alkoxy, C1-C4 monohaloalkoxy, C1-C4 polyhaloalkoxy, C1-C4 acyclic alkylamino, (C1-C4)(C1-C4)dialkylamino, and —CO(C1-C4 acyclic alkyl).

In one aspect, Ar$^1$ is selected from aryl and heteroaryl and substituted with 1, 2, or 3 groups independently selected from halogen, —NO$_2$, —CN, —OH, —SH, —NH$_2$, C1-C8 acyclic alkyl, C1-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, —CO(C1-C8 acyclic alkyl), cyclopropyl, cyclobutyl, and oxetane, wherein the cyclopropyl, cyclobutyl, and oxetane are optionally substituted with 1, 2, or 3 groups independently selected from —OH, C1-C4 alkyl, and C1-C4 alkoxy.

In one aspect, $Ar^1$ is selected from aryl and heteroaryl and substituted with 1, 2, or 3 groups independently selected from halogen, —NO$_2$, —CN, —OH, —SH, —NH$_2$, C1-C8 acyclic alkyl, C1-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, —CO(C1-C8 acyclic alkyl), and cyclopropyl.

In one aspect, $Ar^1$ is selected from furanyl, 3-isopropylisoxazole, 6-isopropylpyridin-2-yl, 5-isopropylpyridin-2-yl, 5-tertbutylpyridin-2-yl, 5-bromopyridin-2-yl, 5-(prop-1-en-2-yl)pyridin-2-yl, 3-pyridinyl, 4-pyridinyl, and pyrimidinyl, and substituted with 0, 1, 2, or 3 groups independently selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino.

In a further aspect, $Ar^1$ is selected from aryl and heteroaryl and substituted with 1 or 2 groups independently selected from halogen, —NO$_2$, —CN, —OH, —SH, —NH$_2$, C1-C8 acyclic alkyl, C1-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, —CO(C1-C8 acyclic alkyl), and cyclopropyl. In a still further aspect, $Ar^1$ is selected from aryl and heteroaryl and monosubstituted with a group selected from halogen, —NO$_2$, —CN, —OH, —SH, —NH$_2$, C1-C8 acyclic alkyl, C1-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, —CO(C1-C8 acyclic alkyl), and cyclopropyl. In yet a further aspect, $Ar^1$ is selected from aryl and heteroaryl and unsubstituted.

In a further aspect, $Ar^1$ is aryl substituted with 1, 2, or 3 groups independently selected from halogen, —NO$_2$, —CN, —OH, —SH, —NH$_2$, C1-C8 acyclic alkyl, C1-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, —CO(C1-C8 acyclic alkyl), and cyclopropyl. In a still further aspect, $Ar^1$ is aryl substituted with 1 or 2 groups independently selected from halogen, —NO$_2$, —CN, —OH, —SH, —NH$_2$, C1-C8 acyclic alkyl, C1-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, —CO(C1-C8 acyclic alkyl), and cyclopropyl. In yet a further aspect, $Ar^1$ is aryl monosubstituted with a group selected from halogen, —NO$_2$, —CN, —OH, —SH, —NH$_2$, C1-C8 acyclic alkyl, C1-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, —CO(C1-C8 acyclic alkyl), and cyclopropyl. In an even further aspect, $Ar^1$ is unsubstituted aryl.

In a further aspect, $Ar^1$ is phenyl substituted with 1, 2, or 3 groups independently selected from halogen, —NO$_2$, —CN, —OH, —SH, —NH$_2$, C1-C8 acyclic alkyl, C1-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, —CO(C1-C8 acyclic alkyl), and cyclopropyl. In a still further aspect, $Ar^1$ is phenyl substituted with 1 or 2 groups independently selected from halogen, —NO$_2$, —CN, —OH, —SH, —NH$_2$, C1-C8 acyclic alkyl, C1-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, —CO(C1-C8 acyclic alkyl), and cyclopropyl. In yet a further aspect, $Ar^1$ is phenyl monosubstituted with a group selected from halogen, —NO$_2$, —CN, —OH, —SH, —NH$_2$, C1-C8 acyclic alkyl, C1-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, —CO(C1-C8 acyclic alkyl), and cyclopropyl. In an even further aspect, $Ar^1$ is unsubstituted phenyl.

In a further aspect, $Ar^1$ is heteroaryl substituted with 1, 2, or 3 groups independently selected from halogen, —NO$_2$, —CN, —OH, —SH, —NH$_2$, C1-C8 acyclic alkyl, C1-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, —CO(C1-C8 acyclic alkyl), and cyclopropyl. In a still further aspect, $Ar^1$ is heteroaryl substituted with 1 or 2 groups independently selected from halogen, —NO$_2$, —CN, —OH, —SH, —NH$_2$, C1-C8 acyclic alkyl, C1-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, —CO(C1-C8 acyclic alkyl), and cyclopropyl. In yet a further aspect, $Ar^1$ is heteroaryl monosubstituted with a group selected from halogen, —NO$_2$, —CN, —OH, —SH, —NH$_2$, C1-C8 acyclic alkyl, C1-C8 acyclic alkenyl, C1-C8 hydroxyalkyl, C1-C8 monohaloalkyl, C1-C8 polyhaloalkyl, C1-C8 alkoxy, C1-C8 monohaloalkoxy, C1-C8 polyhaloalkoxy, C1-C8 acyclic alkylamino, (C1-C8)(C1-C8)dialkylamino, —CO(C1-C8 acyclic alkyl), and cyclopropyl. In an even further aspect, $Ar^1$ is unsubstituted heteroaryl.

In a further aspect, $Ar^1$ is selected from furanyl, 3-isopropylisoxazole, 6-isopropylpyridin-2-yl, 5-isopropylpyridin-2-yl, 5-tertbutylpyridin-2-yl, 5-bromopyridin-2-yl, 5-(prop-1-en-2-yl)pyridin-2-yl, 3-pyridinyl, 4-pyridinyl, and pyrimidinyl, and substituted with 0, 1, or 2 groups independently selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, $Ar^1$ is selected from furanyl, 3-isopropylisoxazole, 6-isopropylpyridin-2-yl, 5-isopropylpyridin-2-yl, 5-tertbutylpyridin-2-yl, 5-bromopyridin-2-yl, 5-(prop-1-en-2-yl)pyridin-2-yl, 3-pyridinyl, 4-pyridinyl, and pyrimidinyl, and substituted with 0 or 1 group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, $Ar^1$ is selected from furanyl, 3-isopropylisoxazole, 6-isopropylpyridin-2-yl, 5-isopropylpyridin-2-yl, 5-tertbutylpyridin-2-yl, 5-bromopyridin-2-yl, 5-(prop-1-en-2-yl)pyridin-2-yl, 3-pyridinyl, 4-pyridinyl, and pyrimidinyl, and monosubstituted with a group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, $Ar^1$ is selected from furanyl, 3-isopropylisoxazole, 6-isopropylpyridin-2-yl, 5-isopropylpyridin-2-yl, 5-tertbutylpyridin-2-yl, 5-bromopyridin-2-yl, 5-(prop-1-en-2-yl)pyridin-2-yl, 3-pyridinyl, 4-pyridinyl, and pyrimidinyl, and unsubstituted.

In a further aspect, $Ar^1$ is furanyl substituted with 0, 1, or 2 groups independently selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, $Ar^1$ is furanyl substituted with 0 or 1 group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, $Ar^1$ is furanyl monosubstituted with a group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, $Ar^1$ is unsubstituted furanyl.

In a further aspect, $Ar^1$ is 3-isopropylisoxazole substituted with 0, 1, or 2 groups independently selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, $Ar^1$ is 3-isopropylisoxazole substituted with 0 or 1 group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, $Ar^1$ is 3-isopropylisoxazole monosubstituted with a group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, $Ar^1$ is unsubstituted 3-isopropylisoxazole.

In a further aspect, $Ar^1$ is 6-isopropylpyridin-2-yl substituted with 0, 1, or 2 groups independently selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, $Ar^1$ is 6-isopropylpyridin-2-yl substituted with 0 or 1 group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, $Ar^1$ is 6-isopropylpyridin-2-yl monosubstituted with a group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, $Ar^1$ is unsubstituted 6-isopropylpyridin-2-yl.

In a further aspect, $Ar^1$ is 5-isopropylpyridin-2-yl substituted with 0, 1, or 2 groups independently selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, $Ar^1$ is 5-isopropylpyridin-2-yl substituted with 0 or 1 group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, $Ar^1$ is 5-isopropylpyridin-2-yl monosubstituted with a group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, $Ar^1$ is unsubstituted 5-isopropylpyridin-2-yl.

In a further aspect, $Ar^1$ is 5-tertbutylpyridin-2-yl substituted with 0, 1, or 2 groups independently selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, $Ar^1$ is 5-tertbutylpyridin-2-yl substituted with 0 or 1 group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, $Ar^1$ is 5-tertbutylpyridin-2-yl monosubstituted with a group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, $Ar^1$ is unsubstituted 5-tertbutylpyridin-2-yl.

In a further aspect, $Ar^1$ is 5-bromopyridin-2-yl substituted with 0, 1, or 2 groups independently selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, $Ar^1$ is 5-bromopyridin-2-yl substituted with 0 or 1 group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, $Ar^1$ is 5-bromopyridin-2-yl monosubstituted with a group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, $Ar^1$ is unsubstituted 5-bromopyridin-2-yl.

In a further aspect, $Ar^1$ is 5-(prop-1-en-2-yl)pyridin-2-yl substituted with 0, 1, or 2 groups independently selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, $Ar^1$ is 5-(prop-1-en-2-yl)pyridin-2-yl substituted with 0 or 1 group selected from halogen, —NO$_2$, —CN, —OH, –SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, $Ar^1$ is 5-(prop-1-en-2-yl)pyridin-2-yl monosubstituted with a group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, $Ar^1$ is unsubstituted 5-(prop-1-en-2-yl)pyridin-2-yl.

In a further aspect, $Ar^1$ is 3-pyridinyl substituted with 0, 1, or 2 groups independently selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, $Ar^1$ is 3-pyridinyl substituted with 0 or 1 group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, $Ar^1$ is 3-pyridinyl monosubstituted with a group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, $Ar^1$ is unsubstituted 3-pyridinyl.

In a further aspect, $Ar^1$ is pyridinyl substituted with 0, 1, or 2 groups independently selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, $Ar^1$ is pyridinyl substituted with 0 or 1 group selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, $Ar^1$ is pyridinyl monosubstituted with a group selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, $Ar^1$ is unsubstituted pyridinyl.

In a further aspect, $Ar^1$ is pyrimidinyl substituted with 0, 1, or 2 groups independently selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, $Ar^1$ is pyrimidinyl substituted with 0 or 1 group selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, $Ar^1$ is pyrimidinyl monosubstituted with a group selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, $Ar^1$ is unsubstituted pyrimidinyl.

t. $AR^2$ Groups

In one aspect, $Ar^2$ is a structure represented by a formula selected from:

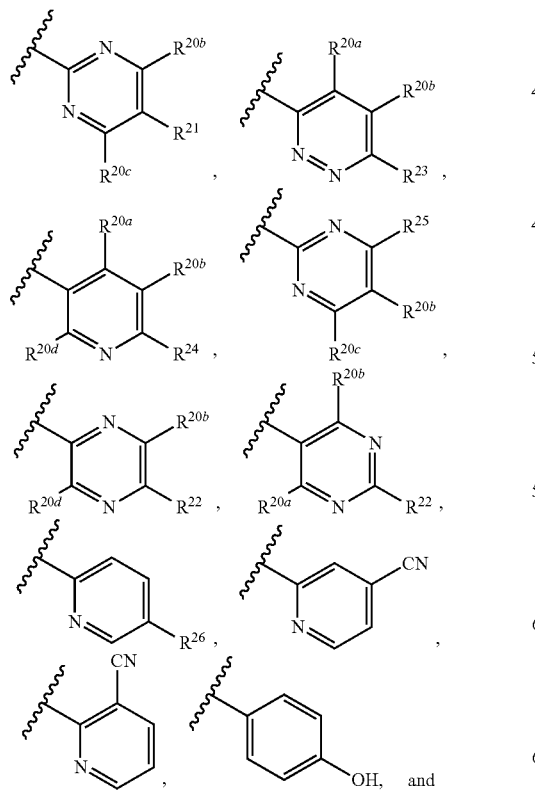

-continued

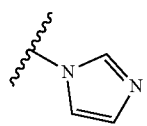

In one aspect, $Ar^2$ is a structure represented by a formula selected from:

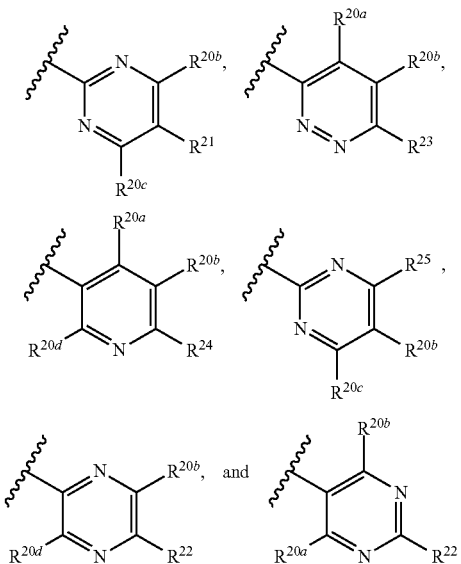

In one aspect, $Ar^2$ is a structure represented by a formula selected from:

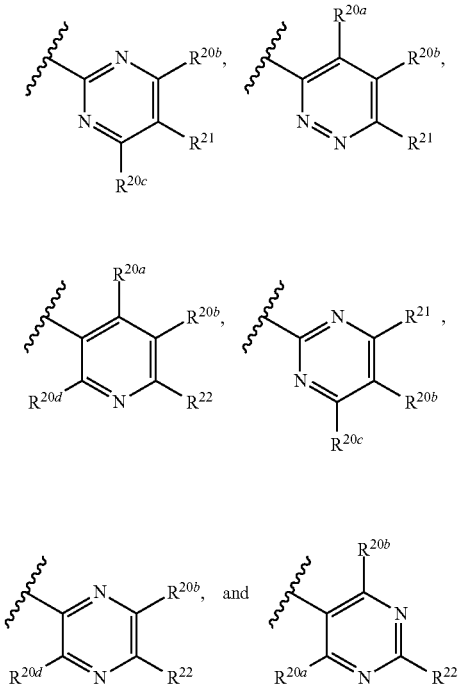

In one aspect, Ar² is a structure represented by a formula selected from:

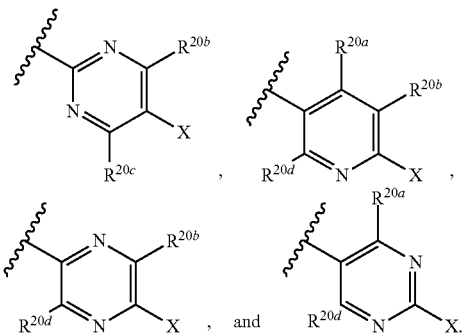

In one aspect, Ar² is a structure represented by a formula:

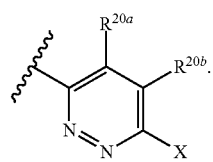

In a further aspect, Ar² is a structure represented by a formula:

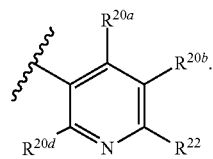

In a still further aspect, Ar² is a structure represented by a formula:

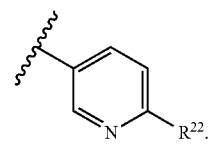

In yet a further aspect, Ar² is a structure represented by a formula selected from:

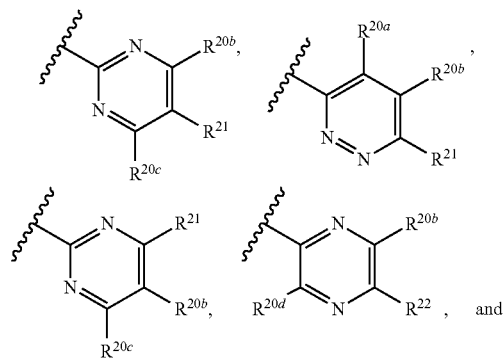

-continued

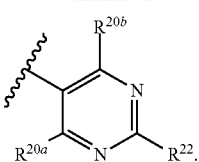

In an even further aspect, Ar² is a structure represented by a formula selected from:

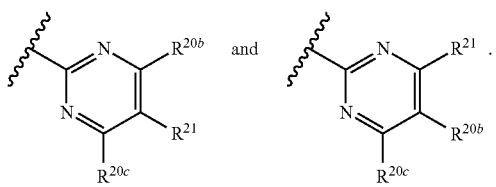

In a still further aspect, Ar² is a structure represented by a formula selected from:

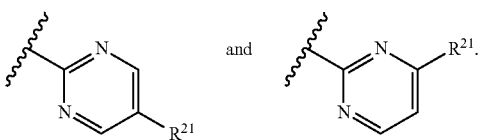

In yet a further aspect, Ar² is a structure represented by a formula selected from:

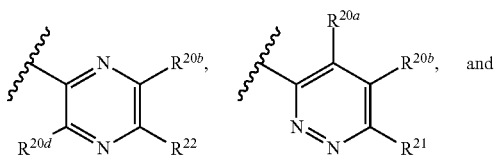

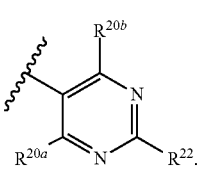

In an even further aspect, Ar² is a structure represented by a formula selected from:

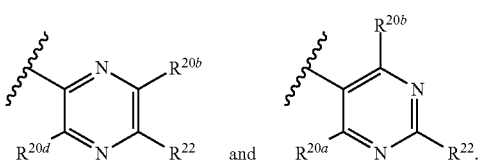

In a still further aspect, Ar² is a structure represented by a formula selected from:

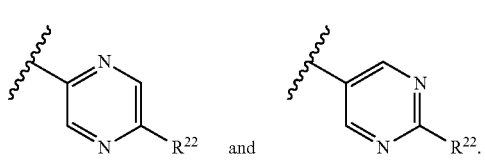

In yet a further aspect, Ar² is a structure represented by a formula:

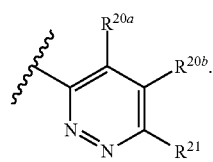

In a further aspect, Ar² is a structure represented by a formula:

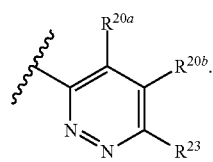

In an even further aspect, Ar² is a structure represented by a formula:

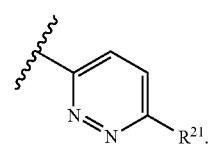

In a further aspect, Ar² is a structure represented by a formula:

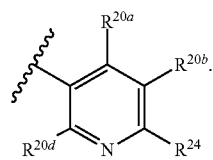

In a further aspect, Ar² is a structure represented by a formula:

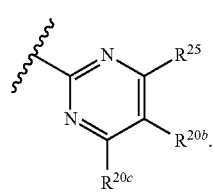

In a further aspect, Ar² is a structure represented by a formula selected from:

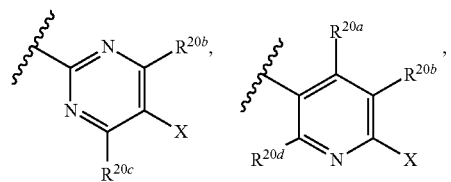

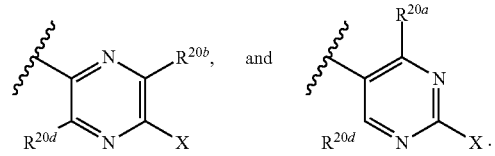

In a still further aspect, Ar² is a structure represented by a formula:

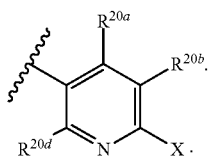

In yet a further aspect, Ar² is a structure represented by a formula:

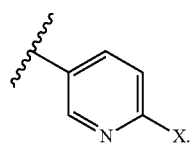

In an even further aspect, Ar² is a structure represented by a formula selected from:

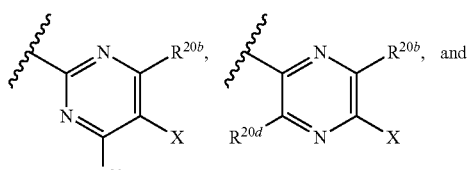

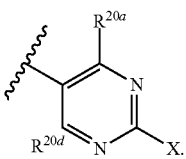

In a still further aspect, Ar² is a structure represented by a formula selected from:

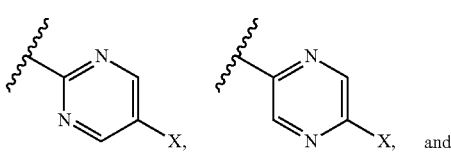

-continued

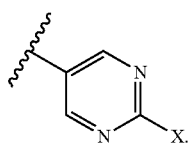

In a further aspect, Ar² is a structure represented by a formula:

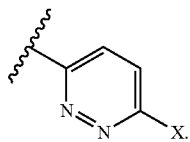

u. AR³ Groups

In one aspect, Ar³ is a structure selected from:

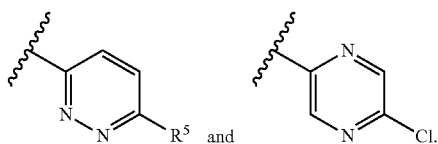

In a further aspect, Ar³ is:

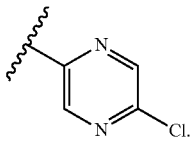 [SMILES: *c1cnc(Cl)cn1]

In a further aspect, Ar³ is:

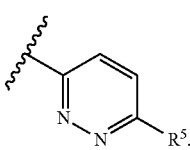

In a further aspect, Ar³ is:

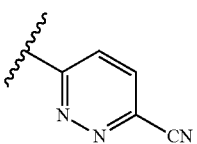 [SMILES: *c1ccc(C#N)nn1]

In a further aspect, Ar³ is:

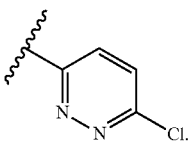 [SMILES: *c1ccc(Cl)nn1]

v. CY¹ Groups

In one aspect, Cy¹, when present, is selected from cycle, heterocycle, aryl, and heteroaryl and substituted with 0, 1, 2, or 3 groups independently selected from halogen, —NO₂, —CN, —OH, —SH, —NH₂, C1-C4 alkyl, C1-C4 monohaloalkyl, C1-C4 polyhaloalkyl, C1-C4 alkoxy, C1-C4 alkylamino, and (C1-C4)(C1-C4)dialkylamino.

In one aspect, Cy¹, when present, is selected from cycloalkyl, heterocycloalkyl, aryl, and heteroaryl and substituted with 0, 1, 2, or 3 groups independently selected from halogen, —NO₂, —CN, —OH, —SH, —NH₂, C1-C4 alkyl, C1-C4 monohaloalkyl, C1-C4 polyhaloalkyl, C1-C4 alkoxy, C1-C4 alkylamino, and (C1-C4)(C1-C4)dialkylamino.

In a further aspect, Cy¹, when present, is selected from cycloalkyl, heterocycloalkyl, aryl, and heteroaryl and substituted with 0, 1, or 2 groups independently selected from halogen, —NO₂, —CN, —OH, —SH, —NH₂, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, Cy¹, when present, is selected from cycloalkyl, heterocycloalkyl, aryl, and heteroaryl and substituted with 0 or 1 group selected from halogen, —NO₂, —CN, —OH, —SH, —NH₂, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, Cy¹, when present, is selected from cycloalkyl, heterocycloalkyl, aryl, and heteroaryl and monosubstituted with a group selected from halogen, —NO₂, —CN, —OH, —SH, —NH₂, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, Cy¹, when present, is selected from cycloalkyl, heterocycloalkyl, aryl, and heteroaryl and unsubstituted.

In a further aspect, Cy¹, when present, is selected from cyclopropyl, imidazolyl, pyrazolyl, pyrrolyl, piperidinyl, morpholinyl, and piperazinyl and substituted with 0, 1, 2, or 3 groups independently selected from halogen, —NO₂, —CN, —OH, —SH, —NH₂, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, Cy¹, when present, is selected from cyclopropyl, imidazolyl, pyrazolyl, pyrrolyl, piperidinyl, morpholinyl, and piperazinyl and substituted with 0, 1, or 2 groups independently selected from halogen, —NO₂, —CN, —OH, —SH, —NH₂, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, Cy¹, when present, is selected from cyclopropyl, imidazolyl, pyrazolyl, pyrrolyl, piperidinyl, morpholinyl, and piperazinyl and substituted with 0 or 1 group selected from halogen, —NO₂, —CN, —OH, —SH, —NH₂, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, Cy¹, when present, is selected from cyclopropyl, imidazolyl, pyrazolyl, pyrrolyl, piperidinyl, morpholinyl, and piperazinyl and monosubstituted with a group selected from halogen, —NO₂, —CN, —OH, —SH, —NH₂, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, $Cy^1$, when present, is selected from cyclopropyl, imidazolyl, pyrazolyl, pyrrolyl, piperidinyl, morpholinyl, and piperazinyl and unsubstituted.

In a further aspect, $Cy^1$, when present, is selected from cycloalkyl and heterocycloalkyl and substituted with 0, 1, or 2 groups independently selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, $Cy^1$, when present, is selected from cycloalkyl and heterocycloalkyl and substituted with 0 or 1 group selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, $Cy^1$, when present, is selected from cycloalkyl and heterocycloalkyl and monosubstituted with a group selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, $Cy^1$, when present, is selected from cycloalkyl and heterocycloalkyl and unsubstituted.

In a further aspect, $Cy^1$, when present, is cycloalkyl substituted with 0, 1, or 2 groups independently selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, $Cy^1$, when present, is cycloalkyl substituted with 0 or 1 group selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, $Cy^1$, when present, is cycloalkyl monosubstituted with a group selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, $Cy^1$, when present, is unsubstituted cycloalkyl.

In a further aspect, $Cy^1$, when present, is cyclopropyl substituted with 0, 1, or 2 groups independently selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, $Cy^1$, when present, is cyclopropyl substituted with 0 or 1 group selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, $Cy^1$, when present, is cyclopropyl monosubstituted with a group selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, $Cy^1$, when present, is unsubstituted cyclopropyl.

In a further aspect, $Cy^1$, when present, is heterocycloalkyl substituted with 0, 1, or 2 groups independently selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, Cy', when present, is heterocycloalkyl substituted with 0 or 1 group selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, $Cy^1$, when present, is heterocycloalkyl monosubstituted with a group selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, $Cy^1$, when present, is unsubstituted heterocycloalkyl.

In a further aspect, $Cy^1$, when present, is morpholinyl substituted with 0, 1, or 2 groups independently selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, $Cy^1$, when present, is morpholinyl substituted with 0 or 1 group selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, $Cy^1$, when present, is morpholinyl monosubstituted with a group selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, $Cy^1$, when present, is unsubstituted morpholinyl.

In a further aspect, $Cy^1$, when present, is piperidinyl substituted with 0, 1, or 2 groups independently selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, $Cy^1$, when present, is piperidinyl substituted with 0 or 1 group selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, $Cy^1$, when present, is piperidinyl monosubstituted with a group selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, $Cy^1$, when present, is unsubstituted piperidinyl.

In a further aspect, $Cy^1$, when present, is piperazinyl substituted with 0, 1, or 2 groups independently selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, $Cy^1$, when present, is piperazinyl substituted with 0 or 1 group selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, $Cy^1$, when present, is piperazinyl monosubstituted with a group selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, $Cy^1$, when present, is unsubstituted piperazinyl.

In a further aspect, $Cy^1$, when present, is selected from aryl and heteroaryl and substituted with 0, 1, or 2 groups independently selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, $Cy^1$, when present, is selected from aryl and heteroaryl and substituted with 0 or 1 group selected from halogen, —$NO_2$, —CN, —OH, —SH, —$NH_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, Cy$^1$, when present, is selected from aryl and heteroaryl and monosubstituted with a group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, Cy$^1$, when present, is selected from aryl and heteroaryl and unsubstituted.

In a further aspect, Cy$^1$, when present, is aryl substituted with 0, 1, or 2 groups independently selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, Cy$^1$, when present, is aryl substituted with 0 or 1 group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, Cy$^1$, when present, is aryl monosubstituted with a group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, Cy$^1$, when present, is unsubstituted aryl.

In a further aspect, Cy$^1$, when present, is heteroaryl substituted with 0, 1, or 2 groups independently selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, Cy$^1$, when present, is heteroaryl substituted with 0 or 1 group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, Cy$^1$, when present, is heteroaryl monosubstituted with a group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, Cy$^1$, when present, is unsubstituted heteroaryl.

In a further aspect, Cy$^1$, when present, is imidazolyl substituted with 0, 1, or 2 groups independently selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, Cy$^1$, when present, is imidazolyl substituted with 0 or 1 group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, Cy$^1$, when present, is imidazolyl monosubstituted with a group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, Cy$^1$, when present, is unsubstituted imidazolyl.

In a further aspect, Cy$^1$, when present, is pyrazolyl substituted with 0, 1, or 2 groups independently selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, Cy$^1$, when present, is pyrazolyl substituted with 0 or 1 group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, Cy$^1$, when present, is pyrazolyl monosubstituted with a group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, Cy$^1$, when present, is unsubstituted pyrazolyl.

In a further aspect, Cy$^1$, when present, is pyrrolyl substituted with 0, 1, or 2 groups independently selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In a still further aspect, Cy$^1$, when present, is pyrrolyl substituted with 0 or 1 group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In yet a further aspect, Cy$^1$, when present, is pyrrolyl monosubstituted with a group selected from halogen, —NO$_2$, —CN, —OH, —SH, —NH$_2$, C1-C4 alkyl, C1-C4 monohaloalkyl, C1-C4 polyhaloalkyl, C1-C4 alkoxy, C1-C4 alkylamino, and (C1-C4)(C1-C4)dialkylamino. In an even further aspect, Cy$^1$, when present, is unsubstituted pyrrolyl.

2. Example Compounds

In one aspect, a compound can be present as one or more of the following structures:

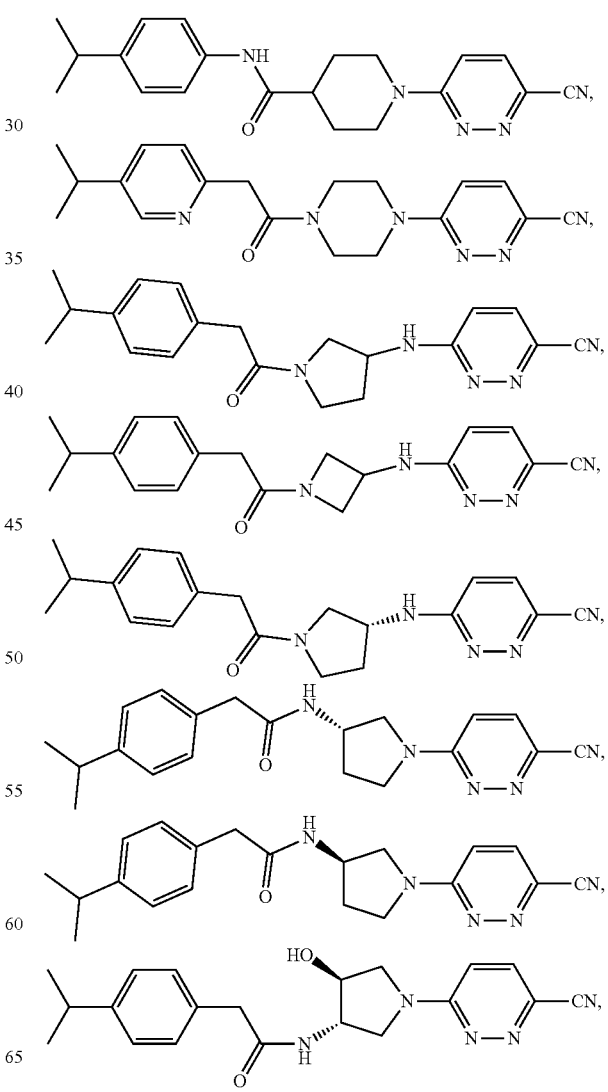

157
-continued
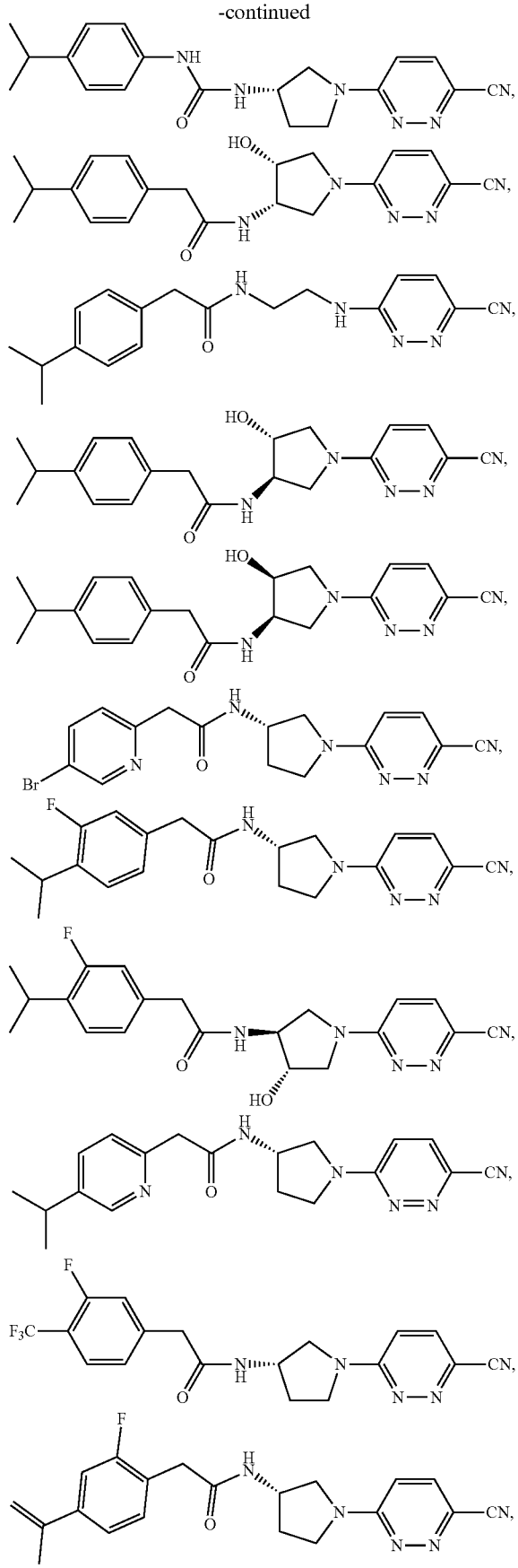
158
-continued
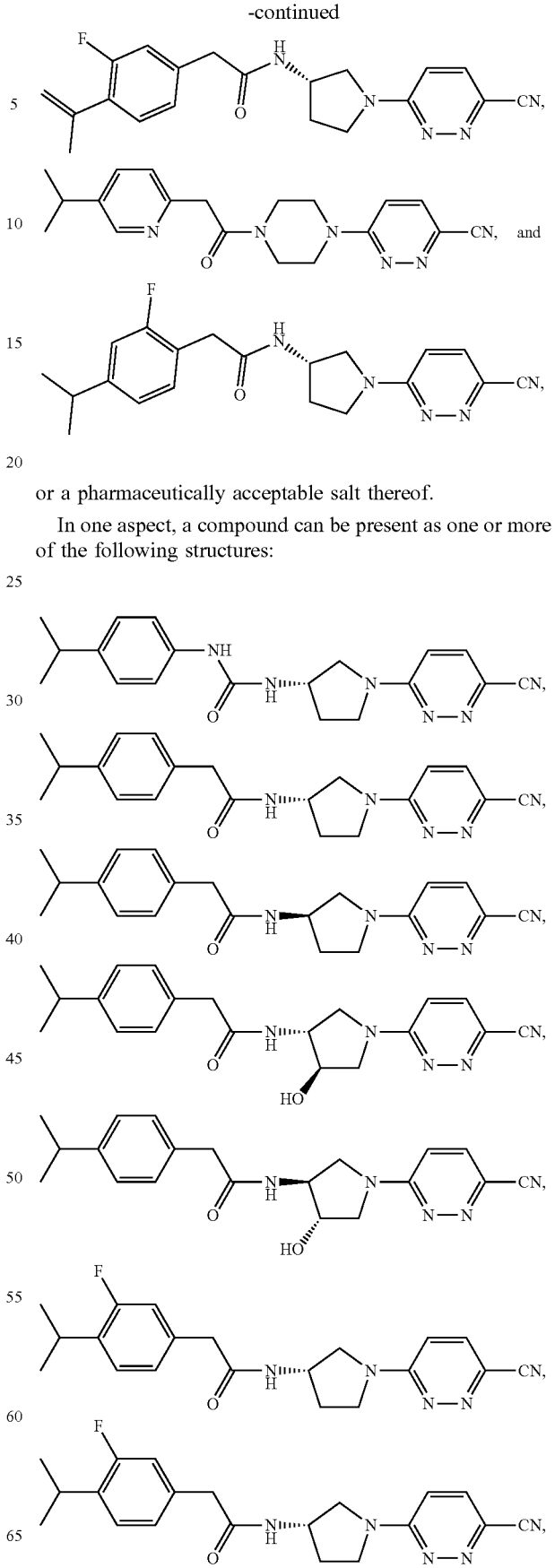
or a pharmaceutically acceptable salt thereof.
In one aspect, a compound can be present as one or more of the following structures:

-continued
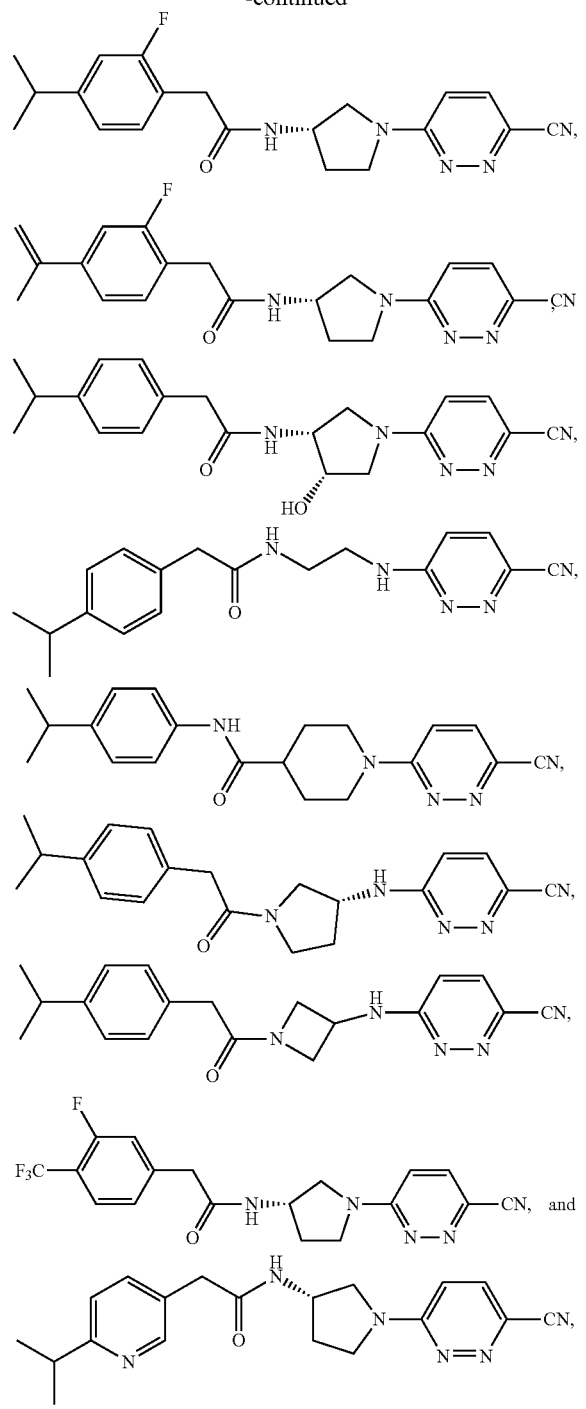
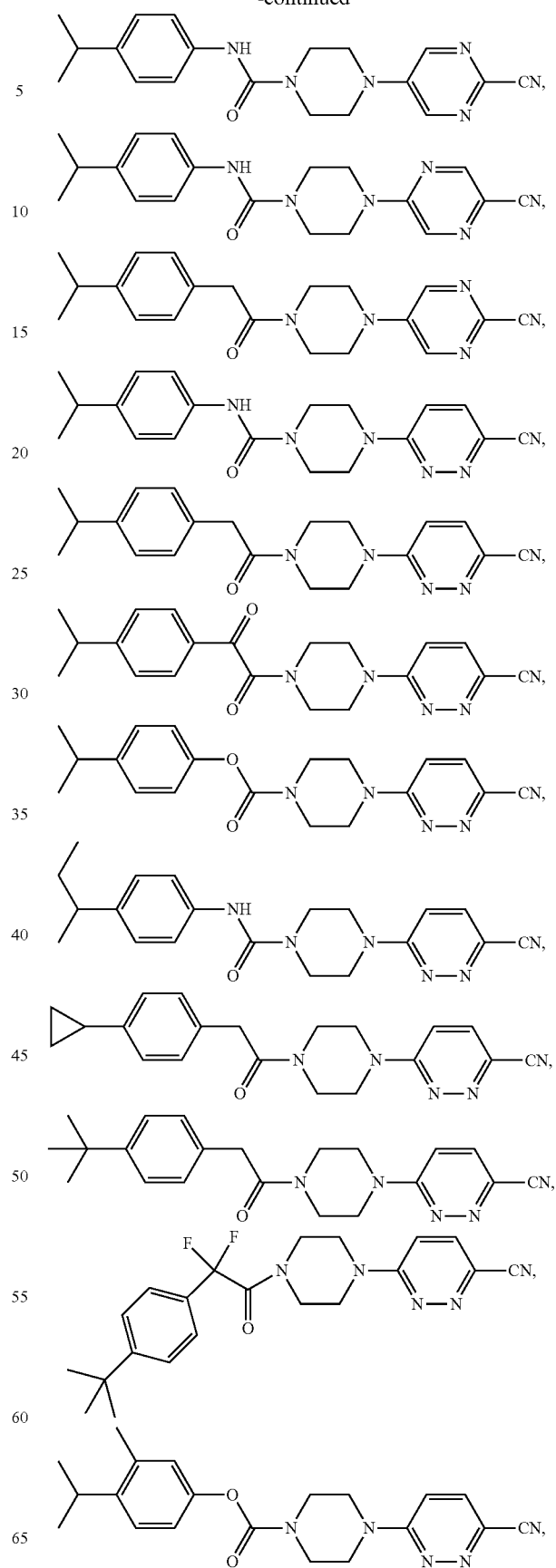
or a pharmaceutically acceptable salt thereof.
In one aspect, a compound can be present as one or more of the following structures:
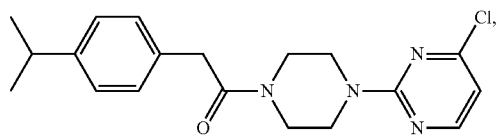
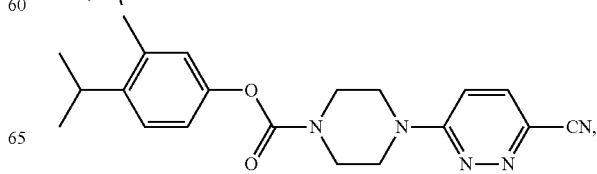

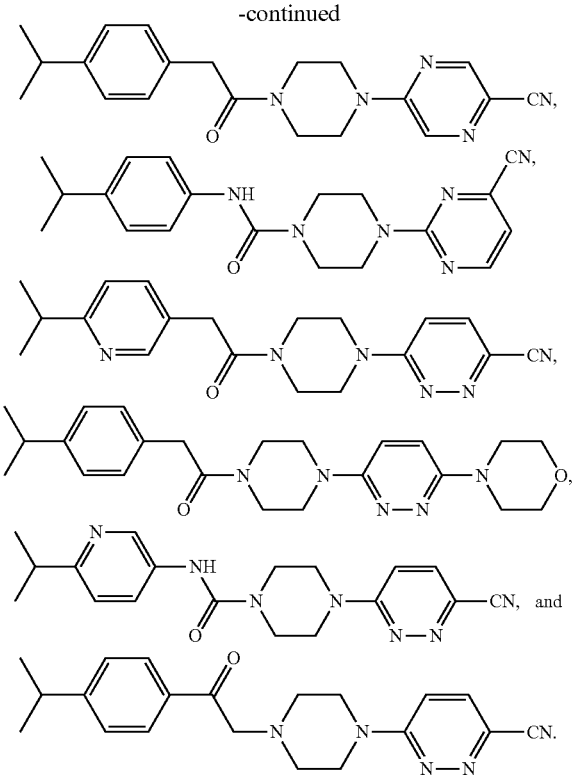

or a pharmaceutically acceptable derivative thereof.

In one aspect, a compound can be present as one or more of the following structures:

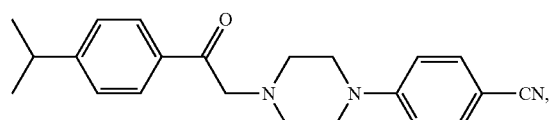

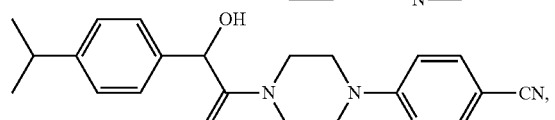

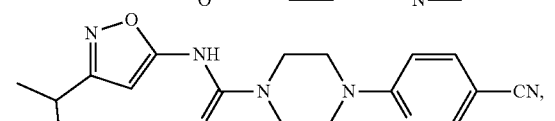

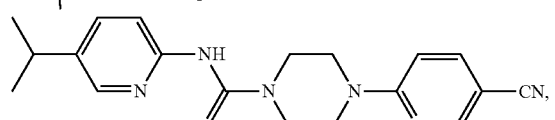

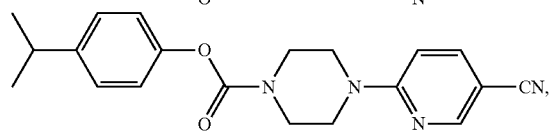

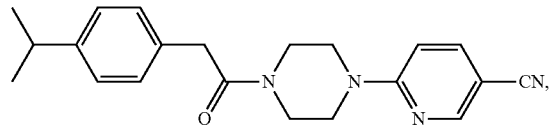

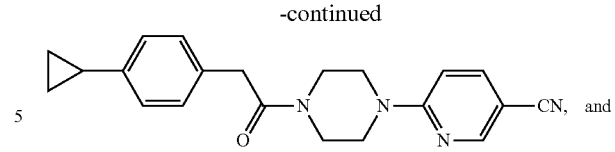

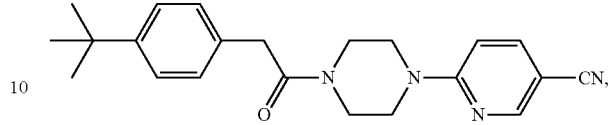

or a pharmaceutically acceptable derivative thereof.

In one aspect, a compound can be present as one or more of the following structures:

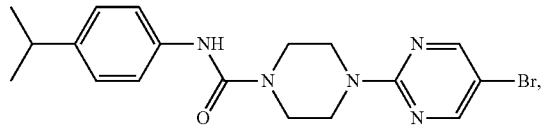

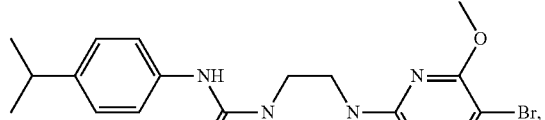

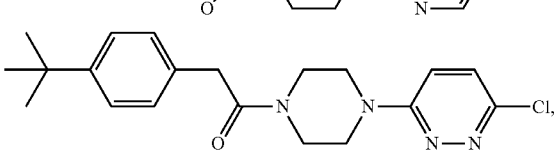

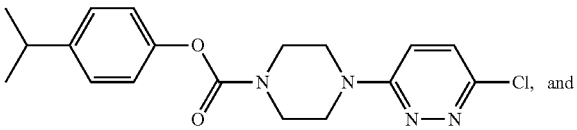

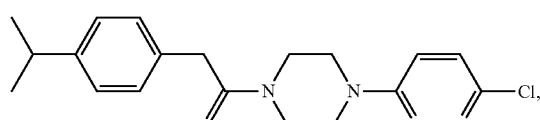

or a pharmaceutically acceptable salt thereof.

In one aspect, a compound can be present as one or more of the following structures:

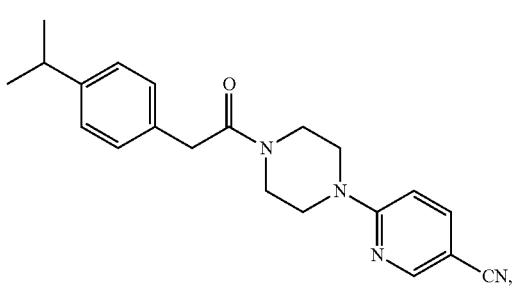

163
-continued
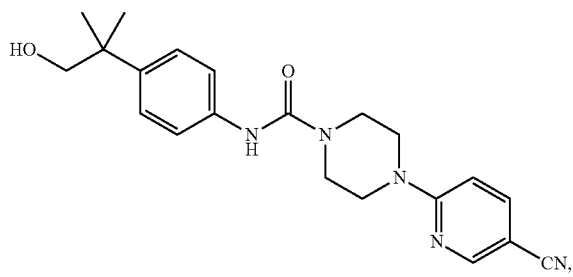
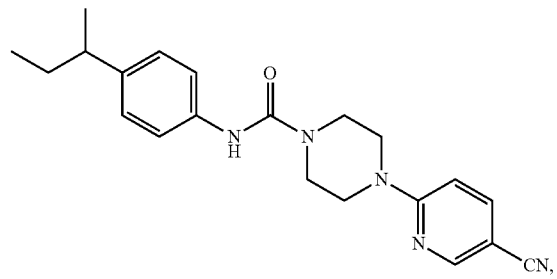
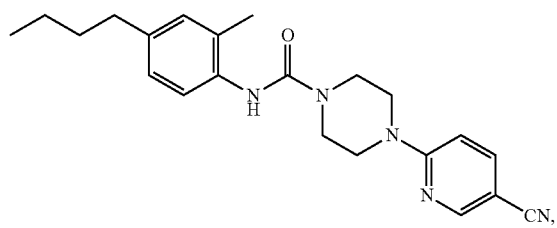
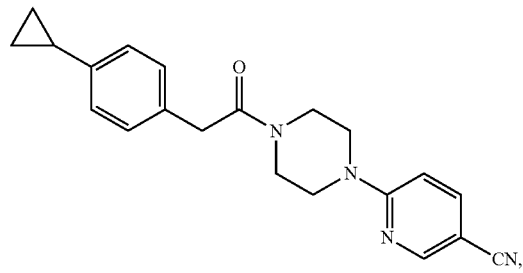
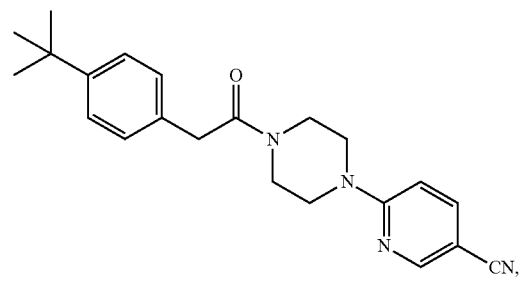
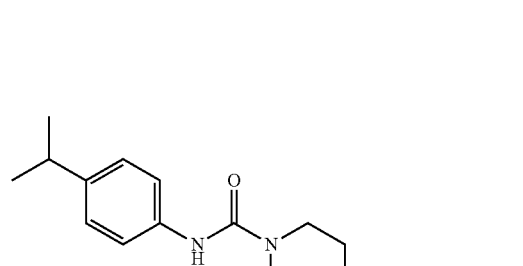
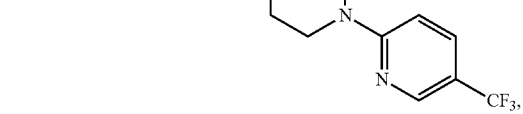
164
-continued
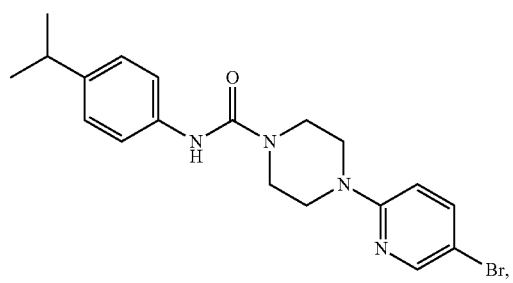
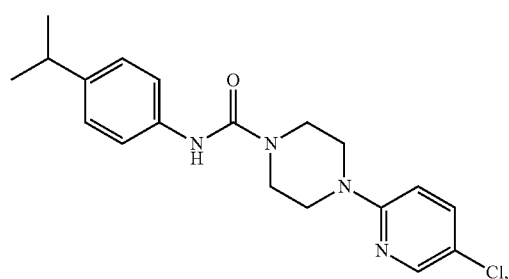
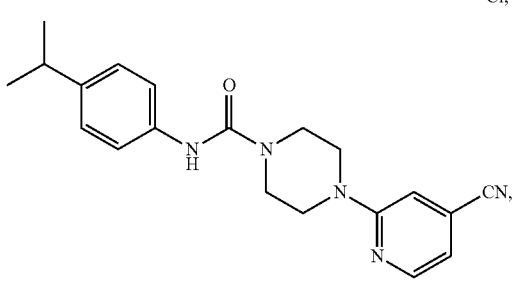
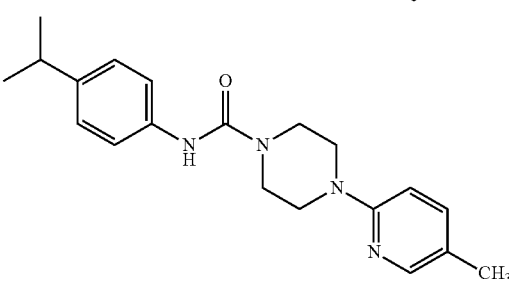
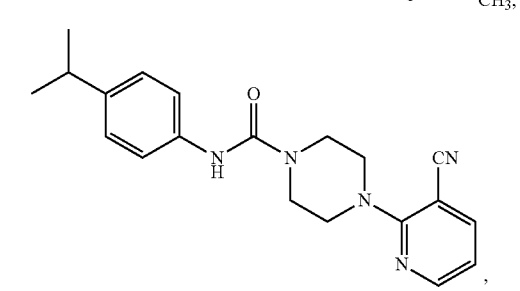
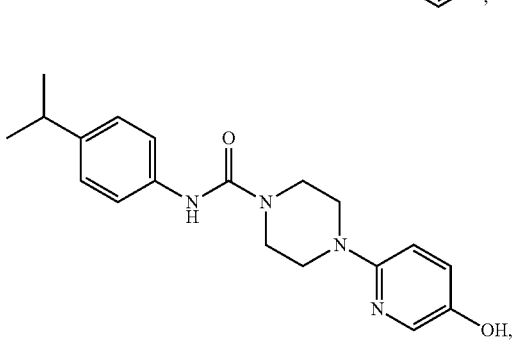

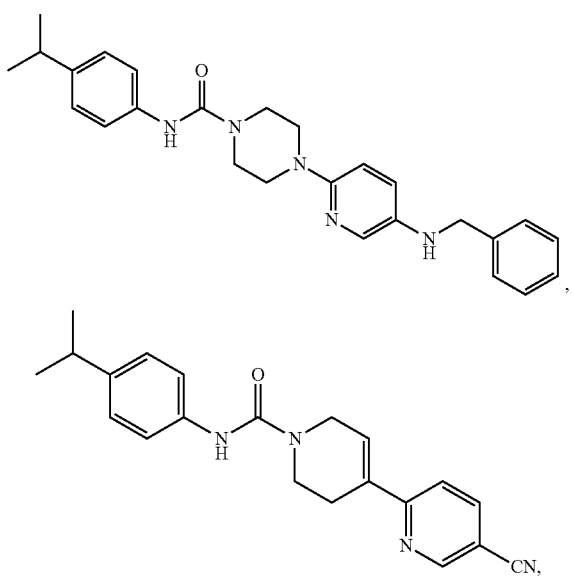
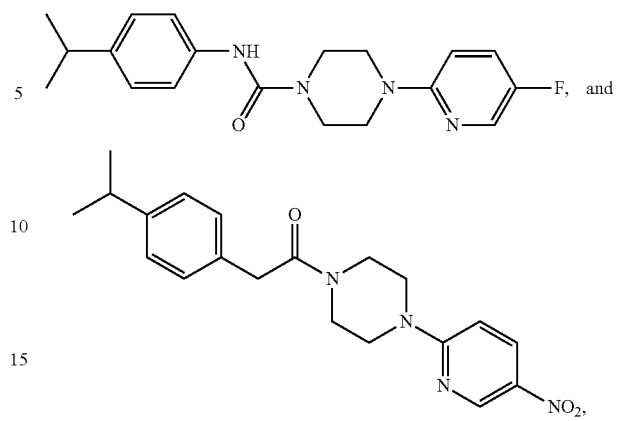
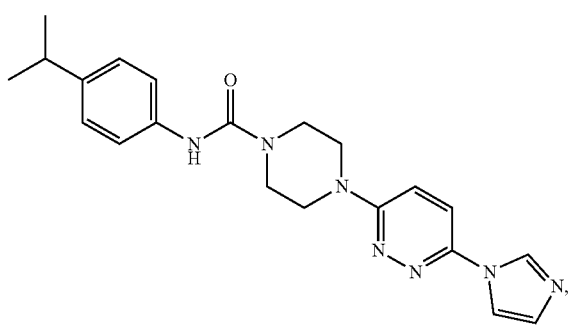
or a pharmaceutically acceptable salt thereof.
In one aspect, a compound can be present as one or more of the following structures:
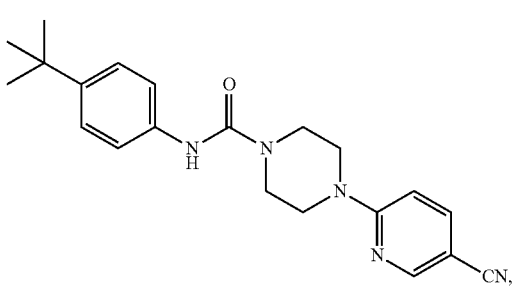
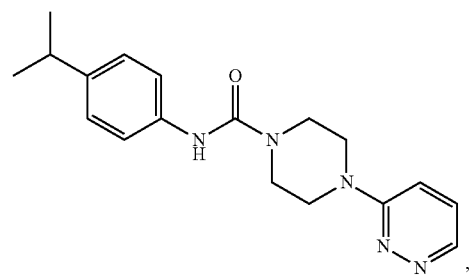
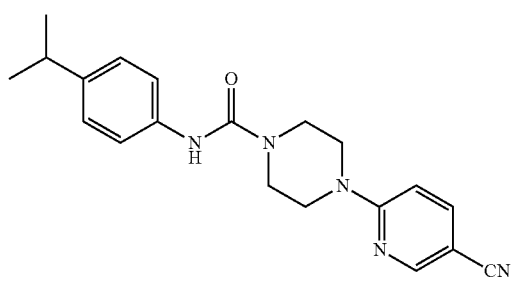
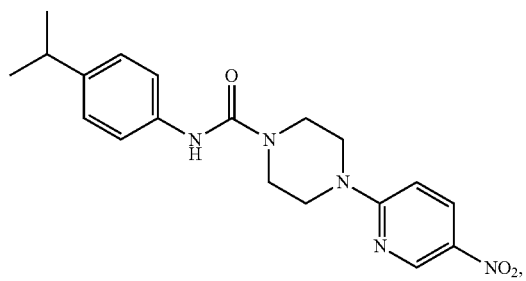
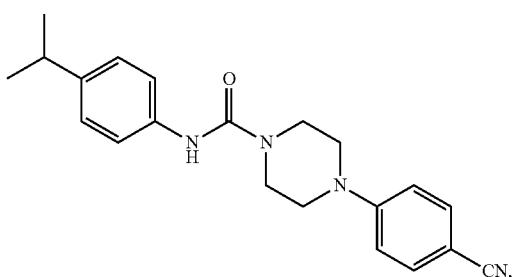
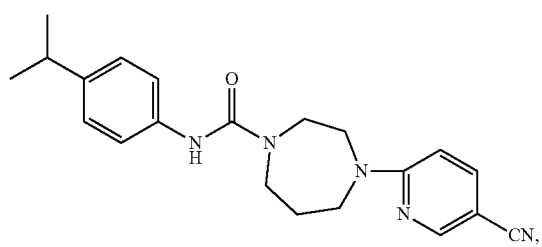
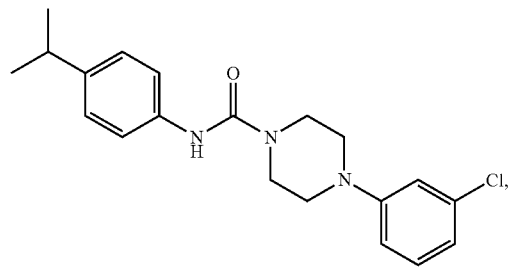

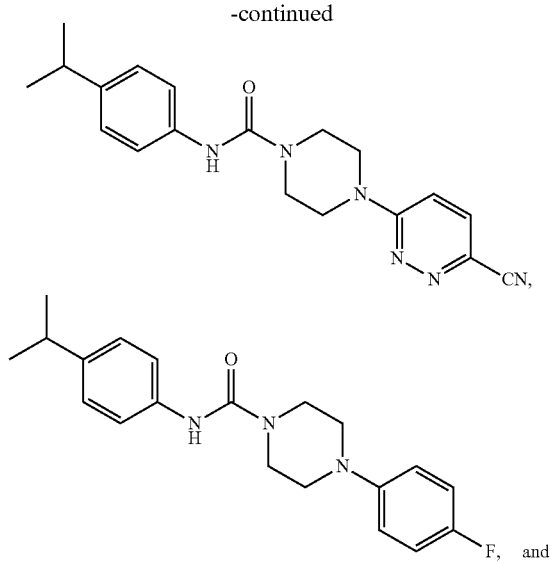
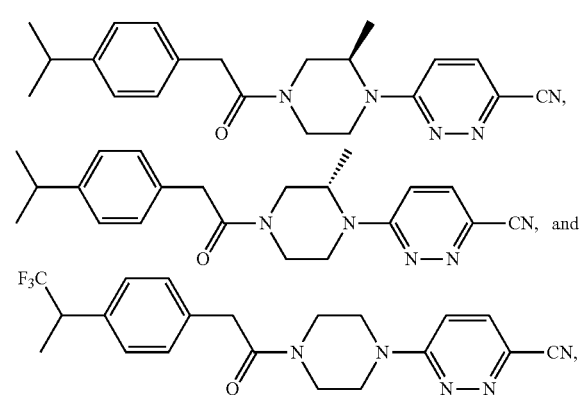
or a pharmaceutically acceptable salt thereof.
In one aspect, a compound can be present as one or more of the following structures:
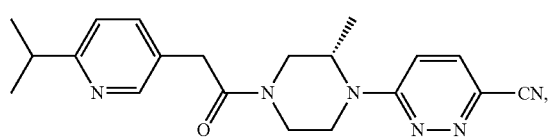
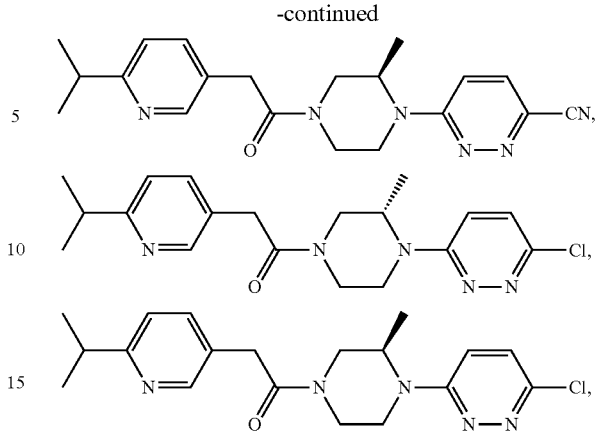
or a pharmaceutically acceptable salt thereof.
In one aspect, a compound can be present as one or more of the following structures:
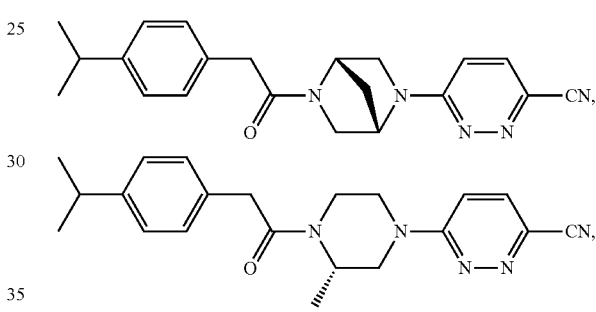
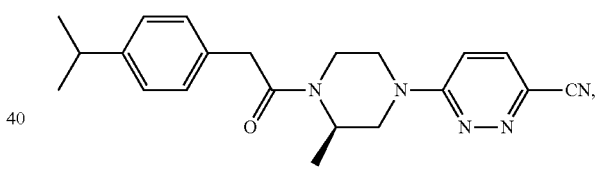
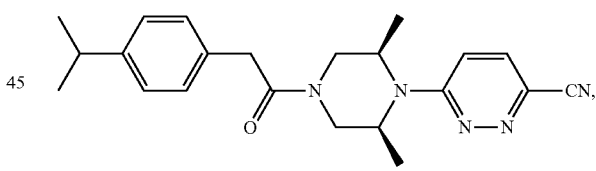
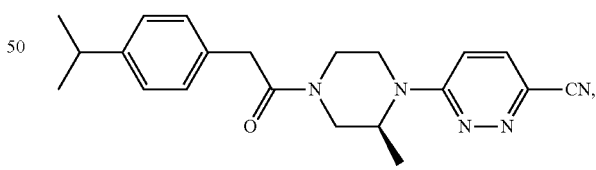
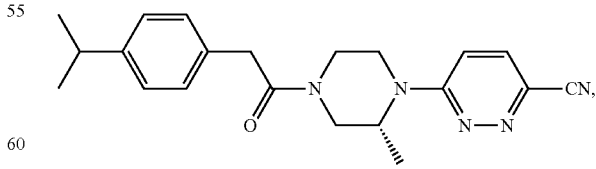

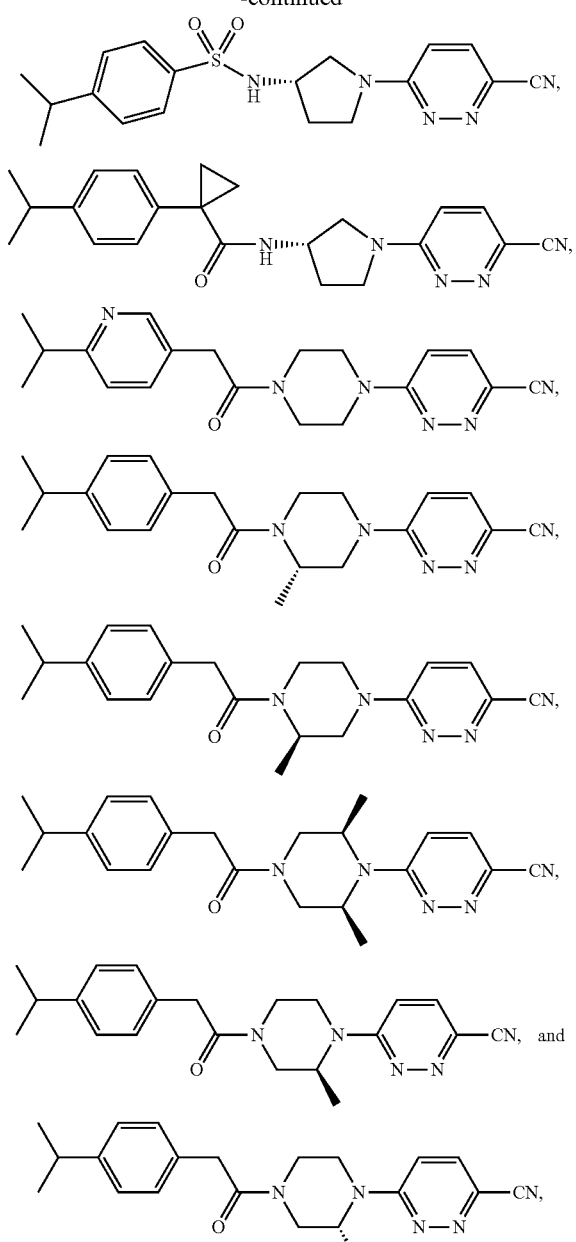
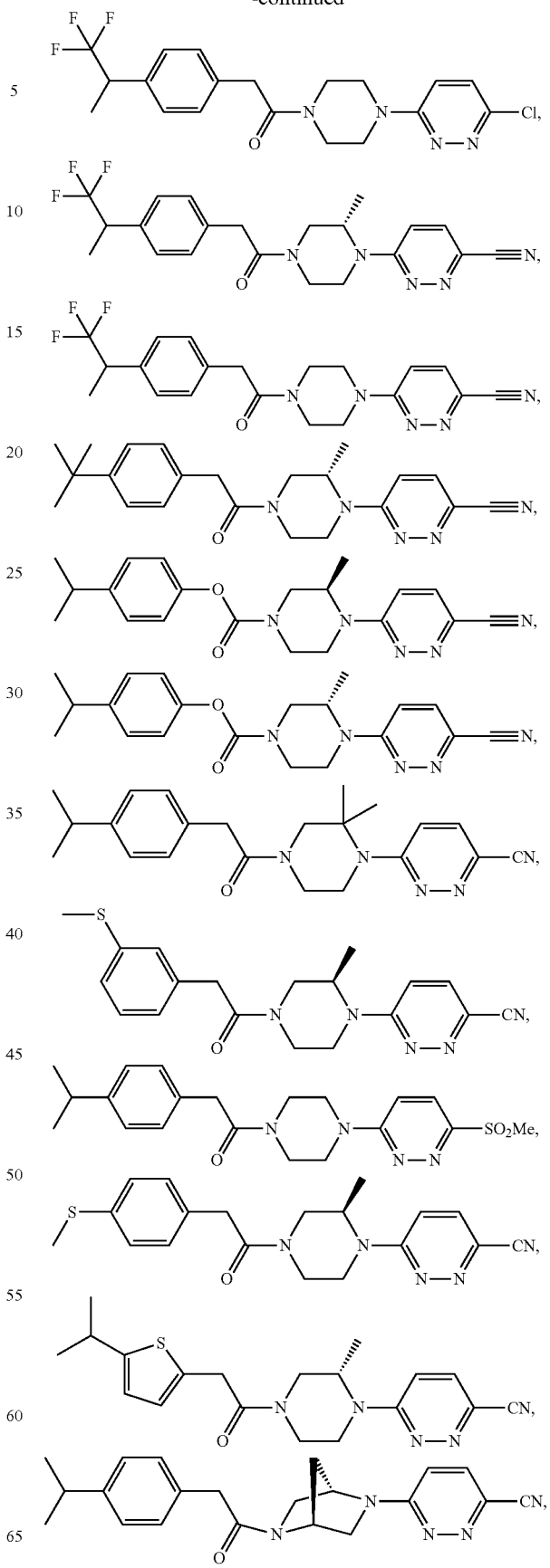
or a pharmaceutically acceptable salt thereof.
In one aspect, a compound can be present as one or more of the following structures:

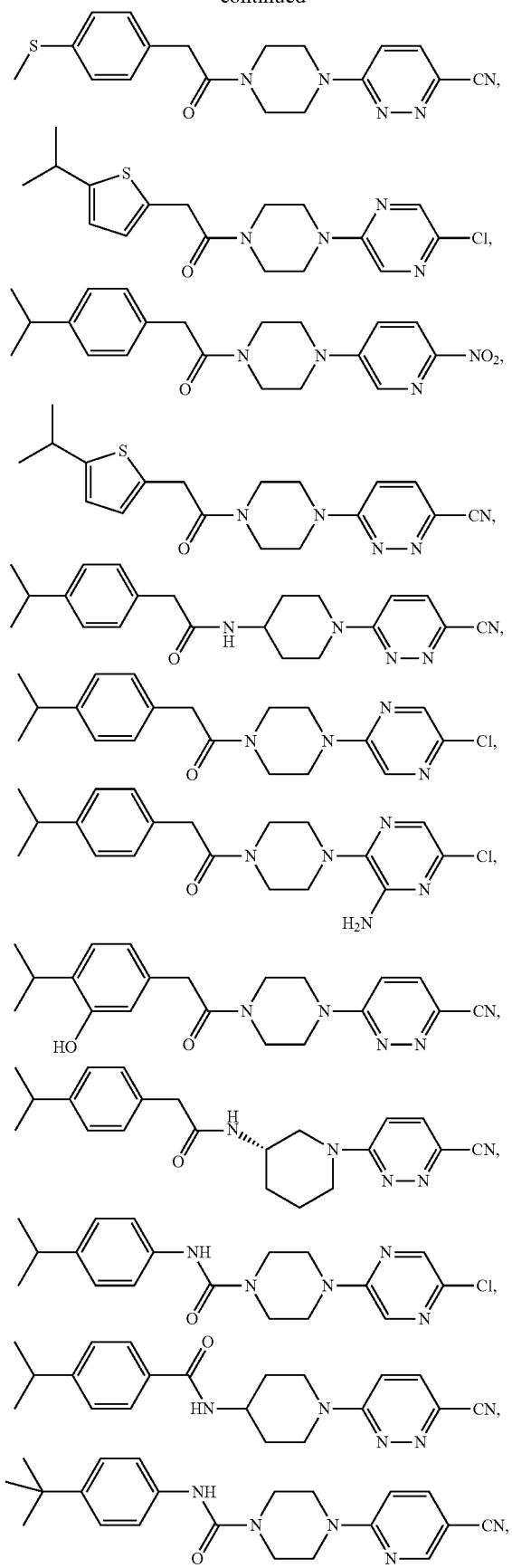
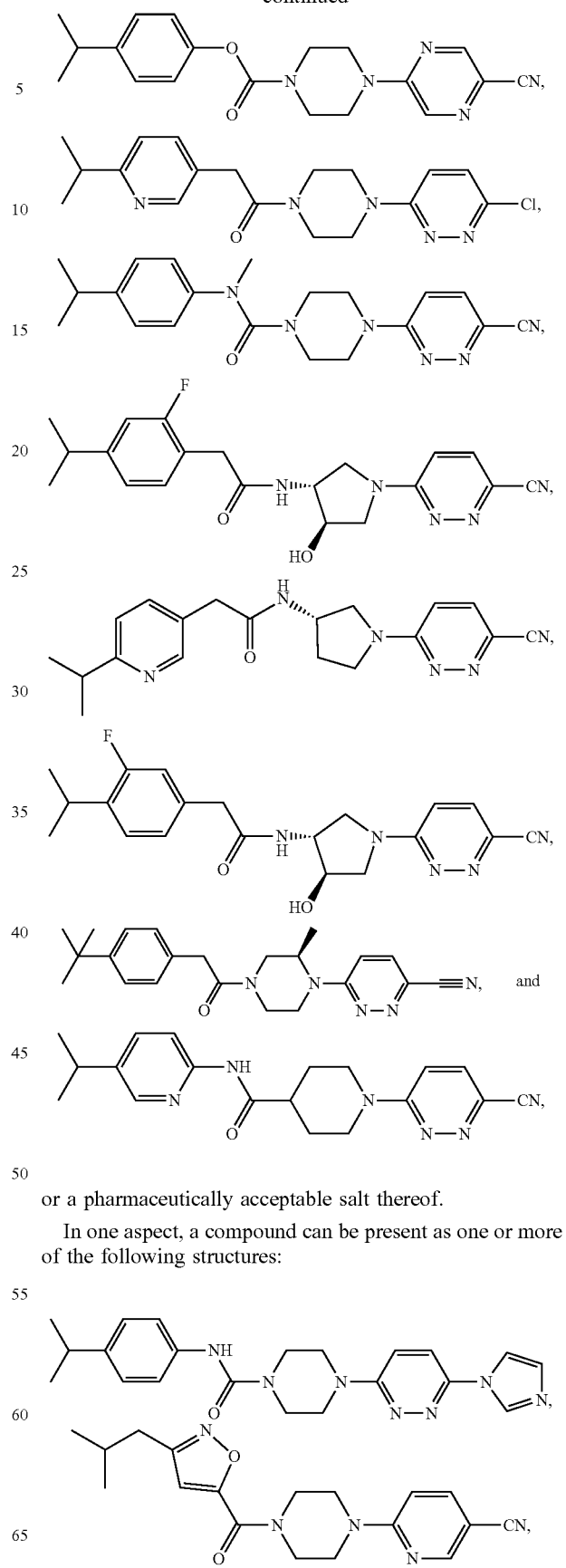
or a pharmaceutically acceptable salt thereof.
In one aspect, a compound can be present as one or more of the following structures:
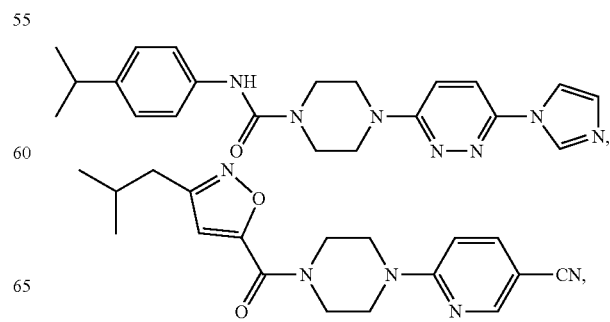

-continued
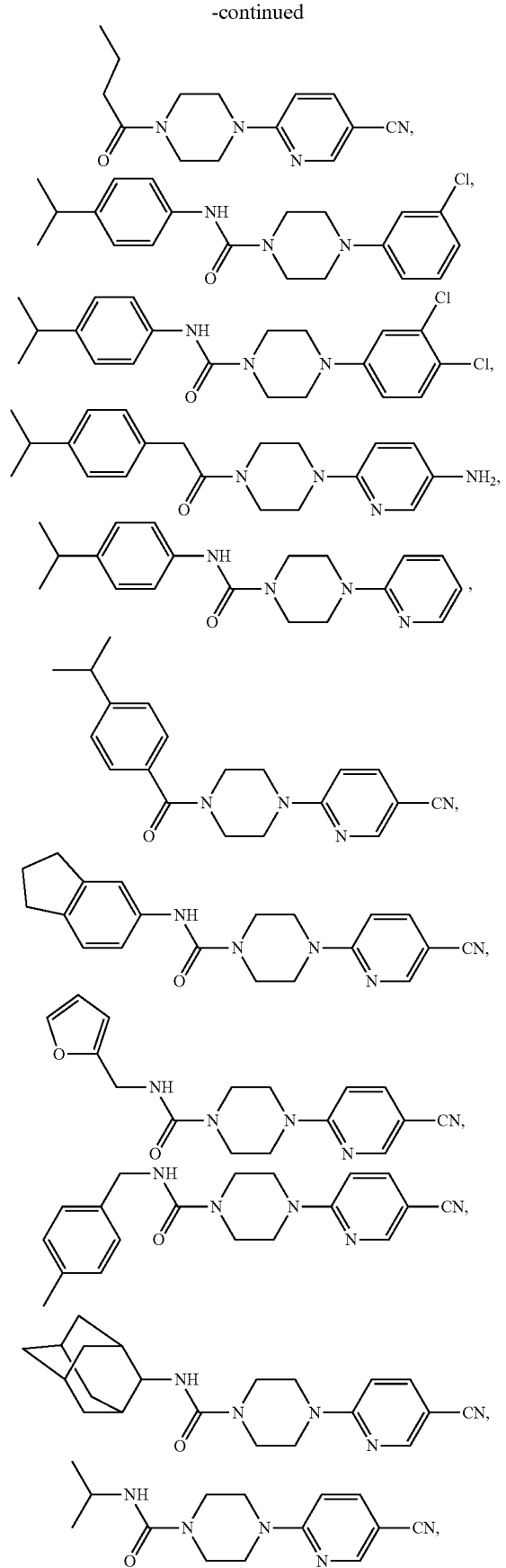
-continued
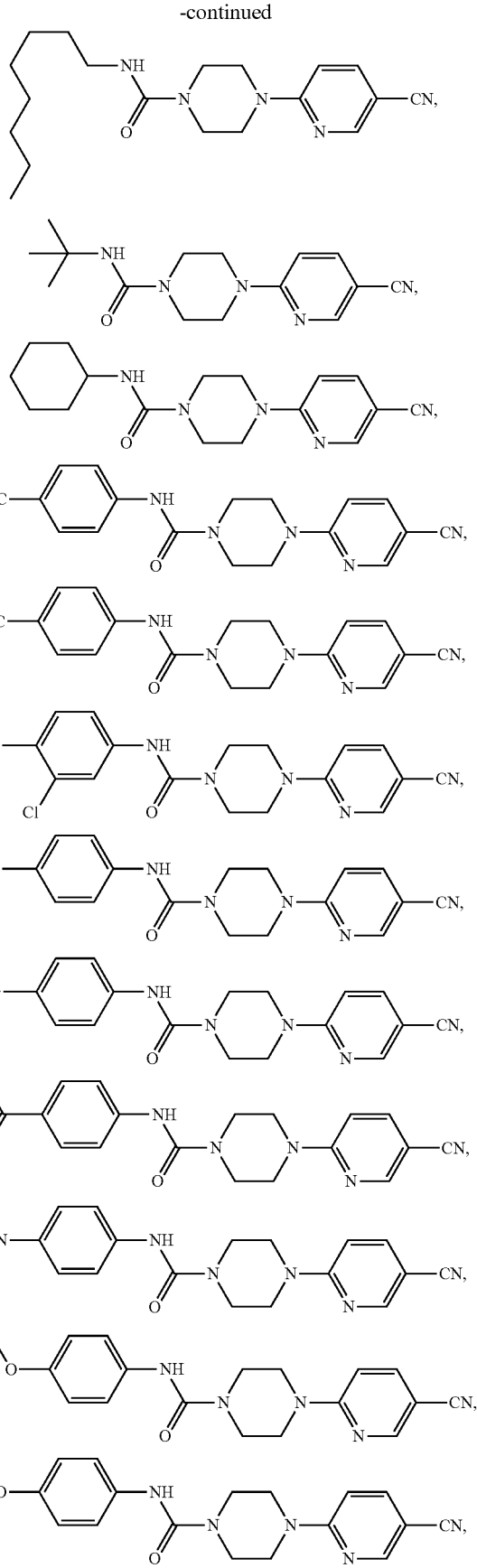

175
-continued

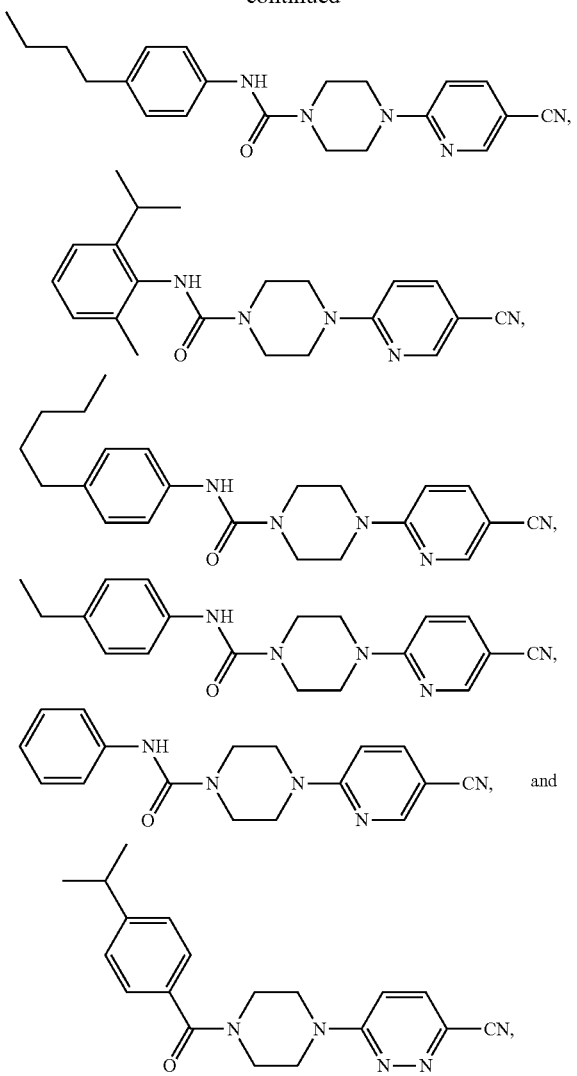

or a pharmaceutically acceptable salt thereof.

In one aspect, a compound can be:

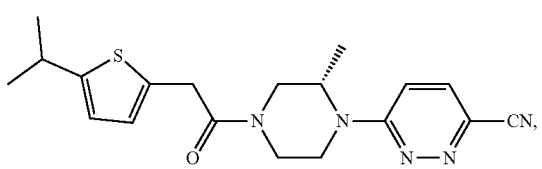 [SMILES: CC(C)c1ccc(CC(=O)N2CCN(c3ccc(C#N)nn3)[C@@H](C)C2)s1]

or a pharmaceutically acceptable salt thereof.

In one aspect, a compound can be:

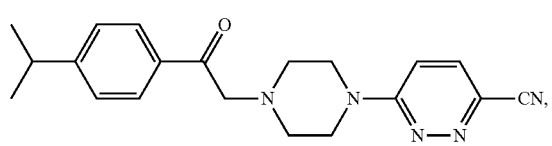 [SMILES: CC(C)c1ccc(C(=O)CN2CCN(c3ccc(C#N)nn3)CC2)cc1]

or a pharmaceutically acceptable salt thereof.

176

In one aspect, a compound can be:

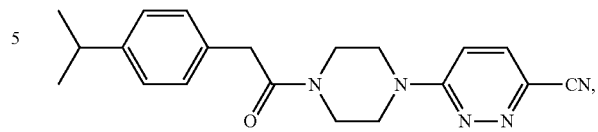

or a pharmaceutically acceptable salt thereof.

In one aspect, a compound can be present as one or more of the following structures:

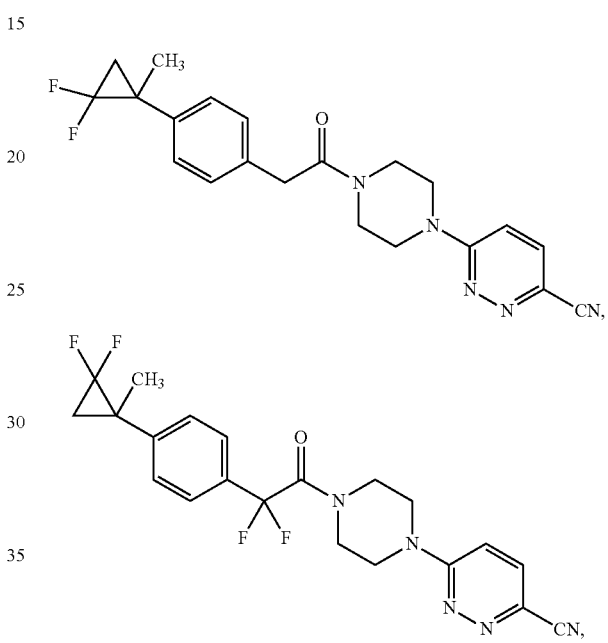

or a pharmaceutically acceptable salt thereof.

In one aspect, a compound can be present as the following structure:
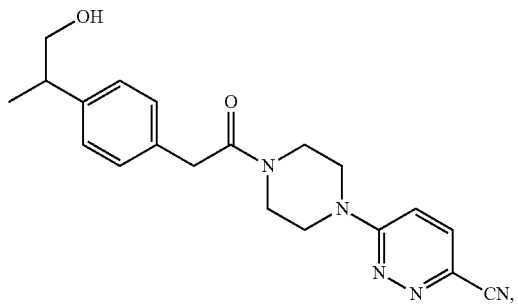 [SMILES: CC(CO)c1ccc(CC(=O)N2CCN(c3ccc(C#N)nn3)CC2)cc1]
or a pharmaceutically acceptable salt thereof.
In one aspect, a compound can be present as one or more of the following structures:
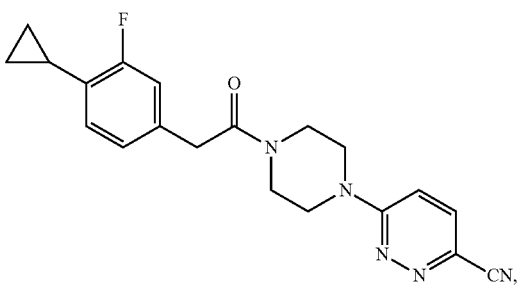
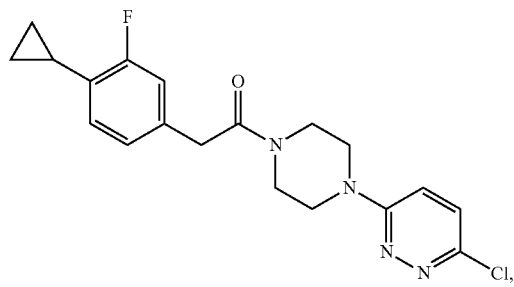
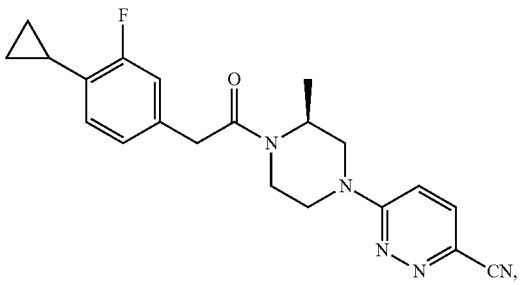
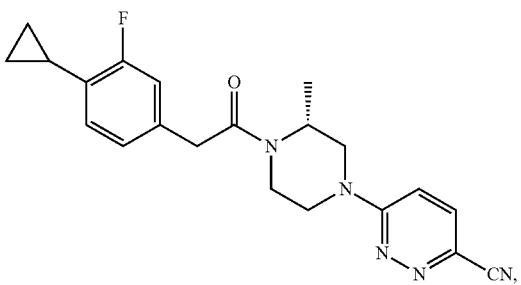
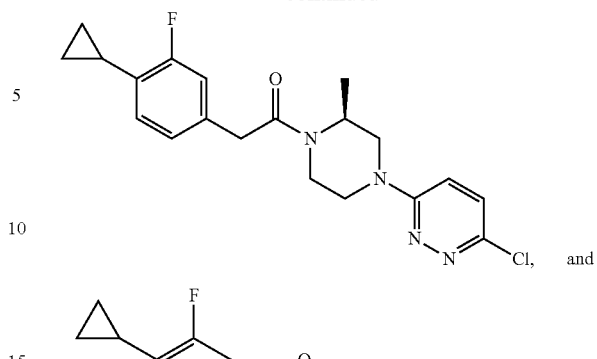
or a pharmaceutically acceptable salt thereof.
In a further aspect, a compound can be present as one or more of the following structures:
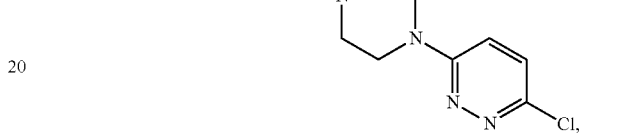

179

-continued

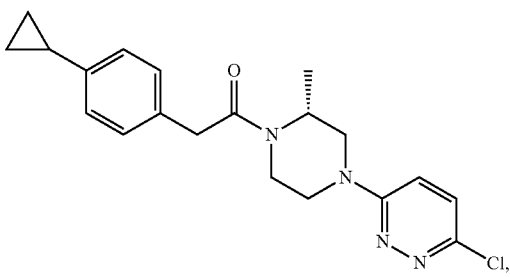

or a pharmaceutically acceptable salt thereof.

D. METHODS OF MAKING A COMPOUND

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Route I and Route II, as described and exemplified below. The following examples are provided so that the invention might be more fully understood, are illustrative only, and should not be construed as limiting.

1. Route I

In one aspect, substituted 4-(5-cyanopyridin-2-yl)-N-arylpiperazine-1-carboxamide derivatives and substituted 4-(5-cyanopyridin-2-yl)-N-arylpiperazine-1-carbothioamide derivatives can be prepared as shown below.

SCHEME 1A.

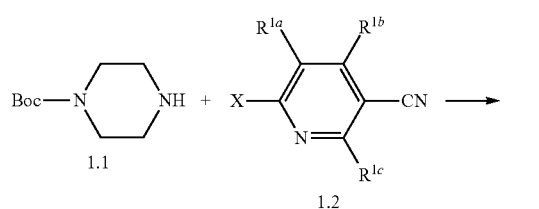

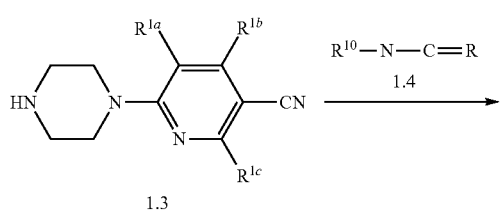

180

-continued

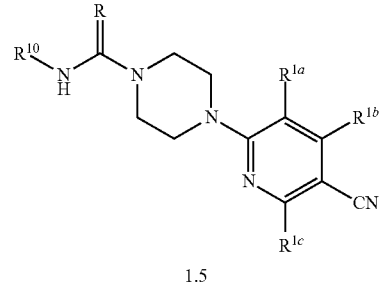

1.5

Compounds are represented in generic form, with substituents as noted in compound descriptions elsewhere herein; wherein X is halogen, wherein $R^{10}$ is akyl, aryl, or heteroaryl; and wherein R is selected from O and S. A more specific example is set forth below.

SCHEME 1B.

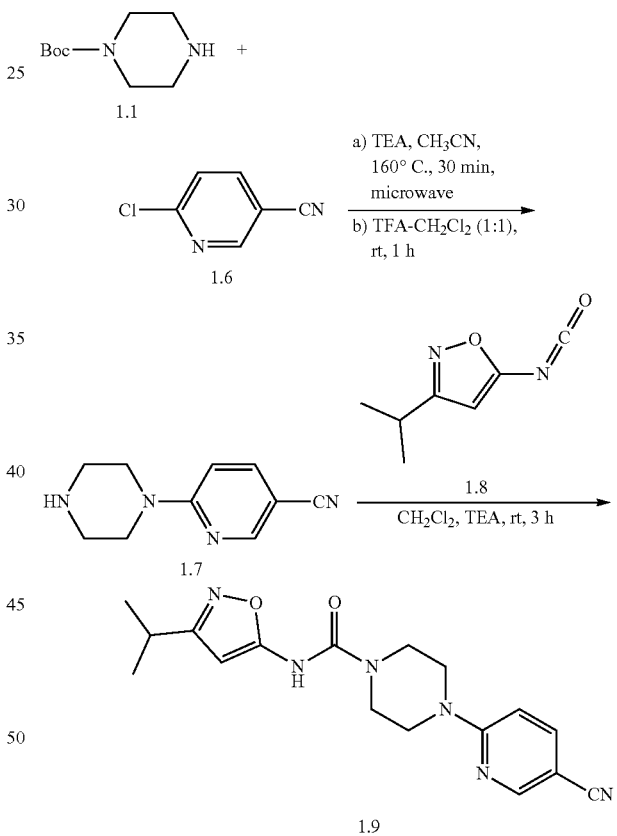

In one aspect, compounds of type 1.9, and similar compounds, can be prepared according to reaction Scheme 1B above. Thus, compounds of type 1.7 are either commercially available or can be prepared by an arylation reaction of an appropriate amine, e.g., 1.1 as shown above, and an appropriate aryl halide, e.g., 1.6 as shown above. Appropriate amines and appropriate aryl halides are commercially available or prepared by methods known to one skilled in the art. The arylation reaction is carried out in the presence of an appropriate base, e.g., triethylamine (TEA), in an appropriate solvent, e.g., acetonitrile, at an appropriate temperature, e.g., 160° C., for an appropriate period of time, e.g., 30 minutes using microwave irradiation. The arylation reaction is followed by a deprotection. The deprotection is carried out in the presence of an appropriate deprotecting agent, e.g., trifluoroacetic acid (TFA), in an appropriate solvent, e.g., dichloromethane, for an appropriate period of time, e.g., 1 hour. Compounds of type 1.9 can be prepared by reaction between an appropriate piperazine, e.g., 1.7 as shown above, and an appropriate isocyanate or isothiocyanate, e.g., 1.8 as shown above. Appropriate isocyanates and isothiocyanates are commercially available or prepared by methods known to one skilled in the art. The urea or thiourea bond formation reaction is carried out in the presence or absence of an appropriate base, e.g., triethylamine, in an appropriate solvent, e.g., dichloromethane or diethyl ether, for an appropriate period of time, e.g., 3 hours. As can be appreciated by one skilled in the art, the above reaction provides an example of a generalized approach wherein compounds similar in structure to the specific reactants above (compounds similar to compounds of type 1.1, 1.2, 1.3, and 1.4), can be substituted in the reaction to provide 4-(5-cyanopyridin-2-yl)-N-arylpiperazine-1-carboxamide derivatives and 4-(5-cyanopyridin-2-yl)-N-arylpiperazine-1-carbothioamide derivatives similar to Formula 1.5.

2. Route II

In one aspect, substituted 4-(5-cyanopyridin-2-yl)-arylpiperazine-1-carboxamide derivatives can be prepared as shown below.

SCHEME 2A.

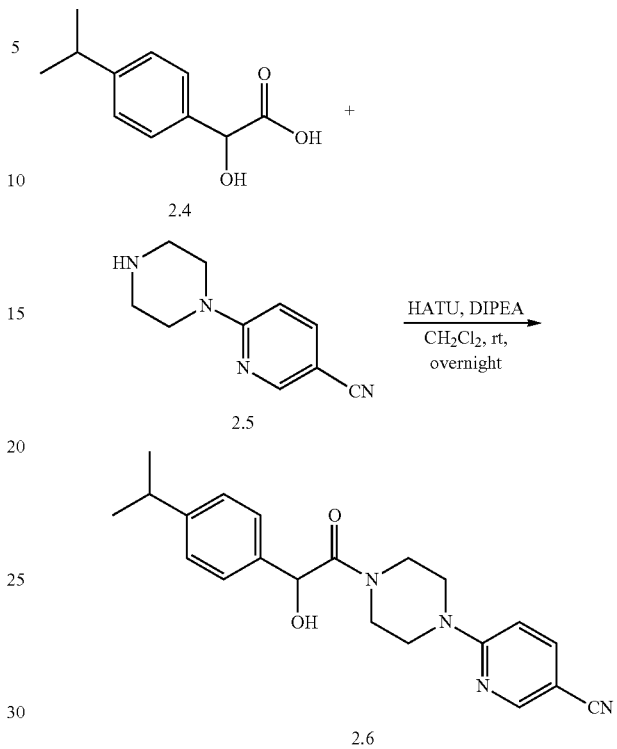

Compounds are represented in generic form, with substituents as noted in compound descriptions elsewhere herein and wherein A is either absent or selected from CH$_2$, CF$_2$, cyclopropyl, and CH(OH). A more specific example is set forth below.

In one aspect, compounds of type 2.6, and similar compounds, can be prepared according to reaction Scheme 2B above. Thus, compounds of type 2.6 can be prepared by a coupling reaction of an appropriate carboxylic acid, e.g., 2.4 as shown above, with an appropriate amine, e.g., 2.5 as shown above. Appropriate carboxylic acids and appropriate amines are commercially available or prepared by methods known to one skilled in the art. The coupling reaction is carried out in the presence of an appropriate coupling agent, e.g., 1-[bis(dimethylamino)methylene]-1H-1,2,3-triazolo[4,5-b]pyridinium 3-oxid hexafluorophosphate (HATU), and an appropriate base, e.g., diisopropylethylamine (DIPEA), in an appropriate solvent, e.g., dichloromethane. As can be appreciated by one skilled in the art, the above reaction provides an example of a generalized approach wherein compounds similar in structure to the specific reactants above (compounds similar to compounds of type 2.1 and 2.2), can be substituted in the reaction to provide 4-(5-cyanopyridin-2-yl)-N-arylpiperazine-1-carboxamide derivatives similar to Formula 2.3.

3. Route III

In one aspect, substituted phenyl 4-arylpiperazine-1-carboxylate derivatives can be prepared as shown below.

SCHEME 3A.

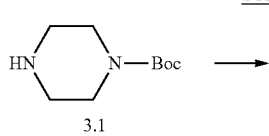

3.1

183
-continued

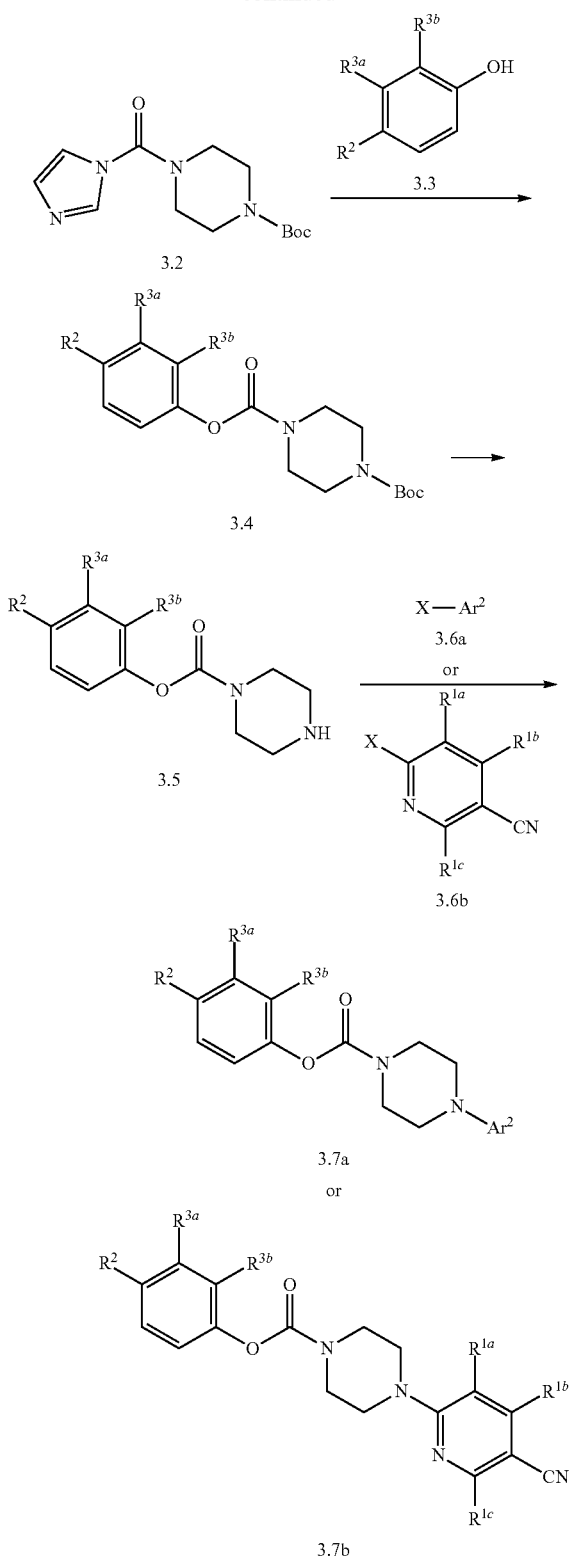

Compounds are represented in generic form, with substituents as noted in compound descriptions elsewhere herein and wherein X is halogen. A more specific example is set forth below.

184

SCHEME 3B.

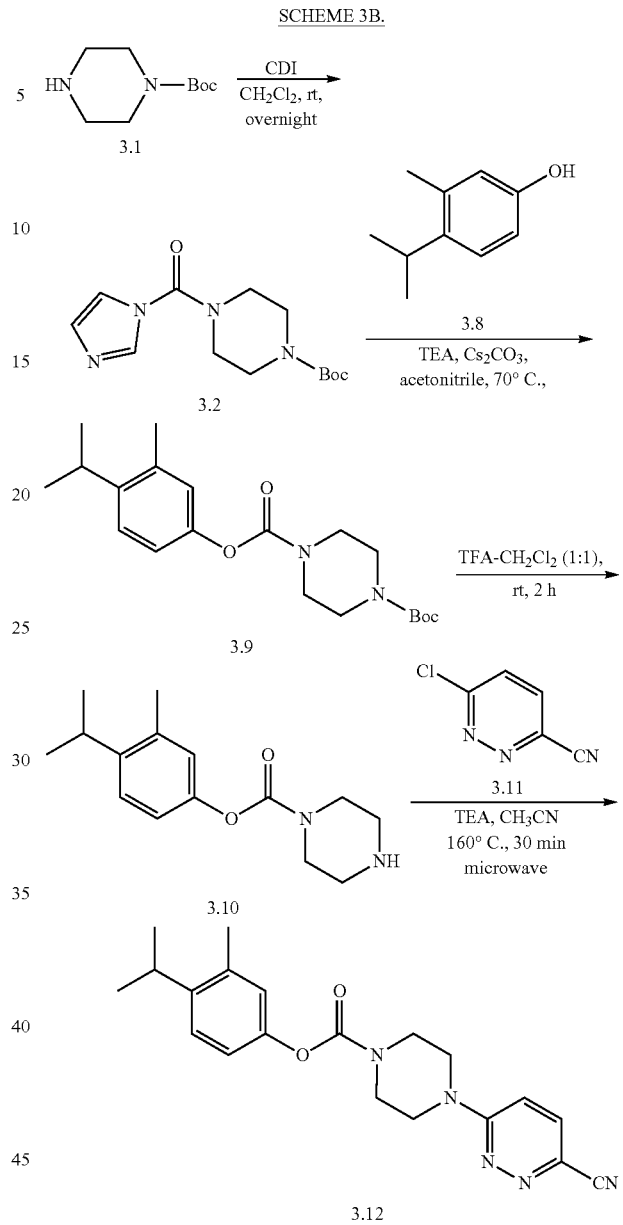

In one aspect, compounds of type 3.12, and similar compounds, can be prepared according to reaction Scheme 3B above. Thus, compounds of type 3.2 can be prepared by a coupling reaction of an appropriate amine, e.g., 3.1 as shown above. Appropriate amines are commercially available or prepared by methods known to one skilled in the art. The coupling reaction is carried out in the presence of an appropriate coupling agent, e.g., N,N-carbonyldiimidazole (CDI), in an appropriate solvent, e.g., dichloromethane. Compounds of type 3.9 can be prepared by a reaction of an appropriate activated -urea, e.g., 3.2, and an appropriate phenol, e.g., 3.8 as shown above. Appropriate phenols are commercially available or prepared by methods known to one skilled in the art. The reaction is carried out in the presence of an appropriate base, e.g., triethylamine and cesium carbonate, in an appropriate solvent, e.g., acetonitrile, at an appropriate temperature, e.g., 70° C., for an appropriate period of time, e.g., 3-4 hours or overnight.

Compounds of type 3.10 can be prepared by a deprotection reaction of an appropriate piperazine, e.g., 3.9 as shown above. The deprotection reaction is carried out in the presence of an appropriate deprotecting agent, e.g., trifluoroacetic acid, and an appropriate solvent, e.g., dichloromethane, for an appropriate period of time, e.g., 2 hours. Compounds of type 3.12 can be prepared by an arylation reaction of an appropriate amine, e.g., 3.10 as shown above, and an appropriate aryl halide, e.g., 3.11 as shown above. Appropriate aryl halides are commercially available or prepared by methods known to one skilled in the art. The arylation reaction is carried out in the presence of an appropriate base, e.g., triethylamine, and an appropriate solvent, e.g., acetonitrile, at an appropriate temperature, e.g., 160° C., for an appropriate period of time, e.g., 30 minutes using microwave irradiations. As can be appreciated by one skilled in the art, the above reaction provides an example of a generalized approach wherein compounds similar in structure to the specific reactants above (compounds similar to compounds of type 3.1, 3.2, 3.3, 3.4, 3.5, 3.6a, and 3.6b), can be substituted in the reaction to provide phenyl 4-arylpiperazine-1-carboxylate derivatives similar to Formula 3.7a and 3.7b.

4. Route IV

In one aspect, substituted 6-(4-(2-oxo-2-phenylethyl)piperazin-1-yl)nicotinonitrile derivatives can be prepared as shown below.

SCHEME 4A.

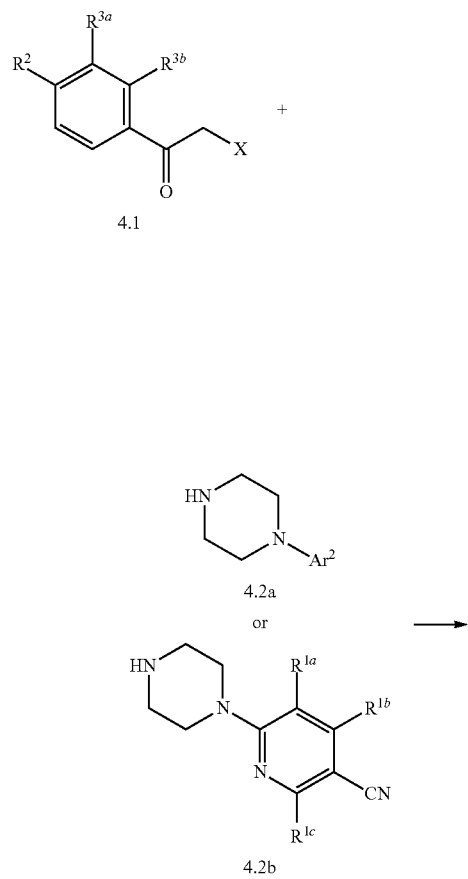

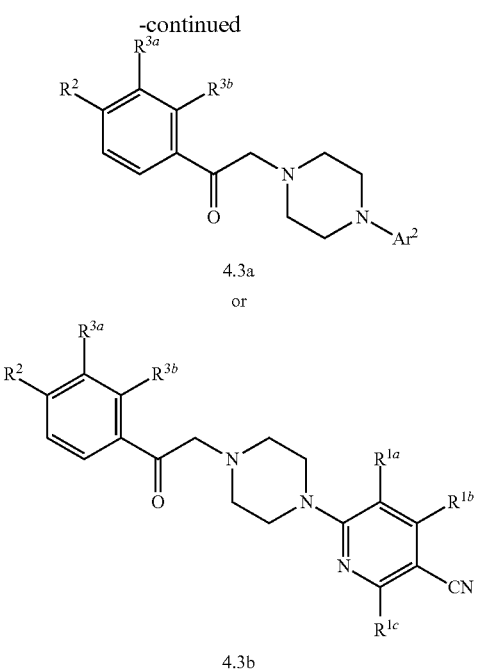

Compounds are represented in generic form, with substituents as noted in compound descriptions elsewhere herein and wherein X is halogen. A more specific example is set forth below.

SCHEME 4B.

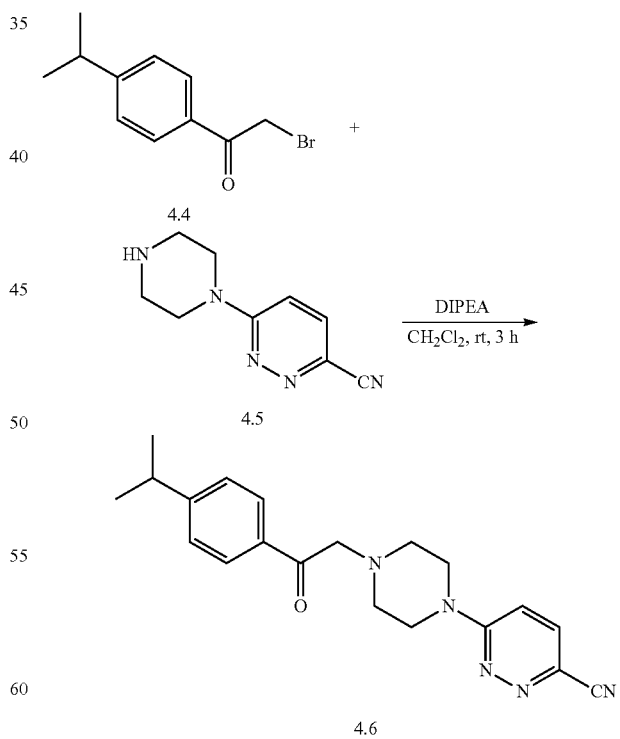

In one aspect, compounds of type 4.6, and similar compounds, can be prepared according to reaction Scheme 4B above. Thus, compounds of type 4.6 can be prepared by an alkylation reaction of an appropriate amine, e.g., 4.5 as shown above, with an appropriate alkyl halide, e.g., 4.4 as shown above. Appropriate amines and appropriate alkyl halides are commercially available or prepared by methods known to one skilled in the art. The alkylation reaction is carried out in the presence of an appropriate base, e.g., diisopropylethylamine, in an appropriate solvent, e.g., dichloromethane, for an appropriate period of time, e.g., 3 hours. As can be appreciated by one skilled in the art, the above reaction provides an example of a generalized approach wherein compounds similar in structure to the specific reactants above (compounds similar to compounds of type 4.1, 4.2a, and 4.2b), can be substituted in the reaction to provide 6-(4-(2-oxo-2-phenylethyl)piperazin-1-yl)nicotinonitrile derivatives similar to Formula 4.3a and 4.3b.

5. Route V

In one aspect, substituted 4-aryl-N-phenylpiperazine-1-carboxamide derivatives can be prepared as shown below.

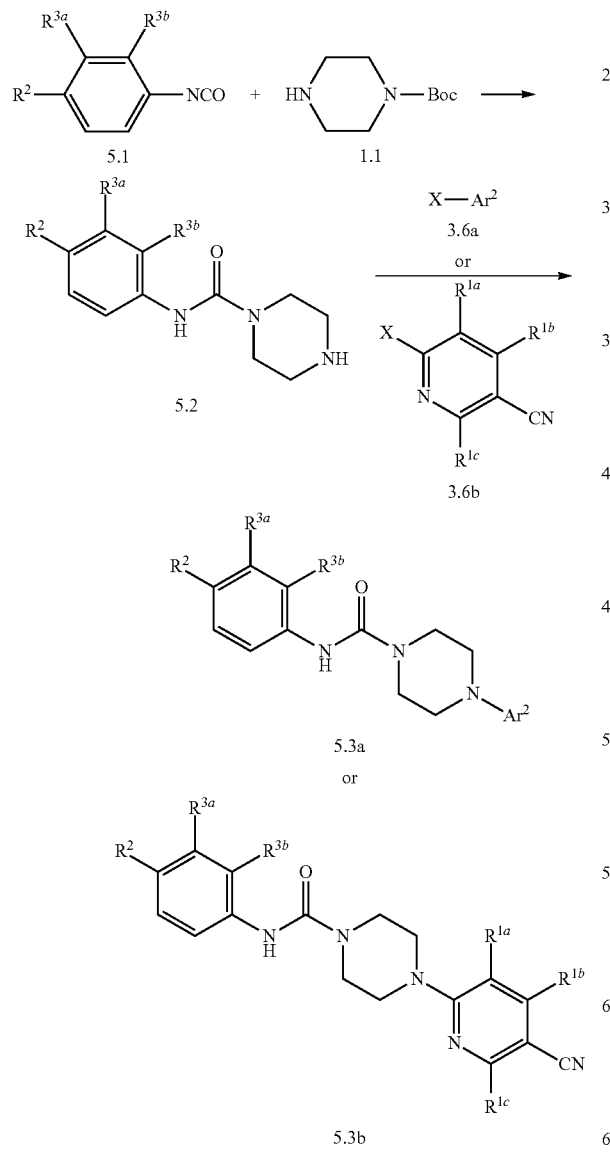

Compounds are represented in generic form, with substituents as noted in compound descriptions elsewhere herein and wherein X is halogen. A more specific example is set forth below.

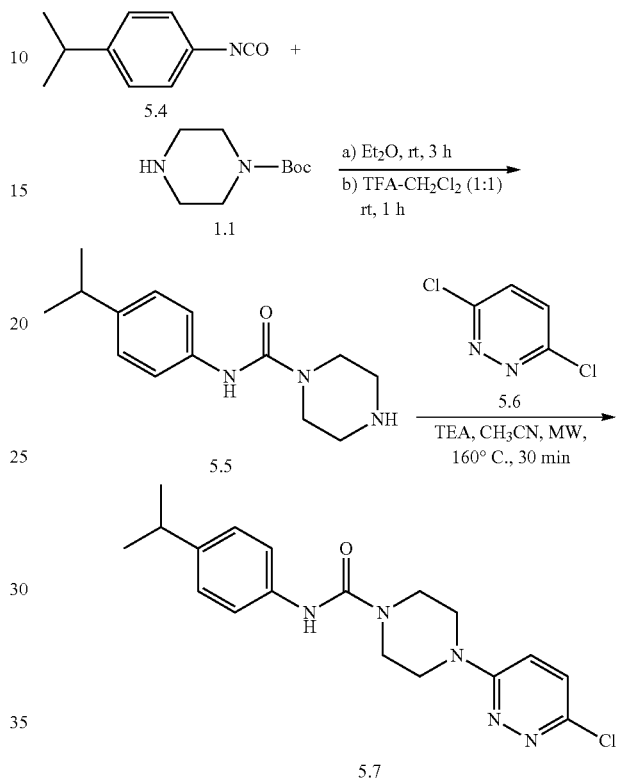

In one aspect, compounds of type 5.5, and similar compounds, can be prepared according to reaction Scheme 5B above. Thus, compounds of type 5.5 can be prepared by a urea bond formation reaction between an appropriate amine, e.g., 1.1 as shown above, and an appropriate isocyanate, e.g., 5.4 as shown above. Appropriate amines and appropriate isocyanates are commercially available or prepared by methods known to one skilled in the art. The nucleophilic substitution is carried out in the presence of an appropriate solvent, e.g., diethyl ether, for an appropriate period of time, e.g., 3 hours. The nucleophilic substitution is followed by a deprotection reaction. The deprotection reaction is carried out in the presence of an appropriate deprotecting agent, e.g., trifluoroacetic acid, in an appropriate solvent, e.g., dichloromethane, for an appropriate period of time, e.g., 1 hour. Compounds of type 5.7 can be prepared by an arylation reaction of appropriate amine, e.g., 5.5 as shown above, and an appropriate aryl halide, e.g., 5.6 as shown above. Appropriate aryl halides are commercially available or prepared by methods known to one skilled in the art. The arylation reaction is carried out in the presence of an appropriate base, e.g., triethylamine, in an appropriate solvent, e.g., acetonitrile, at an appropriate temperature, e.g., 160° C., for an appropriate period of time, e.g., 30 minutes using microwave irradiations. As can be appreciated by one skilled in the art, the above reaction provides an example of a generalized approach wherein compounds similar in structure to the specific reactants above (compounds similar to compounds of type 1.1, 3.6a, 3.6b, 5.1, and 5.2), can be substituted in the reaction to provide 4-aryl-N-phenylpiperazine-1-carboxamide derivatives similar to Formula 5.3a and 5.3b.

6. Route VI

In one aspect, 4-substituted-arylpiperazine-1-carboxamide derivatives can be prepared as shown below.

SCHEME 6A.

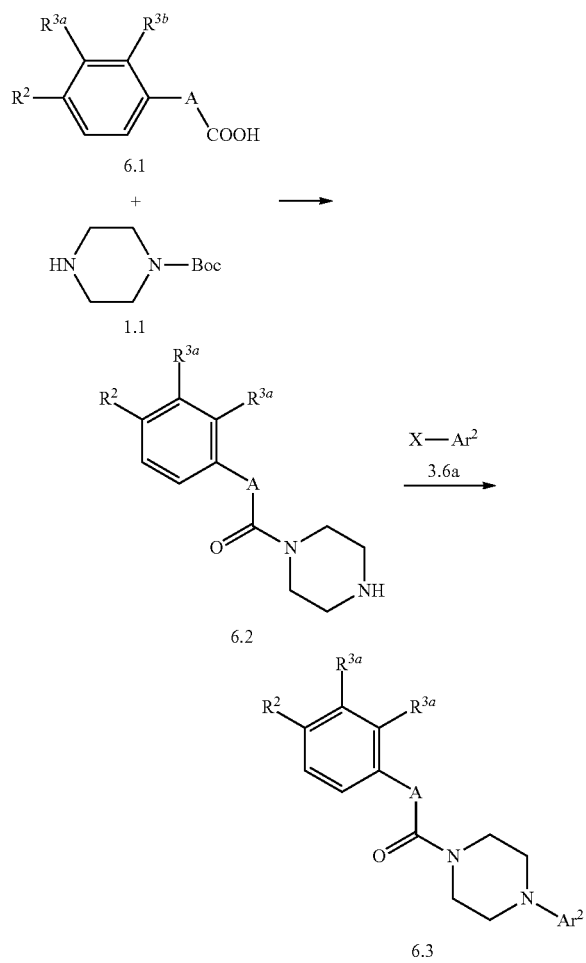

Compounds are represented in generic form, with substituents as noted in compound descriptions elsewhere herein and wherein X is halogen. A more specific example is set forth below.

SCHEME 6B.

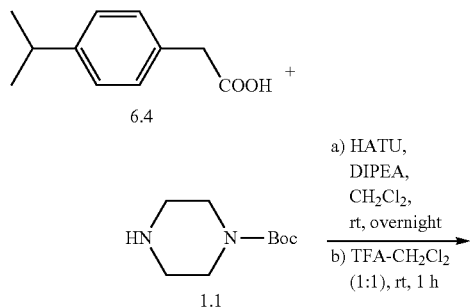

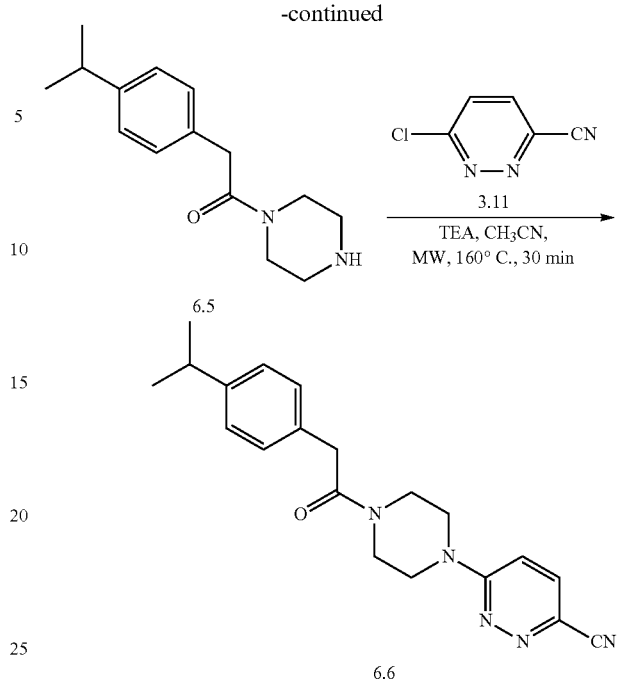

In one aspect, compounds of type 6.6, and similar compounds, can be prepared according to reaction Scheme 6B above. Thus, compounds of type 6.5 can be prepared by a coupling reaction of an appropriate amine, e.g., 1.1 as shown above, and an appropriate carboxylic acid, e.g., 6.4 as shown above. Appropriate amines and appropriate carboxylic acids are commercially available or prepared by methods known to one skilled in the art. The coupling reaction is carried out in the presence of an appropriate coupling agent, e.g., HATU, and an appropriate base, e.g., DIPEA, in an appropriate solvent, e.g., dichloromethane. The coupling reaction is followed by a deprotection reaction. The deprotection reaction is carried out in the presence of an appropriate deprotecting agent, e.g., trifluoroacetic acid, in an appropriate solvent, e.g., dichloromethane, for an appropriate period of time, e.g., 1 hour. Compounds of type 6.6 can be prepared by an arylation reaction of an appropriate amine, e.g., 6.5, and an appropriate aryl halide, e.g., 3.11 as shown above. Appropriate aryl halides are commercially available or prepared by methods known to one skilled in the art. The arylation reaction is carried out in the presence of an appropriate base, e.g., triethylamine, in an appropriate solvent, e.g., acetonitrile, at an appropriate temperature, e.g., 160° C., for an appropriate period of time, e.g., 30 minutes using microwave irradiations. As can be appreciated by one skilled in the art, the above reaction provides an example of a generalized approach wherein compounds similar in structure to the specific reactants above (compounds similar to compounds of type 1.1, 3.6a, 6.1, and 6.2), can be substituted in the reaction to provide 4-substituted-arylpiperazine-1-carboxamide derivatives similar to Formula 6.3.

7. Route VII

In one aspect, N-substituted-5-pyridazinyl-carboxamide derivatives can be prepared as shown below.

SCHEME 7A.

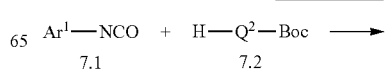

-continued

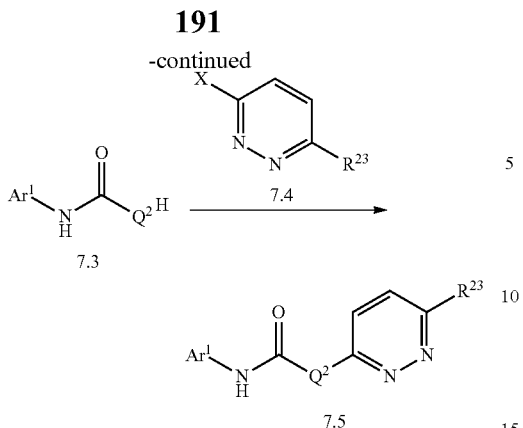

7.3

7.5

Compounds are represented in generic form, with substituents as noted in compound descriptions elsewhere herein and wherein X is halogen. A more specific example is set forth below.

SCHEME 7B.

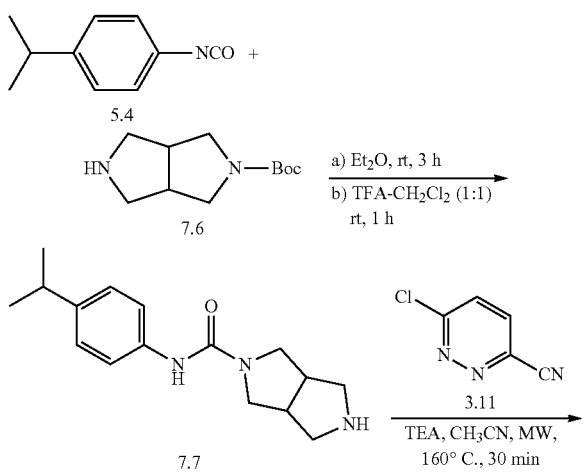

-continued

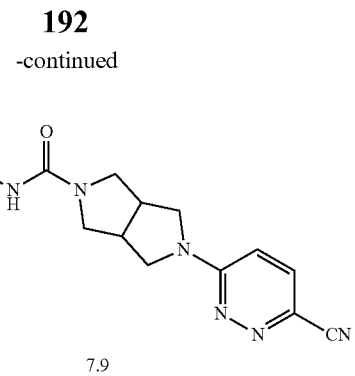

7.9

In one aspect, compounds of type 7.9, and similar compounds, can be prepared according to reaction Scheme 7B above. Thus, the urea compounds of type 7.7 can be prepared by reactingan appropriate amine, e.g., 7.6 as shown above, with an appropriate isocyanate, e.g., 5.4 as shown above. Appropriate amines and appropriate isocyanates are commercially available or prepared by methods known to one skilled in the art. The urea bond formation reaction is carried out in the presence of an appropriate solvent, e.g., diethyl ether, for an appropriate period of time, e.g., 3 hours. Compounds of type 7.9 can be prepared by an arylation reaction of an appropriate amine, e.g., 7.7 as shown above, and an aryl halide, e.g., 3.11 as shown above. Appropriate aryl halides are commercially available or prepared by methods known to one skilled in the art. The arylation reaction is carried out in the presence of an appropriate base, e.g., triethylamine, and an appropriate solvent, e.g., acetonitrile, at an appropriate temperature, e.g., 160° C., for an appropriate period of time, e.g., 30 minutes using microwave irradiation. As can be appreciated by one skilled in the art, the above reaction provides an example of a generalized approach wherein compounds similar in structure to the specific reactants above (compounds similar to compounds of type 7.1, 7.2, 7.3, and 7.4), can be substituted in the reaction to provide N-substituted-5-pyridazinyl-carboxamide derivatives similar to Formula 7.5.

8. Route VIII

In one aspect, 4-substituted-N-arylpiperazine-1-carboxamide derivatives can be prepared as shown below.

SCHEME 8A.

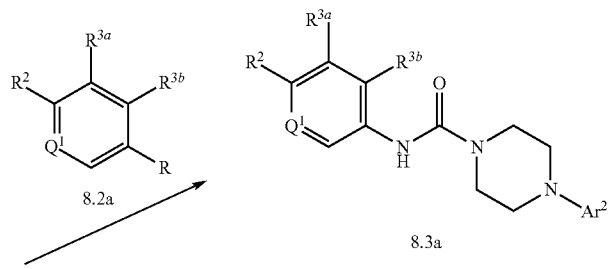

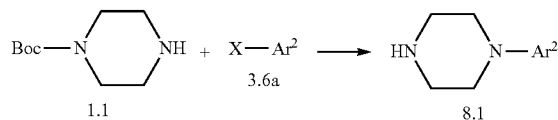

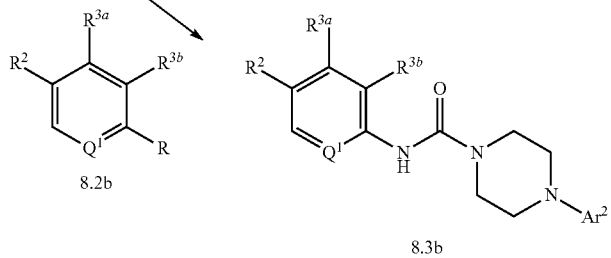

Compounds are represented in generic form, with substituents as noted in compound descriptions elsewhere herein and wherein X is halogen and R is selected from —NH₂ and —COOH. A more specific example is set forth below.

SCHEME 8B.

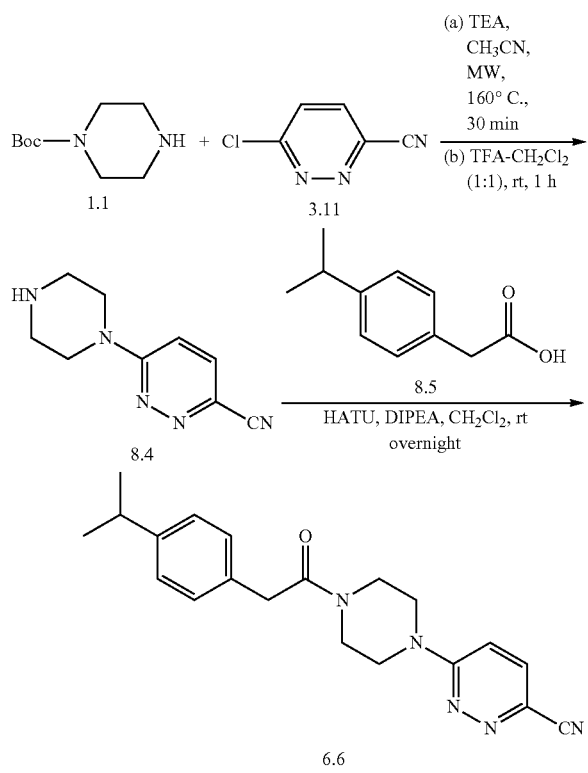

In one aspect, compounds of type 6.6, and similar compounds, can be prepared according to reaction Scheme 8B above. Thus, compounds of type 8.4 can be prepared by a arylation reaction of an appropriate amine, e.g., 1.1 as shown above, with an appropriate aryl halide, e.g., 3.11 as shown above. Appropriate amines and appropriate aryl halides are commercially available or prepared by methods known to one skilled in the art. The arylation reaction is carried out in the presence of an appropriate base, e.g., triethylamine, and an appropriate solvent, e.g., acetonitrile, at an appropriate temperature, e.g., 160° C., for an appropriate period of time, e.g., 30 minutes using microwave irradiation. The arylation reaction is followed by a deprotecting reaction. The deprotection reaction is carried out in the presence of an appropriate deprotecting agent, e.g., trifluoroacetic acid, in an appropriate solvent, dichloromethane, for an appropriate period of time, e.g., 1 hour. Compounds of type 6.6 can be prepared by a coupling reaction of an appropriate carboxylic acid, e.g., 8.5, in the presence of an appropriate amine, e.g., 8.4, as shown above. The reaction is carried out in the presence of an appropriate coupling agent, e.g., 1-[bis(dimethylamino)methylene]-1H-1,2,3-triazolo[4,5-b]pyridinium 3-oxid hexafluorophosphate (HATU) and an appropriate base, e.g., N,N-diisopropylethylamine (DIPEA), and an appropriate solvent, e.g., dichloromethane. As can be appreciated by one skilled in the art, the above reaction provides an example of a generalized approach wherein compounds similar in structure to the specific reactants above (compounds similar to compounds of type 1.1, 3.6a, 8.1, and 8.2), can be substituted in the reaction to provide 4-substituted-N-arylpiperazine-1-carboxamide derivatives similar to Formula 8.3.

9. Route IX

In one aspect, substituted pyridazinyl-N-aryl-4-carboxamide derivatives can be prepared as shown below.

SCHEME 9A.

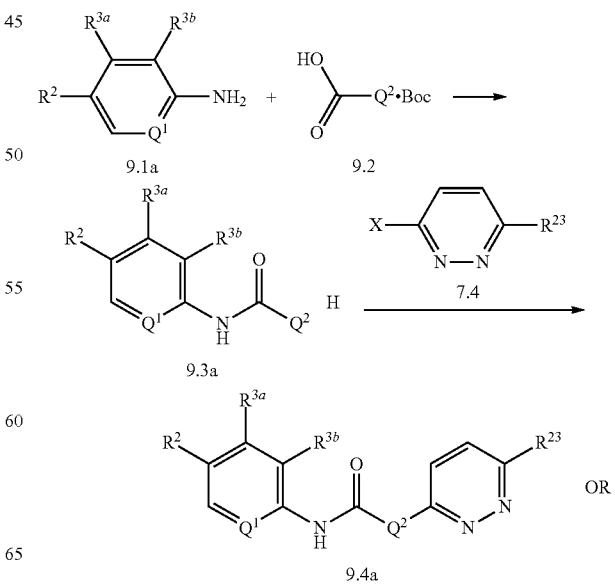

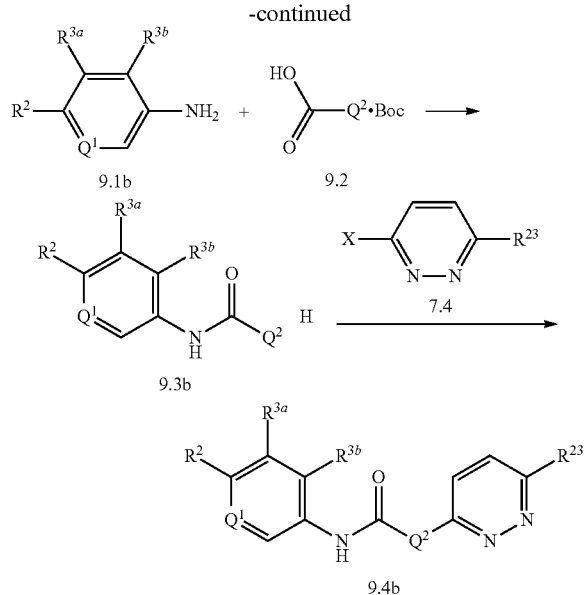

Compounds are represented in generic form, with substituents as noted in compound descriptions elsewhere herein and wherein X is halogen. A more specific example is set forth below.

SCHEME 9B.

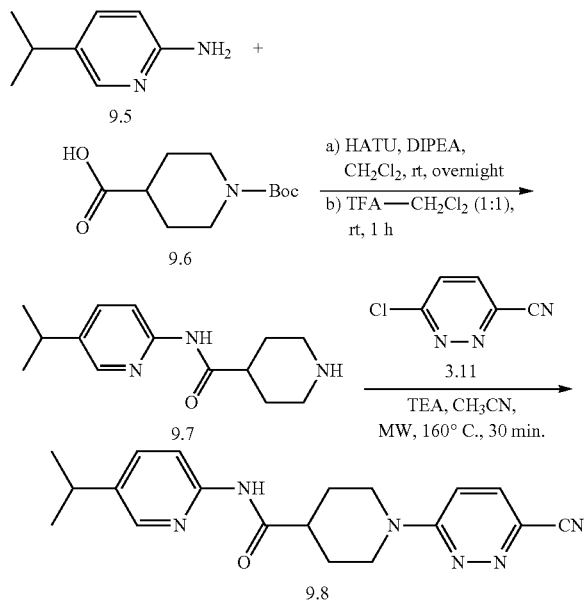

In one aspect, compounds of type 9.8, and similar compounds, can be prepared according to reaction Scheme 9B above. Thus, compounds of type 9.7 can be prepared by a coupling reaction of an appropriate amine, e.g., 9.5 as shown above, with an appropriate carboxylic acid, e.g., 9.6 as shown above. Appropriate amines and appropriate carboxylic acids are commercially available or prepared by methods known to one skilled in the art. The coupling reaction is carried out in the presence of an appropriate coupling agent, e.g., HATU, and an appropriate base, e.g., DIPEA, in an appropriate solvent, e.g., dichloromethane. Compounds of type 9.8 can be prepared by an arylation reaction of an appropriate amine, e.g., 9.7, and an appropriate aryl halide, e.g., 3.11 as shown above. Appropriate aryl halides are commercially available or prepared by methods known to one skilled in the art. The arylation reaction is carried out in the presence of an appropriate base, e.g., triethylamine, in an appropriate solvent, e.g., acetonitrile, at an appropriate temperature, e.g., 160° C., for an appropriate period of time, e.g., 30 minutes using microwave irradiation. As can be appreciated by one skilled in the art, the above reaction provides an example of a generalized approach wherein compounds similar in structure to the specific reactants above (compounds similar to compounds of type 7.4, 9.1, 9.2, and 9.3), can be substituted in the reaction to provide pyridazinyl-N-aryl-4-carboxamide derivatives similar to Formula 9.4.

10. Route X

In one aspect, 1-(6-substituted-pyridazin-3yl)-aryl derivatives can be prepared as shown below.

SCHEME 10A.

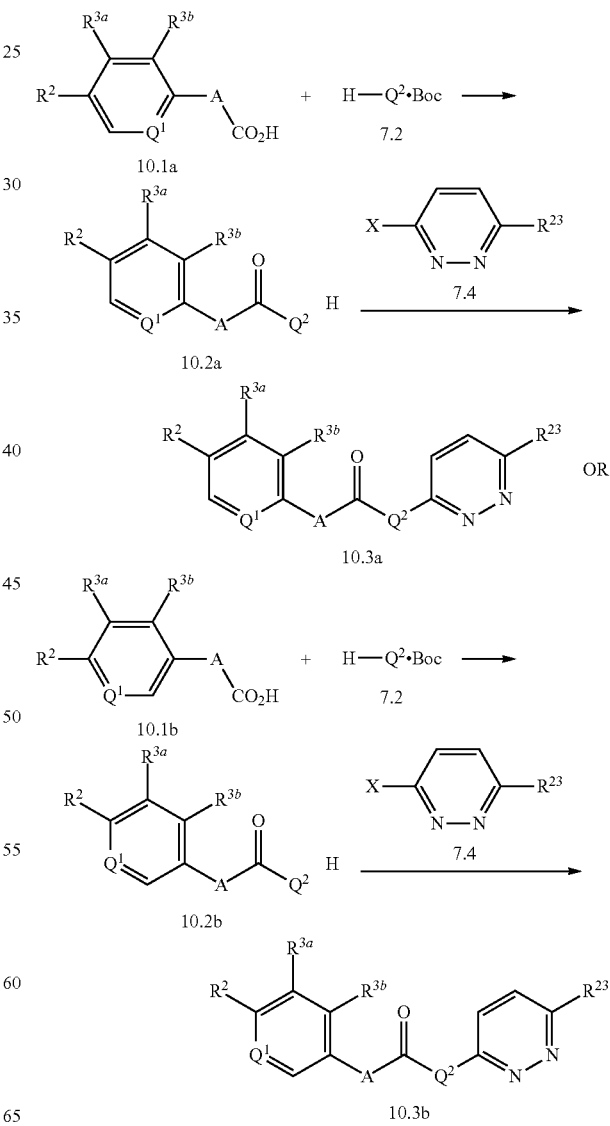

Compounds are represented in generic form, with substituents as noted in compound descriptions elsewhere herein and wherein X is halogen. A more specific example is set forth below.

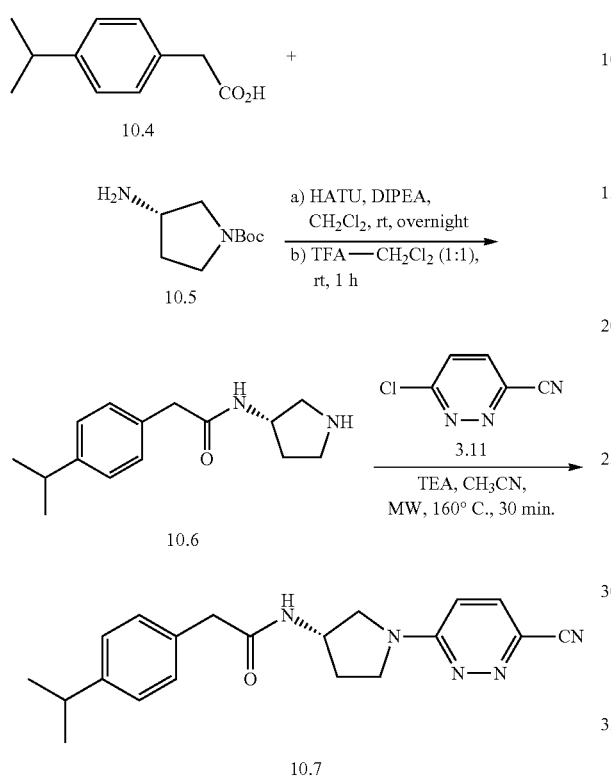

SCHEME 10B.

In one aspect, compounds of type 10.7, and similar compounds, can be prepared according to reaction Scheme 10B above. Thus, compounds of type 10.6 can be prepared by a coupling reaction of an appropriate carboxylic acid, e.g., 10.4 as shown above, with an appropriate amine, e.g., 10.5 as shown above. Appropriate carboxylic acids and appropriate amines are commercially available or prepared by methods known to one skilled in the art. The coupling reaction is carried out in the presence of an appropriate coupling agent, e.g., HATU, and an appropriate base, e.g., DIPEA, in an appropriate solvent, e.g., dichloromethane. Compounds of type 10.7 can be prepared by an arylation reaction of an appropriate amine, e.g., 10.6, and an appropriate aryl halide, e.g., 3.11 as shown above. Appropriate aryl halides are commercially available or prepared by methods known to one skilled in the art. The arylation reaction is carried out in the presence of an appropriate base, e.g., triethylamine, in an appropriate solvent, e.g., acetonitrile, at an appropriate temperature, e.g., 160° C., for an appropriate period of time, e.g., 30 minutes. As can be appreciated by one skilled in the art, the above reaction provides an example of a generalized approach wherein compounds similar in structure to the specific reactants above (compounds similar to compounds of type 7.2, 7.4, 10.1, and 10.2), can be substituted in the reaction to provide 1-(6-substituted-pyridazin-3yl)-aryl derivatives derivatives similar to Formula 10.3.

11. Route XI

In one aspect, substituted 4-(pyridazin-3-yl)piperazine derivatives can be prepared as shown below.

SCHEME 11A.

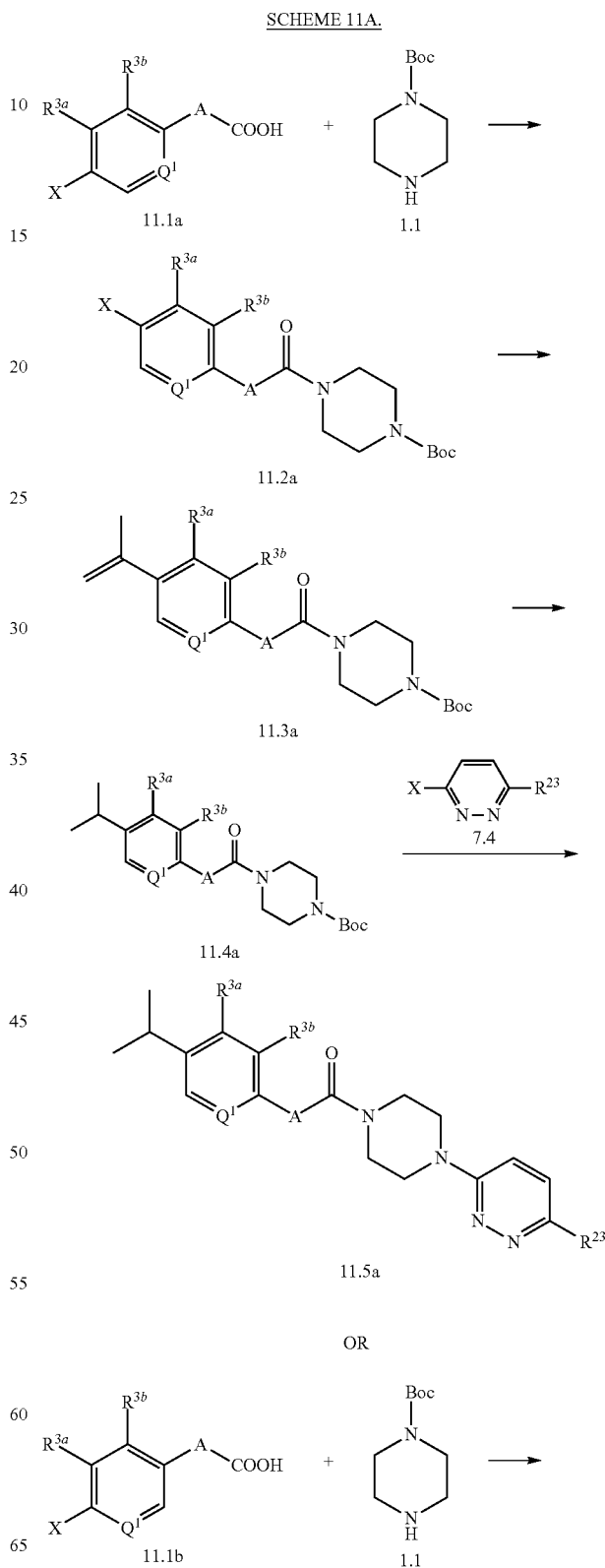

-continued

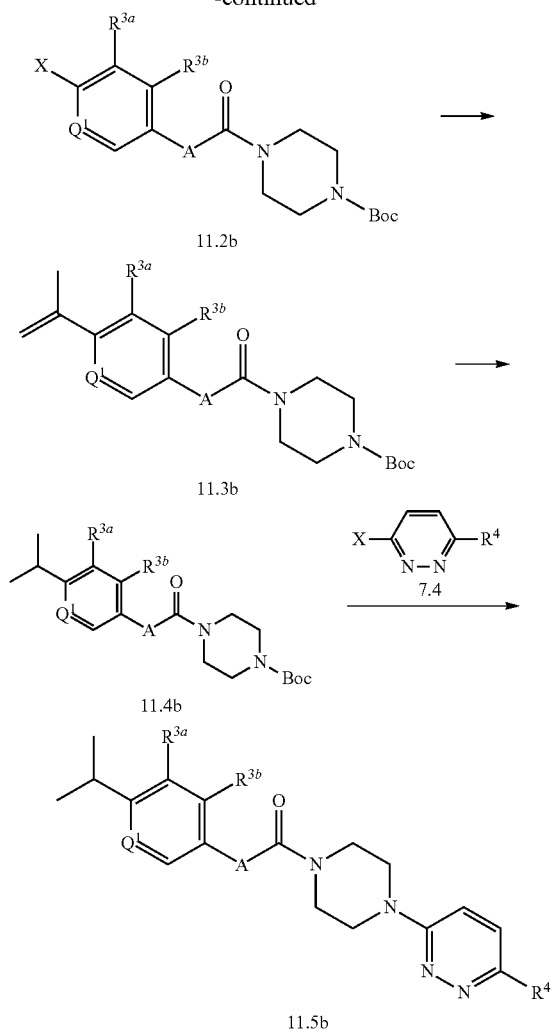

Compounds are represented in generic form, with substituents as noted in compound descriptions elsewhere herein and wherein each X is independently halogen. A more specific example is set forth below.

SCHEME 11B.

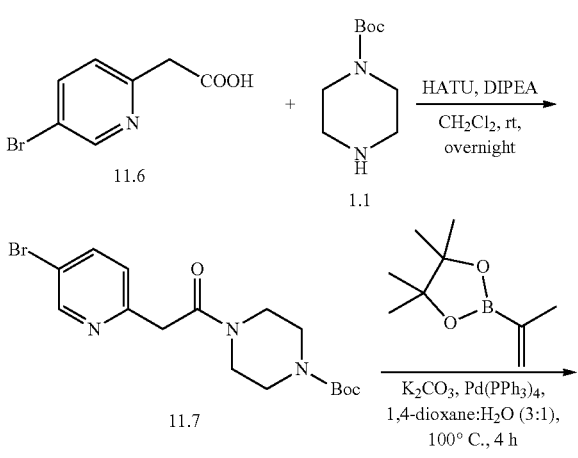

-continued

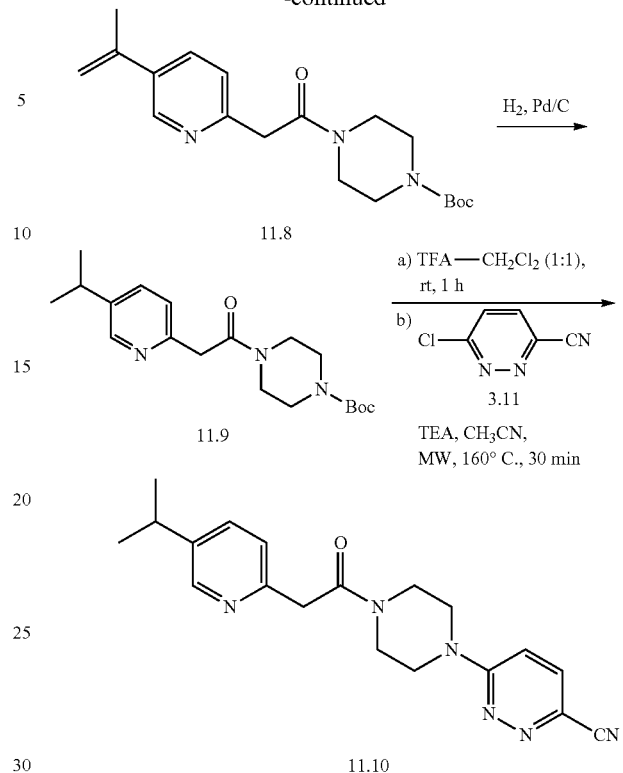

In one aspect, compounds of type 11.10, and similar compounds, can be prepared according to reaction Scheme 11B above. Thus, compounds of type 11.7 can be prepared by a coupling reaction of an appropriate amine, e.g., 1.1 as shown above, with an appropriate carboxylic acid, e.g., 11.6 as shown above. Appropriate amines and appropriate carboxylic acids are commercially available or prepared by methods known to one skilled in the art. The coupling reaction is carried out in the presence of an appropriate coupling agent, e.g., HATU, and an appropriate base, e.g., DIPEA, in an appropriate solvent, e.g., dichloromethane. Compounds of type 11.8 can be prepared by a coupling reaction of an appropriate aryl halide, e.g., 11.7, and an appropriate alkene, e.g., 4,4,5,5-tetramethyl-2-(prop-1-en-2-yl)-1,3,2-dioxaborolane as shown above. Appropriate alkenes are commercially available or prepared by methods known to one skilled in the art. The coupling reaction is carried out in the presence of an appropriate base, e.g., potassium carbonate, and an appropriate catalyst, e.g., tetrakis(triphenylphosphine)palladium (0), at an appropriate temperature, e.g., 100° C., for an appropriate period of time, e.g., 4 hours, in appropriate solvent system, e.g. dioxane-water (3:1 by volume). Compounds of type 11.9 can be prepared by reduction of an appropriate alkene, e.g., 11.8 as shown above. The reduction is carried out in the presence of an appropriate hydrogen source, e.g., hydrogen gas, and an appropriate catalyst, e.g., palladium on carbon. Compounds of type 11.10 can be prepared by deprotection, followed by an arylation reaction of an appropriate amine, e.g., 11.9 as shown above, and an appropriate aryl halide, e.g., 11.10 as shown above. Appropriate aryl halides are commercially available or prepared by methods known to one skilled in the art. The deprotection is carried out in the presence of an appropriate deprotecting agent, e.g., trifluoroacetic acid, in an appropriate solvent, e.g., dichloromethane, for an appropriate period of time, e.g., 1 hour. The arylation reaction is carried out in the presence of an appropriate base, e.g., triethylamine, in an appropriate solvent, e.g., acetonitrile, at an appropriate temperature, e.g., 160° C., for an appropriate period of time, e.g., 30 minutes. As can be appreciated by one skilled in the art, the above reaction provides an example of a generalized approach wherein compounds similar in structure to the specific reactants above (compounds similar to compounds of type 1.1, 7.4, 11.1, 11.2, 11.3, and 11.4), can be substituted in the reaction to provide substituted 4-(pyridazin-3-yl)piperazine derivatives similar to Formula 11.5.

12. Route XII

In one aspect, phenyl 6-substituted-nicotinonitrile derivatives can be prepared as shown below.

SCHEME 12A.

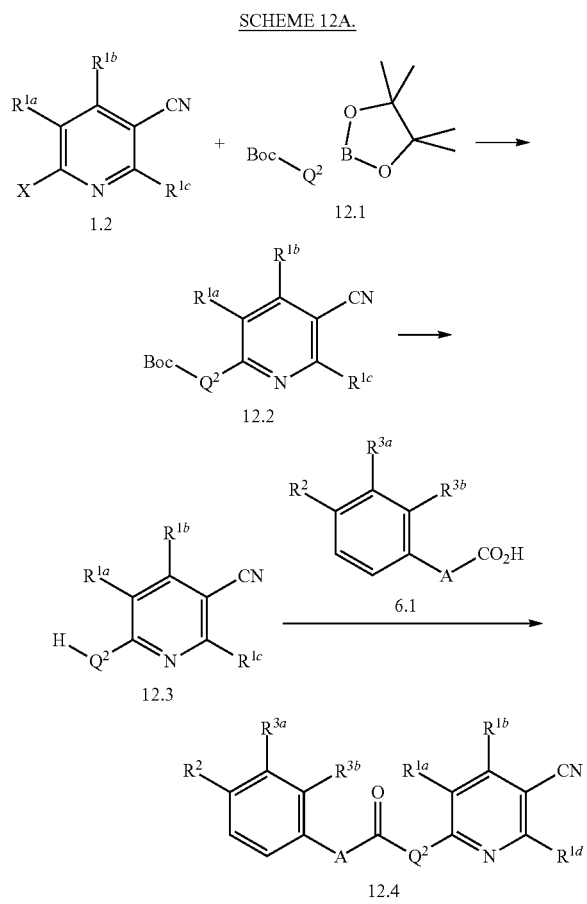

Compounds are represented in generic form, with substituents as noted in compound descriptions elsewhere herein. A more specific example is set forth below.

SCHEME 12B.

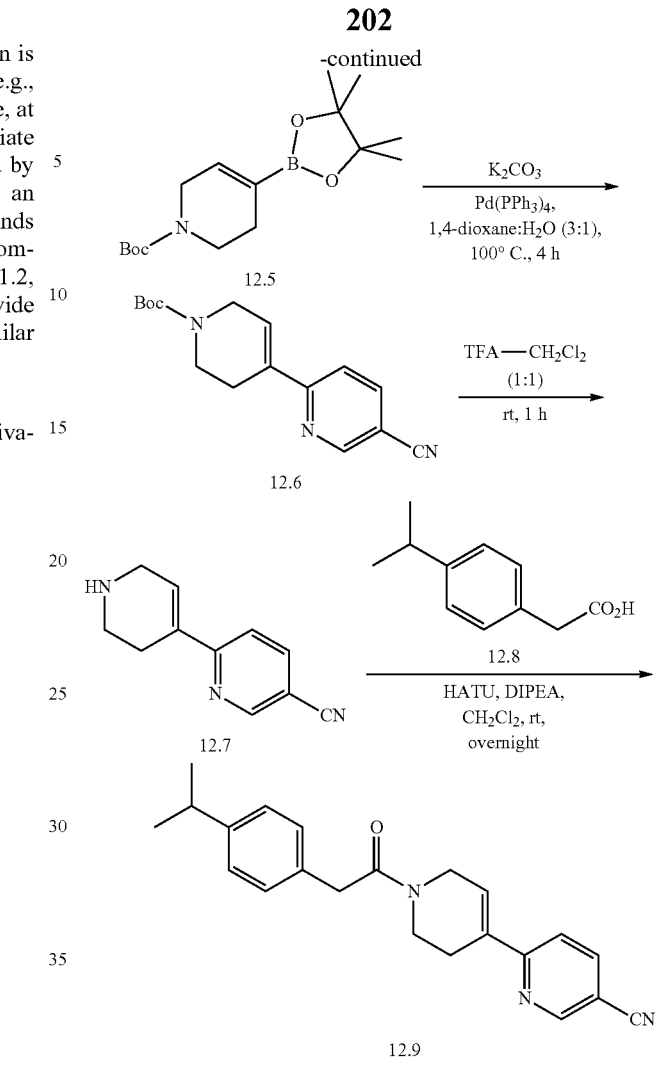

In one aspect, compounds of type 12.9, and similar compounds, can be prepared according to reaction Scheme 12B above. Thus, compounds of type 12.6 can be prepared by a coupling reaction of an appropriate aryl halide, e.g., 1.6 as shown above, with an appropriate boron derivative, e.g., 12.5 as shown above. Appropriate aryl halides and appropriate boron derivatives are commercially available or prepared by methods known to one skilled in the art. The coupling reaction is carried out in the presence of an appropriate base, e.g., potassium carbonate, and an appropriate catalyst, tetrakis(triphenylphosphine)palladium (0), at an appropriate temperature, e.g., 100° C., for an appropriate period of time, e.g., 4 hours, in appropriate solvent system, e.g. dioxane-water (3:1 by volume). Compounds of type 12.7 can be prepared by deprotection reaction of an appropriate amine, e.g., 12.6 as shown above. The deprotection reaction is carried out in the presence of an appropriate deprotecting agent, e.g., trifluoroacetic acid, in an appropriate solvent, e.g., dichloromethane, for an appropriate period of time, e.g., 1 hour. Compounds of type 12.9 can be prepared by a coupling reaction of an appropriate amine, e.g., 12.7, and an appropriate carboxylic acid, e.g., 12.8. Appropriate carboxylic acids are commercially available or prepared by methods known to one skilled in the art. The coupling reaction is carried out in the presence of an appropriate coupling agent, e.g., HATU, and an appropriate base, e.g., DIPEA, in an appropriate solvent, e.g., dichloromethane. As can be appreciated by one skilled in the art, the above reaction provides an example of a generalized approach wherein compounds similar in structure to the specific reactants above (compounds similar to compounds of type 1.2, 6.1, 12.1, 12.2, and 12.3), can be substituted in the reaction to provide phenyl 6-substituted-nicotinonitrile derivatives similar to Formula 12.4.

13. Route XIII

In one aspect, haloaryl 6-substituted-pyridazine derivatives can be prepared as shown below.

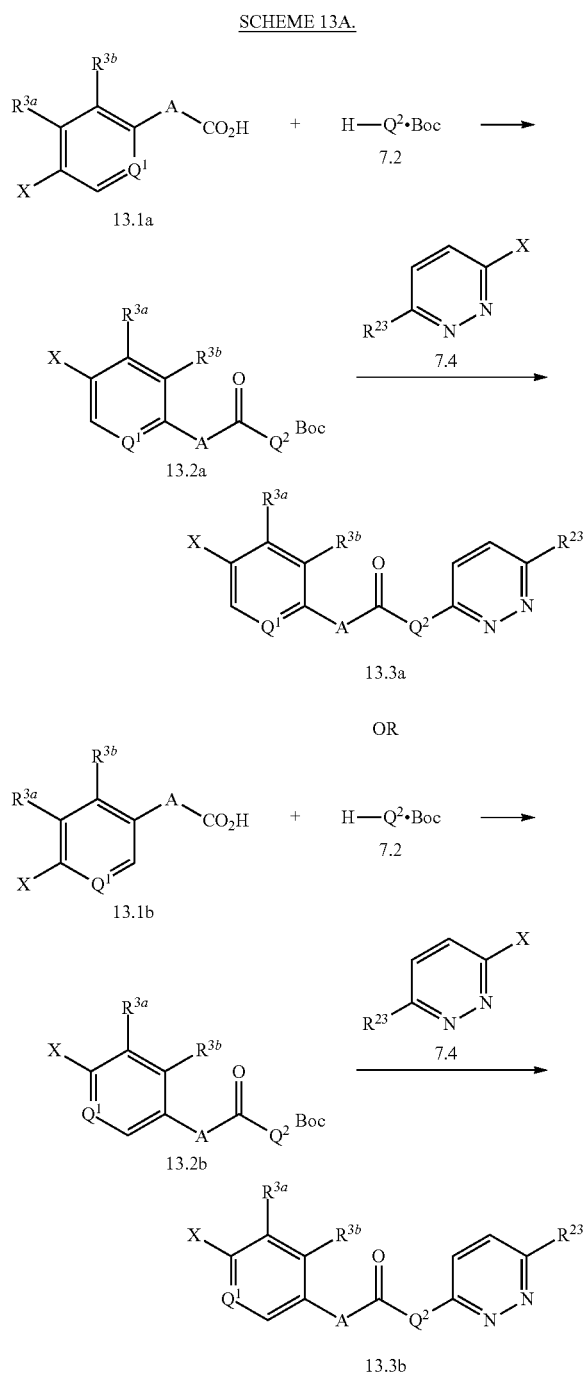

Compounds are represented in generic form, with substituents as noted in compound descriptions elsewhere herein and wherein each X is independently halogen. A more specific example is set forth below.

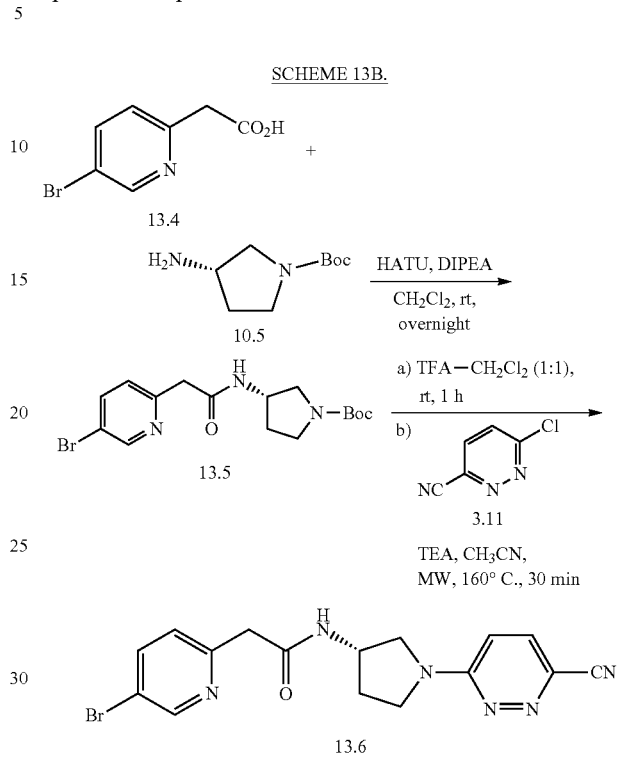

In one aspect, compounds of type 13.6, and similar compounds, can be prepared according to reaction Scheme 13B above. Thus, compounds of type 13.5 can be prepared by a coupling reaction of an appropriate amine, e.g., 10.5 as shown above, with an appropriate carboxylic acid, e.g., 13.4 as shown above. Appropriate amines and appropriate carboxylic acids are commercially available or prepared by methods known to one skilled in the art. The coupling reaction is carried out in the presence of an appropriate coupling agent, e.g., HATU, and an appropriate base, e.g., DIPEA, in an appropriate solvent, e.g., dichloromethane. Compounds of type 13.6 can be prepared by a deprotection reaction, followed by an arylation reaction of an appropriate amine, e.g., 13.5, and an appropriate aryl halide, e.g., 3.11. Appropriate aryl halides are commercially available or prepared by methods known to one skilled in the art. The deprotection is carried out in the presence of an appropriate deprotecting agent, e.g., trifluoroacetic acid, in an appropriate solvent, e.g., dichloromethane, for an appropriate period of time, e.g., 1 hour. The arylation reaction is carried out in the presence of an appropriate base, e.g., triethylamine, in an appropriate solvent, e.g., acetonitrile, at an appropriate temperature, e.g., 160° C., for an appropriate period of time, e.g., 30 minutes using microwave irradiations. As can be appreciated by one skilled in the art, the above reaction provides an example of a generalized approach wherein compounds similar in structure to the specific reactants above (compounds similar to compounds of type 7.2, 7.4, 13.1, and 13.2), can be substituted in the reaction to provide haloaryl 6-substituted-pyridazine derivatives similar to Formula 13.3.

14. Route XIV

In one aspect, alkenylaryl 6-substituted-pyridazine derivatives can be prepared as shown below.

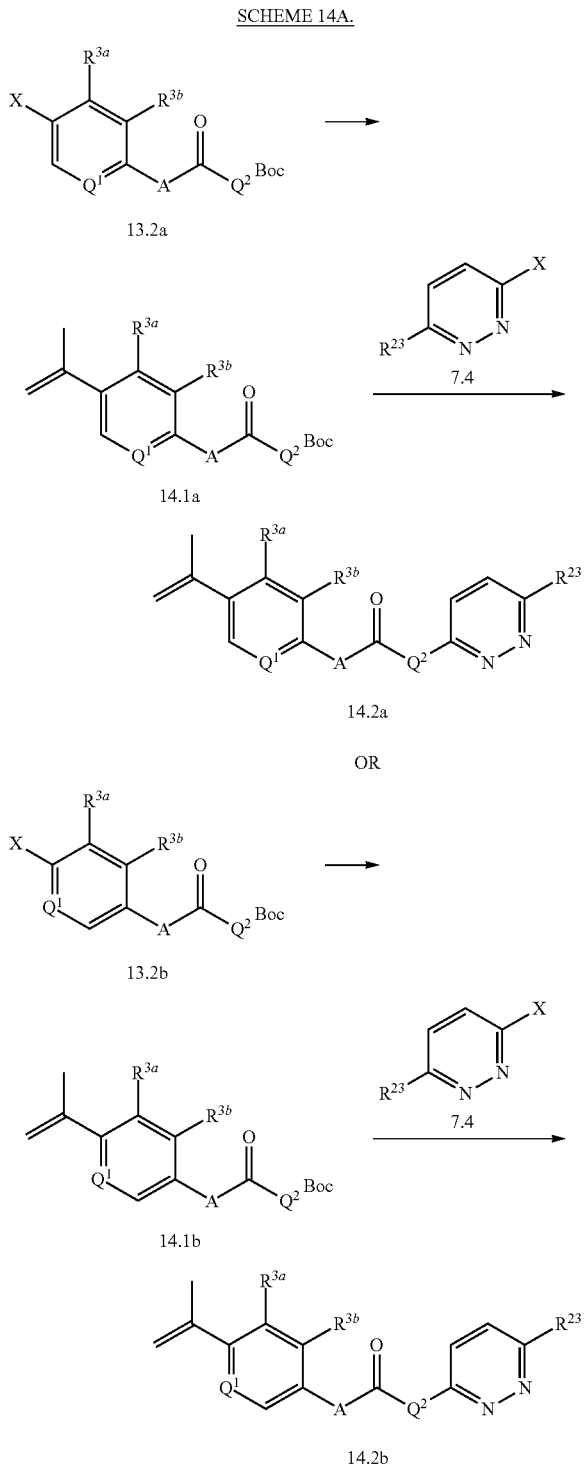

SCHEME 14A.

13.2a 14.1a

OR 13.2b 14.1b 14.2b

Compounds are represented in generic form, with substituents as noted in compound descriptions elsewhere herein and wherein each X is independently halogen. A more specific example is set forth below.

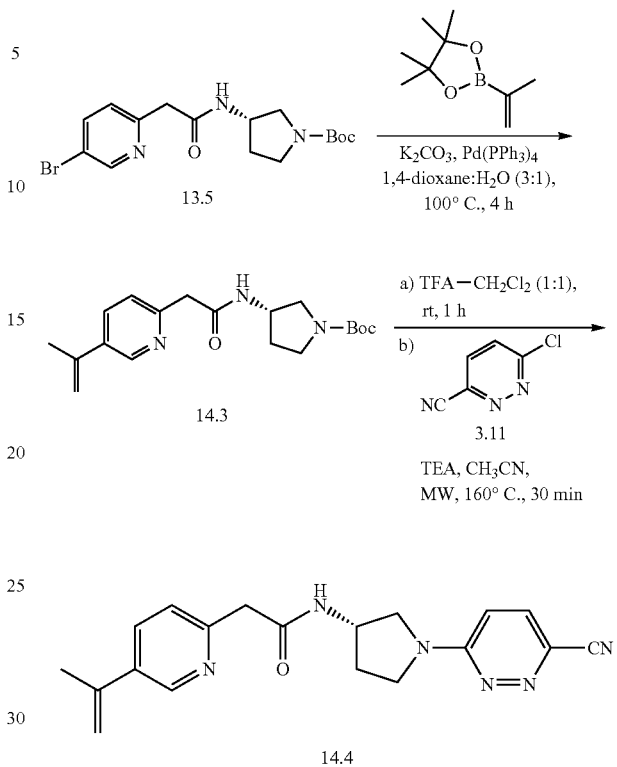

SCHEME 14B.

13.5

14.3

14.4

In one aspect, compounds of type 14.4, and similar compounds, can be prepared according to reaction Scheme 14B above. Thus, compounds of type 14.3 can be prepared by a coupling reaction of an appropriate aryl halide, e.g., 13.5 as shown above, with an appropriate boron derivative, e.g., 4,4,5,5-tetramethyl-2-(prop-1-en-2-yl)-1,3,2-dioxaborolane as shown above. Appropriate aryl halides and appropriate boron derivatives are commercially available or prepared by methods known to one skilled in the art. The coupling reaction is carried out in the presence of an appropriate base, e.g., potassium carbonate, and an appropriate catalyst, e.g., tetrakis(triphenylphosphine)palladium (0), at an appropriate temperature, e.g., 100° C., for an appropriate period of time, e.g., 4 hours. Compounds of type 14.4 can be prepared by a deprotection reaction, followed by an arylation reaction of an appropriate amine, e.g., 14.3, and an appropriate aryl halide, e.g., 3.11 as shown above. The deprotection reaction is carried out in the presence of an appropriate deprotecting agent, e.g., trifluoroacetic acid, in an appropriate solvent, e.g., dichloromethane, for an appropriate period of time, e.g., 1 hour. The arylation reaction is carried out in the presence of an appropriate base, e.g., triethylamine, in an appropriate solvent, e.g., acetonitrile, at an appropriate temperature, e.g., 160° C., for an appropriate period of time, e.g., 30 minutes using microwave irradiations. As can be appreciated by one skilled in the art, the above reaction provides an example of a generalized approach wherein compounds similar in structure to the specific reactants above (compounds similar to compounds of type 7.4, 13.2, and 14.1), can be substituted in the reaction to provide alkenylaryl 6-substituted-pyridazine derivatives similar to Formula 14.2.

15. Route XV

In one aspect, alkylaryl 6-substituted-pyridazine derivatives can be prepared as shown below.

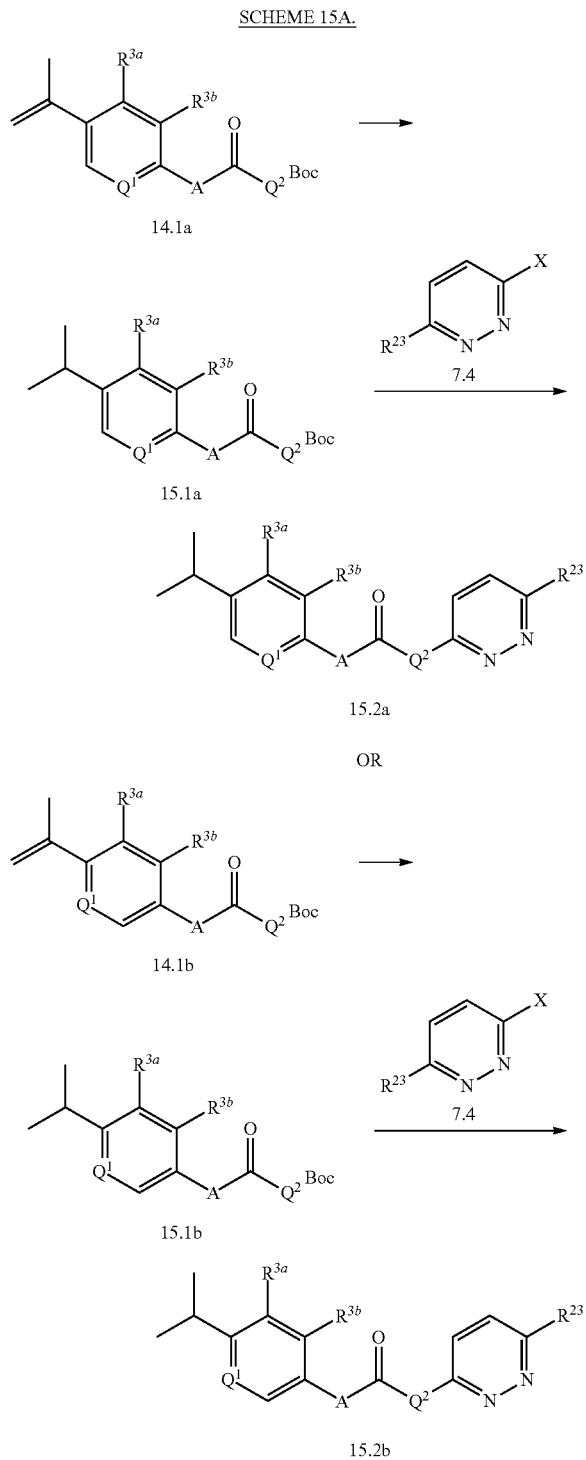

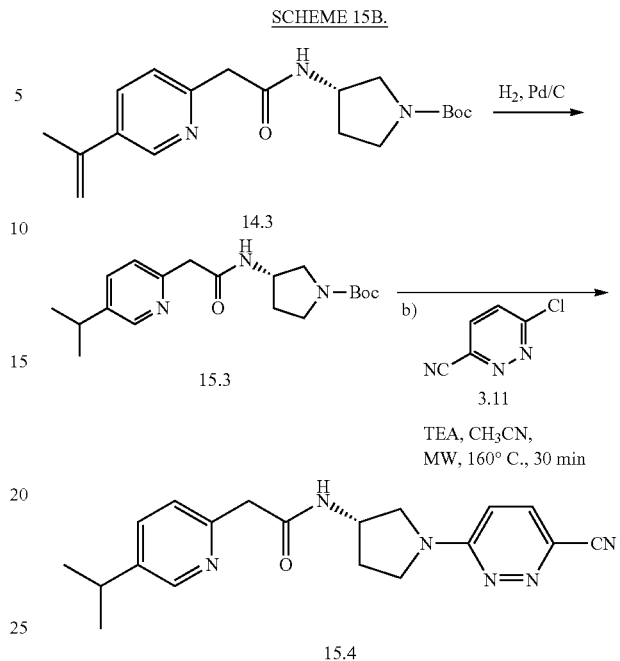

In one aspect, compounds of type 15.4, and similar compounds, can be prepared according to reaction Scheme 15B above. Thus, compounds of type 15.3 can be prepared by reduction of an appropriate alkene, e.g., 14.3 as shown above. The reduction is carried out in the presence of an appropriate hydrogen source, e.g., hydrogen gas, and an appropriate catalyst, e.g., palladium on carbon. Compounds of type 15.4 can be prepared by a deprotection reaction, followed by an arylation reaction of an appropriate amine, e.g., 15.3, and an appropriate aryl halide, e.g., 3.11. Appropriate aryl halides are commercially available or prepared by methods known to one skilled in the art. The deprotection reaction is carried out in the presence of an appropriate deprotecting agent, e.g., trifluoroacetic acid, in an appropriate solvent, e.g., dichloromethane, for an appropriate period of time, e.g., 1 hour. The arylation reaction is carried out in the presence of an appropriate base, e.g., triethylamine, in an appropriate solvent, e.g., acetonitrile, at an appropriate temperature, e.g., 160° C., for an appropriate period of time, e.g., 30 minutes. As can be appreciated by one skilled in the art, the above reaction provides an example of a generalized approach wherein compounds similar in structure to the specific reactants above (compounds similar to compounds of type 7.4, 14.1, and 15.1), can be substituted in the reaction to provide alkylaryl 6-substituted-pyridazine derivatives similar to Formula 15.2.

16. Route XVI

In one aspect, N-substituted-5-pyridazinyl-N-methyl carboxamide derivatives can be prepared as shown below:

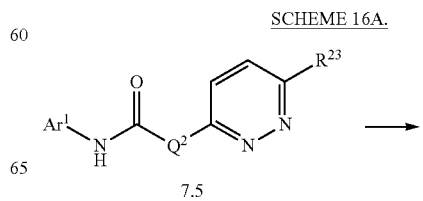

Compounds are represented in generic form, with substituents as noted in compound descriptions elsewhere herein and wherein each X is independently halogen. A more specific example is set forth below.

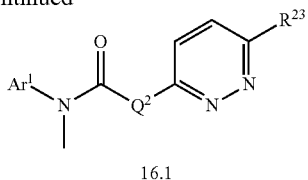

16.1

Compounds are represented in generic form, with substituents as noted in compound descriptions elsewhere herein and wherein $R_4$ is halogen, CN or $NO_2$. A more specific example is set forth below.

SCHEME 16B.

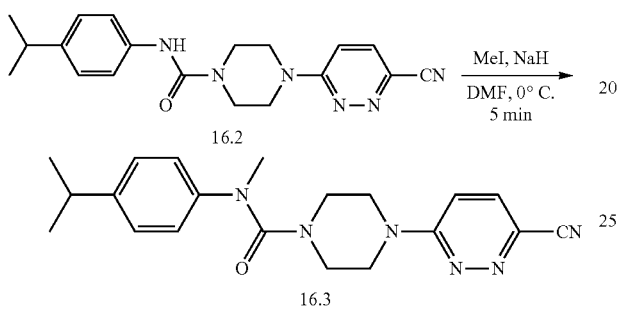

In one aspect, compounds of type 16.3, and similar compounds, can be prepared according to reaction Scheme 16B above. Thus, the N-methylated compounds of type 16.3 can be prepared by reacting an appropriate urea, e.g., 16.2 as shown above, with an iodomethane. Appropriate ureas can be prepared by the method described previously in Route VII, and iodomethane is commercially available. The N-methylation reaction is carried out in the presence of an appropriate solvent, e.g., N,N-Dimethylformamide (DMF), for an appropriate period of time, e.g., 5 min at 0° C. As can be appreciated by one skilled in the art, the above reaction provides an example of a generalized approach wherein compounds similar in structure to the specific reactants above (compounds similar to compounds of type 7.5), can be substituted in the reaction to provide N-substituted-5-pyridazinyl-N-methyl carboxamide derivatives similar to Formula 16.1.

17. Route XVII

In one aspect, 1-(6-substituted-pyridazin-3yl)-aryl sulfonamide derivatives can be prepared as shown below.

SCHEME 17A.

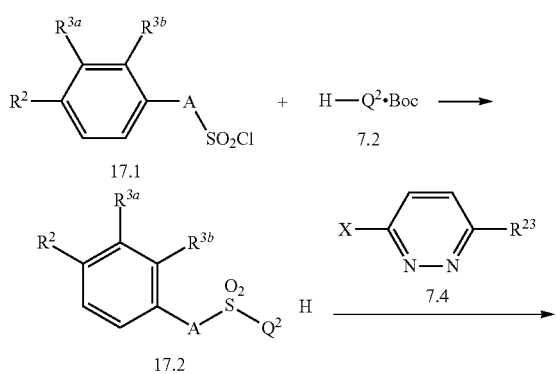

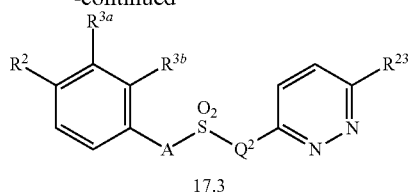

17.3

Compounds are represented in generic form, with substituents as noted in compound descriptions elsewhere herein and wherein X is halogen. A more specific example is set forth below.

SCHEME 17B.

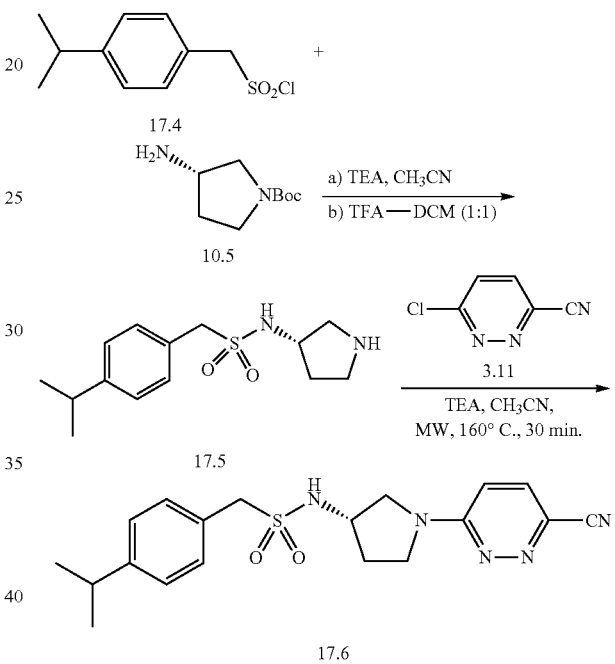

In one aspect, compounds of type 17.6, and similar compounds, can be prepared according to reaction Scheme 17B above. Thus, compounds of type 17.5 can be prepared by a coupling reaction of appropriate sulfonyl chlorides, e.g., 17.4 as shown above, with an appropriate amine, e.g., 10.5 as shown above. Appropriate sulfonyl chlorides and appropriate amines are commercially available or prepared by methods known to one skilled in the art. The coupling reaction is carried out in the presence of an appropriate base, e.g., triethyl amine, in an appropriate solvent, e.g., acetonitrile. The coupling reaction is followed by a deprotection. The deprotection is carried out in the presence of an appropriate deprotecting agent, e.g., trifluoroacetic acid (TFA), in an appropriate solvent, e.g., dichloromethane, for an appropriate period of time, e.g., 1 hour. Compounds of type 17.6 can be prepared by an arylation reaction of an appropriate amine, e.g., 17.5, and an appropriate aryl halide, e.g., 3.11 as shown above. Appropriate aryl halides are commercially available or prepared by methods known to one skilled in the art. The arylation reaction is carried out in the presence of an appropriate base, e.g., triethylamine, in an appropriate solvent, e.g., acetonitrile, at an appropriate temperature, e.g., 160° C., for an appropriate period of time, e.g., 30 minutes.

As can be appreciated by one skilled in the art, the above reaction provides an example of a generalized approach wherein compounds similar in structure to the specific reactants above (compounds similar to compounds of type 17.2, 17.3, 17.5, and 17.6), can be substituted in the reaction to provide 1-(6-substituted-pyridazin-3y1)-aryl sulfonamide derivatives similar to Formula 17.3.

18. Route XVIII

In one aspect, substituted arylpiperazine-1-carboxamide derivatives can be prepared as shown below.

SCHEME 18A.

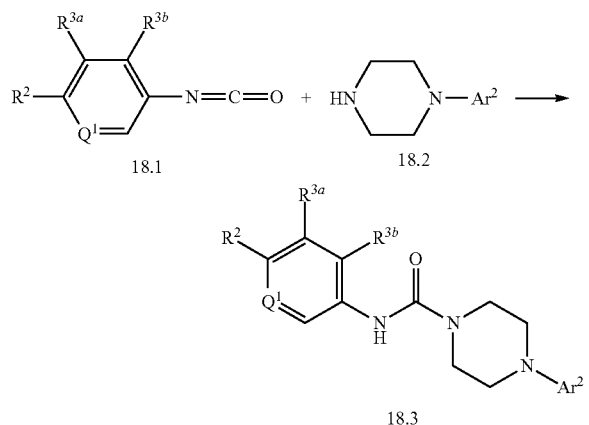

Compounds are represented in generic form, with substituents as noted in compound descriptions elsewhere herein. A more specific example is set forth below.

SCHEME 18B.

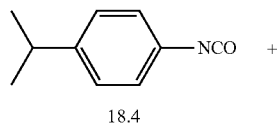

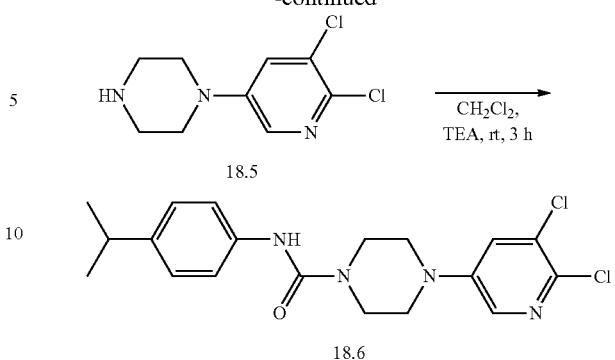

In one aspect, compounds of type 18.6, and similar compounds, can be prepared according to reaction Scheme 18B above. Thus, compounds of type 18.6 can be prepared by a urea bond formation reaction of an appropriate isocyanate, e.g., 18.4 as shown above, with an appropriate amine, e.g., 18.5 as shown above. Appropriate isocyanates and appropriate amines are commercially available or prepared by methods known to one skilled in the art. The coupling reaction is carried out in the presence of an appropriate base, e.g., triethyl amine, in an appropriate solvent, e.g., acetonitrile. The urea bond formation reaction is carried out in the presence of an appropriate base, e.g., triethylamine, in an appropriate solvent, e.g., dichloromethane, for an appropriate period of time, e.g., 3 hours. As can be appreciated by one skilled in the art, the above reaction provides an example of a generalized approach wherein compounds similar in structure to the specific reactants above (compounds similar to compounds of type 18.1 and 18.2), can be substituted in the reaction to provide substituted arylpiperazine-1-carboxamide derivatives similar to Formula 18.3.

19. Route XIX

In one aspect, 4-substituted-N-arylpiperazine-1-carboxamide derivatives can be prepared as shown below.

SCHEME 19A.

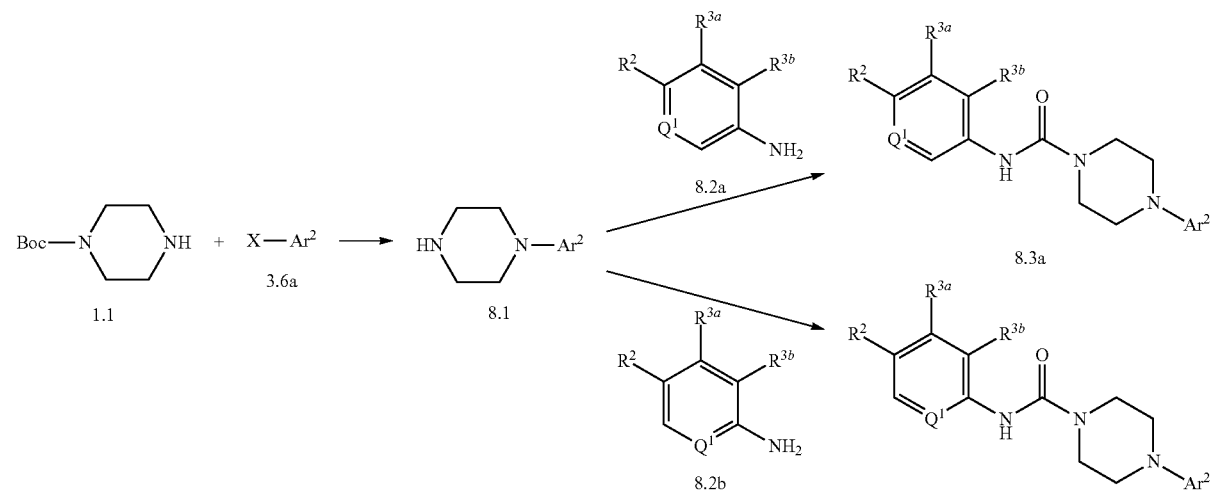

Compounds are represented in generic form, with substituents as noted in compound descriptions elsewhere herein and wherein X is halogen. A more specific example is set forth below.

SCHEME 19B.

In one aspect, compounds of type 19.4, and similar compounds, can be prepared according to reaction Scheme 19B above. Thus, compounds of type 19.2 can be prepared by arylation reaction of an appropriate amine, e.g., 1.1 as shown above, with an appropriate aryl halide, e.g., 19.1 as shown above, followed by a deprotection reaction. Appropriate amines and appropriate aryl halides are commercially available or prepared by methods known to one skilled in the art. The arylation reaction is carried out in the presence of an appropriate catalyst, e.g., Tris(dibenzylideneacetone)dipalladium(0), an appropriate base, e.g., sodium tert-butoxide, an appropriate ligand, e.g., Xantphos, and an appropriate solvent, e.g., 1,4-Dioxane, at an appropriate temperature, e.g., 150° C., for an appropriate period of time, e.g., 60 minutes using microwave irradiation. The arylation reaction is followed by a deprotection reaction. The deprotection reaction is carried out in the presence of an appropriate deprotecting agent, e.g., trifluoroacetic acid, in an appropriate solvent, dichloromethane, for an appropriate period of time, e.g., 1 hour. Compounds of type 19.4 can be prepared by urea bond formation reaction. The urea bond formation reaction is carried out between an appropriate amine, e.g., 19.2, and an isocyanate derivative (formed in situ from an appropriate amine, e.g., 19.3, and an appropriate phosgene derivative, e.g., bis(trichloromethyl) carbonate) in the presence of an appropriate base, e.g., pyridine, and an appropriate solvent, e.g., dichloromethane. As can be appreciated by one skilled in the art, the above reaction provides an example of a generalized approach wherein compounds similar in structure to the specific reactants above (compounds similar to compounds of type 1.1, 3.6a, 8.1, and 8.2), can be substituted in the reaction to provide 4-substituted-N-arylpiperazine-1-carboxamide derivatives similar to Formula 8.3.

20. Route XX

In one aspect, 4-substituted-arylpiperazine-1-carboxamide derivatives can be prepared as shown below.

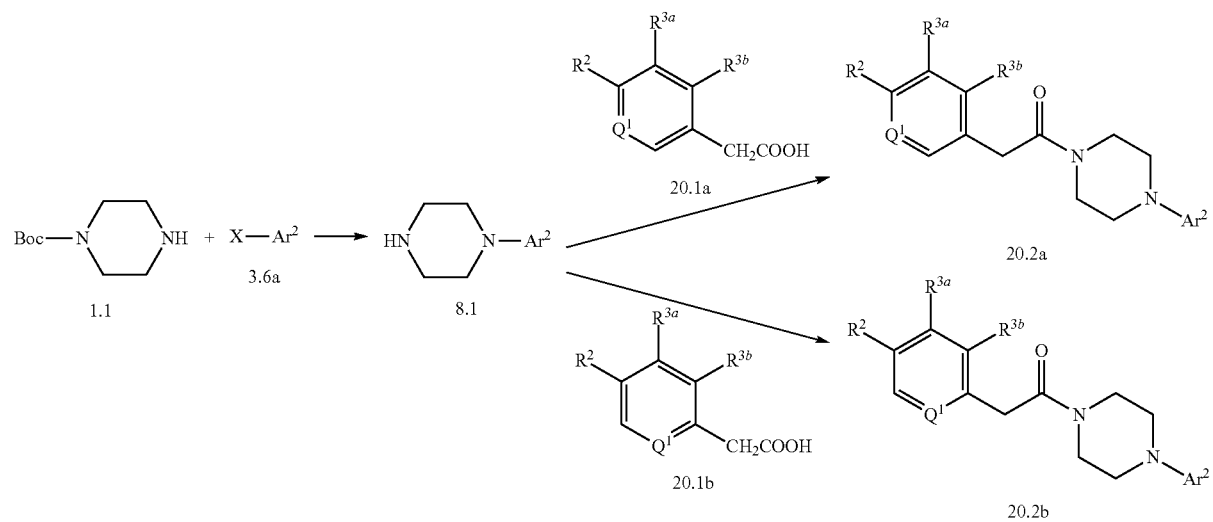

SCHEME 20A.

Compounds are represented in generic form, with substituents as noted in compound descriptions elsewhere herein. A more specific example is set forth below.

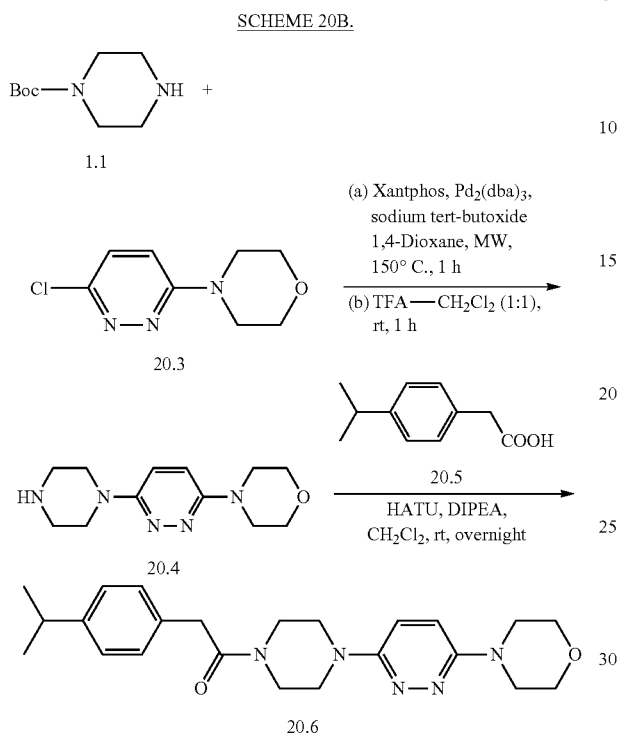

21. Route XXI

In one aspect, substituted arylpyridazinyl or heteroaryl pyridazinyl derivatives can be prepared as shown below.

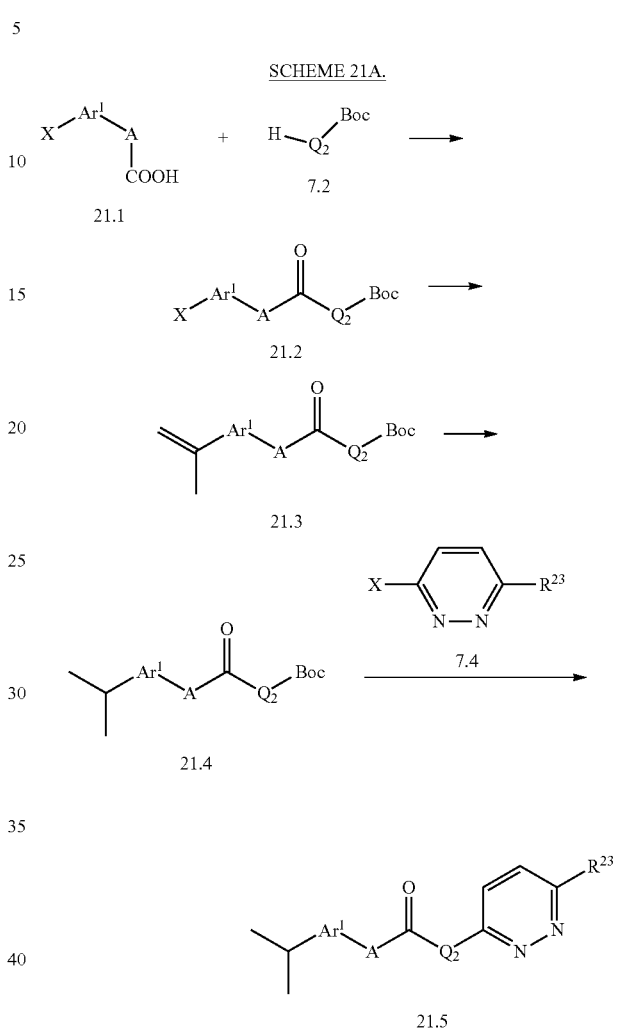

In one aspect, compounds of type 20.6, and similar compounds, can be prepared according to reaction Scheme 20B above. Thus, compounds of type 20.4 can be prepared by arylation reaction of an appropriate amine, e.g., 1.1 as shown above, with an appropriate aryl halide, e.g., 20.3 as shown above, followed by a deprotection reaction. Appropriate amines and appropriate aryl halides are commercially available or prepared by methods known to one skilled in the art. The arylation reaction is carried out in the presence of an appropriate catalyst, e.g., Tris(dibenzylideneacetone)dipalladium(0), an appropriate base, e.g., sodium tert-butoxide, an appropriate ligand, e.g., Xantphos, and an appropriate solvent, e.g., 1,4-Dioxane, at an appropriate temperature, e.g., 150° C., for an appropriate period of time, e.g., 60 minutes using microwave irradiation. The deprotection reaction is carried out in the presence of an appropriate deprotecting agent, e.g., trifluoroacetic acid, in an appropriate solvent, dichloromethane, for an appropriate period of time, e.g., 1 hour. Compounds of type 20.6 can be prepared by coupling reaction of amine 20.4 with appropriate carboxylic acid, e.g. 20.5, as shown above. The coupling reaction is carried out in the presence of an appropriate coupling agent, e.g., HATU, and an appropriate base, e.g., DIPEA, in an appropriate solvent, e.g., dichloromethane As can be appreciated by one skilled in the art, the above reaction provides an example of a generalized approach wherein compounds similar in structure to the specific reactants above (compounds similar to compounds of type 1.1, 3.6a, 8.1, and 20.1), can be substituted in the reaction to provide 4-substituted-arylpiperazine-1-carboxamide derivatives similar to Formula 20.2a and 20.2b.

Compounds are represented in generic form, with substituents as noted in compound descriptions elsewhere herein and wherein each X is independently halogen. A more specific example is set forth below.

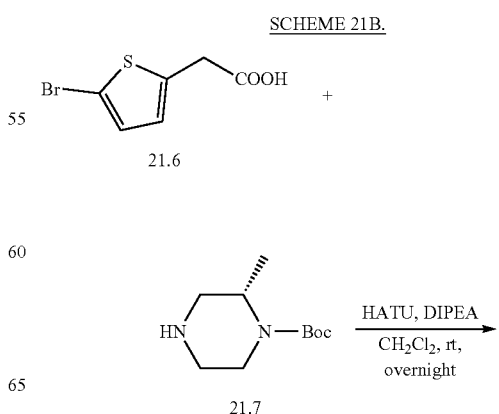

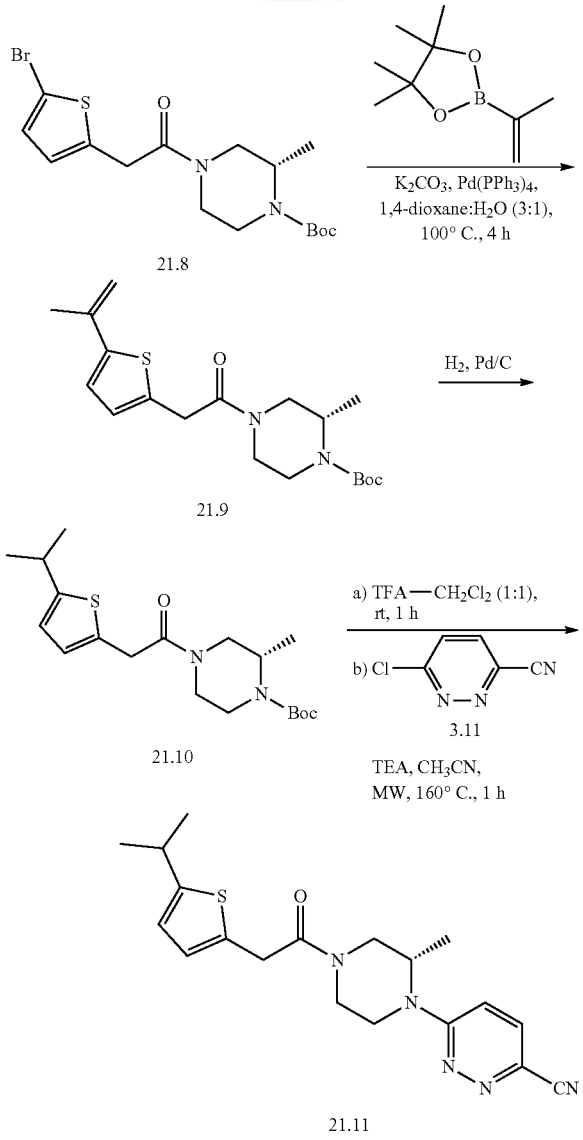

e.g., 4 hours, in appropriate solvent system, e.g. dioxane-water (3:1 by volume). Compounds of type 21.10 can be prepared by reduction of an appropriate alkene, e.g., 21.9 as shown above. The reduction is carried out in the presence of an appropriate hydrogen source, e.g., hydrogen gas, and an appropriate catalyst, e.g., palladium on carbon. Compounds of type 21.11 can be prepared by deprotection, followed by an arylation reaction of an appropriate amine, e.g., 21.10 as shown above, and an appropriate aryl halide, e.g., 3.11 as shown above. Appropriate aryl halides are commercially available or prepared by methods known to one skilled in the art. The deprotection is carried out in the presence of an appropriate deprotecting agent, e.g., trifluoroacetic acid, in an appropriate solvent, e.g., dichloromethane, for an appropriate period of time, e.g., 1 hour. The arylation reaction is carried out in the presence of an appropriate base, e.g., triethylamine, in an appropriate solvent, e.g., acetonitrile, at an appropriate temperature, e.g., 160° C., for an appropriate period of time, e.g., 1 hour. As can be appreciated by one skilled in the art, the above reaction provides an example of a generalized approach wherein compounds similar in structure to the specific reactants above (compounds similar to compounds of type 7.2, 7.4, 21.1, 21.2, 21.3, and 21.4), can be substituted in the reaction to provide substituted arylpyridazinyl or heteroaryl pyridazinyl derivatives similar to Formula 21.5.

22. Route XXII

In one aspect, substituted 4-aryl-N-phenyl carboxamide derivatives can be prepared as shown below.

In one aspect, compounds of type 21.11, and similar compounds, can be prepared according to reaction Scheme 21B above. Thus, compounds of type 21.8 can be prepared by a coupling reaction of an appropriate amine, e.g., 21.7 as shown above, with an appropriate carboxylic acid, e.g., 21.6 as shown above. Appropriate amines and appropriate carboxylic acids are commercially available or prepared by methods known to one skilled in the art. The coupling reaction is carried out in the presence of an appropriate coupling agent, e.g., HATU, and an appropriate base, e.g., DIPEA, in an appropriate solvent, e.g., dichloromethane. Compounds of type 21.9 can be prepared by a coupling reaction of an appropriate aryl halide, e.g., 21.8, and an appropriate alkene, e.g., 4,4,5,5-tetramethyl-2-(prop-1-en-2-yl)-1,3,2-dioxaborolane as shown above. Appropriate alkenes are commercially available or prepared by methods known to one skilled in the art. The coupling reaction is carried out in the presence of an appropriate base, e.g., potassium carbonate, and an appropriate catalyst, e.g., tetrakis(triphenylphosphine)palladium (0), at an appropriate temperature, e.g., 100° C., for an appropriate period of time,

SCHEME 22A.

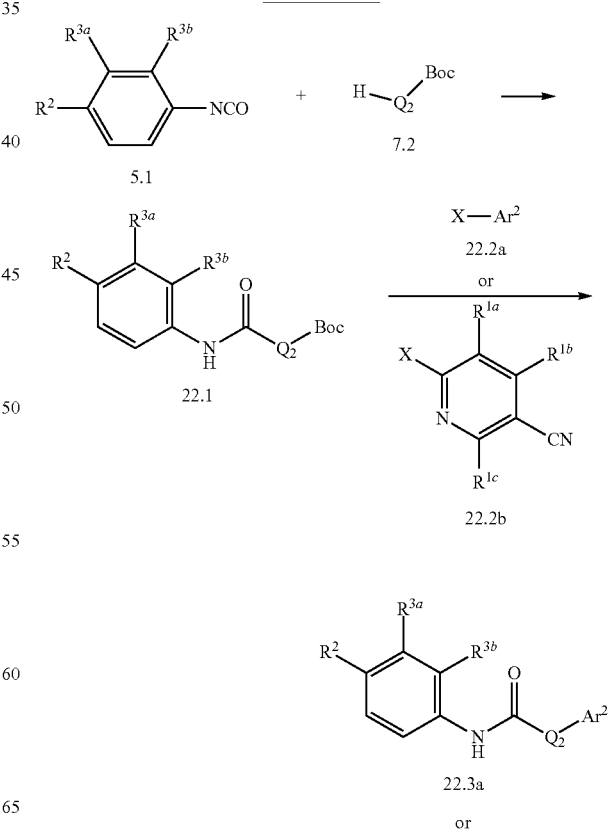

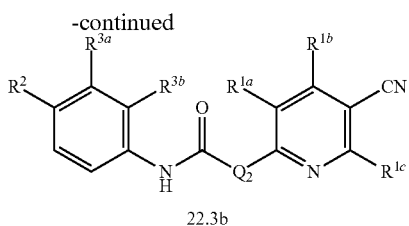

22.3b

Compounds are represented in generic form, with substituents as noted in compound descriptions elsewhere herein and wherein X is halogen. A more specific example is set forth below.

SCHEME 22B.

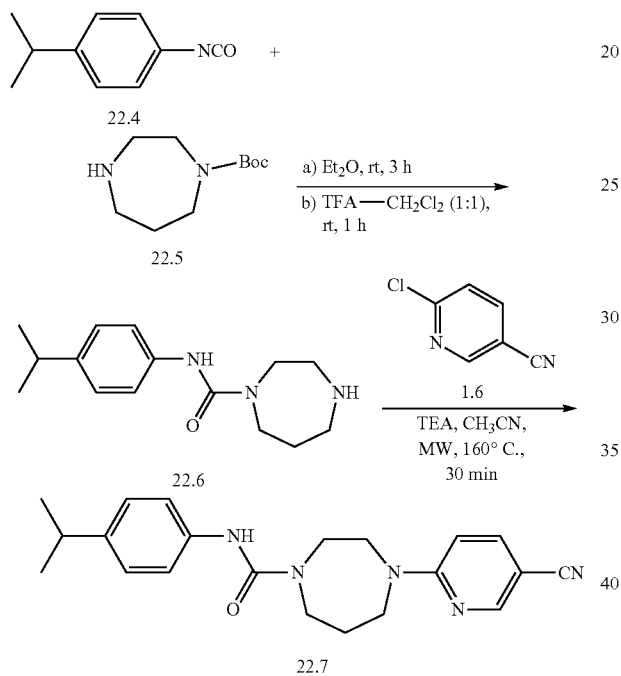

In one aspect, compounds of type 22.7, and similar compounds, can be prepared according to reaction Scheme 22B above. Thus, compounds of type 22.6 can be prepared by a urea bond formation reaction between an appropriate amine, e.g., 22.5 as shown above, and an appropriate isocyanate, e.g., 22.4 as shown above. Appropriate amines and appropriate isocyanates are commercially available or prepared by methods known to one skilled in the art. The urea bond formation reaction is carried out in the presence of an appropriate solvent, e.g., diethyl ether, for an appropriate period of time, e.g., 3 hours. The nucleophilic substitution is followed by a deprotection reaction. The deprotection reaction is carried out in the presence of an appropriate deprotecting agent, e.g., trifluoroacetic acid, in an appropriate solvent, e.g., dichloromethane, for an appropriate period of time, e.g., 1 hour. Compounds of type 22.7 can be prepared by an arylation reaction of appropriate amine, e.g., 22.6 as shown above, and an appropriate aryl halide, e.g., 1.6 as shown above. Appropriate aryl halides are commercially available or prepared by methods known to one skilled in the art. The arylation reaction is carried out in the presence of an appropriate base, e.g., triethylamine, in an appropriate solvent, e.g., acetonitrile, at an appropriate temperature, e.g, 160° C., for an appropriate period of time, e.g., 30 minutes using microwave irradiations. As can be appreciated by one skilled in the art, the above reaction provides an example of a generalized approach wherein compounds similar in structure to the specific reactants above (compounds similar to compounds of type 5.1, 7.2, 22.1 and 22.2), can be substituted in the reaction to provide 4-aryl-N-phenyl carboxamide derivatives similar to Formula 22.3a and 22.3b.

23. Route XXIII

In one aspect, alkylaryl 6-substituted-pyridazine derivatives can be prepared as shown below.

SCHEME 23A.

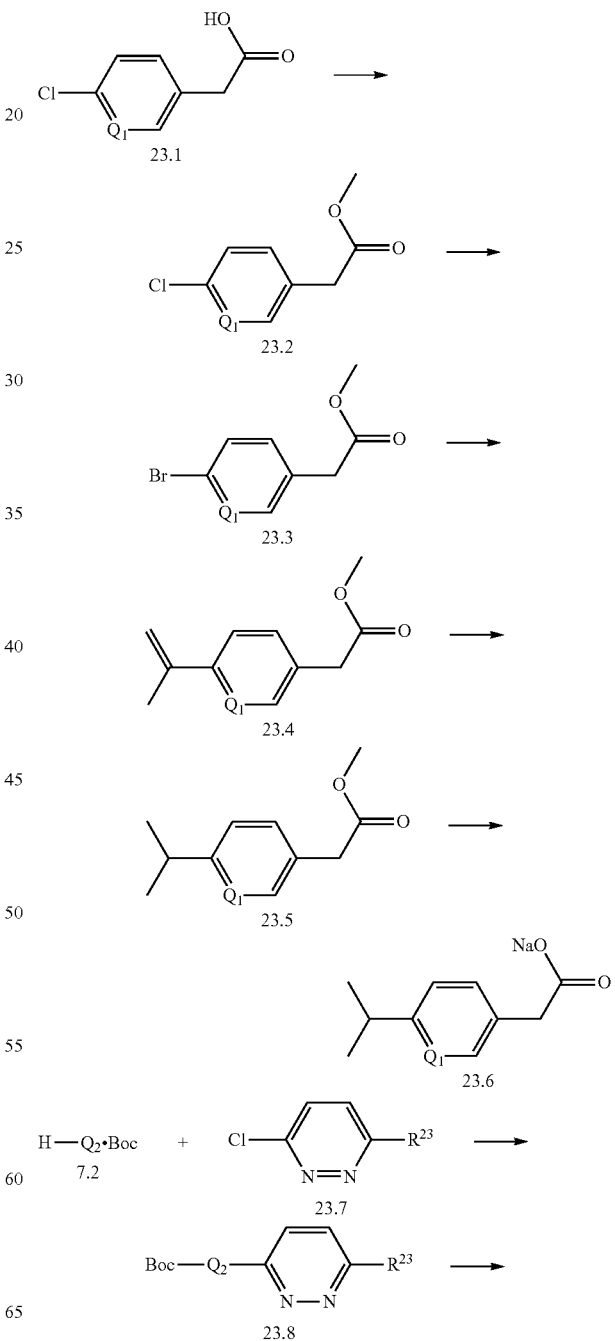

221
-continued

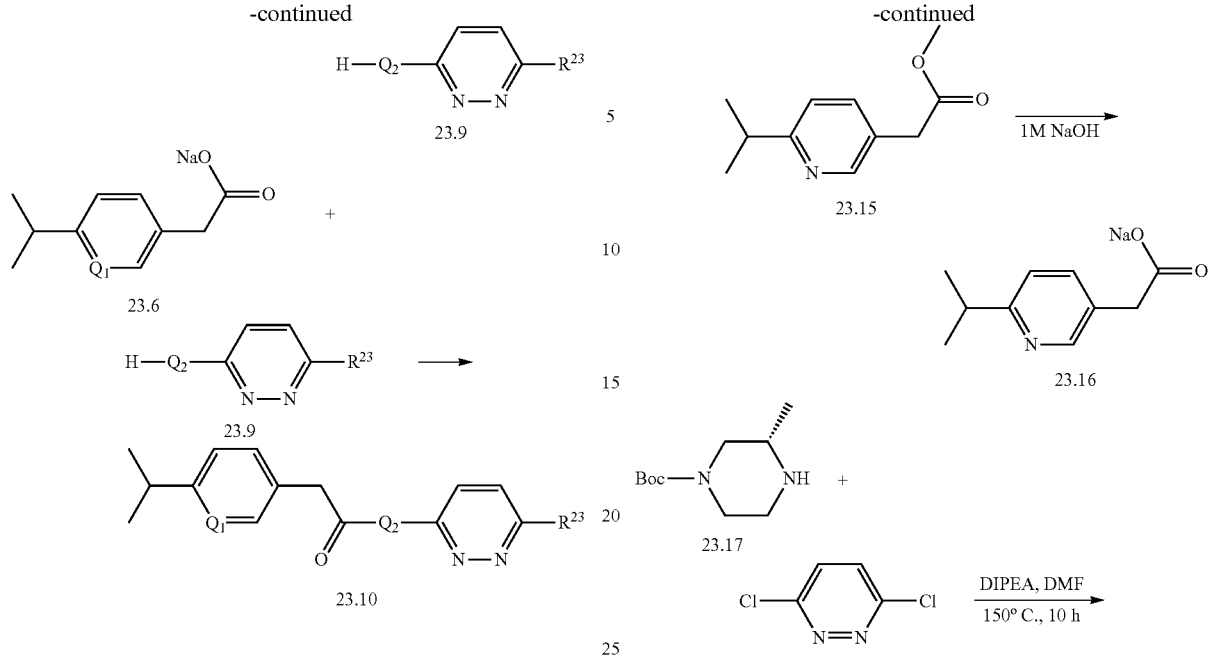

Compounds are represented in generic form, with substituents as noted in compound descriptions elsewhere herein. A more specific example is set forth below.

SCHEME 23B.

222
-continued

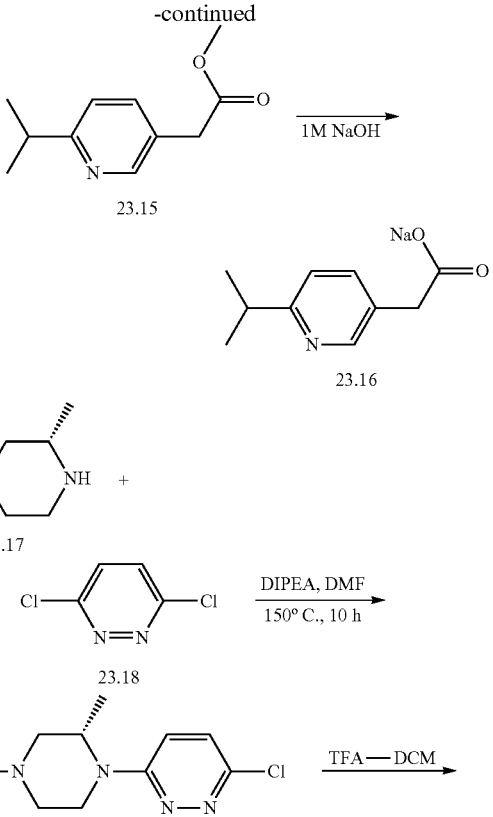

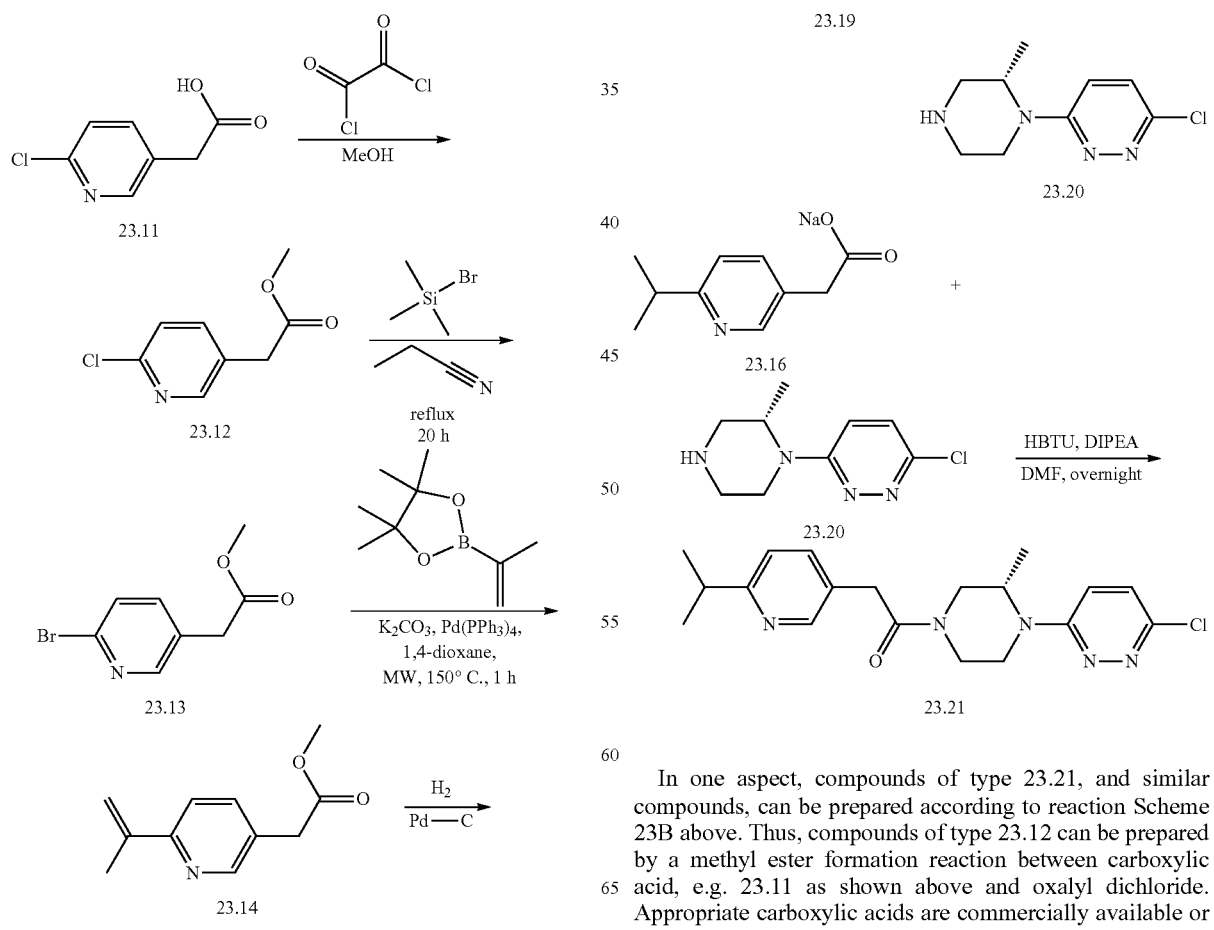

In one aspect, compounds of type 23.21, and similar compounds, can be prepared according to reaction Scheme 23B above. Thus, compounds of type 23.12 can be prepared by a methyl ester formation reaction between carboxylic acid, e.g. 23.11 as shown above and oxalyl dichloride. Appropriate carboxylic acids are commercially available or prepared by methods known to one skilled in the art. The methyl ester formation reaction is carried out in the presence of an appropriate solvent e.g. methanol, for an appropriate period of time, e.g. 1 hour. Compound of type 23.13 can be prepared by a chloride displacement reaction between appropriate heteroarylchloride, e.g., 23.12 and bromotrimethylsilane. The chloride displacement reaction is carried out in an appropriate solvent, e.g. propiononitrile, at an appropriate temperature, e.g., 110° C., for an appropriate period of time, e.g. 20 hours. Compounds of type 23.14 can be prepared by a coupling reaction of an appropriate aryl halide, e.g., 23.13, and an appropriate alkene, e.g., 4,4,5,5-tetramethyl-2-(prop-1-en-2-yl)-1,3,2-dioxaborolane as shown above. Appropriate alkenes are commercially available or prepared by methods known to one skilled in the art. The coupling reaction is carried out in the presence of an appropriate base, e.g., potassium carbonate, and an appropriate catalyst, e.g., tetrakis(triphenylphosphine)palladium (0), at an appropriate temperature, e.g., 150° C., for an appropriate period of time, e.g., 1 hours, in appropriate solvent system, e.g. dioxane using microwave irradiations. Compounds of type 23.15 can be prepared by reduction of an appropriate alkene, e.g., 23.14 as shown above. The reduction is carried out in the presence of an appropriate hydrogen source, e.g., hydrogen gas, and an appropriate catalyst, e.g., palladium on carbon. Compounds of type 23.16 can be prepared by ester deprotection reaction of an appropriate ester, e.g., 23.15 as shown above. The ester deprotection reaction is carried out using appropriate base, e.g. sodium hydroxide.

Compounds of type 23.19 can be prepared by an arylation reaction of appropriate amine, e.g., 23.17 as shown above, and an appropriate aryl halide, e.g., 23.18 as shown above. Appropriate aryl halides are commercially available or prepared by methods known to one skilled in the art. The arylation reaction is carried out in the presence of an appropriate base, e.g., diisopropylethylamine, in an appropriate solvent, e.g., dimethylformamide, at an appropriate temperature, e.g, 150° C., for an appropriate period of time, e.g., 10 hour. Compounds of type 23.20 can be prepared by a deprotection reaction. The deprotection reaction is carried out in the presence of an appropriate deprotecting agent, e.g., trifluoroacetic acid, in an appropriate solvent, e.g., dichloromethane, for an appropriate period of time, e.g., 1 hour.

Compounds of type 23.21 can be prepared by a coupling reaction of an appropriate amine, e.g., 23.20 as shown above, with an appropriate sodium salt of carboxylic acid, e.g., 23.16 as shown above. The coupling reaction is carried out in the presence of an appropriate coupling agent, e.g., HATU, and an appropriate base, e.g., DIPEA, in an appropriate solvent, e.g., dichloromethane.

As can be appreciated by one skilled in the art, the above reaction provides an example of a generalized approach wherein compounds similar in structure to the specific reactants above (compounds similar to compounds of type 7.2, 23.1, 23.2, 23.3, 23.4, 23.5, 23.6, 23.7, 23.8 and 23.9), can be substituted in the reaction to provide 4-aryl-N-phenyl carboxamide derivatives similar to Formula 23.10.

24. Route XXIV

In one aspect, 4-substituted-arylpiperazine-1-carboxamide derivatives can be prepared as shown below.

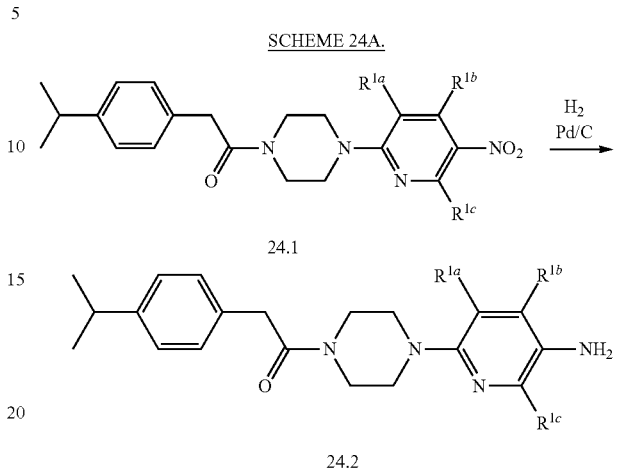

SCHEME 24A.

24.1

24.2

Compounds are represented in generic form, with substituents as noted in compound description elsewhere herein. A more specific example is set forth below.

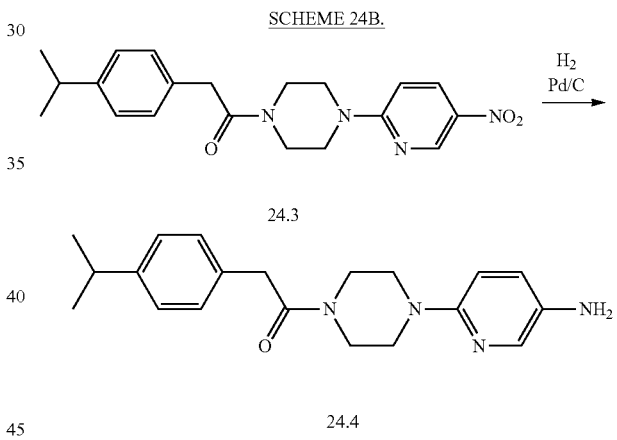

SCHEME 24B.

24.3

24.4

In one aspect, compounds of type 24.4, and similar compounds, can be prepared according to reaction Scheme 24B above. Thus, compound type 24.4 can be prepared by reaction by reduction of an appropriate nito compound, e.g., 24.3 as shown above. The reduction of nitro is carried out in the presence of an appropriate hydrogen source, e.g., hydrogen gas, and an appropriate catalyst, e.g., palladium on carbon. As can be appreciated by one skilled in the art, the above reaction provides an example of a generalized approach wherein compounds similar in structure to the specific reactants above (compounds similar to compounds of type 24.3), can be substituted in the reaction to provide 4-substituted-arylpiperazine-1-carboxamide derivatives similar to Formula 24.4.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

E. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. PZ-2891 Prevents Inhibition of Purified Human PANK3 by Propionyl-CoA

Figure 1B:
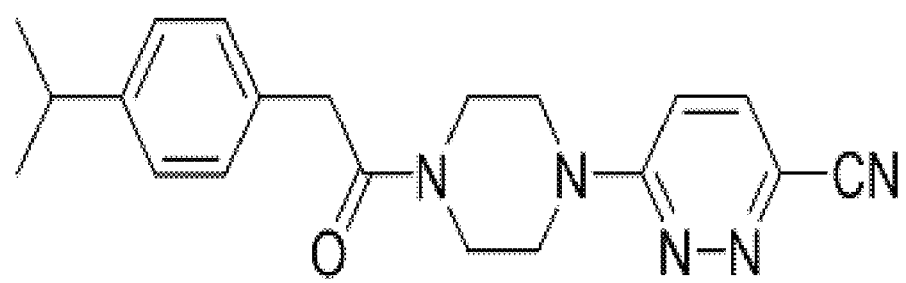
FIG. 1B shows the structure of PZ-2891.

Referring to FIG. 1A, PANK3 protein (1 μg) was incubated with 1 mM ATP, 10 mM $MgCl_2$, 45 μM [$^{14}C$]-pantothenate, 100 mM Tris-HCl pH 7.5 for 10 minutes at 37° C., either with or without 2.5 μM PZ-2891 (FIG. 1B), and at the indicated concentration of propionyl-coenzyme A (C3-CoA). The [$^{14}C$]-phosphopantothenate product of the PANK3 reaction was measured by DE-81 filter disc assay (Vallari et al. (1987) *J. Biol. Chem.* 262: 2468-2472) and the amount of product without added propionyl-coenzyme A (C3-CoA) was defined as 100% maximal activity.

2. Reduction of Blood Ammonia Levels in Response to PZ-2891 Treatment

Figure 2:
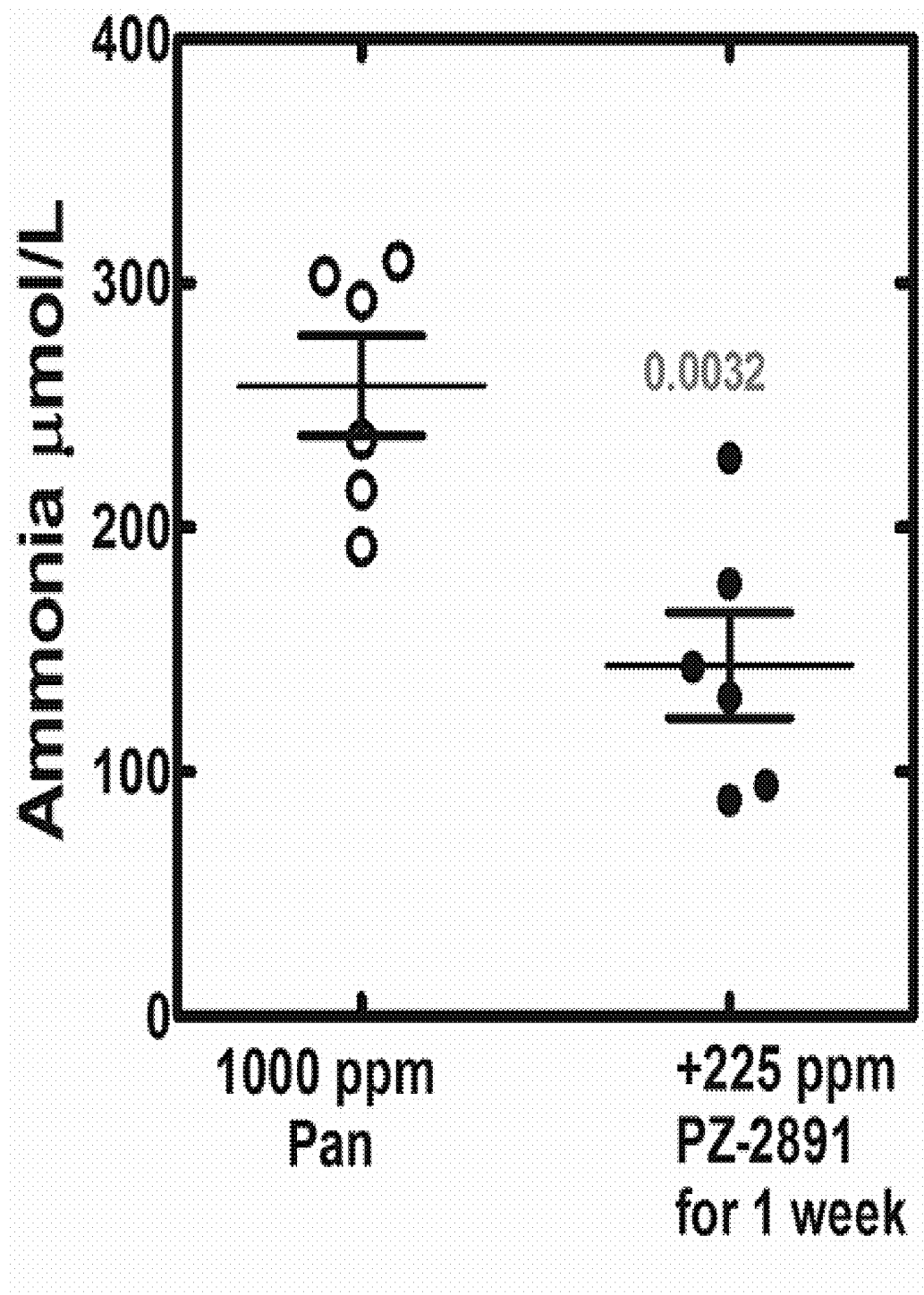
FIG. 2 shows representative data demonstrating reduction of blood ammonia levels in response to PZ-2891 treatment.

Referring to FIG. 2, a mouse model of propionic acidemia, the Pcca−/−(A138T) (Guensel et al. (2013) *Mol. Ther.* 21: 1316-1323), was fed chow containing either 1000 ppm pantothenate (Pan) or 225 ppm PZ-2891 plus 1000 ppm Pan for 7 days. Blood was drawn from 6 mice per group and blood ammonia levels were determined using a GM7 MicroStat Analyser (Analox Instruments, www.analox.com) and the Analox Blood Ammonia Reagent kit according to the manufacturer's instructions. Statistical analysis was performed using the Students unpaired t-test and p=0.0032.

3. Reduction of CoA Levels in the Livers of the Pcca Mouse Model are Elevated by PZ-3022 Treatment.

Figure 3:
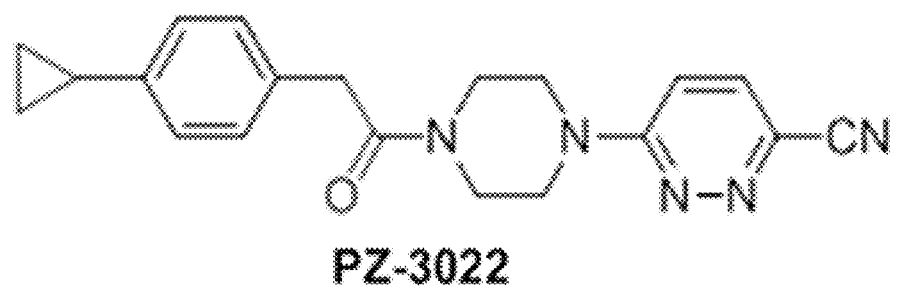
FIG. 3 shows the structure of PZ-3022.

The structure of PZ-3022 is shown in FIG. 3.

Figure 4:
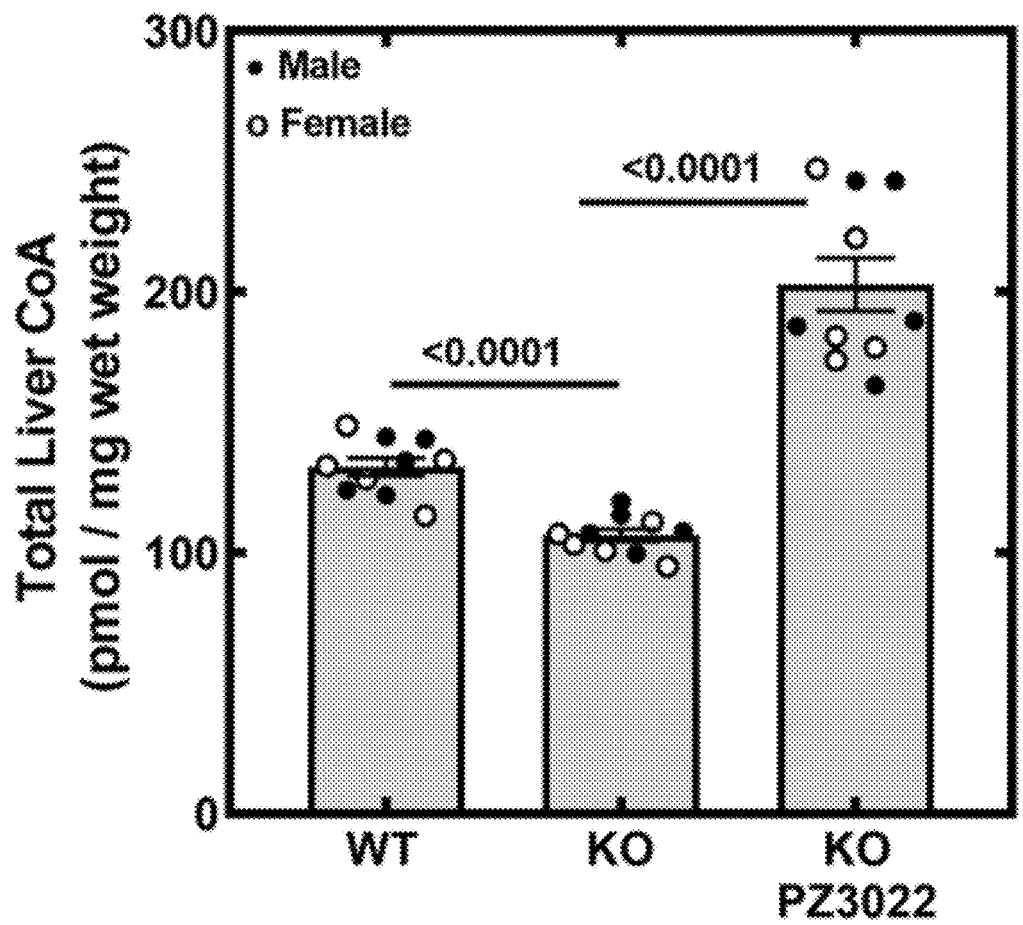
FIG. 4 shows representative data demonstrating the total CoA levels in the livers of wild-type, Pcca, and PZ-3022-treated Pcca mice.

Referring to FIG. 4, a mouse model of propionic acidemia, the Pcca−/−(A138T) mouse (Guensel et al. (2013) *Mol. Ther.* 21: 1316-23) was fed chow or chow containing 1000 ppm pantothenate plus 75 ppm PZ-3022 beginning at day 21. At 70 days, the liver CoA levels were measured. The Pcca mice had reduced liver CoA compared to wild-type and in the PZ-3022-treated Pcca mice the CoA levels were elevated.

4. PZ-3022 Elevates CoA and Acetyl-CoA in the Livers of the Pcca Mouse Model

Figure 5:
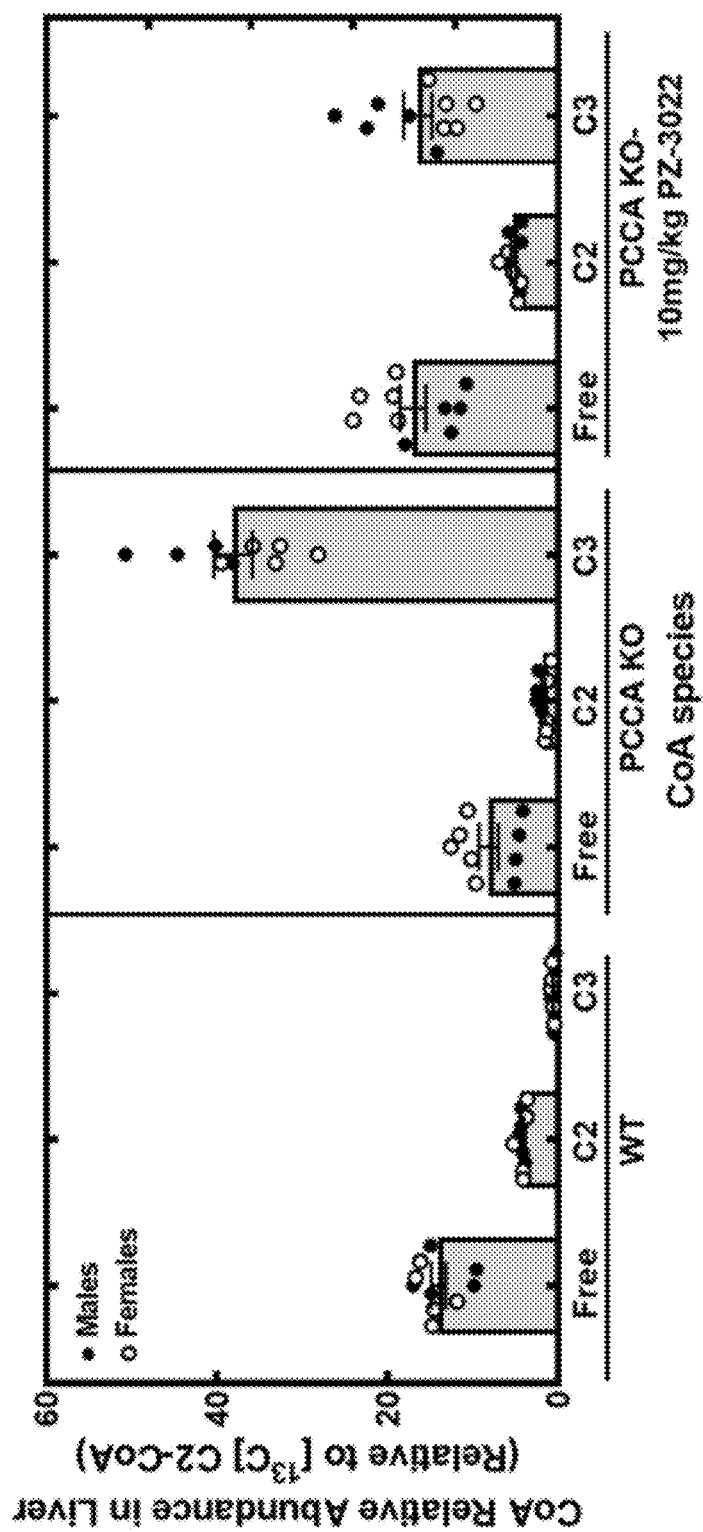
FIG. 5 shows representative data demonstrating CoA (Free), acetyl-CoA (C2), and propionyl-CoA (C3) levels in the livers of wild-type, Pcca, and PZ-3022-treated Pcca mice.

Referring to FIG. 5, a mouse model of propionic acidemia, the Pcca−/−(A138T) (mouse Guensel et al. (2013) *Mol. Ther.* 21: 1316-23) was fed chow or chow containing 1000 ppm pantothenate plus 75 ppm PZ-3022 beginning at day 21. At 70 days, the liver CoA, acetyl-CoA and propionyl-CoA levels were measured. The Pcca mice had lower free CoA, lower acetyl-CoA and very elevated propionyl-CoA compared to wild-type. PZ-3022 treatment of the Pcca mice elevated free CoA and acetyl-CoA, and propionyl-CoA was reduced.

Figure 6A:
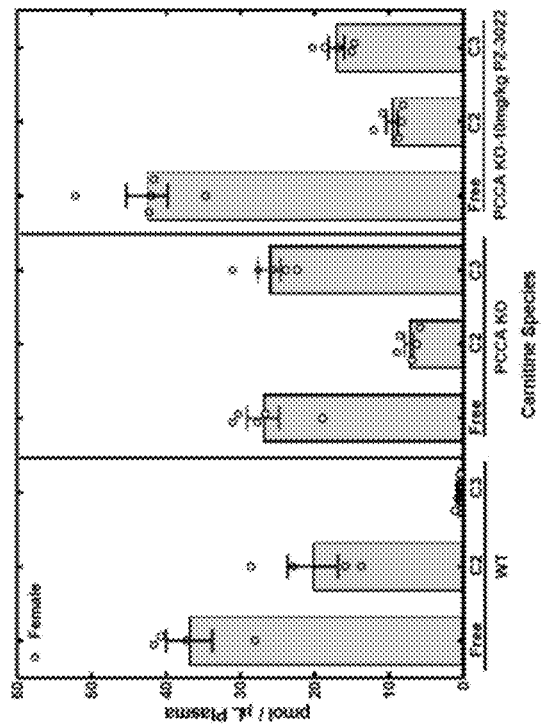
FIG. 6A and FIG. 6B shows representative data demonstrating carnitine (free), acetyl-carnitine (C2), and propionyl-carnitine (C3) levels in the plasma of wild-type, Pcca, and PZ-3022-treated Pcca male (FIG. 6A) and female (FIG. 6B) mice.
Figure 6B:
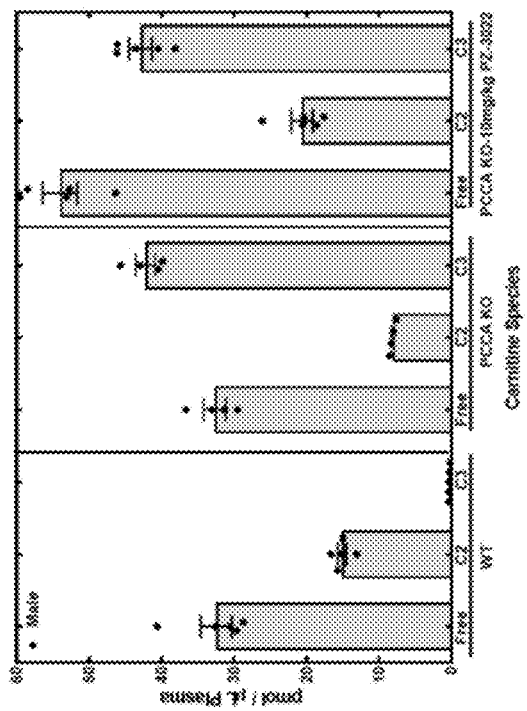

5. PZ-3022 Treatment Normalizes the Levels of Acyl-Carnitines in the Pcca Mouse Model Referring to FIG. 6A and FIG. 6B, a mouse model of propionic acidemia, the Pcca−/−(A138T) (mouse Guensel et al. (2013) *Mol. Ther.* 21: 1316-23) was fed chow or chow containing 1000 ppm pantothenate plus 75 ppm PZ-3022 beginning at day 21. At 70 days, the plasma was analyzed for the levels of acyl-carnitines. The Pcca mice had lower levels of acetyl-carnitine and significantly elevated levels of propionyl-carnitine. PZ-3022 treatment elevated acetyl-carnitine.

Figure 7:
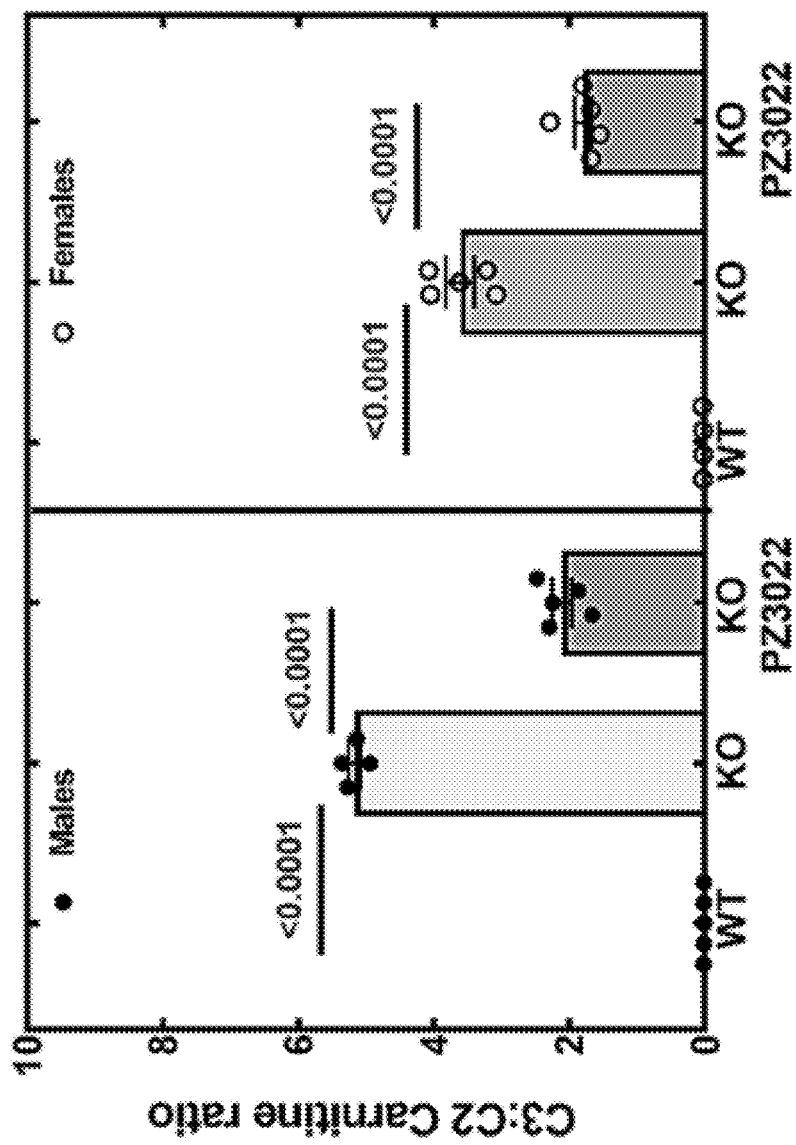
FIG. 7 shows representative data demonstrating the C3:C2 ration of plasma carnitines in wild-type, Pcca, and PZ-3022-treated Pcca mice.

Referring to FIG. 7, the data in FIG. 5 are presented as the C3:C2 ration of plasma carnitines. PZ-3022 therapy reduced the highly elevated C3:C2 ratio in the Pcca mouse model.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating propionic acidemia (PA) in a subject in need thereof, the method comprising administering to the subject a therapeutically effective amount of a compound having a structure represented by a formula:

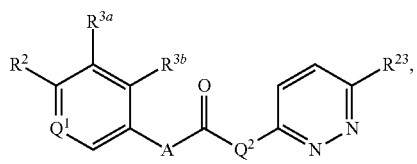

or a pharmaceutically acceptable salt thereof, wherein:

A is $CH_2$;

$Q^1$ is CH; and $R^2$ is selected from —$SCH_3$, C1-C8 acyclic alkyl, C2-C8 acyclic alkenyl, C1-C8 monohaloalkyl, C1-C8 polyhaloalkyl, C1-C8 alkoxyhaloalkyl, cyclopropyl, cyclobutyl, and oxetane, wherein the cyclopropyl, cyclobutyl, and oxetane are optionally substituted with 1, 2, or 3 groups independently selected from —OH, C1-C4 alkyl, and C1-C4 alkoxy; or $Q^1$ is N; and $R^2$ is selected from halogen, —$SCH_3$, C1-C8 acyclic alkyl, C2-C8 acyclic alkenyl, C1-C8 monohaloalkyl, C1-C8 polyhaloalkyl, C1-C8 alkoxyhaloalkyl, cyclopropyl, cyclobutyl, and oxetane, wherein the cyclopropyl, cyclobutyl, and oxetane are optionally substituted with 1, 2, or 3 groups independently selected from —OH, C1-C4 alkyl, and C1-C4 alkoxy;

$Q^2$ is a structure selected from:
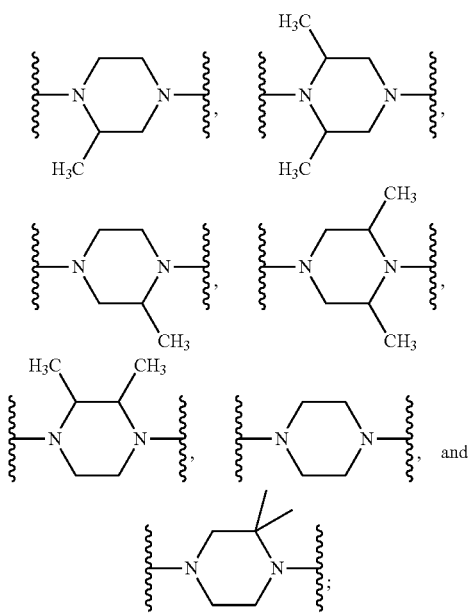
each of $R^{3a}$ and $R^{3b}$ is independently selected from hydrogen, halogen, —OH, C1-C4 alkoxy, and C1-C4 alkyl; and
$R^{23}$ is selected from halogen and —CN.
2. The method of claim 1, wherein the compound has a structure represented by a formula:
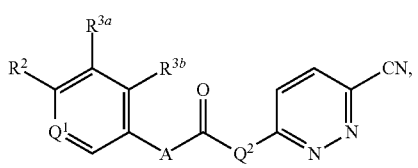
or a pharmaceutically acceptable salt thereof.
3. The method of claim 1, wherein the compound is selected from:
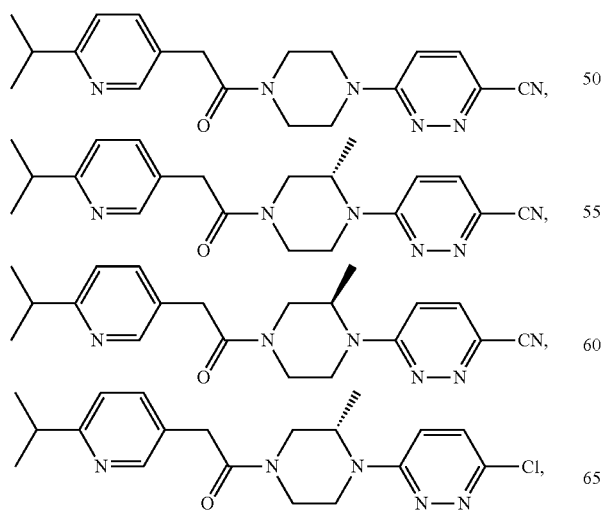
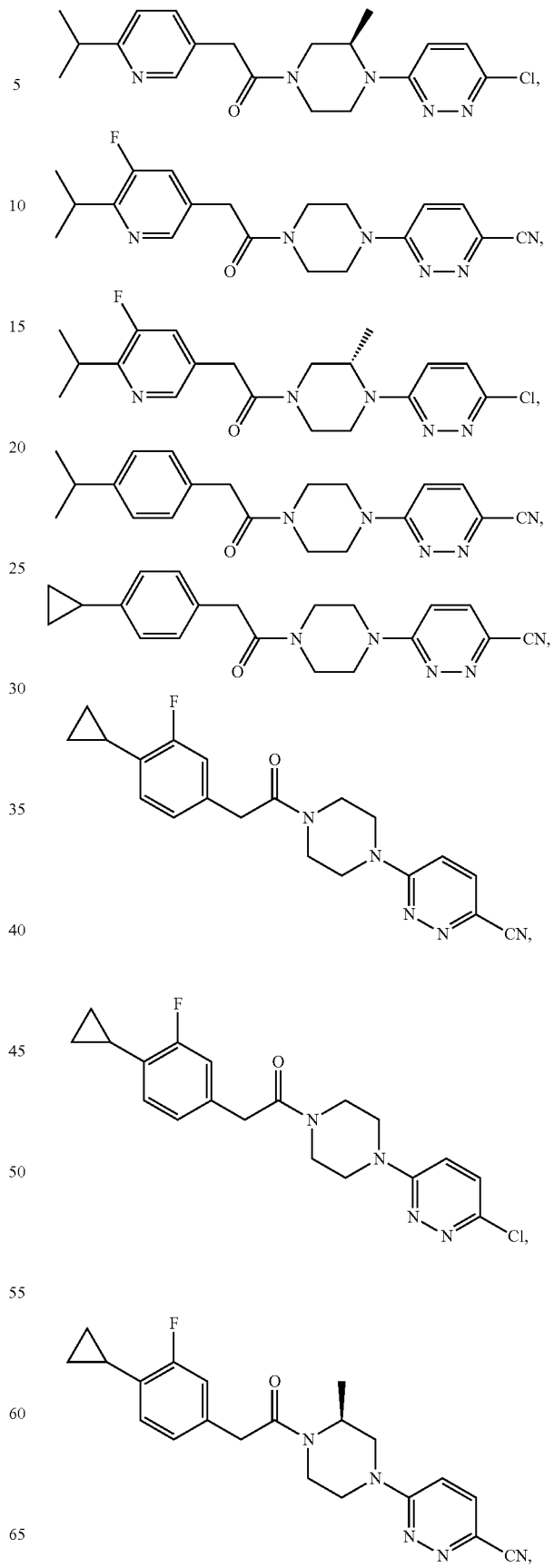

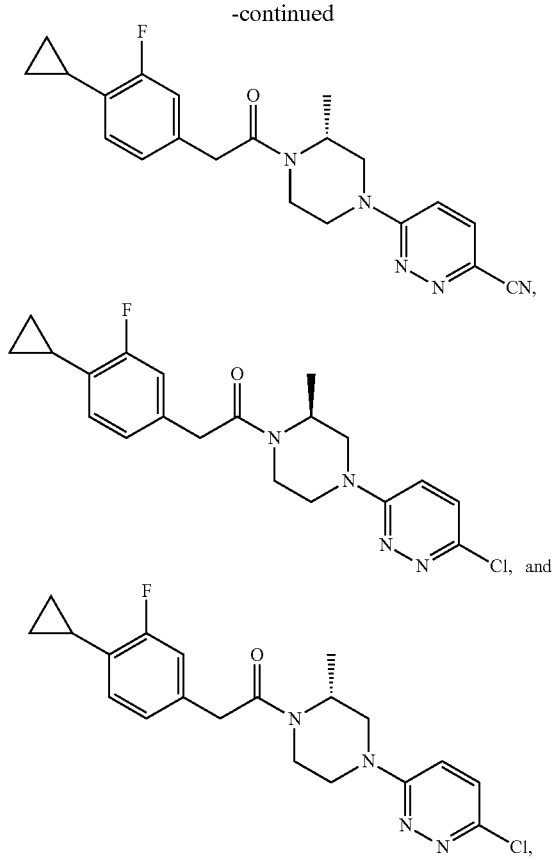

or a pharmaceutically acceptable salt thereof.

4. The method of claim 1, wherein the subject is a mammal.

5. The method of claim 1, wherein the mammal is a human.

6. The method of claim 1, further comprising the step of administering to the subject a therapeutically effective amount of carnitine, pantothenate, and/or pantothenic acid.

7. The method of claim 1, wherein the PA is hereditary.

8. The method of claim 1, wherein the PA is acquired.

9. A kit for treating propionic acidemia (PA) in a subject in need thereof, comprising:

(a) an effective amount of a compound of claim 1; and (b) at least one agent known to treat the PA, together with instructions for effective administration.

10. The kit of claim 9, wherein the at least one agent is carnitine, pantothenate, or pantothenic acid.

11. The kit of claim 9, wherein the compound is represented by the formula:

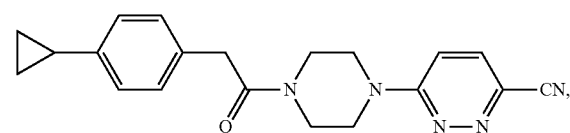 [SMILES: N#Cc1ccc(N2CCN(C(=O)Cc3ccc(C4CC4)cc3)CC2)nn1]

or a pharmaceutically acceptable salt thereof.

12. The kit of claim 9, wherein the compound is represented by the formula:

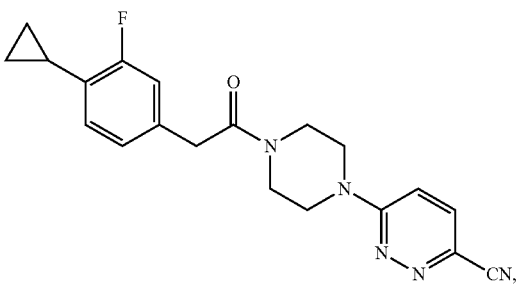 [SMILES: N#Cc1ccc(N2CCN(C(=O)Cc3ccc(C4CC4)c(F)c3)CC2)nn1]

or a pharmaceutically acceptable salt thereof.

13. The kit of claim 9, wherein the compound is represented by the formula:

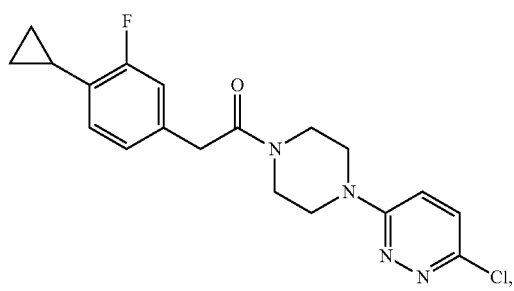 [SMILES: O=C(Cc1ccc(C2CC2)c(F)c1)N1CCN(c2ccc(Cl)nn2)CC1]

or a pharmaceutically acceptable salt thereof.

14. The method of claim 1, wherein $Q^1$ is CH.

15. The method of claim 1, wherein $R^2$ is cyclopropyl.

16. The method of claim 1, wherein $Q^2$ is a structure:

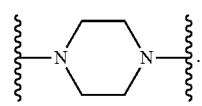

17. The method of claim 1, wherein the compound is represented by the formula:

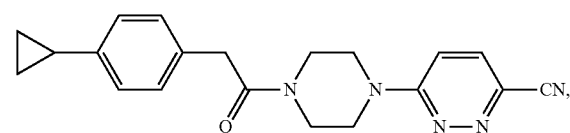 [SMILES: N#Cc1ccc(N2CCN(C(=O)Cc3ccc(C4CC4)cc3)CC2)nn1]

or a pharmaceutically acceptable salt thereof.

18. The method of claim 1, wherein the compound is represented by the formula:
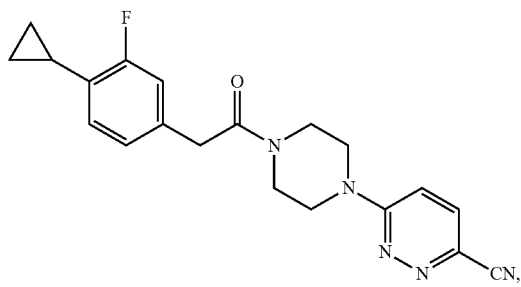 [SMILES: N#Cc1ccc(N2CCN(C(=O)Cc3ccc(C4CC4)c(F)c3)CC2)nn1]
or a pharmaceutically acceptable salt thereof.
19. The method of claim 1, wherein the compound is represented by the formula:
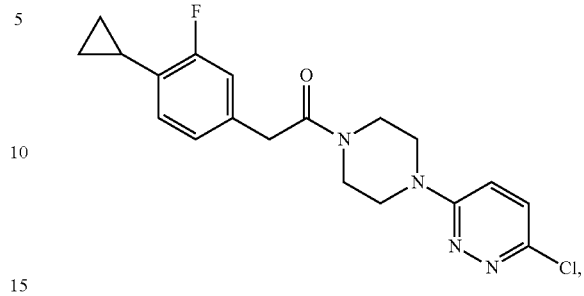
or a pharmaceutically acceptable salt thereof.
* * * * *